US009802918B2

(12) United States Patent
Vechorkin et al.

(10) Patent No.: US 9,802,918 B2
(45) Date of Patent: Oct. 31, 2017

(54) PYRIDINEAMINE COMPOUNDS USEFUL AS PIM KINASE INHIBITORS

(71) Applicant: Incyte Corporation, Wilmington, DE (US)

(72) Inventors: Oleg Vechorkin, Wilmington, DE (US); Yun-Long Li, Chadds Ford, PA (US); Jincong Zhuo, Garnet Valley, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/353,312

(22) Filed: Nov. 16, 2016

(65) Prior Publication Data

US 2017/0158670 A1    Jun. 8, 2017

Related U.S. Application Data

(63) Continuation of application No. 15/166,380, filed on May 27, 2016, now Pat. No. 9,540,347.

(60) Provisional application No. 62/168,230, filed on May 29, 2015.

(51) Int. Cl.
*C07D 401/14*    (2006.01)

(52) U.S. Cl.
CPC ................. *C07D 401/14* (2013.01)

(58) Field of Classification Search
None
See application file for complete search history.

(56) References Cited

U.S. PATENT DOCUMENTS

| | | | |
|---|---|---|---|
| 8,168,794 B2 | 5/2012 | Burger et al. | |
| 8,329,732 B2 | 12/2012 | Burger et al. | |
| 9,200,004 B2 | 12/2015 | Xue | |
| 9,278,950 B2 | 3/2016 | Li et al. | |
| 9,340,546 B2 | 5/2016 | Ahmad | |
| 9,540,347 B2 | 1/2017 | Vechorkin et al. | |
| 9,550,765 B2 | 1/2017 | Xue et al. | |
| 9,556,197 B2 | 1/2017 | Li et al. | |
| 9,580,418 B2 | 2/2017 | Sun et al. | |
| 2011/0059961 A1 | 3/2011 | Wang et al. | |
| 2012/0114663 A1 | 5/2012 | Gelfand et al. | |
| 2012/0225062 A1 | 9/2012 | Burger et al. | |
| 2013/0057956 A1 | 3/2013 | Iwasa | |
| 2014/0086941 A1 | 3/2014 | Burch et al. | |
| 2014/0088117 A1 | 3/2014 | Reddy et al. | |
| 2014/0163000 A1 | 6/2014 | Ahmad | |
| 2014/0200216 A1 | 7/2014 | Li et al. | |
| 2014/0200227 A1* | 7/2014 | Xue ...................... A61K 31/444 514/255.05 |
| 2015/0057265 A1 | 2/2015 | Li et al. | |
| 2015/0329534 A1 | 11/2015 | Xue et al. | |
| 2016/0009714 A1 | 1/2016 | Sun et al. | |
| 2016/0009726 A1 | 1/2016 | Vechorkin et al. | |
| 2016/0137626 A1 | 5/2016 | Li et al. | |
| 2016/0347735 A1 | 12/2016 | Vechorkin et al. | |
| 2017/0096411 A1 | 4/2017 | Vechorkin et al. | |
| 2017/0121310 A1 | 5/2017 | Jia et al. | |

FOREIGN PATENT DOCUMENTS

| | | |
|---|---|---|
| CN | 102985426 | 3/2013 |
| CN | 103664878 | 3/2014 |
| EP | 2637650 | 9/2013 |
| EP | 2743269 | 6/2014 |
| WO | WO 02/00196 | 1/2002 |
| WO | WO 02/055489 | 7/2002 |
| WO | WO 02/093173 | 11/2002 |
| WO | WO 03/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |

(Continued)

OTHER PUBLICATIONS

Amson et al., "The human protooncogene product p33pim is expressed during fetal hematopoiesis and in diverse leukemias," Proc. Nat. Acad. Sci., USA, 1989, 86:8857-61.

Arunesh et al., "Small molecule inhibitors of PIM1 kinase: Jul. 2009 to Feb. 2013 patent update," Expert Opin Ther Pat, Jan. 2014, 24(1): 5-17.

Asano et al., "The serine/threonine kinase Pim-2 is a novel anti-apoptotic mediator in myeloma cells," Leukemia, 2011, 25: 1182-1188.

Bamborough, "Assessment of Chemical Coverage of Kinome Space and Its Implications for Kinase Drug Discovery," J. Med. Chem., 2008, 51: 7898-7914.

Baron et al., "PIM1 gene cooperates with human BCL6 gene to promote the development of lymphomas," PNAS, Apr. 2012, 109(15): 5735-5739.

Berge et al., "Pharmaceutical Salts," J. Pharm. Sci., 1977, 66(1):1-19.

Blanco-Aparicio, Biochemical Pharmacology, vol. 85, pp. 629-643, 2013.

(Continued)

*Primary Examiner* — Karl J Puttlitz
(74) *Attorney, Agent, or Firm* — Fish & Richardson P.C.

(57) ABSTRACT

The present disclosure describes pyridineamine compounds, as well as their compositions and methods of use. The compounds inhibit the activity of the Pim kinases, and are useful in the treatment of diseases related to the activity of Pim kinases including, e.g., cancer and other diseases.

16 Claims, No Drawings

(56) References Cited

FOREIGN PATENT DOCUMENTS

| | | |
|---|---|---|
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/020370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2015/021153 | 2/2015 |
| WO | WO 2015/027124 | 2/2015 |

(56) References Cited

FOREIGN PATENT DOCUMENTS

| WO | WO 2015/131031 | 9/2015 |
|---|---|---|
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump At Column Dilution Configuration for Preparative Liquid Chromatography—Mass Spectrometry," J. Comb. Chem., 2002, 4:295-301.
Brault et al., "PIM kinases are progression markers and emerging therapeutic targets in diffuse large B-cell lymphoma," British Journal of Cancer, 2012, 107: 491-500.
Burger et al. "Structure Guided Optimization, in Vitro Activity, and in Vivo Activity of Pan-PIM Kinase Inhibitors," ACS Med Chem Lett., 2013, 4:1193-1197.
Caira, "Crystalline Polymorphism of Organic Compounds," Topics in Current Chemistry, Jan. 1998, 198: 163-208.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chilean Office Action, Patent Application No. 1985-2015, dated Jul. 7, 2016, 22 pages (English Translation).
Chinese Office Action in Chinese Application No. 201480012783.3. dated Sep. 6, 2016, 16 pages (English Translation).
Claudio et al., "A molecular compendium of genes expressed in multiple myeloma," Blood, 2002, 100:2175-86.
Colombian Office Action in Colombian Application No. 15-168. 544, dated Aug. 10, 2016, 10 pages.
Coperet, "A simple and efficient method for the preparation of pyridine N-Oxides," The Journal of Organic Chemistry, Jan. 1998, 63: 1740-1741.
Damia "Contemporary pre-clinical development of anticancer agents—What are the optimal preclinical models?" European Journal of Cancer, 2009, 45, 2768-2781.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface p. 1-15.
Freshney, Culture of Animal Cells, A Manual of Basic Technique, Alan R. Liss, Inc., 1983, New York, p. 4.
Fujii et al., "Aberrant expression of serine-threonine kinase Pim-3 in hepatocellular carcinoma development and its role in the proliferation of human hepatoma cell lines," Int. J. Canc., 2005, 114:209-18.
Georg Pilz, "Modern multiple sclerosis treatment—what is approved, what is on the horizon" Drug Discovery Today Dec. 2008, vol. 13, Nos. 23/24 1013-1025.

Gomez-Abad et al., "PIM2 inhibition as a rational therapeutic approach in B-cell lymphoma," Blood, 2011, 118:5517-27.
Gozgit et al., "Effects of the JAK2 Inhibitor, AZ960, on Pim/BAD/BCL-xL, Survival Signaling in the Human JAK2 V617F Cell Line SET-2," Journal of Biological Chemistry, Nov. 2008, 283(47): 32334-32343.
Gu and Li, "A concise synthesis of (2S,4R)- and (2S,4R)-4-methylglutamic acid," Tetrahedron Lett., 2003, 44:3203-3205.
Hammerman et al., "Lymphocyte Transformation by Pim-2 Is Dependent on Nuclear Factor-kB Activation," Cancer Research, Nov. 2004, 64: 8341-8348.
Hsi et al., "Ki67 and PIM1 expression predict outcome in mantle cell lymphoma treated with high dose therapy, stem cell transplantation and rituximab: a Cancer and Leukemia Group B 59909 correlative science study," Leuk. Lymph., 2008, 49:2081-90.
Hsu et al., "Pim-1 knockdown potentiates paclitaxel-induced apoptosis in human hormone-refractory prostate cancers through inhibition of NHEJ DNA repair," Cancer Lett., 2012, 319:214-222.
Huang et al., "Structure-based design and optimization of 2-aminothiazole-4-carboxamide as a new class of CHK1 inhibitors," Bioorganic Med Chem Lett., Mar. 2013, 23(9):2590-2594.
International Preliminary Report on Patentability in International Application No. PCT/US2014/011486, dated Jul. 21, 2015, 7 pages.
International Preliminary Report on Patentability in International Application No. PCT/US2014/011487, dated Jul. 23, 2015, 6 pages.
International Preliminary Report on Patentability in International Application No. PCT/US2014/052214, dated Feb. 23, 2016, 7 pages.
International Preliminary Report on Patentability in International Application No. PCT/US2015/040146, dated Jan. 17, 2017, 8 pages.
International Search Report and Written Opinion in International Application No. PCT/US2014/011486, dated Mar. 17, 2014, 12 pages.
International Search Report and Written Opinion in International Application No. PCT/US2014/011487, dated Apr. 4, 2014, 11 pages.
International Search Report and Written Opinion in International Application No. PCT/US2014/052214, dated Oct. 28, 2014, 13 pages.
International Search Report and Written Opinion in International Application No. PCT/US2015/040146, dated Oct. 5, 2015, 12 pages.
International Search Report and Written Opinion in International Application No. PCT/US2016/034520, dated Jul. 12, 2016, 11 pages.
International Search Report and Written Opinion in International Application No. PCT/US2016/050925, dated Oct. 21, 2016, 13 pages.
International Search Report and Written Opinion in International Application No. PCT/US2016/054779, dated Dec. 9, 2016, 12 pages.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Jiang et al., "3,5-Disubstituted quinolines as novel c-Jun N-terminal kinase inhibitors," Bioorganic & Medicinal Chemistry Letters, 2007, 17: 6378-6382.
Johnson et al., "Relationship between drug activity in NCI preclinical in vitro and in vivo models and early clinical trials" British Journal of Cancer, 2001, 84, 1424-1437.
Katano et al., "Synthesis and biological activity of (cyclopentenopyridinium)thiomethylcephalosporins," The Journal of Antibiotics, Jan. 1990, 43(9): 1150-1159.
Kelly et al., "Targeting PIM kinase activity significantly augments the efficacy of cytarabine," British Journal of Haematology, 2011, 156, 129-152.
Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.

(56) References Cited

OTHER PUBLICATIONS

Lam et al., "New aryl/heteroaryl C N bond cross-coupling reactions via arylboronic acid/cupric acetate arylation," Tetrahedron Letters, May 1998, 39(19): 2941-2944.

Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.

Liu et al., "Overexpression of Pim-1 is associated with poor prognosis in patients with esophageal squamous cell carcinoma," J. Surg. Oncol., 2010,102:683-88.

Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594

Lu et al., "Pim2 is required for maintaining multiple myeloma cell growth through modulating TSC2 phosphorylation," Blood, Aug. 2013, 122(9): 1610-1620.

Merkel et al., "PIM1 kinase as a target for cancer therapy," Exp. Opin. Investig. Drugs, 2012, 21:425-38.

Michelotti et al., "Two classes of p38a MAP kinase inhibitors having a common diphenylether core but exhbiting divergent binding modes," 2005, 15: 5274-5279.

Mikkers et al., "High-throughput retroviral tagging to identify components of specific signaling pathways in cancer," Nature Genet., 2002, 32:153-159.

Mikkers et al., "Mice deficient for all PIM kinases display reduced body size and impaired responses to hematopoietic growth factors," Mol. Cell. Biol., 2004, 24:6104-15.

Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistry Letters, 2007, 17: 250-254.

Mizuki et al., "Suppression of myeloid transcription factors and induction of STAT response genes by AML-specific Flt3 mutations," Blood, 2003, 101:3164-73.

Morwick, "Pim kinase inhibitors: a survey of the patent literature," Exp. Opin. Ther. Patents, 2010, 20(2):193-212.

Mulvihill et al., "Novel 2-phenylquinolin-7-yl-derived imidazo[1,5-a]pyrazines as potent insulin-like growth factor-I receptor (IFG-IR) inhibitors," Bioorganic & Medicinal Chemistry, 2008, 16: 1359-1375.

Ocana, A. "Preclinical development of molecular targeted agents for cancer" Nat. Rev. Clin. Oncol. 2011, 8, 200-209.

Ogawa et al., "Insights from Pim1 structure for anti-cancer drug design," Expert Opin Drug Discov, Dec. 2012, 7(12): 1177-92.

Peltola et al., "Pim-1 kinase expression predicts radiation response in squamocellular carcinoma of head and neck and is under the control of epidermal growth factor receptor," Neoplasia, 2009, 11:629-36.

Peturssion, "Protecting Groups in Carbohydrate Chemistry," J. Chem. Educ., 1997, 74(11):1297-1303.

Ravin, "Preformulation," Remington's Pharmaceutical Sciences, 17th Ed., (Mack Publishing Company, Easton, 1985), p. 1409-1423.

Robinson et al., "A Dual PIM 1/3 Kinase Inhibitor Demonstrates Efficacy in Murine Models of Lupus and Multiple Sclerosis," J. Immunol., 2012, 188:119.9.

Schatz, et al., "Targeting cap-dependent translation blocks converging survival signals by AKT and PIM kinases in lymphoma," J. Exp. Med., 2011, 208:1799-1807.

Schwemmers et al., "JAK2$^{V617F}$-negative ET Patients do not display constitutively active JAK/STAT signaling," Exp. Hematol., Nov. 2007, 35(11): 1695-1703.

Search Report, Jul. 2, 2014, 6 pages.

Search Report, Jul. 3, 2014, 4 pages.

Search Report, Jul. 8, 2014, 4 pages.

Sharma "Cell line-based platforms to evaluate the therapeutic efficacy of candidate anticancer agents" Nature Reviews Cancer Apr. 2010, vol. 10, 241-253.

Shen et al., "Inhibition of Pim-1 kinase ameliorates dextran sodium sulfate-induced colitis in mice," Dig. Dis. Sci., 2012, 57:1822-31.

Shinto et al., "Moloney murine leukemia virus infection accelerates lymphomagenesis in Eµ-bc1-2 transfenic mice," Oncogene, 1995, 11:1729-36.

Simone, Oncology: Introduction, Cecil Textbook of Medicine, 20th Edition, 1996 vol. 1, pp. 1004-1010.

Swords et al., "The Pim kinases: new targets for drug development," Curr. Drug Targets, 2011, 12(14):2059-66.

United States Office Action in U.S. Appl. No. 14/155,134, dated Jul. 27, 2015, 12 pages.

Venkatesh et al., "Role of the Development Scientist in Compound Lead Selection and Optimization," J. Pharm. Sci., 2000, 89:145-54.

Wang et al., "Inhibition of Pim1 kinase prevents peanut allergy by enhancing Runx3 expression and suppressing T(H)2 and T(H)17 T-cell differentiation," J. All. Clin. Immunol., 2012, 130:932-44 www.leukaemia.org' [online]. "Myeloproliferative neoplasms (MPN)," 2016, [retrieved on Dec. 5, 2016]. Retrieved from the Internet: URL<http://www.leukaemia.org.au/blood-cancers/myeloproliferative-neoplasms-mpn>, 3 pages.

Yang et al., "Proviral integration site 2 is required for interleukin-6 expression induced by interleukin-1, tumour necrosis factor-α and lipopolysaccharide," Immunol., 2010, 131:174-182.

Zippo, et al., "PIM1-dependent phosphorylation of histone H3 at serine 10 is required for MYC-dependent transcriptional activation and oncogenic transformation," Nature Cell Biol., 2007, 9:932-44.

Eurasian Office Action in Eurasian Application No. 201690458/28, dated Jan. 25, 2017, 11 pages (with English translation).

Cancer [online], [retrieved on Jul. 6, 2007] Retrieved from the Internet, URL: http://www.nlm.nih.gov/medlineplus/cancer.html.

Golub et al., "Molecular Classification of Cancer: Class Discovery and Class Prediction by Gene Expression Monitoring," Science, 1999, 286: 531-537.

Lala et al., "Role of nitric oxide in tumor progression: Lessons from experimental tumors," Cancer and Metastasis Reviews, 1998, 17: 91-106.

Chinese Office Action in Chinese Application No. 201480057613.7, dated Apr. 5, 2017, 15 pages (English Translation).

\* cited by examiner

US 9,802,918 B2

PYRIDINEAMINE COMPOUNDS USEFUL AS PIM KINASE INHIBITORS

TECHNICAL FIELD

The present application is concerned with pharmaceutically useful pyridineamine compounds, as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bcl2-transgenic mice. Mikkers et al., Nature Genet., 2002, 32, 153-159; Shinto et al., Oncogene, 1995, 11, 1729-35.

The three non-receptor serine/threonine kinases Pim1, Pim2 and Pim3 regulate cell proliferation and survival by impacting gene transcription and protein translation. Zippo, et al., Nature Cell Biol., 2007, 9, 932-44; Schatz, et al., J. Exp. Med., 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., Blood, 2002, 100, 2175-86; Amson et al., Proc. Nat. Acad. Sci., USA, 1989, 86, 8857-61; Mizuki et al., Blood, 2003, 101, 3164-73; Li et al., Canc. Res., 2006, 66, 6741-7; Fujii et al., Int. J. Canc., 2005, 114, 209-18. Pim1 overexpression is associated with poor prognosis in mantle cell lymphoma, esophageal and head and neck cancers. Hsi et al., Leuk. Lymph., 2008, 49, 2081-90; Liu et al., J. Surg. Oncol., 2010, 102, 683-88; Peltola et al., Neoplasia, 2009, 11, 629-36. Pim2 overexpression is associated with an aggressive clinical course in a subset of DLBCL patients. Gomez-Abad et al., Blood, 2011, 118, 5517-27. Overexpression is often seen where Myc is overexpressed and Pim kinases can convey resistance to traditional chemotherapeutic agents and radiation. Chen et al., Blood, 2009, 114, 4150-57; Isaac et al., Drug Resis. Updates, 2011, 14, 203-11; Hsu et al., Cancer Lett., 2012, 319, 214; Peltola et al., Neoplasia, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., Mol. Cell. Biol., 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., Dig. Dis. Sci., 2012, 57, 1822-31), peanut allergy (Wang et al., J. All. Clin. Immunol., 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., J. Immunol., 2012, 188, 119.9) and rheumatoid arthritis (Yang et al., Immunol. 2010, 131, 174-182) and other immunological and inflammatory disorders.

The Pim kinases have therefore been identified as useful targets for drug development efforts. Swords et al., Curr. Drug Targets, 2011, 12(14), 2059-66; Merkel et al., Exp. Opin. Investig. Drugs, 2012, 21, 425-38; Morwick et al., Exp. Opin. Ther. Patents, 2010, 20(2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of Formula (I):

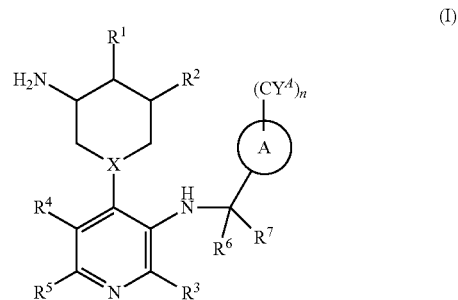

or a pharmaceutically acceptable salt thereof; wherein the variables are as defined below.

The present disclosure also provides a pharmaceutical composition comprising a compound of Formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DETAILED DESCRIPTION

I. Compounds

The present disclosure provides, inter alia, a compound of Formula (I):

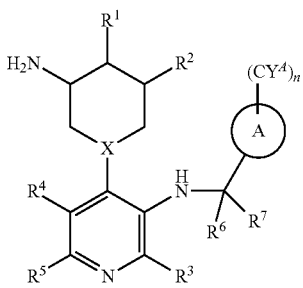

or a pharmaceutically acceptable salt thereof, wherein:

X is N or CH;

ring A is $C_{6\text{-}10}$ aryl or 5-10 membered heteroaryl, said heteroaryl group consisting of one or more carbon atoms and 1, 2, or 3 heteroatoms selected from N, O and S, wherein the $C_{6\text{-}10}$ aryl or 5-10 membered heteroaryl is optionally substituted with 1 or 2 substituents independently selected from $R^A$;

$R^A$ is halogen, cyano, amino, or $C_{1\text{-}3}$ alkyl;

n is 0 or 1;

$Cy^A$, when present, is selected from $C_{6\text{-}10}$ aryl, 5-10 membered heteroaryl, $C_{3\text{-}7}$ cycloalkyl, and 4-10 membered heterocycloalkyl, wherein the ring atoms of the 5-10 membered heteroaryl or 4-10 membered heterocycloalkyl forming $Cy^A$ consist of one or more carbon atoms and 1, 2, or 3 heteroatoms selected from N, O and S, and wherein the $C_{6\text{-}10}$ aryl, 5-10 membered heteroaryl, $C_{3\text{-}7}$ cycloalkyl, and 4-10 membered heterocycloalkyl forming $Cy^A$ are each optionally substituted by 1, 2 or 3 substituents independently selected from $R^{CyA}$;

$R^{CyA}$ is halogen, $C_{1\text{-}4}$ alkyl, $C_{2\text{-}4}$ alkenyl, $C_{2\text{-}4}$ alkynyl, $C_{1\text{-}4}$ haloalkyl, $Cy^B$, -L-$Cy^B$, =O, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ or $S(O)_2NR^{c1}R^{d1}$; wherein the $C_{1\text{-}4}$ alkyl, $C_{2\text{-}4}$ alkenyl, and $C_{2\text{-}4}$ alkynyl forming $R^{CyA}$ are each optionally substituted with 1, 2 or 3 substituents independently selected from halogen, $C_{1\text{-}3}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$;

$Cy^B$ is selected from $C_{6\text{-}10}$ aryl, 5-10 membered heteroaryl, $C_{3\text{-}7}$ cycloalkyl, and 4-10 membered heterocycloalkyl, wherein the ring atoms of the 5-10 membered heteroaryl or 4-10 membered heterocycloalkyl forming $Cy^B$ consist of one or more carbon atoms and 1, 2, or 3 heteroatoms selected from N, O and S, and wherein the $C_{6\text{-}10}$ aryl, 5-10 membered heteroaryl, $C_{3\text{-}7}$ cycloalkyl, and 4-10 membered heterocycloalkyl forming $Cy^B$ are each optionally substituted with 1, 2, or 3 substituents independently selected from $R^{CyB}$;

$R^{CyB}$ is halogen, $C_{1\text{-}4}$ alkyl, $C_{2\text{-}4}$ alkenyl, $C_{2\text{-}4}$ alkynyl, $C_{1\text{-}4}$ haloalkyl, CN, OH, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$ or $S(O)_2NR^{c2}R^{d2}$, wherein the $C_{1\text{-}4}$ alkyl, $C_{2\text{-}4}$ alkenyl, and $C_{2\text{-}4}$ alkynyl forming $R^{CyB}$ are each optionally substituted with 1, 2 or 3 substituents independently selected from halogen, $C_{1\text{-}3}$ haloalkyl, CN, OH, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$;

L is $C_{1\text{-}4}$ alkylene, $L^1$-O-$L^1$, $L^1$-C(=O)-$L^1$, $L^1$-OC(=O)-$L^1$, $L^1$-C(=O)O-$L^1$, $L^1$-NHC(=O)-$L^1$, $L^1$-C(=O)NH-$L^1$, $L^1$-NH-$L^1$, $L^1$-N(CH$_3$)-$L^1$, $L^1$-NHC(=O)NH-$L^1$, $L^1$-NHC(=O)O-$L^1$, $L^1$-S-$L^1$, $L^1$-S(=O)-$L^1$, $L^1$-S(=O)$_2$-$L^1$, $L^1$-NHS(=O)$_2$-$L^1$, $L^1$-S(=O)$_2$NH-$L^1$, $L^1$-NHS(=O)$_2$NH-$L^1$, wherein $L^1$, at each occurrence, is independently selected from a bond and $C_{1\text{-}2}$ alkylene; and wherein the $C_{1\text{-}2}$ alkylene forming $L^1$ is optionally substituted with 1 or 2 substituents independently selected from F, Cl, CN, OH, O($C_{1\text{-}3}$ alkyl), NH$_2$, NH($C_{1\text{-}3}$ alkyl) and N($C_{1\text{-}3}$ alkyl)$_2$;

$R^1$ is H, F, Cl, CN, OH, $C_{1\text{-}3}$ alkoxy, —OC(O)O($C_{1\text{-}3}$ alkyl), —OC(O)NH($C_{1\text{-}3}$ alkyl), $C_{1\text{-}3}$ alkyl, $C_{1\text{-}3}$ haloalkyl, or $C_{3\text{-}6}$ cycloalkyl;

$R^2$ is H, $C_{1\text{-}3}$ alkyl, $C_{1\text{-}3}$ haloalkyl or cyclopropyl;

$R^3$, $R^4$, and $R^5$ are each independently selected from H, halogen, OH, CN, amino, NH($C_1$-4 alkyl), N($C_{1\text{-}4}$ alkyl)$_2$, $C_{1\text{-}4}$ alkyl, $C_{1\text{-}4}$ alkoxy, $C_{1\text{-}4}$ haloalkyl and $C_{1\text{-}4}$ haloalkoxy; alternatively, $R^4$ and $R^5$ in combination, together with the carbon atoms to which they are attached, form a 5, 6, or 7-membered fused aryl, a 5, 6, or 7-membered fused cycloalkyl, a 5, 6, or 7-membered fused heteroaryl, or a 5, 6, or 7-membered fused heterocycloalkyl, each optionally substituted by 1, 2 or 3 substituents independently selected from halogen, OH, CN, amino, NH($C_{1\text{-}4}$ alkyl), N($C_{1\text{-}4}$ alkyl)$_2$, $C_{1\text{-}4}$ alkyl, $C_{1\text{-}4}$ alkoxy, $C_{1\text{-}4}$ haloalkyl and $C_{1\text{-}4}$ haloalkoxy;

$R^6$ and $R^7$ are each independently selected from H, halogen, $C_{1\text{-}4}$ alkyl, $C_{2\text{-}4}$ alkenyl, $C_{2\text{-}4}$ alkynyl, and $C_{1\text{-}4}$ haloalkyl; wherein said $C_{1\text{-}4}$ alkyl forming $R^6$ or $R^7$ is optionally substituted with 1, 2, or 3 substituents independently selected from halogen, OH, CN, $C_{1\text{-}3}$ haloalkyl, $C_{1\text{-}4}$ alkoxy, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$ and $S(O)_2NR^{c1}R^{d1}$;

alternatively, $R^6$ and $R^7$, together with the carbon atom to which they are both attached, form a $C_{3\text{-}6}$ cycloalkyl group that is optionally substituted with 1, 2, or 3 substituents independently selected from halogen, OH, CN, and $C_{1\text{-}4}$ alkyl;

$R^{a1}$, $R^{b1}$, $R^{c1}$ and $R^{d1}$, at each occurrence, are independently selected from H, $C_{1\text{-}4}$ alkyl, $C_{2\text{-}4}$ alkenyl, $C_{2\text{-}4}$ alkynyl, wherein said $C_{1\text{-}4}$ alkyl, $C_{2\text{-}4}$ alkenyl, $C_{2\text{-}4}$ alkynyl groups forming $R^{a1}$, $R^{b1}$, $R^{c1}$ and $R^{d1}$ are each optionally substituted with 1, 2, or 3 substituents independently selected from $C_{1\text{-}4}$ alkyl, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$;

or $R^{c1}$ and $R^{d1}$ attached to the same N atom, together with the N atom to which they are both attached, form a 4-, 5-, 6-, or 7-membered heterocycloalkyl group that is optionally substituted with 1, 2, or 3 substituents independently selected from $C_{1-6}$ alkyl, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$; and $R^{a2}$, $R^{b2}$, $R^{c2}$ and $R^{d2}$ are each independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{1-6}$ haloalkyl, $C_{2-6}$ alkenyl, and $C_{2-6}$ alkynyl forming $R^{a2}$, $R^{b2}$, $R^{c2}$ and $R^{d2}$ are each optionally substituted with 1, 2, or 3 substituents independently selected from halo, OH, CN, amino, $NH(C_{1-6}$ alkyl), $N(C_{1-6}$ alkyl)$_2$, $C_{1-6}$ alkyl, $C_{1-6}$ alkoxy, $C_{1-6}$ haloalkyl and $C_{1-6}$ haloalkoxy.

In some embodiments, ring A is $C_{6-10}$ aryl optionally substituted with 1 or 2 substituents each independently selected from $R^A$.

In some embodiments, phenyl optionally substituted with 1 or 2 substituents each independently selected from $R^A$.

In some embodiments, ring A is 5-10 membered heteroaryl optionally substituted with 1 or 2 substituents each independently selected from $R^A$.

In some embodiments, ring A is a pyridinyl, pyrimidinyl, thiazolyl, quinolinyl, or furopyridinyl, each optionally substituted with 1 or 2 substituents each independently selected from $R^A$.

In some embodiments, each $R^A$ is independently selected from F, $NH_2$, and isopropyl.

In some embodiments, each $R^A$ is F.

In some embodiments, n is 0.

In some embodiments, n is 1.

In some embodiments, $Cy^A$ is $C_{6-10}$ aryl optionally substituted by 1, 2, or 3 substituents independently selected from $R^{CyA}$.

In some embodiments, $Cy^A$ is phenyl optionally substituted by 1, 2, or 3 substituents independently selected from $R^{CyA}$.

In some embodiments, $Cy^A$ is 2-fluorophenyl optionally substituted by 1 or 2 substituents independently selected from $R^{CyA}$.

In some embodiments, $Cy^A$ is 5-10 membered heteroaryl optionally substituted by 1, 2, or 3 substituents independently selected from $R^{CyA}$.

In some embodiments, $Cy^A$ is pyridinyl, benzothienyl, indolyl, dihydroindolyl, dihydrobenzofuranyl, imidazopyridinyl, or quinolinyl, each optionally substituted by 1, 2, or 3 substituents independently selected from $R^{CyA}$.

In some embodiments, $Cy^A$ is pyridinyl, benzothien-5-yl, indolyl, dihydroindol-6-yl, 1,3-dihydro-2H-indolinyl, 2,3-dihydrobenzofuran-6-yl, imidazo[1,2-a]pyridin-7-yl, or quinolinyl, each optionally substituted by 1, 2, or 3 substituents independently selected from $R^{CyA}$.

In some embodiments, $Cy^A$ is $C_{3-7}$ cycloalkyl optionally substituted by 1, 2, or 3 substituents independently selected from $R^{CyA}$.

In some embodiments, $Cy^A$ is cyclopropyl, cyclobutyl, cyclopentyl, cyclohexyl or cyclohexenyl, each optionally substituted by 1, 2, or 3 substituents independently selected from $R^{CyA}$.

In some embodiments, $Cy^A$ is 4-10 membered heterocycloalkyl optionally substituted by 1, 2, or 3 substituents independently selected from $R^{CyA}$.

In some embodiments, the compound is according to any one of the following formulae (II-A) to (II-C):

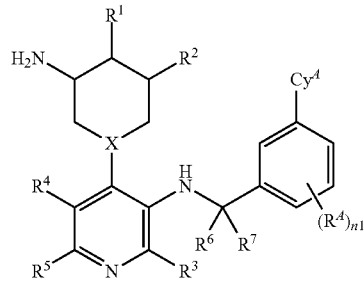
(II-A)

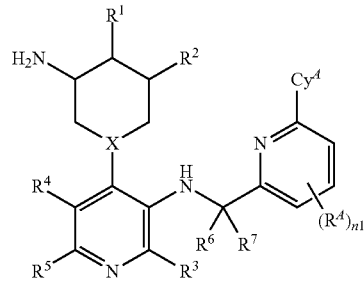
(II-B)

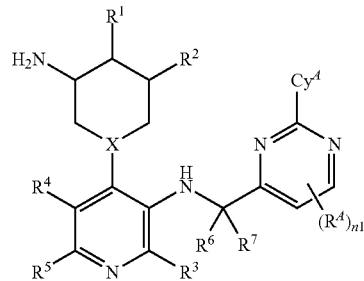
(II-C)

wherein each n1 is 0, 1, or 2.

In some embodiments, the compound is according to any one of the following formulae (II-D) to (II-K):

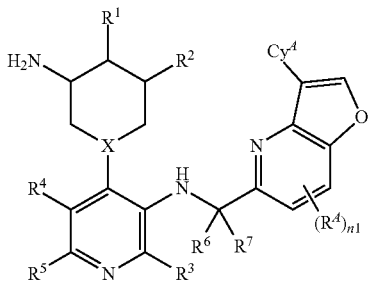
(II-D)

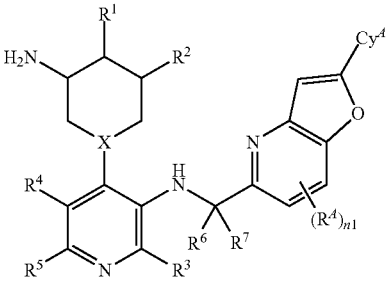
(II-E)

(II-F)
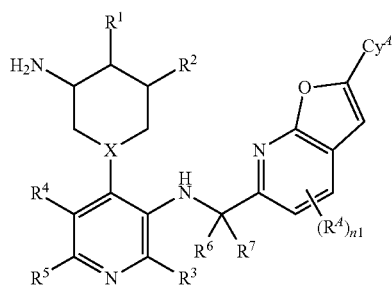
(II-G)
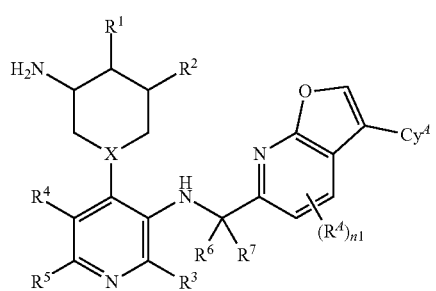
(II-H)
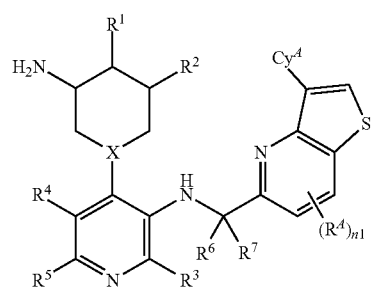
(II-I)
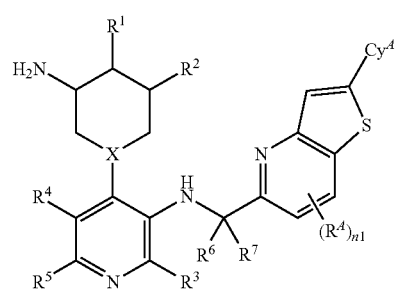
(II-J)
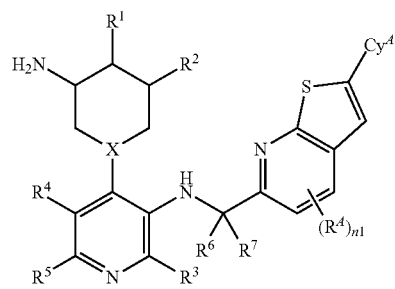
(II-K)
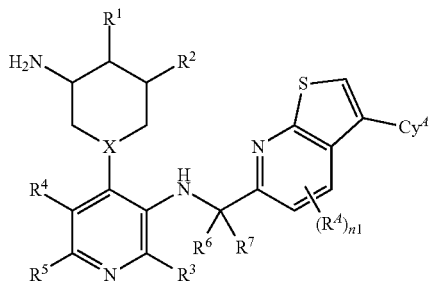
wherein each n1 is 0, 1, or 2.
In some embodiments, n1 is 0.
In some embodiments, n1 is 1
In some embodiments, the compound is according to any one of the following formulae (II-DA) to (II-KA):
(II-DA)
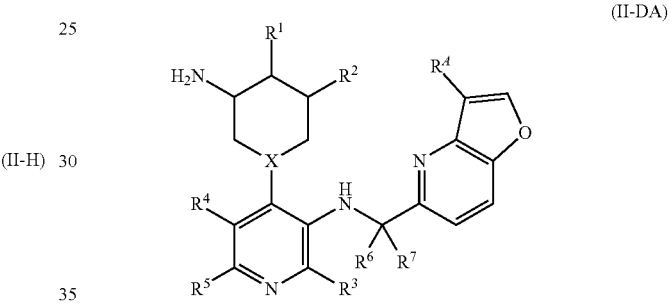
(II-EA)
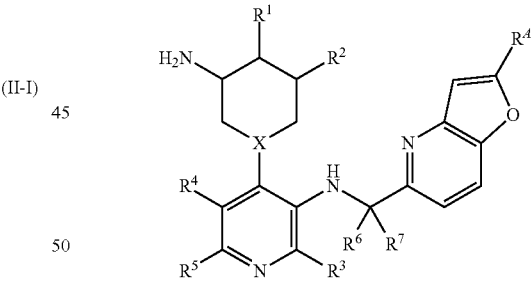
(II-FA)
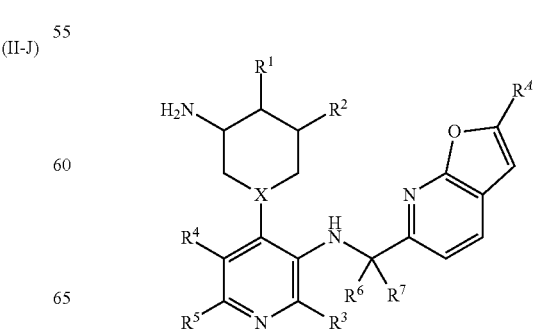

-continued
(II-GA)
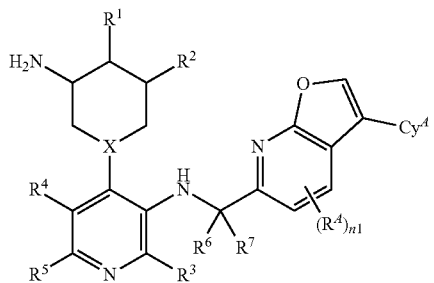
(II-HA)
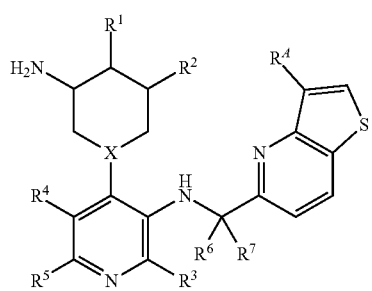
(II-IA)
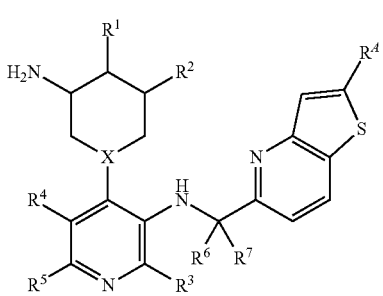
(II-JA)
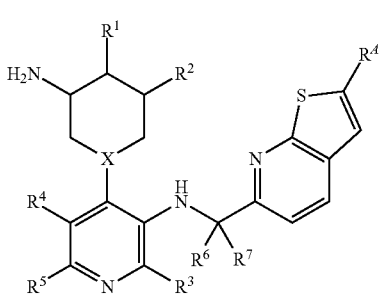
(II-KA)
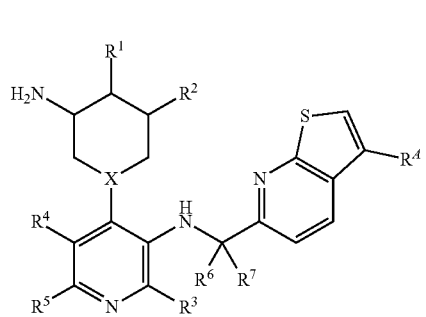
In some embodiments, the compound is according to any one of the following formulae (III-A) and (III-B):
(III-A)
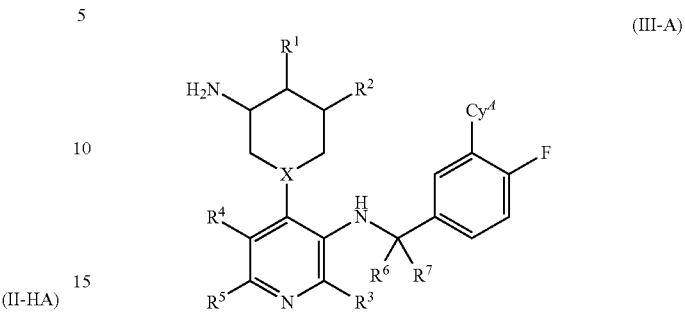
(III-B)
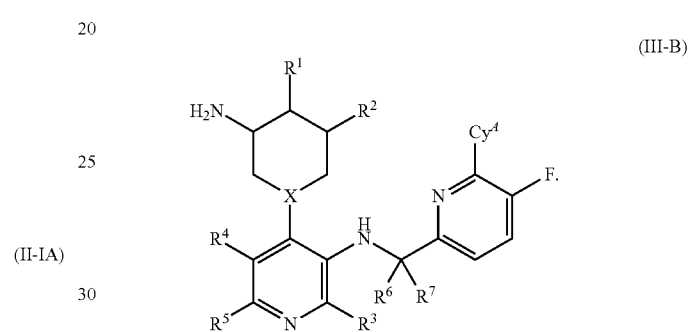
In some embodiments, the compound is according to any one of the following formulae (IV-A) to (IV-C):
(IV-A)
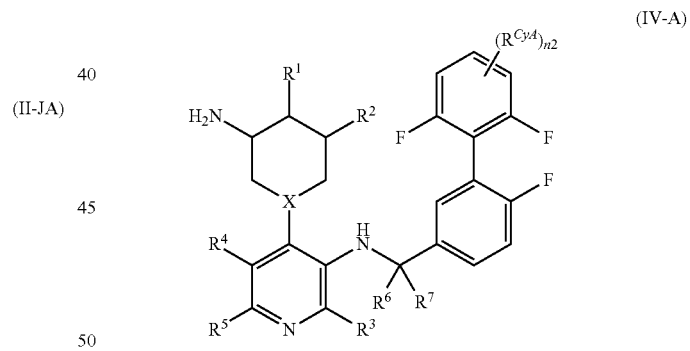
(IV-B)
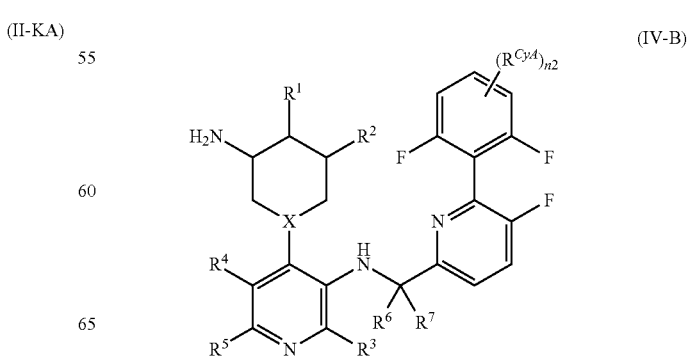

-continued

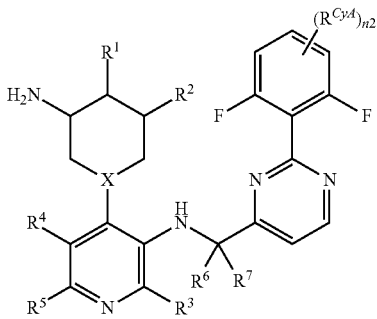

(IV-C)

wherein each n2 is 0 or 1.

In some embodiments, the compound is according to any one of the following formulae (V-A) to (V-C):

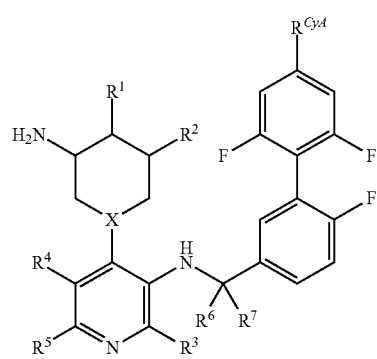

(V-A)

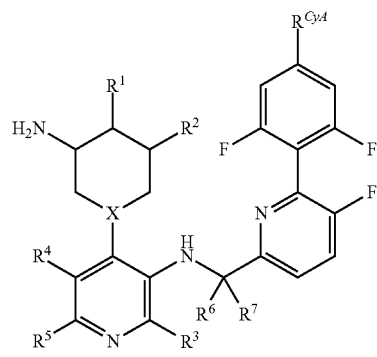

(V-B)

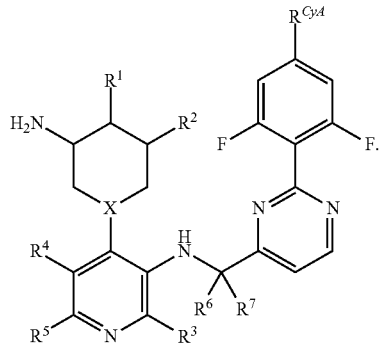

(V-C)

In some embodiments, each $R^{CyA}$ is halogen, $C_{1-4}$ alkyl, $Cy^B$, -L-$Cy^B$, CN, or $OR^{a1}$; wherein each $C_{1-4}$ alkyl forming $R^{CyA}$ is optionally substituted with 1, 2, or 3 substituents independently selected from halogen, $OR^{a1}$ and $NR^{c1}R^{d1}$.

In some embodiments, $Cy^A$ is substituted by 1, 2 or 3 substituents wherein one of the substituents is selected from $Cy^B$.

In some embodiments, $Cy^A$ is substituted by 1, 2 or 3 substituents wherein one of the substituents is selected from -L-$Cy^B$.

In some embodiments, $Cy^A$ is substituted by 1 substituent wherein the substituent is selected from $R^{CyA}$.

In some embodiments, $Cy^A$ is substituted by 1 substituent wherein the substituent is selected from $Cy^B$.

In some embodiments, $Cy^A$ is substituted by 1 substituent wherein the substituent is selected from -L-$Cy^B$.

In some embodiments, L is $C_{1-4}$ alkylene, $L^1$-O-$L^1$, $L^1$-NH-$L^1$ or $L^1$-N(CH$_3$)-$L^1$.

In some embodiments, each $L^1$ is independently selected from a bond and $C_{1-2}$ alkylene.

In some embodiments, each $L^1$ is a bond.

In some embodiments, L is $C_{1-4}$ alkylene.

In some embodiments, L is CH$_2$.

In some embodiments, L is O.

In some embodiments, $Cy^B$ is $C_{6-10}$ aryl optionally substituted with 1, 2, or 3 substituents independently selected from $R^{CyB}$.

In some embodiments, $Cy^B$ is phenyl optionally substituted with 1, 2, or 3 substituents independently selected from $R^{CyB}$.

In some embodiments, $Cy^B$ is 5-10 membered heteroaryl, optionally substituted with 1, 2, or 3 substituents independently selected from $R^{CyB}$.

In some embodiments, $Cy^B$ is pyridinyl, pyrazolyl, or quinolinyl, each optionally substituted with 1, 2, or 3 substituents independently selected from $R^{CyB}$.

In some embodiments, $Cy^B$ is $C_{3-7}$ cycloalkyl, optionally substituted with 1, 2, or 3 substituents independently selected from $R^{CyB}$.

In some embodiments, $Cy^B$ is cyclopropyl, cyclobutyl, cyclopentyl, cyclohexyl or cyclohexenyl, each optionally substituted with 1, 2, or 3 substituents independently selected from $R^{CyB}$.

In some embodiments, $Cy^B$ is 4-10 membered heterocycloalkyl, optionally substituted with 1, 2, or 3 substituents independently selected from $R^{CyB}$.

In some embodiments, $Cy^B$ is tetrahydrofuranyl, tetrahydropyranyl, morpholinyl, azetidinyl, pyrrolidinyl, or piperidinyl, each optionally substituted with 1, 2, or 3 substituents independently selected from $R^{CyB}$.

In some embodiments, $R^{CyB}$ is H, halogen, $C_{1-4}$ alkyl, CN, OH, or $OR^{a2}$.

In some embodiments, $R^1$ is H, F, or OH.

In some embodiments, $R^1$ is H.

In some embodiments, $R^1$ is OH.

In some embodiments, $R^2$ is H.

In some embodiments, $R^2$ is $C_{1-3}$ alkyl.

In some embodiments, $R^2$ is methyl.

In some embodiments, $R^2$ is $C_{1-3}$ haloalkyl.

In some embodiments, $R^2$ is trifluoromethyl.

In some embodiments, $R^2$ is cyclopropyl.

In some embodiments, the ring substituted by $R^1$ and $R^2$ is selected from rings of the following formulae (B-1) to (B-26):

(B-1) 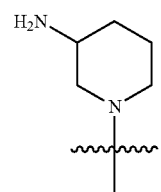
(B-2) 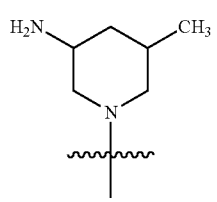
(B-3) 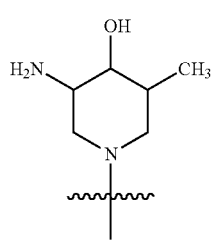
(B-4) 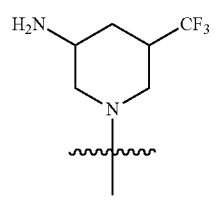
(B-5) 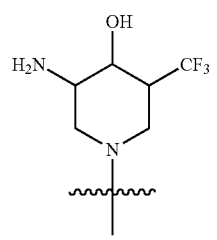
(B-6) 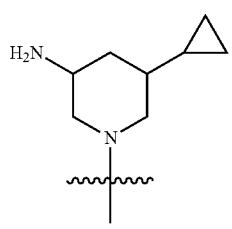
(B-7) 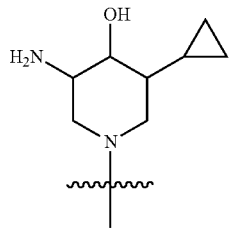
(B-8) 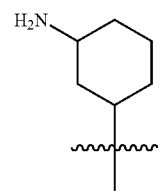
(B-9) 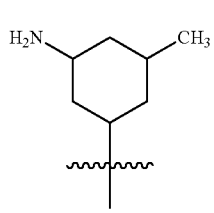
(B-10) 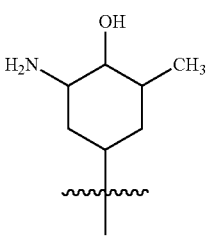
(B-11) 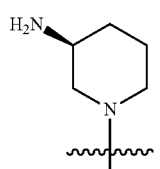
(B-12) 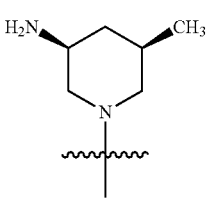
(B-13) 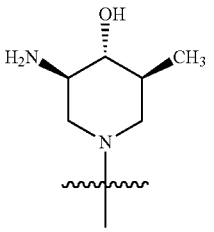
(B-14) 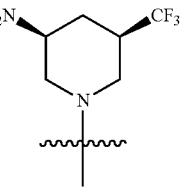

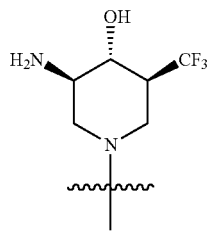
(B-15)

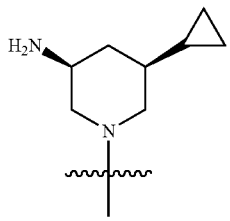
(B-16)

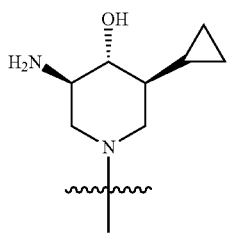
(B-17)

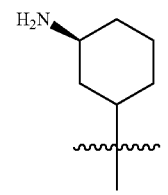
(B-18)

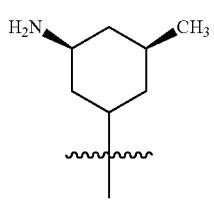
(B-19)

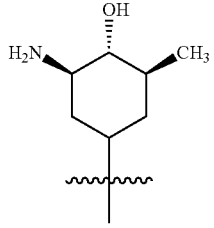
(B-20)

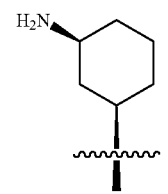
(B-21)

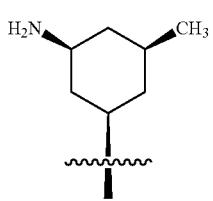
(B-22)

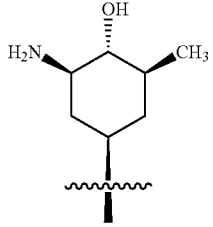
(B-23)

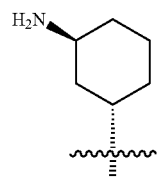
(B-24)

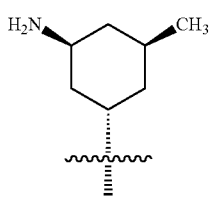
(B-25)

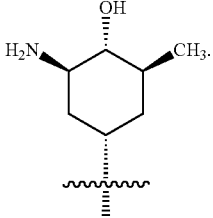
(B-26)

In some embodiments, $R^3$, $R^4$, and $R^5$ are each independently selected from H, halo, OH, CN, amino, NH($C_{1-4}$ alkyl), N($C_{1-4}$ alkyl)$_2$, $C_{1-4}$ alkyl, $C_{1-4}$ alkoxy, $C_{1-4}$ haloalkyl and $C_{1-4}$ haloalkoxy.

In some embodiments, $R^3$ is hydrogen.

In some embodiments, $R^4$ is hydrogen.

In some embodiments, $R^5$ is H.

In some embodiments, $R^6$ is selected from H, halogen, $C_{1-4}$ alkyl, $C_{2-4}$ alkenyl, $C_{2-4}$ alkynyl, and $C_{1-4}$ haloalkyl; wherein said $C_{1-4}$ alkyl forming $R^6$ is optionally substituted with 1, 2 or 3 substituents each independently selected from halogen, OH, CN, $C_{1-3}$ haloalkyl, $C_{1-4}$ alkoxy, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, S(O)R$^{b1}$, S(O)NR$^{c1}$R$^{d1}$, S(O)$_2$R$^{b1}$, NR$^{c1}$S(O)$_2$R$^{b1}$ and S(O)$_2$NR$^{c1}$R$^{d1}$; and wherein $R^7$ is H or $C_{1-4}$ alkyl.

In some embodiments, $R^6$ and $R^7$ are each independently selected from H and $C_{1-4}$ alkyl.

In some embodiments, $R^6$ is H.

In some embodiments, $R^7$ is H.

In some embodiments, $R^6$ and $R^7$, together with the carbon atom to which they are both attached, form a $C_{3-6}$ cycloalkyl group that is optionally substituted with 1, 2 or 3 substituents each independently selected from halogen, OH, CN, and $C_{1-4}$ alkyl.

In some embodiments, $R^6$ and $R^7$, together with the carbon atom to which they are both attached, form an unsubstituted $C_{3-6}$ cycloalkyl.

In some embodiments, $R^6$ and $R^7$, together with the carbon atom to which they are both attached, form an unsubstituted cyclopropyl group.

In some embodiments, $R^{a1}$, $R^{b1}$, $R^{c1}$, $R^{d1}$, $R^{a2}$, $R^{b2}$, $R^{c2}$ and $R^{d2}$ are each independently selected from H and $C_{1-6}$ alkyl.

Examples of the compounds of Formula (I) include the following compounds and or pharmaceutically acceptable salts thereof:

3-amino-1-{3-[({6-[2,6-difluoro-4-(3-hydroxytetrahydro-furan-3-yl)phenyl]-5-fluoropyridin-2-yl}methyl)amino]pyridin-4-yl}-5-methylpiperidin-4-ol;

3-amino-1-(3-(((6-(2,6-difluoro-4-(1-hydroxycyclobutyl)phenyl)-5-fluoropyridin-2-yl)methyl)amino)pyridin-4-yl)-5-methylpiperidin-4-ol;

3-amino-1-(3-(((6-(2,6-difluoro-4-(4-hydroxytetrahydro-2H-pyran-4-yl)phenyl)-5-fluoropyridin-2-yl)methyl)amino)pyridin-4-yl)-5-methylpiperidin-4-ol;

3-(4-{6-[({4-[3-amino-5-methylpiperidin-1-yl]pyridin-3-yl}amino)methyl]-3-fluoropyridin-2-yl}-3,5-difluorophenyl)tetrahydrofuran-3-ol;

1-(4-(6-((4-(3-amino-5-methylpiperidin-1-yl)pyridin-3-ylamino)methyl)-3-fluoropyridin-2-yl)-3,5-difluorophenyl)cyclobutanol;

4-(4-(6-((4-(3-amino-5-methylpiperidin-1-yl)pyridin-3-ylamino)methyl)-3-fluoropyridin-2-yl)-3,5-difluorophenyl)tetrahydro-2H-pyran-4-ol;

1-(4-{6-[({4-[3-amino-5-(trifluoromethyl)piperidin-1-yl]pyridin-3-yl}amino)methyl]-3-fluoropyridin-2-yl}-3,5-difluorophenyl)cyclobutanol;

3-amino-1-{3-[({6-[2,6-difluoro-4-(1-hydroxycyclopropyl)phenyl]-5-fluoropyridin-2-yl}methyl)amino]pyridin-4-yl}-5-methylpiperidin-4-ol;

3-amino-1-(3-(((6-(2,6-difluoro-3-(1-hydroxycyclopropyl)phenyl)-5-fluoropyridin-2-yl)methyl)amino)pyridin-4-yl)-5-methylpiperidin-4-ol;

1-(4-{6-[({4-[3-amino-5-methylpiperidin-1-yl]pyridin-3-yl}amino)methyl]-3-fluoropyridin-2-yl}-3,5-difluorophenyl)cyclopropanol;

1-(3-(6-((4-(3-amino-5-methylpiperidin-1-yl)pyridin-3-ylamino)methyl)-3-fluoropyridin-2-yl)-2,4-difluorophenyl)cyclopropanol;

3-amino-1-{3-[({6-[2,6-difluoro-4-(2-hydroxy-2-methylpropyl)phenyl]-5-fluoropyridin-2-yl}methyl)amino]pyridin-4-yl}-5-methylpiperidin-4-ol;

1-(4-{6-[({4-[3-amino-5-methylpiperidin-1-yl]pyridin-3-yl}amino)methyl]-3-fluoropyridin-2-yl}-3,5-difluorophenyl)-2-methylpropan-2-ol;

3-amino-1-[3-({[6-(2,6-difluorophenyl)-5-fluoropyridin-2-yl]methyl}amino)pyridin-4-yl]-5-methylpiperidin-4-ol;

3-amino-1-(3-(((5-fluoro-6-(2-fluoro-6-methoxyphenyl)pyridin-2-yl)methyl)amino)pyridin-4-yl)-5-methylpiperidin-4-ol;

3-amino-5-methyl-1-(3-(((3,3',5'-trifluoro-[2,4'-bipyridin]-6-yl)methyl)amino)pyridin-4-yl)piperidin-4-ol;

2-(6-((4-(3-amino-4-hydroxy-5-methylpiperidin-1-yl)pyridin-3-ylamino)methyl)-3-fluoropyridin-2-yl)-3-fluorobenzonitrile;

3-amino-1-(3-(((5-fluoro-6-(2-fluorophenyl)pyridin-2-yl)methyl)amino)pyridin-4-yl)-5-methylpiperidin-4-ol;

4-[3-amino-5-methylpiperidin-1-yl]-N-{[6-(2,6-difluorophenyl)-5-fluoropyridin-2-yl]methyl}pyridin-3-amine;

4-(3-amino-5-methylpiperidin-1-yl)-N-((5-fluoro-6-(2-fluoro-6-methoxyphenyl)pyridin-2-yl)methyl)pyridin-3-amine;

4-(3-amino-5-methylpiperidin-1-yl)-N-((3,3',5'-trifluoro-2,4'-bipyridin-6-yl)methyl)pyridin-3-amine;

2-(6-((4-(3-amino-5-methylpiperidin-1-yl)pyridin-3-ylamino)methyl)-3-fluoropyridin-2-yl)-3-fluorobenzonitrile;

4-(3-amino-5-methylpiperidin-1-yl)-N-((5-fluoro-6-(2-fluorophenyl)pyridin-2-yl)methyl)pyridin-3-amine;

2-(4-{6-[({4-[3-amino-4-hydroxy-5-methylpiperidin-1-yl]pyridin-3-yl}amino)methyl]-3-fluoropyridin-2-yl}-3,5-difluorophenyl)-2-methylpropanenitrile;

2-(4-{6-[({4-[3-amino-5-methylpiperidin-1-yl]pyridin-3-yl}amino)methyl]-3-fluoropyridin-2-yl}-3,5-difluorophenyl)-2-methylpropanenitrile;

3-amino-5-methyl-1-(3-{[(2',6,6'-trifluorobiphenyl-3-yl)methyl]amino}pyridin-4-yl)piperidin-4-ol;

4-[3-amino-5-methylpiperidin-1-yl]-N-[(2',6,6'-trifluorobiphenyl-3-yl)methyl]pyridin-3-amine;

1-(5'-((4-(3-amino-5-methylpiperidin-1-yl)pyridin-3-ylamino)methyl)-2,2',6-trifluorobiphenyl-4-yl)cyclobutanol;

4-(5'-((4-(3-amino-5-methylpiperidin-1-yl)pyridin-3-ylamino)methyl)-2,2',6-trifluorobiphenyl-4-yl)tetrahydro-2H-pyran-4-ol;

3-amino-1-[3-({[6-(2,6-difluorophenyl)pyridin-2-yl]methyl}amino)pyridin-4-yl]-5-methylpiperidin-4-ol;

4-[3-amino-5-methylpiperidin-1-yl]-N-{[6-(2,6-difluorophenyl)pyridin-2-yl]methyl}pyridin-3-amine;

3-amino-1-[3-({[2-(2,6-difluorophenyl)pyrimidin-4-yl]methyl}amino)pyridin-4-yl]-5-methylpiperidin-4-ol;

4-[3-amino-5-methylpiperidin-1-yl]-N-{[2-(2,6-difluorophenyl)pyrimidin-4-yl]methyl}pyridin-3-amine;

3-amino-1-(3-(((6-(2,6-difluoro-4-morpholinophenyl)-5-fluoropyridin-2-yl)methyl)amino)pyridin-4-yl)-5-methylpiperidin-4-ol;

4-(3-amino-5-methylpiperidin-1-yl)-N-((6-(2,6-difluoro-4-morpholinophenyl)-5-fluoropyridin-2-yl)methyl)pyridin-3-amine;

4-(3-amino-5-(trifluoromethyl)piperidin-1-yl)-N-((6-(2,6-difluoro-4-morpholinophenyl)-5-fluoropyridin-2-yl)methyl)pyridin-3-amine;

3-amino-1-{3-[({6-[2,6-difluoro-4-(hydroxymethyl)phenyl]-5-fluoropyridin-2-yl}methyl)amino]pyridin-4-yl}-5-methylpiperidin-4-ol;

(4-{6-[({4-[3-amino-5-methylpiperidin-1-yl]pyridin-3-yl}amino)methyl]-3-fluoropyridin-2-yl}-3,5-difluorophenyl)methanol;

3-amino-1-[3-({[6-(5,7-difluoroquinolin-6-yl)-5-fluoropyridin-2-yl]methyl}amino)pyridin-4-yl]-5-methylpiperidin-4-ol;

4-[3-amino-5-methylpiperidin-1-yl]-N-{[6-(5,7-difluoroquinolin-6-yl)-5-fluoropyridin-2-yl]methyl}pyridin-3-amine;

3-amino-1-{3-[({6-[2,6-difluoro-4-(morpholin-4-ylmethyl)phenyl]-5-fluoropyridin-2-yl}methyl)amino]pyridin-4-yl}-5-methylpiperidin-4-ol;

3-amino-1-(3-(((6-(2,6-difluoro-4-((methylamino)methyl)phenyl)-5-fluoropyridin-2-yl)methyl)amino)pyridin-4-yl)-5-methylpiperidin-4-ol;

3-amino-1-(3-(((6-(4-(azetidin-1-ylmethyl)-2,6-difluorophenyl)-5-fluoropyridin-2-yl)methyl)amino)pyridin-4-yl)-5-methylpiperidin-4-ol;

3-amino-1-(3-(((6-(2,6-difluoro-4-((3-hydroxypyrrolidin-1-yl)methyl)phenyl)-5-fluoropyridin-2-yl)methyl)amino)pyridin-4-yl)-5-methylpiperidin-4-ol;
1-(4-(6-((4-(3-amino-4-hydroxy-5-methylpiperidin-1-yl)pyridin-3-ylamino)methyl)-3-fluoropyridin-2-yl)-3,5-difluorobenzyl)pyrrolidine-3-carbonitrile;
3-amino-1-(3-(((6-(2,6-difluoro-4-((3-fluoropyrrolidin-1-yl)methyl)phenyl)-5-fluoropyridin-2-yl)methyl)amino)pyridin-4-yl)-5-methylpiperidin-4-ol;
4-[3-amino-5-methylpiperidin-1-yl]-N-({6-[2,6-difluoro-4-(morpholin-4-ylmethyl)phenyl]-5-fluoropyridin-2-yl}methyl)pyridin-3-amine;
4-(3-amino-5-methylpiperidin-1-yl)-N-((6-(2,6-difluoro-4-((methylamino)methyl)phenyl)-5-fluoropyridin-2-yl)methyl)pyridin-3-amine;
4-(3-amino-5-methylpiperidin-1-yl)-N-((6-(4-(azetidin-1-ylmethyl)-2,6-difluorophenyl)-5-fluoropyridin-2-yl)methyl)pyridin-3-amine;
1-(4-(6-((4-(3-amino-5-methylpiperidin-1-yl)pyridin-3-ylamino)methyl)-3-fluoropyridin-2-yl)-3,5-difluorobenzyl)pyrrolidin-3-ol;
1-(4-(6-((4-(3-amino-5-methylpiperidin-1-yl)pyridin-3-ylamino)methyl)-3-fluoropyridin-2-yl)-3,5-difluorobenzyl)pyrrolidine-3-carbonitrile;
4-(3-amino-5-methylpiperidin-1-yl)-N-((6-(2,6-difluoro-4-((3-fluoropyrrolidin-1-yl)methyl)phenyl)-5-fluoropyridin-2-yl)methyl)pyridin-3-amine;
3-amino-1-(3-{[(6-cyclohex-1-en-1-yl-5-fluoropyridin-2-yl)methyl]amino}pyridin-4-yl)-5-methylpiperidin-4-ol;
4-[3-amino-5-methylpiperidin-1-yl]-N-[(6-cyclohexyl-5-fluoropyridin-2-yl)methyl]pyridin-3-amine;
3-amino-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-4-ol;
4-[3-amino-5-methylpiperidin-1-yl]-N-({6-[2,6-difluoro-4-(4-methoxytetrahydro-2H-pyran-4-yl)phenyl]-5-fluoropyridin-2-yl}methyl)pyridin-3-amine;
3-amino-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-4-ol;
4-[3-amino-5-methylpiperidin-1-yl]-N-({6-[2,6-difluoro-4-(4-fluorotetrahydro-2H-pyran-4-yl)phenyl]-5-fluoropyridin-2-yl}methyl)pyridin-3-amine;
3-amino-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-4-ol;
4-[3-amino-5-methylpiperidin-1-yl]-N-({6-[2,6-difluoro-4-(tetrahydro-2H-pyran-4-yl)phenyl]-5-fluoropyridin-2-yl}methyl)pyridin-3-amine;
4-(3-amino-5-(trifluoromethyl)piperidin-1-yl)-N-((6-(2,6-difluoro-4-(tetrahydro-2H-pyran-4-yl)phenyl)-5-fluoropyridin-2-yl)methyl)pyridin-3-amine;
4-[3-amino-5-methylcyclohexyl]-N-{[6-(2,6-difluorophenyl)-5-fluoropyridin-2-yl]methyl}pyridin-3-amine;
1-(4-{6-[({4-[3-amino-5-methylcyclohexyl]pyridin-3-yl}amino)methyl]-3-fluoropyridin-2-yl}-3,5-difluorophenyl)cyclobutanol;
4-[3-amino-5-methylcyclohexyl]-N-{[6-(2,6-difluoro-4-morpholin-4-ylphenyl)-5-fluoropyridin-2-yl]methyl}pyridin-3-amine;
N-{[5-amino-2-(2,6-difluorophenyl)-1,3-thiazol-4-yl]methyl}-4-[3-amino-5-methylpiperidin-1-yl]pyridin-3-amine;
4-[3-amino-5-methylpiperidin-1-yl]-N-[(6-{2,6-difluoro-4-[3-fluoropyrrolidin-1-yl]phenyl}-5-fluoropyridin-2-yl)methyl]pyridin-3-amine;
4-[3-amino-5-methylpiperidin-1-yl]-N-({6-[2,6-difluoro-4-(3-fluoropiperidin-1-yl)phenyl]-5-fluoropyridin-2-yl}methyl)pyridin-3-amine;
1-(4-{6-[({4-[3-amino-5-methylpiperidin-1-yl]pyridin-3-yl}amino)methyl]-3-fluoropyridin-2-yl}-3,5-difluorophenyl)-3-methylazetidin-3-ol;
3-amino-1-(3-{[(6-{2,6-difluoro-4-[tetrahydrofuran-3-yloxy]phenyl}-5-fluoropyridin-2-yl)methyl]amino}pyridin-4-yl)-5-methylpiperidin-4-ol;
4-[3-amino-5-methylpiperidin-1-yl]-N-[(6-{2,6-difluoro-4-[tetrahydrofuran-3-yloxy]phenyl}-5-fluoropyridin-2-yl)methyl]pyridin-3-amine;
3-amino-1-{3-[({6-[2,6-difluoro-4-(tetrahydro-2H-pyran-4-yloxy)phenyl]-5-fluoropyridin-2-yl}methyl)amino]pyridin-4-yl}-5-methylpiperidin-4-ol;
4-[3-amino-5-methylpiperidin-1-yl]-N-({6-[2,6-difluoro-4-(tetrahydro-2H-pyran-4-yloxy)phenyl]-5-fluoropyridin-2-yl}methyl)pyridin-3-amine;
4-[3-amino-5-methylpiperidin-1-yl]-N-[(6-{2,6-difluoro-4-[(1-methylpiperidin-4-yl)oxy]phenyl}-5-fluoropyridin-2-yl)methyl]pyridin-3-amine;
3-amino-1-(3-{[(6-{4-[(3,3-difluorocyclobutyl)oxy]-2,6-difluorophenyl}-5-fluoropyridin-2-yl)methyl]amino}pyridin-4-yl)-5-methylpiperidin-4-ol;
4-[3-amino-5-methylpiperidin-1-yl]-N-[(6-{4-[(3,3-difluorocyclobutyl)oxy]-2,6-difluorophenyl}-5-fluoropyridin-2-yl)methyl]pyridin-3-amine;
3-amino-1-[3-({[6-(2,6-difluoro-4-methoxyphenyl)-5-fluoropyridin-2-yl]methyl}amino)pyridin-4-yl]-5-methylpiperidin-4-ol;
4-[3-amino-5-methylpiperidin-1-yl]-N-{[6-(2,6-difluoro-4-methoxyphenyl)-5-fluoropyridin-2-yl]methyl}pyridin-3-amine;
4-{6-[({4-[3-amino-5-methylpiperidin-1-yl]pyridin-3-yl}amino)methyl]-3-fluoropyridin-2-yl}-3-fluorobenzonitrile;
4-[3-amino-5-methylpiperidin-1-yl]-N-{[6-(1-benzothien-5-yl)-5-fluoropyridin-2-yl]methyl}pyridin-3-amine;
6-{6-[({4-[3-amino-5-methylpiperidin-1-yl]pyridin-3-yl}amino)methyl]-3-fluoropyridin-2-yl}-1,3-dihydro-2H-indol-2-one;
4-[3-amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol;
3-amino-1-[5-({[6-(2,6-difluorophenyl)-5-fluoropyridin-2-yl]methyl}amino)-2,3-dihydrofuro[2,3-b]pyridin-4-yl]-5-methylpiperidin-4-ol;
4-[3-amino-5-methylpiperidin-1-yl]-N-{[6-(2,6-difluorophenyl)-5-fluoropyridin-2-yl]methyl}-6,7-dihydro-5H-cyclopenta[b]pyridin-3-amine;
4-[3-amino-4-fluoropiperidin-1-yl]-N-{[6-(2,6-difluorophenyl)-5-fluoropyridin-2-yl]methyl}pyridin-3-amine;
4-[3-amino-5-methylpiperidin-1-yl]-N-{[7-(2,3-dihydro-1-benzofuran-6-yl)quinolin-2-yl]methyl}pyridin-3-amine;
4-[3-amino-5-methylpiperidin-1-yl]-N-[(7-imidazo[1,2-a]pyridin-7-ylquinolin-2-yl)methyl]pyridin-3-amine;
3-amino-1-(3-{[(7-imidazo[1,2-a]pyridin-7-ylquinolin-2-yl)methyl]amino}pyridin-4-yl)-5-methylpiperidin-4-ol;
3-amino-1-{3-[({6-[2,6-difluoro-4-(1-methyl-1H-pyrazol-4-yl)phenyl]-5-fluoropyridin-2-yl}methyl)amino]pyridin-4-yl}-5-methylpiperidin-4-ol;
3-amino-1-(3-{[(3-isopropylfuro[3,2-b]pyridin-5-yl)methyl]amino}pyridin-4-yl)-5-methylpiperidin-4-ol;
3-amino-1-(3-(((3-(2,6-difluoro-4-(hydroxymethyl)phenyl)furo[3,2-b]pyridin-5-yl)methyl)amino)pyridin-4-yl)-5-methylpiperidin-4-ol;

3-amino-1-(3-(((3-(2-fluoro-4-(hydroxymethyl)phenyl)furo[3,2-b]pyridin-5-yl)methyl)amino)pyridin-4-yl)-5-methylpiperidin-4-ol;

4-[3-amino-5-methylpiperidin-1-yl]-N-[(3-isopropylfuro[3,2-b]pyridin-5-yl)methyl]pyridin-3-amine;

(4-(5-((4-(3-amino-5-methylpiperidin-1-yl)pyridin-3-ylamino)methyl)furo[3,2-b]pyridin-3-yl)-3,5-difluorophenyl)methanol;

(4-(5-((4-(3-amino-5-methylpiperidin-1-yl)pyridin-3-ylamino)methyl)furo[3,2-b]pyridin-3-yl)-3-fluorophenyl)methanol;

3-amino-1-(3-{[(3-cyclopropylfuro[3,2-b]pyridin-5-yl)methyl]amino}pyridin-4-yl)-5-methylpiperidin-4-ol;

4-[3-amino-5-methylpiperidin-1-yl]-N-[(3-cyclopropylfuro[3,2-b]pyridin-5-yl)methyl]pyridin-3-amine;

1-(4-{6-[({4-[3-amino-5-methylpiperidin-1-yl]pyridin-3-yl}amino)methyl]-3-fluoropyridin-2-yl}-3,5-difluorophenoxy)-2-methylpropan-2-ol;

3-amino-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-4-ol;

2-(4-{6-[({4-[3-amino-5-methylpiperidin-1-yl]pyridin-3-yl}amino)methyl]-3-fluoropyridin-2-yl}-3,5-difluorophenyl)propan-2-ol;

3-amino-1-{3-[({6-[2,6-difluoro-4-(1-hydroxy-1-methylethyl)phenyl]-5-fluoropyridin-2-yl}methyl)amino]pyridin-4-yl}-5-methylpiperidin-4-ol;

4-{2-[({4-[3-amino-4-hydroxy-5-methylpiperidin-1-yl]pyridin-3-yl}amino)methyl]quinolin-7-yl}-3-fluoro-1-methylpyridin-2(1H)-one;

2-[({4-[3-amino-5-methylpiperidin-1-yl]pyridin-3-yl}amino)methyl]-6-(2,6-difluorophenyl)-5-fluoropyridin-3-amine;

2-[({4-[3-amino-5-(trifluoromethyl)piperidin-1-yl]pyridin-3-yl}amino)methyl]-6-(2,6-difluorophenyl)-5-fluoropyridin-3-amine;

4-[3-amino-5-methylpiperidin-1-yl]-N-{[6-(2,6-difluorophenyl)-5-fluoropyridin-2-yl]methyl}-2-fluoropyridin-3-amine; and 4-[3-amino-5-methylpiperidin-1-yl]-N-{1-[6-(2,6-difluorophenyl)-5-fluoropyridin-2-yl]ethyl}pyridin-3-amine.

Examples of the compounds of Formula (I) also include the following compounds and or pharmaceutically acceptable salts thereof:

(3R,4R,5S)-3-amino-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-4-ol;

(3R,4R,5S)-3-amino-1-(3-(((6-(2,6-difluoro-4-(1-hydroxycyclobutyl)phenyl)-5-fluoropyridin-2-yl)methyl)amino)pyridin-4-yl)-5-methylpiperidin-4-ol;

(3R,4R,5S)-3-amino-1-(3-(((6-(2,6-difluoro-4-(4-hydroxytetrahydro-2H-pyran-4-yl)phenyl)-5-fluoropyridin-2-yl)methyl)amino)pyridin-4-yl)-5-methylpiperidin-4-ol;

3-(4-{6-[({4-[(3S,5R)-3-amino-5-methylpiperidin-1-yl]pyridin-3-yl}amino)methyl]-3-fluoropyridin-2-yl}-3,5-difluorophenyl)tetrahydrofuran-3-ol;

1-(4-(6-((4-((3S,5R)-3-amino-5-methylpiperidin-1-yl)pyridin-3-ylamino)methyl)-3-fluoropyridin-2-yl)-3,5-difluorophenyl)cyclobutanol;

4-(4-(6-((4-((3S,5R)-3-amino-5-methylpiperidin-1-yl)pyridin-3-ylamino)methyl)-3-fluoropyridin-2-yl)-3,5-difluorophenyl)tetrahydro-2H-pyran-4-ol;

1-(4-{6-[({4-[(3S,5R)-3-amino-5-(trifluoromethyl)piperidin-1-yl]pyridin-3-yl}amino)methyl]-3-fluoropyridin-2-yl}-3,5-difluorophenyl)cyclobutanol;

(3R,4R,5S)-3-amino-1-{3-[({6-[2,6-difluoro-4-(1-hydroxycyclopropyl)phenyl]-5-fluoropyridin-2-yl}methyl)amino]pyridin-4-yl}-5-methylpiperidin-4-ol;

(3R,4R,5S)-3-amino-1-(3-(((6-(2,6-difluoro-3-(1-hydroxycyclopropyl)phenyl)-5-fluoropyridin-2-yl)methyl)amino)pyridin-4-yl)-5-methylpiperidin-4-ol;

1-(4-{6-[({4-[(3S,5R)-3-amino-5-methylpiperidin-1-yl]pyridin-3-yl}amino)methyl]-3-fluoropyridin-2-yl}-3,5-difluorophenyl)cyclopropanol;

1-(3-(6-((4-((3S,5R)-3-amino-5-methylpiperidin-1-yl)pyridin-3-ylamino)methyl)-3-fluoropyridin-2-yl)-2,4-difluorophenyl)cyclopropanol;

(3R,4R,5S)-3-amino-1-{3-[({6-[2,6-difluoro-4-(2-hydroxy-2-methylpropyl)phenyl]-5-fluoropyridin-2-yl}methyl)amino]pyridin-4-yl}-5-methylpiperidin-4-ol;

1-(4-{6-[({4-[(3S,5R)-3-amino-5-methylpiperidin-1-yl]pyridin-3-yl}amino)methyl]-3-fluoropyridin-2-yl}-3,5-difluorophenyl)-2-methylpropan-2-ol;

(3R,4R,5S)-3-amino-1-[3-({[6-(2,6-difluorophenyl)-5-fluoropyridin-2-yl]methyl}amino)pyridin-4-yl]-5-methylpiperidin-4-ol;

(3R,4R,5S)-3-amino-1-(3-(((5-fluoro-6-(2-fluoro-6-methoxyphenyl)pyridin-2-yl)methyl)amino)pyridin-4-yl)-5-methylpiperidin-4-ol;

(3R,4R,5S)-3-amino-5-methyl-1-(3-(((3,3',5'-trifluoro-[2,4'-bipyridin]-6-yl)methyl)amino)pyridin-4-yl)piperidin-4-ol;

2-(6-((4-((3R,4R,5S)-3-amino-4-hydroxy-5-methylpiperidin-1-yl)pyridin-3-ylamino)methyl)-3-fluoropyridin-2-yl)-3-fluorobenzonitrile;

(3R,4R,5S)-3-amino-1-(3-(((5-fluoro-6-(2-fluorophenyl)pyridin-2-yl)methyl)amino)pyridin-4-yl)-5-methylpiperidin-4-ol;

4-[(3S,5R)-3-amino-5-methylpiperidin-1-yl]-N-{[6-(2,6-difluorophenyl)-5-fluoropyridin-2-yl]methyl}pyridin-3-amine;

4-((3S,5R)-3-amino-5-methylpiperidin-1-yl)-N-((5-fluoro-6-(2-fluoro-6-methoxyphenyl)pyridin-2-yl)methyl)pyridin-3-amine;

4-((3S,5R)-3-amino-5-methylpiperidin-1-yl)-N-((3,3',5'-trifluoro-2,4'-bipyridin-6-yl)methyl)pyridin-3-amine;

2-(6-((4-((3S,5R)-3-amino-5-methylpiperidin-1-yl)pyridin-3-ylamino)methyl)-3-fluoropyridin-2-yl)-3-fluorobenzonitrile;

4-((3S,5R)-3-amino-5-methylpiperidin-1-yl)-N-((5-fluoro-6-(2-fluorophenyl)pyridin-2-yl)methyl)pyridin-3-amine;

2-(4-{6-[({4-[(3R,4R,5S)-3-amino-4-hydroxy-5-methylpiperidin-1-yl]pyridin-3-yl}amino)methyl]-3-fluoropyridin-2-yl}-3,5-difluorophenyl)-2-methylpropanenitrile;

2-(4-{6-[({4-[(3S,5R)-3-amino-5-methylpiperidin-1-yl]pyridin-3-yl}amino)methyl]-3-fluoropyridin-2-yl}-3,5-difluorophenyl)-2-methylpropanenitrile;

(3R,4R,5S)-3-amino-5-methyl-1-(3-{[(2',6,6'-trifluorobiphenyl-3-yl)methyl]amino}pyridin-4-yl)piperidin-4-ol;

4-[(3S,5R)-3-amino-5-methylpiperidin-1-yl]-N-[(2',6,6'-trifluorobiphenyl-3-yl)methyl]pyridin-3-amine;

1-(5'-((4-((3S,5R)-3-amino-5-methylpiperidin-1-yl)pyridin-3-ylamino)methyl)-2,2',6-trifluorobiphenyl-4-yl)cyclobutanol;

4-(5'-((4-((3S,5R)-3-amino-5-methylpiperidin-1-yl)pyridin-3-ylamino)methyl)-2,2',6-trifluorobiphenyl-4-yl)tetrahydro-2H-pyran-4-ol;

(3R,4R,5S)-3-amino-1-[3-({[6-(2,6-difluorophenyl)pyridin-2-yl]methyl}amino)pyridin-4-yl]-5-methylpiperidin-4-ol;

4-[(3S,5R)-3-amino-5-methylpiperidin-1-yl]-N-{[6-(2,6-difluorophenyl)pyridin-2-yl]methyl}pyridin-3-amine;

(3R,4R,5S)-3-amino-1-[3-({[2-(2,6-difluorophenyl)pyrimidin-4-yl]methyl}amino)pyridin-4-yl]-5-methylpiperidin-4-ol;

4-[(3S,5R)-3-amino-5-methylpiperidin-1-yl]-N-{[2-(2,6-difluorophenyl)pyrimidin-4-yl]methyl}pyridin-3-amine;

(3R,4R,5S)-3-amino-1-(3-(((6-(2,6-difluoro-4-morpholinophenyl)-5-fluoropyridin-2-yl)methyl)amino)pyridin-4-yl)-5-methylpiperidin-4-ol;

4-((3S,5R)-3-amino-5-methylpiperidin-1-yl)-N-((6-(2,6-difluoro-4-morpholinophenyl)-5-fluoropyridin-2-yl)methyl)pyridin-3-amine;

4-((3S,5R)-3-amino-5-(trifluoromethyl)piperidin-1-yl)-N-((6-(2,6-difluoro-4-morpholinophenyl)-5-fluoropyridin-2-yl)methyl)pyridin-3-amine;

(3R,4R,5S)-3-amino-1-{3-[({6-[2,6-difluoro-4-(hydroxymethyl)phenyl]-5-fluoropyridin-2-yl}methyl)amino]pyridin-4-yl}-5-methylpiperidin-4-ol;

(4-{6-[({4-[(3S,5R)-3-amino-5-methylpiperidin-1-yl]pyridin-3-yl}amino)methyl]-3-fluoropyridin-2-yl}-3,5-difluorophenyl)methanol;

(3R,4R,5S)-3-amino-1-[3-({[6-(5,7-difluoroquinolin-6-yl)-5-fluoropyridin-2-yl]methyl}amino)pyridin-4-yl]-5-methylpiperidin-4-ol;

4-[(3S,5R)-3-amino-5-methylpiperidin-1-yl]-N-{[6-(5,7-difluoroquinolin-6-yl)-5-fluoropyridin-2-yl]methyl}pyridin-3-amine;

(3R,4R,5S)-3-amino-1-{3-[({6-[2,6-difluoro-4-(morpholin-4-ylmethyl)phenyl]-5-fluoropyridin-2-yl}methyl)amino]pyridin-4-yl}-5-methylpiperidin-4-ol;

(3R,4R,5S)-3-amino-1-(3-(((6-(2,6-difluoro-4-((methylamino)methyl)phenyl)-5-fluoropyridin-2-yl)methyl)amino)pyridin-4-yl)-5-methylpiperidin-4-ol;

(3R,4R,5S)-3-amino-1-(3-(((6-(4-(azetidin-1-ylmethyl)-2,6-difluorophenyl)-5-fluoropyridin-2-yl)methyl)amino)pyridin-4-yl)-5-methylpiperidin-4-ol;

(3R,4R,5S)-3-amino-1-(3-(((6-(2,6-difluoro-4-(((R)-3-hydroxypyrrolidin-1-yl)methyl)phenyl)-5-fluoropyridin-2-yl)methyl)amino)pyridin-4-yl)-5-methylpiperidin-4-ol;

(3R,4R,5S)-3-amino-1-(3-(((6-(2,6-difluoro-4-(((S)-3-hydroxypyrrolidin-1-yl)methyl)phenyl)-5-fluoropyridin-2-yl)methyl)amino)pyridin-4-yl)-5-methylpiperidin-4-ol;

(R)-1-(4-(6-((4-((3R,4R,5S)-3-amino-4-hydroxy-5-methylpiperidin-1-yl)pyridin-3-ylamino)methyl)-3-fluoropyridin-2-yl)-3,5-difluorobenzyl)pyrrolidine-3-carbonitrile;

(S)-1-(4-(6-((4-((3R,4R,5S)-3-amino-4-hydroxy-5-methylpiperidin-1-yl)pyridin-3-ylamino)methyl)-3-fluoropyridin-2-yl)-3,5-difluorobenzyl)pyrrolidine-3-carbonitrile;

(3R,4R,5S)-3-amino-1-(3-(((6-(2,6-difluoro-4-(((R)-3-fluoropyrrolidin-1-yl)methyl)phenyl)-5-fluoropyridin-2-yl)methyl)amino)pyridin-4-yl)-5-methylpiperidin-4-ol;

(3R,4R,5S)-3-amino-1-(3-(((6-(2,6-difluoro-4-(((S)-3-fluoropyrrolidin-1-yl)methyl)phenyl)-5-fluoropyridin-2-yl)methyl)amino)pyridin-4-yl)-5-methylpiperidin-4-ol;

4-[(3S,5R)-3-amino-5-methylpiperidin-1-yl]-N-({6-[2,6-difluoro-4-(morpholin-4-ylmethyl)phenyl]-5-fluoropyridin-2-yl}methyl)pyridin-3-amine;

4-((3S,5R)-3-amino-5-methylpiperidin-1-yl)-N-((6-(2,6-difluoro-4-((methylamino)methyl)phenyl)-5-fluoropyridin-2-yl)methyl)pyridin-3-amine;

4-((3S,5R)-3-amino-5-methylpiperidin-1-yl)-N-((6-(4-(azetidin-1-ylmethyl)-2,6-difluorophenyl)-5-fluoropyridin-2-yl)methyl)pyridin-3-amine;

(R)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidin-3-ol;

(S)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidin-3-ol;

(R)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidine-3-carbonitrile;

(S)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidine-3-carbonitrile;

4-((3S,5R)-3-amino-5-methylpiperidin-1-yl)-N-((6-(2,6-difluoro-4-(((R)-3-fluoropyrrolidin-1-yl)methyl)phenyl)-5-fluoropyridin-2-yl)methyl)pyridin-3-amine;

4-((3S,5R)-3-amino-5-methylpiperidin-1-yl)-N-((6-(2,6-difluoro-4-(((S)-3-fluoropyrrolidin-1-yl)methyl)phenyl)-5-fluoropyridin-2-yl)methyl)pyridin-3-amine;

(3R,4R,5S)-3-amino-1-(3-{[(6-cyclohex-1-en-1-yl-5-fluoropyridin-2-yl)methyl]amino}pyridin-4-yl)-5-methylpiperidin-4-ol;

4-[(3S,5R)-3-amino-5-methylpiperidin-1-yl]-N-[(6-cyclohexyl-5-fluoropyridin-2-yl)methyl]pyridin-3-amine;

(3R,4R,5S)-3-amino-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-4-ol;

4-[(3S,5R)-3-amino-5-methylpiperidin-1-yl]-N-({6-[2,6-difluoro-4-(4-methoxytetrahydro-2H-pyran-4-yl)phenyl]-5-fluoropyridin-2-yl}methyl)pyridin-3-amine;

(3R,4R,5S)-3-amino-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-4-ol;

4-[(3S,5R)-3-amino-5-methylpiperidin-1-yl]-N-({6-[2,6-difluoro-4-(4-fluorotetrahydro-2H-pyran-4-yl)phenyl]-5-fluoropyridin-2-yl}methyl)pyridin-3-amine;

(3R,4R,5S)-3-amino-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-4-ol;

4-[(3S,5R)-3-amino-5-methylpiperidin-1-yl]-N-({6-[2,6-difluoro-4-(tetrahydro-2H-pyran-4-yl)phenyl]-5-fluoropyridin-2-yl}methyl)pyridin-3-amine;

4-((3S,5R)-3-amino-5-(trifluoromethyl)piperidin-1-yl)-N-((6-(2,6-difluoro-4-(tetrahydro-2H-pyran-4-yl)phenyl)-5-fluoropyridin-2-yl)methyl)pyridin-3-amine;

4-[(1R,3S,5S)-3-amino-5-methylcyclohexyl]-N-{[6-(2,6-difluorophenyl)-5-fluoropyridin-2-yl]methyl}pyridin-3-amine;

1-(4-{6-[({4-[(1R,3S,5S)-3-amino-5-methylcyclohexyl]pyridin-3-yl}amino)methyl]-3-fluoropyridin-2-yl}-3,5-difluorophenyl)cyclobutanol;

4-[(1R,3S,5S)-3-amino-5-methylcyclohexyl]-N-{[6-(2,6-difluoro-4-morpholin-4-ylphenyl)-5-fluoropyridin-2-yl]methyl}pyridin-3-amine;

N-{[5-amino-2-(2,6-difluorophenyl)-1,3-thiazol-4-yl]methyl}-4-[(3S,5R)-3-amino-5-methylpiperidin-1-yl]pyridin-3-amine;

4-[(3S,5R)-3-amino-5-methylpiperidin-1-yl]-N-[(6-{2,6-difluoro-4-[(3R)-3-fluoropyrrolidin-1-yl]phenyl}-5-fluoropyridin-2-yl)methyl]pyridin-3-amine;

4-[(3S,5R)-3-amino-5-methylpiperidin-1-yl]-N-({6-[2,6-difluoro-4-(3-fluoropiperidin-1-yl)phenyl]-5-fluoropyridin-2-yl}methyl)pyridin-3-amine;

1-(4-{6-[({4-[(3S,5R)-3-amino-5-methylpiperidin-1-yl]pyridin-3-yl}amino)methyl]-3-fluoropyridin-2-yl}-3,5-difluorophenyl)-3-methylazetidin-3-ol;

(3R,4R,5S)-3-amino-1-(3-{[(6-{2,6-difluoro-4-[(3R)-tetrahydrofuran-3-yloxy]phenyl}-5-fluoropyridin-2-yl)methyl]amino}pyridin-4-yl)-5-methylpiperidin-4-ol;

4-[(3S,5R)-3-amino-5-methylpiperidin-1-yl]-N-[(6-{2,6-difluoro-4-[(3R)-tetrahydrofuran-3-yloxy]phenyl}-5-fluoropyridin-2-yl)methyl]pyridin-3-amine;

(3R,4R,5S)-3-amino-1-(3-{[(6-{2,6-difluoro-4-[(3S)-tetrahydrofuran-3-yloxy]phenyl}-5-fluoropyridin-2-yl)methyl]amino}pyridin-4-yl)-5-methylpiperidin-4-ol;

4-[(3S,5R)-3-amino-5-methylpiperidin-1-yl]-N-[(6-{2,6-difluoro-4-[(3S)-tetrahydrofuran-3-yloxy]phenyl}-5-fluoropyridin-2-yl)methyl]pyridin-3-amine;

(3R,4R,5S)-3-amino-1-{3-[({6-[2,6-difluoro-4-(tetrahydro-2H-pyran-4-yloxy)phenyl]-5-fluoropyridin-2-yl}methyl)amino]pyridin-4-yl}-5-methylpiperidin-4-ol;

4-[(3S,5R)-3-amino-5-methylpiperidin-1-yl]-N-({6-[2,6-difluoro-4-(tetrahydro-2H-pyran-4-yloxy)phenyl]-5-fluoropyridin-2-yl}methyl)pyridin-3-amine;

4-[(3S,5R)-3-amino-5-methylpiperidin-1-yl]-N-[(6-{2,6-difluoro-4-[(1-methylpiperidin-4-yl)oxy]phenyl}-5-fluoropyridin-2-yl)methyl]pyridin-3-amine;

(3R,4R,5S)-3-amino-1-(3-{[(6-{4-[(3,3-difluorocyclobutyl)oxy]-2,6-difluorophenyl}-5-fluoropyridin-2-yl)methyl]amino}pyridin-4-yl)-5-methylpiperidin-4-ol;

4-[(3S,5R)-3-amino-5-methylpiperidin-1-yl]-N-[(6-{4-[(3,3-difluorocyclobutyl)oxy]-2,6-difluorophenyl}-5-fluoropyridin-2-yl)methyl]pyridin-3-amine;

(3R,4R,5S)-3-amino-1-[3-({[6-(2,6-difluoro-4-methoxyphenyl)-5-fluoropyridin-2-yl]methyl}amino)pyridin-4-yl]-5-methylpiperidin-4-ol;

4-[(3S,5R)-3-amino-5-methylpiperidin-1-yl]-N-{[6-(2,6-difluoro-4-methoxyphenyl)-5-fluoropyridin-2-yl]methyl}pyridin-3-amine;

4-{6-[({4-[(3S,5R)-3-amino-5-methylpiperidin-1-yl]pyridin-3-yl}amino)methyl]-3-fluoropyridin-2-yl}-3-fluorobenzonitrile;

4-[(3S,5R)-3-amino-5-methylpiperidin-1-yl]-N-{[6-(1-benzothien-5-yl)-5-fluoropyridin-2-yl]methyl}pyridin-3-amine;

6-{6-[({4-[(3S,5R)-3-amino-5-methylpiperidin-1-yl]pyridin-3-yl}amino)methyl]-3-fluoropyridin-2-yl}-1,3-dihydro-2H-indol-2-one;

(7R)-4-[(3S,5R)-3-amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol;

(3R,4R,5S)-3-amino-1-[5-({[6-(2,6-difluorophenyl)-5-fluoropyridin-2-yl]methyl}amino)-2,3-dihydrofuro[2,3-b]pyridin-4-yl]-5-methylpiperidin-4-ol;

4-[(3S,5R)-3-amino-5-methylpiperidin-1-yl]-N-{[6-(2,6-difluorophenyl)-5-fluoropyridin-2-yl]methyl}-6,7-dihydro-5H-cyclopenta[b]pyridin-3-amine;

4-[(3R,4R)-3-amino-4-fluoropiperidin-1-yl]-N-{[6-(2,6-difluorophenyl)-5-fluoropyridin-2-yl]methyl}pyridin-3-amine;

4-[(3S,5R)-3-amino-5-methylpiperidin-1-yl]-N-{[7-(2,3-dihydro-1-benzofuran-6-yl)quinolin-2-yl]methyl}pyridin-3-amine;

4-[(3S,5R)-3-amino-5-methylpiperidin-1-yl]-N-[(7-imidazo[1,2-a]pyridin-7-ylquinolin-2-yl)methyl]pyridin-3-amine;

(3R,4R,5S)-3-amino-1-(3-{[(7-imidazo[1,2-a]pyridin-7-ylquinolin-2-yl)methyl]amino}pyridin-4-yl)-5-methylpiperidin-4-ol;

(3R,4R,5S)-3-amino-1-{3-[({6-[2,6-difluoro-4-(1-methyl-1H-pyrazol-4-yl)phenyl]-5-fluoropyridin-2-yl}methyl)amino]pyridin-4-yl}-5-methylpiperidin-4-ol;

(3R,4R,5S)-3-amino-1-(3-{[(3-isopropylfuro[3,2-b]pyridin-5-yl)methyl]amino}pyridin-4-yl)-5-methylpiperidin-4-ol;

(3R,4R,5S)-3-amino-1-(3-(((3-(2,6-difluoro-4-(hydroxymethyl)phenyl)furo[3,2-b]pyridin-5-yl)methyl)amino)pyridin-4-yl)-5-methylpiperidin-4-ol;

(3R,4R,5S)-3-amino-1-(3-(((3-(2-fluoro-4-(hydroxymethyl)phenyl)furo[3,2-b]pyridin-5-yl)methyl)amino)pyridin-4-yl)-5-methylpiperidin-4-ol;

4-[(3S,5R)-3-amino-5-methylpiperidin-1-yl]-N-[(3-isopropylfuro[3,2-b]pyridin-5-yl)methyl]pyridin-3-amine;

(4-(5-((4-((3S,5R)-3-amino-5-methylpiperidin-1-yl)pyridin-3-ylamino)methyl)furo[3,2-b]pyridin-3-yl)-3,5-difluorophenyl)methanol;

(4-(5-((4-((3S,5R)-3-amino-5-methylpiperidin-1-yl)pyridin-3-ylamino)methyl)furo[3,2-b]pyridin-3-yl)-3-fluorophenyl)methanol;

(3R,4R,5S)-3-amino-1-(3-{[(3-cyclopropylfuro[3,2-b]pyridin-5-yl)methyl]amino}pyridin-4-yl)-5-methylpiperidin-4-ol;

4-[(3S,5R)-3-amino-5-methylpiperidin-1-yl]-N-[(3-cyclopropylfuro[3,2-b]pyridin-5-yl)methyl]pyridin-3-amine;

1-(4-{6-[({4-[(3S,5R)-3-amino-5-methylpiperidin-1-yl]pyridin-3-yl}amino)methyl]-3-fluoropyridin-2-yl}-3,5-difluorophenoxy)-2-methylpropan-2-ol;

(3R,4R,5S)-3-amino-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-4-ol;

2-(4-{6-[({4-[(3S,5R)-3-amino-5-methylpiperidin-1-yl]pyridin-3-yl}amino)methyl]-3-fluoropyridin-2-yl}-3,5-difluorophenyl)propan-2-ol;

(3R,4R,5S)-3-amino-1-{3-[({6-[2,6-difluoro-4-(1-hydroxy-1-methylethyl)phenyl]-5-fluoropyridin-2-yl}methyl)amino]pyridin-4-yl}-5-methylpiperidin-4-ol;

4-{2-[({4-[(3R,4R,5S)-3-amino-4-hydroxy-5-methylpiperidin-1-yl]pyridin-3-yl}amino)methyl]quinolin-7-yl}-3-fluoro-1-methylpyridin-2(1H)-one;

2-[({4-[(3S,5R)-3-amino-5-methylpiperidin-1-yl]pyridin-3-yl}amino)methyl]-6-(2,6-difluorophenyl)-5-fluoropyridin-3-amine;

2-[({4-[(3S,5R)-3-amino-5-(trifluoromethyl)piperidin-1-yl]pyridin-3-yl}amino)methyl]-6-(2,6-difluorophenyl)-5-fluoropyridin-3-amine;

4-[(3S,5R)-3-amino-5-methylpiperidin-1-yl]-N-{[6-(2,6-difluorophenyl)-5-fluoropyridin-2-yl]methyl}-2-fluoropyridin-3-amine; and 4-[(3S,5R)-3-amino-5-methylpiperidin-1-yl]-N-{1-[6-(2,6-difluorophenyl)-5-fluoropyridin-2-yl]ethyl}pyridin-3-amine.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl, and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —NH$_2$.

The term "carbamyl" refers to a group of formula —C(O)NH$_2$.

The term "carbonyl", employed alone or in combination with other terms, refers to a —C(=O)— group, which also may be written as C(O).

The term "cyano" or "nitrile" refers to a group of Formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo is F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of Formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

The term "arylalkyl," employed alone or in combination with other terms, refers to a group of formula -alkylene-aryl. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl, pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridinyl), indolyl, benzothiophenyl, benzofuranyl, benzisoxazolyl, imidazo[1,2-b]thiazolyl, purinyl, or the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "heteroarylalkyl," employed alone or in combination with other terms, refers to a group of formula -alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen.

The term "cycloalkyl," employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "cycloalkylalkyl," employed alone or in combination with other terms, refers to a group of formula -alkylene-cycloalkyl. In some embodiments, cycloalkylalkyl is $C_{3-7}$ cycloalkyl-$C_{1-3}$ alkyl, wherein the cycloalkyl portion is monocyclic or bicyclic. In some embodiments, cycloalkylalkyl is $C_{3-7}$ cycloalkyl-$C_{1-4}$ alkyl, wherein the cycloalkyl portion is monocyclic or bicyclic.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-12 ring members, 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfide group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidine, azepane, dihydrobenzofuran, dihydrofuran, dihydropyran, morpholine, 3-oxa-9-azaspiro[5.5]undecane, 1-oxa-8-azaspiro[4.5]decane, piperidine, piperazine, pyran, pyrrolidine, quinuclidine, tetrahydrofuran, tetrahydropyran, 1,2,3,4-tetrahydroquinoline, tropane, and thiomorpholine.

As used herein, the term "heterocycloalkylalkyl," employed alone or in combination with other terms, refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is $C_{2-9}$ heterocycloalkyl-$C_{1-4}$ alkyl, wherein the heterocycloalkyl portion is monocyclic or bicyclic and has 1, 2, 3, or 4 heteroatom ring members independently selected from nitrogen, sulfur and oxygen.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical Formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences, 17th* Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); aq. (aqueous); atm. (atmosphere(s)); Boc (t-butoxycarbonyl); BOP ((benzotriazol-1-yloxy)tris(dimethylamino)phosphonium hexafluorophosphate); $Br_2$ (bromine); Cbz (carboxybenzyl); calc. (calculated); $CeCl_3 \cdot 7H_2O$ (cerium (III) chloride heptahydrate); CuI (copper (I) iodide); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMAP (4-dimethylaminopyridine); DMF (N,N-dimethylformamide); Et (ethyl); $Et_2O$ (diethyl ether); EtOAc (ethyl acetate); EtOH (ethanol); Fmoc (9-fluorenylmethylmethoxycarbonyl); g (gram(s)); h (hour(s)); $H_2$ (hydrogen gas); HATU (N,N,N',N'-tetramethyl-O-(7-azabenzotriazol-1-yl)uronium hexafluorophosphate); HCl (hydrochloric acid/hydrogen choride); HPLC (high performance liquid chromatography); $H_2SO_4$ (sulfuric acid); Hz (hertz); $I_2$ (iodine); IPA (isopropyl alcohol); J (coupling constant); KOH (potassium hydroxide); $K_3PO_4$ (potassium phosphate); $K_3PO_4 \cdot H_2O$ (tripotassium phosphate hydrate); LiHMDS (lithium hexamethyldisilazide); LCMS (liquid chromatography-mass spectrometry); $LiAlH_4$ (lithium tetrahydroaluminate); $LiBH_4$ (lithium tetrahydroborate); LiOH (lithium hydroxide); m (multiplet); M (molar); MeI (methyl iodide); MS (Mass spectrometry); Me (methyl); MeCN (acetonitrile); MeOH (methanol); mg (milligram(s)); min. (minutes(s)); mL (milliliter(s)); mmol (millimole(s)); $MnO_2$ (manganese (IV) oxide); $MoSO_4$ (molybdenum sulfate); N (normal); $NaBH_4$ (sodium tetrahydroborate); $Na_2CO_3$ (sodium carbonate); $NH_3$ (ammonia); $NaHCO_3$ (sodium bicarbonate); NaOH (sodium hydroxide); $Na_2S$ (sodium sulfide); $Na_2SO_4$ (sodium sulfate); $Na_2S_2O_3$ (sodium thiosulfate); $NH_4OH$ (ammonium hydroxide); nM (nanomolar); NMR (nuclear magnetic resonance spectroscopy); Pd (palladium); $Pd(OAc)_2$ (palladium acetate); pM (picomolar); $PPh_3$ (triphenylphosphine); RP-HPLC (reverse phase high performance liquid chromatography); t (triplet or tertiary); t-Bu (tert-butyl); TEA (triethylamine); TFA (trifluoroacetic acid); THF (tetrahydrofuran); $TiCl_4$ (titanium tetrachloride); TLC (thin layer chromatography); g (microgram(s)); L (microliter(s)); M (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure, 6th* Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

A general syntheses of compounds of Formula (I) is shown in Scheme 1. Suzuki, Buchwald or Stille coupling of compound 1-1 (Lv=Cl, Br, I) results in the formation of the compound 1-2. Reduction of the ester to alcohol followed by oxidation of the resulting alcohol moiety to aldehyde leads to compound 1-3. Reductive amination of aldehyde 1-3 with a desired amine 1-4 followed by global deprotection of the protective groups results in the formation of the compounds of formula 1-5.

Scheme 1

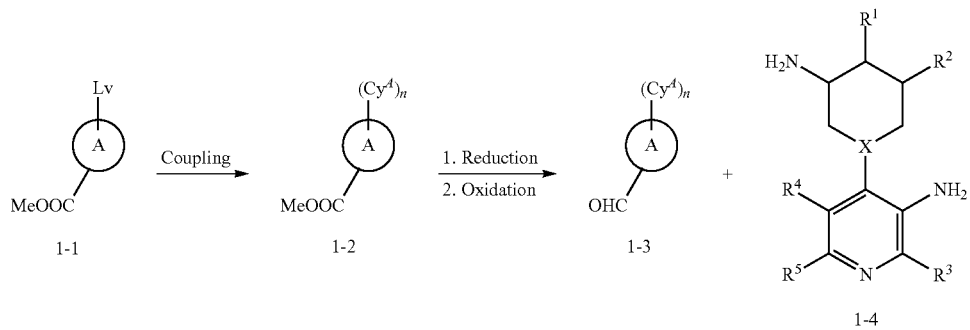

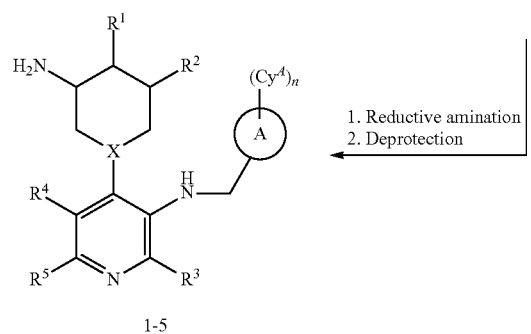

Alternatively, compounds of formula 1-5 can be synthesized according to Scheme 2. Reduction of the ester 2-1 to an alcohol followed by oxidation of the resulting alcohol moiety to aldehyde leads to compound 2-2. Reductive amination of the obtained aldehyde with the amine 1-4 gives the compound 2-3. Suzuki, Buchwald or Stille coupling of the compound 2-3 followed by global deprotection of the protective groups results in the formation of the compounds of formula 1-5. To provide for selectivity, the amine attached to the piperidine or cyclohexyl ring of compound 1-4 can be protected for the reductive amination reaction (e.g., with a carbamate protecting group such as BOC).

Scheme 2

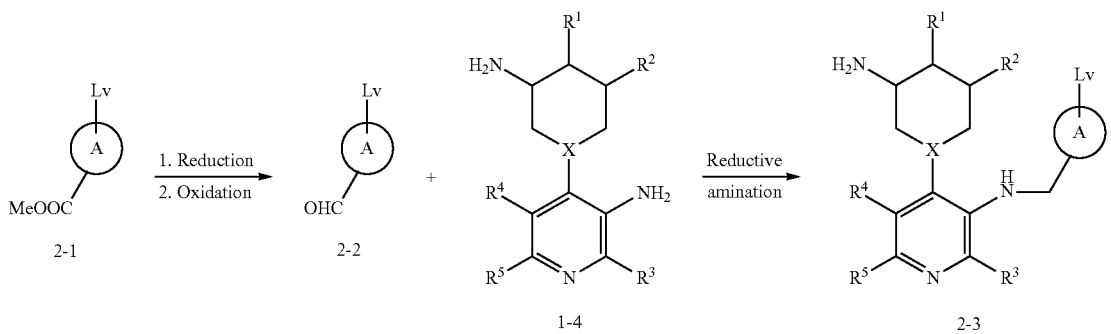

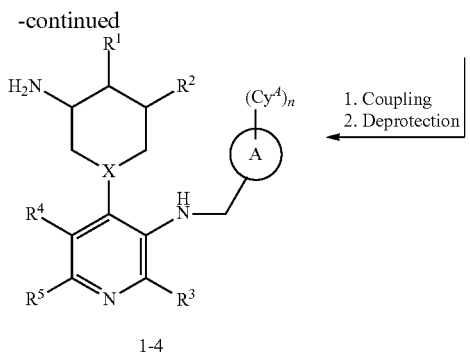

1-4

Amine compounds 3-5 (wherein X=N) can be prepared as shown in Scheme 3. A suitably substituted 4-chloro-3-nitropyridine 3-1 can react with a suitably substituted piperidine 3-2 in the presence of a suitable base or an organometallic catalyst to give compounds of formula 3-4. Reduction of the nitro group, e.g., in the presence of iron in acetic acid, provides amine 3-5 (X=N). Cyclohexyl analogues (compounds of formula 3-3 wherein X=CH) can be prepared by analogous by organometallic cross-coupling, e.g., with a compound of formula 3-3 followed by reduction of the olefinic C=C bond. To provide for selectivity, the amine attached to the piperidine or cyclohexyl ring of compound 3-2 or 3-3 can be protected for the cross-coupling reaction (e.g., with a carbamate protecting group such as BOC) which would provide compound 3-5 in suitable protected form for a selective reductive amination reaction as described above.

Scheme 3

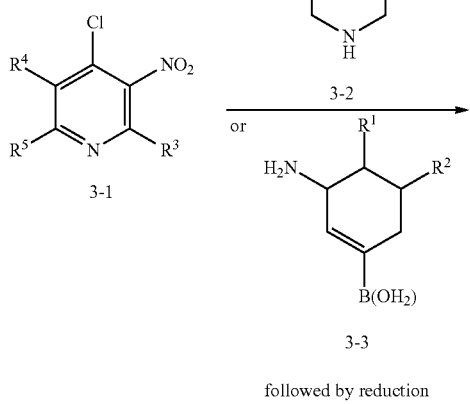

followed by reduction

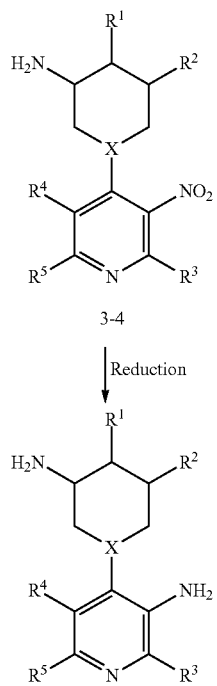

The compounds Formula (I) where A is furopyridine can be prepared as illustrated in Scheme 4. Esterification of 5-hydroxypicolinic acid 4-1 can be performed in methanol in the presence of catalytic amount of concentrated sulfuric acid. Iodination of the resulted ester 4-2 yields compound 4-3. Sonogashira coupling then leads to the formation of the furan ring in the compound 4-4. TMS removal by potassium carbonate in methanol affords compound 4-5. Bromination of the double bond followed by treatment of the resulting product 4-6 with base gives the compound 4-7. Reduction of the acid to alcohol followed by oxidation of the resultant alcohol moiety to aldehyde leads to compound 4-8. Reductive amination of the aldehyde 4-8 with a desired amine gives the compound 4-9. Bromo-compound 4-9 can then be subjected to Suzuki coupling with desired boronic acid or ester (or another functional group interconversion) to provide compounds 4-10 wherein R can be various groups. In cases where alkenyl boronic esters are used for the Suzuki coupling, an extra step of the reduction of the double bond is performed via catalytic hydrogenation. Finally, global deprotection of the protective groups results in the formation of the compounds of formula 4-10.

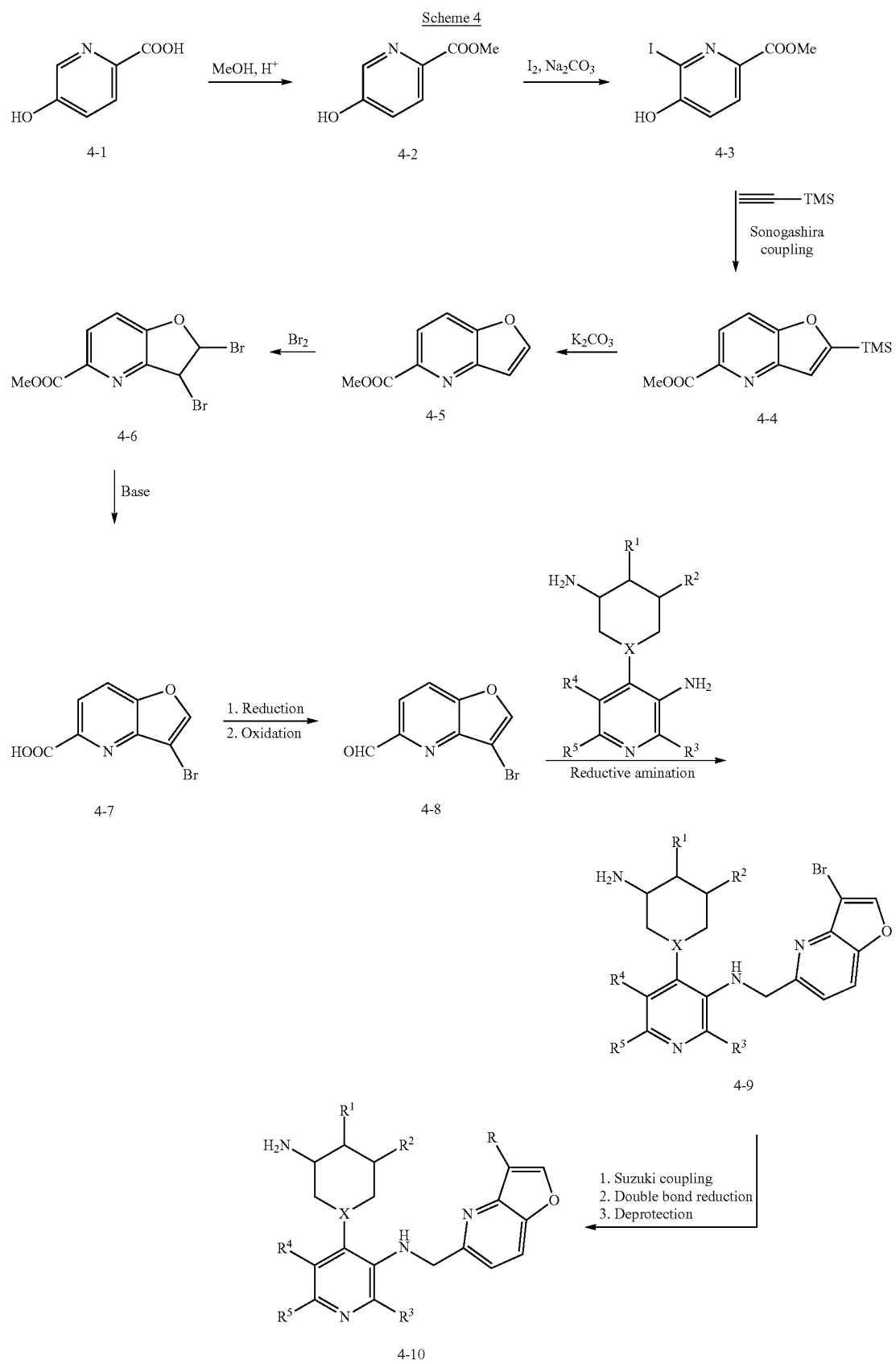

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of the invention, or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a Pim kinase-associated disease or disorder. Also provided is the use of a compound of the invention, or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or Bcl2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase associated diseases that can be treated using the compounds of the invention also include myelodysplastic syndrome, including refractory anemia (RA), refractory cytopenia with unilineage dysplasia (refractory anemia, Refractory neutropenia, and Refractory thrombocytopenia), refactory anemia with ringed sideroblasts (RARS), refractory anemia with ring sideroblasts-thrombocytosis (RARS-t), Refractory cytopenia with multilineage dysplasia (RCMD), refactory anemia with excess blasts (RAEB) (including refactory anemia with excess blasts-I (RAEB-I) and refactory anemia with excess blasts-II (RAEB-II), refactory anemia with excess blasts in transofmration (RAEB-t), 5q-syndrome, myelodysplasia unclassifiable refractory cytopenia of childhood and chronic myelomonocytic leukemia (CMML).

Pim kinase-associated diseases that can be treated using the compounds of the invention also include myelodysplastic/myeloproliferative diseases. Myelodysplastic/myeloproliferative diseases include myeloid disorders that have both dysplastic and proliferative features, such as chronic myelomonocytic leukemia (CMML), atypical chronic myeloid leukemia, juvenile myelomonocytic leukemia, and unclassifiable myelodysplastic/myeloproliferative disease.

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The Pim inhibitors of the present invention can be used in combination with one or more other BET bromodomain inhibitors such a BRD2, BRD3, BRD4 and BRDT that are useful for the treatment of diseases, such as cancer.

In some embodiments Pim inhibitors of the invention can be combined with inhibitors selective for JAK1 and/or JAK2 (e.g., ruxolitinib, baricitinib, momelotinib, filgotinib, pacritinib, INCB039110, INCB052793, INCB054707, CYT387, ABT494, AZD1480, XL019, CEP-33779, AZ 960, TG101209, and gandotinib). In some embodiments Pim inhibitors of the invention can be combined with inhibitors selective for JAK1 (e.g. INCB039110, INCB052793, INCB054707, and ABT494) such as those disclosed in e.g., WO 2010/135650, WO 2011/028685, WO 2011/112662, WO 2012/068450, WO 2012/068440, WO 2012/177606, WO 2013/036611, WO 2013/026025, WO 2014/138168, WO 2013/173720, WO 2015/021153, WO 2014/071031, WO 2014/106706, WO 2015/131031, WO 2015/168246, and WO 2015/184305. In some embodiments Pim inhibitors of the invention can be combined with inhibitors selective for JAK2 (e.g., pacritinib, AZD1480, XL019, CEP-33779, AZ 960, TG101209, and gandotinib).

In some embodiments Pim inhibitors of the invention can be combined with inhibitors selective for PI3K delta (e.g., idelalisib, INCB040093, INCB050465, and TGR 1202) such as those disclosed in e.g., WO 2011/0008487, WO 2011/075643, WO 2011/075630, WO 2011/163195, WO 2011/130342, WO 2012/087881, WO 2012/125629, WO 2012/135009, WO 2013/033569, WO2013/151930, WO 2014/134426, WO 2015/191677, and WO 2015/157257.

The Pim inhibitors of the present invention can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments Pim inhibitors of the invention can be combined with cytarabine.

Other anti-cancer agent(s) include antibody therapeutics such as trastuzumab (Herceptin), antibodies to costimulatory molecules such as CTLA-4, 4-1BB, PD-1 and PD-L1, or antibodies to cytokines (IL-10, TGF-β, etc.).

The Pim inhibitors of the present invention can further be used in combination with one or more anti-inflammatory agents, steroids, immunosuppressants or therapeutic antibodies.

The Pim inhibitors of the present invention can be used in combination with one or more immune check point inhibitors. Exemplary immune checkpoint inhibitors include inhibitors against immune checkpoint molecules such as CD27, CD28, CD40, CD122, CD96, CD73, CD47, OX40, GITR, CSF1R, JAK (e.g., JAK1 and/or JAK2), PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, immune checkpoint inhibitors include inhibitors against immune checkpoint molecules such as JAK1 and/or JAK2.

In some embodiments, immune checkpoint inhibitors include inhibitors against immune checkpoint molecules such as CD96.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166. In some embodiments, the anti-GITR antibody is INCAGN01876.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383. In some embodiments, the anti-OX40 antibody is INCAGN01949.

In some embodiments, the inhibitor of an immune checkpoint molecule is an inhibitor of TIM3, e.g., an anti-TIM3 antibody.

In some embodiments Pim inhibitors of the invention can be combined with TIGIT inhibitors.

The Pim inhibitors of the present invention can be used in combination with one or more other anti-cancer agents including BET inhibitors (e.g., INCB054329, OTX015, and CPI-0610), LSD1 inhibitors (e.g., GSK2979552 and INCB059872), HDAC inhibitors (e.g., panobinostat, vorinostat, and entinostat), DNA methyl transferase inhibitors (e.g., azacitidine and decitabine), and other epigenetic modulators.

In some embodiments Pim inhibitors of the invention can be combined with BET inhibitors. In some embodiments Pim inhibitors of the invention can be combined with LSD1 inhibitors. In some embodiments Pim inhibitors of the invention can be combined with HDAC inhibitors. In some embodiments Pim inhibitors of the invention can be combined with DNA methyl transferase inhibitors.

The Pim inhibitors of the present invention can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a Formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the Formulation, e.g., about 40 mesh.

The compounds of the invention may be milled using known milling procedures such as wet milling to obtain a particle size appropriate for tablet formation and for other Formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The Formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to Formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or Formulated under Good Manufacturing Practice standards as defined in the applicable regulations of the U.S. Food and Drug Administration. For example, suitable Formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, Formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preFormulation composition containing a homogeneous mixture of a compound of the present invention. When referring to these preFormulation compositions as homogeneous, the active ingredient is typically dispersed evenly throughout the composition so that the composition can be readily subdivided into equally effective unit dosage forms such as tablets, pills and capsules. This solid preFormulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the Formulation in an appropriate manner.

Topical Formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be Formulated using isopropyl alcohol and water, suitably in combination with other components such as, e.g., glycerol, hydroxyethyl cellulose, and the like. In some embodiments, topical Formulations contain at least about 0.1, at least about 0.25, at least about 0.5, at least about 1, at least about 2 or at least about 5 wt % of the compound of the invention. The topical Formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, Formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro Pim kinase labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 min. with flow rate 1.5 mL/min.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/min., the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/min.

pH=10 purifications: Waters XBridge™ C$_{18}$ 5 μm, 19×100 mm column, eluting with mobile phase A: 0.15% NH$_4$OH in water and mobile phase B: 0.15% NH$_4$OH in acetonitrile; the flow rate was 30 mL/min., the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/min.

Intermediate 1 tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate

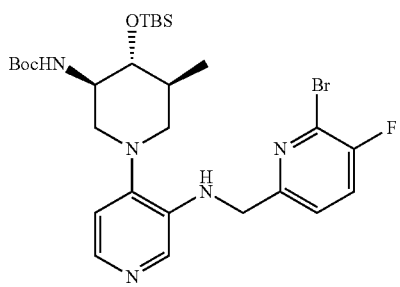 [SMILES: C[C@H]1CN(c2ccncc2NCc2ccc(F)c(Br)n2)C[C@@H](NC(=O)OC(C)(C)C)[C@@H]1O[Si](C)(C)C(C)(C)C]

Step 1. (6-Bromo-5-fluoropyridin-2-yl)methanol

Methyl 6-bromo-5-fluoropyridine-2-carboxylate (Frontier Scientific, 2.50 g, 10.7 mmol) was dissolved in methanol (20.0 mL) and the reaction mixture was cooled to 0° C. Then sodium tetrahydroborate (1.2 g, 32 mmol) was slowly added to the reaction mixture and the reaction mixture was allowed to warm to room temperature and stirring continued for 1 h at room temperature. After this time, water was added to the reaction mixture and product was extracted with EtOAc. Combined organic fractions were washed with brine, dried over Na$_2$SO$_4$ and solvents were evaporated under reduced pressure. The resulting product was used in the next step without further purification (2.2 g, 98%). LCMS calc. for C$_6$H$_6$BrFNO (M+H)$^+$ m/z=206.0; found 205.9.

Step 2. 6-Bromo-5-fluoropyridine-2-carbaldehyde

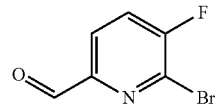

To a stirred solution of (6-bromo-5-fluoropyridin-2-yl)methanol (2.15 g, 10.4 mmol) in DCM (70 mL) at 0° C. were added pyridine (1.0 mL, 12 mmol) and Dess-Martin periodinane (4.65 g, 11.0 mmol). The reaction mixture was stirred at room temperature for 3 h. Then saturated solutions of NaHCO$_3$ in water (40 mL) and Na$_2$S$_2$O$_3$ in water (20 mL) were added and the reaction mixture was stirred for 30 min. Then product was extracted with DCM. Combined organic fractions were washed with brine, dried over Na$_2$SO$_4$ and solvents were evaporated under reduced pressure. The crude product was purified by Biotage Isolera to give the desired compound (1.8 g, 85%). LCMS calc. for C$_6$H$_4$BrFNO (M+H)$^+$ m/z=204.0; found: 204.0.

Step 3. tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate

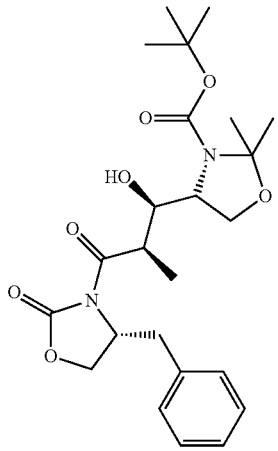

To a solution of (R)-3-(1-oxopropyl)-4-benzyl-2-oxazolidinone (12 g, 51 mmol) in DCM (300 mL) (0.13M), 1.0M TiCl$_4$ in DCM (51 mL, 51 mmol) was added at −40° C. The mixture was stirred at −40° C. for 10 min., then DIPEA (22 mL, 130 mmol) was added, forming a dark red solution. The mixture was stirred at 0° C. for 20 min. tert-Butyl (4R)-4-formyl-2,2-dimethyl-1,3-oxazolidine-3-carboxylate (12 g, 51 mmol) in DCM (100 mL) (0.5M) was then added dropwise and the resulting mixture was stirred for 1.5 h at 0° C. LCMS showed 2 peaks with a mass corresponding to the sub-title compound, one major peak and one min. or peak (5:2). The reaction mixture was quenched by the addition of aq. NH$_4$Cl solution and the mixture was extracted with DCM. The organic phase was separated, washed with brine, dried over MgSO$_4$, concentrated under reduced pressure, and purified by chromatography on silica gel (0-40% EtOAc/hexane) to give 8 g (30% yield) of the sub-title compound as a colorless oil. LCMS calc. for $C_{24}H_{35}N_2O_7$ (M+H)$^+$: m/z=463.2; found: 463.1.

Step 4. tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

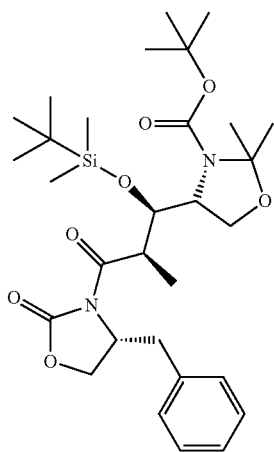

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (12.1 g, 26.2 mmol) and 2,6-lutidine (5.4 mL, 47 mmol) in DCM (260 mL) (0.1M) was added tert-butyldimethylsilyl trifluoromethanesulfonate (8.41 mL, 36.6 mmol) at −40° C. The mixture was stirred at −40° C. for 2 h. The reaction mixture was diluted with DCM, washed with saturated aq. NaHCO$_3$ solution, dried over Na$_2$SO$_4$, concentrated under reduced pressure, and purified by chromatography on silica gel (0-20% EtOAc/hexane) to give 14 g (92.8% yield) of the sub-title compound as a colorless gel. LCMS calc. for $C_{25}H_{41}N_2O_5Si$ (M+H-Boc+H)$^+$: m/z=477.3; found: 477.1.

Step 5. tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate

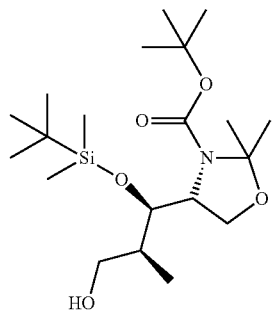

To a solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate (14.0 g, 24.3 mmol) and EtOH (4.2 mL, 73 mmol) in THF (300 mL) (0.09M) was added LiBH$_4$ (1.6 g, 73 mmol) at −30° C. The mixture allowed to warm to 0° C. and stirred overnight. The reaction mixture was diluted with Et$_2$O and 1M NaOH was added. The resulting mixture was extracted with EtOAc and the organic extract was washed with brine, dried over Na$_2$SO$_4$, concentrated under reduced pressure, and purified by chromatography on silica gel (0-20% EtOAc/hexane) to give 4.1 g (42% yield) of the sub-title compound as a colorless oil. LCMS calc. for $C_{15}H_{34}NO_3Si$ (M+H-Boc+H)$^+$: m/z=304.2; found: 304.1.

Step 6. tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate

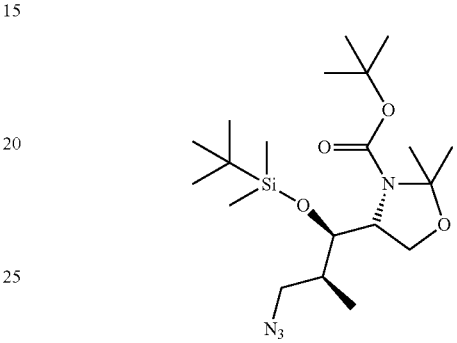

To a mixture of tert-butyl (4R)-4-((1R,2S)-1-{[tert-butyl(dimethyl)silyl]oxy}-3-hydroxy-2-methylpropyl)-2,2-dimethyl-1,3-oxazolidine-3-carboxylate (8.20 g, 20.3 mmol), diisopropyl azodicarboxylate (8.0 mL, 41 mmol) and PPh$_3$ (11 g, 41 mmol) in THF (100 mL) (0.18M), diphenylphosphonic azide (8.8 mL, 41 mmol) was added. The mixture was stirred at room temperature overnight. The mixture was concentrated under reduced pressure, and the residue was purified by chromatography on silica gel (0-15% EtOAc/hexane) to give 5.2 g (60% yield) of the sub-title compound as a yellowish oil. LCMS calc. for $C_{20}H_{41}N_4O_4Si$ (M+H)$^+$: m/z=429.3; found: 429.1.

Step 7. tert-butyl [(1R,2R,3S)-4-azido-2-{[tert-butyl(dimethyl)silyl]oxy}-1-(hydroxymethyl)-3-methylbutyl]carbamate

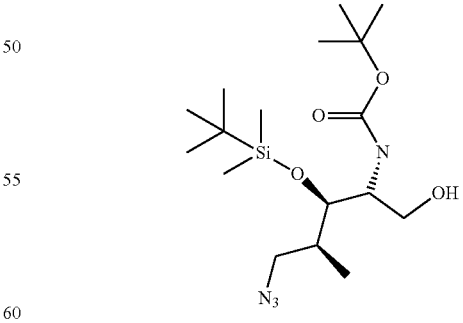

A solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (10.5 g, 24.5 mmol) in EtOH (70 mL) was added pyridinium p-toluenesulfonate (12.3 g, 49.0 mmol) and the mixture was heated under reflux for 2 days.

The volatiles were removed under reduced pressure and the residue was dissolved in DCM (200 mL) (0.1M). To the resulting solution were added DIPEA (8.53 mL, 49.0 mmol) and di-tert-butyldicarbonate (6.42 g, 29.4 mmol). The reaction mixture was stirred at room temperature for 5 h. The mixture was concentrated under reduced pressure and purified by chromatography on silica gel (0-25% EtOAc/Hexane) to give 5.8 g (61% yield) of the sub-title compound as a colorless oil. LCMS calc. for $C_{12}H_{29}N_4O_2Si$ (M+H-Boc+H)$^+$: m/z=289.2; found: 289.1.

Step 8. (2R,3R,4S)-5-azido-2-[(tert-butoxycarbonyl)amino]-3-{[tert-butyl(dimethyl)silyl]oxy}-4-methyl-pentyl methanesulfonate

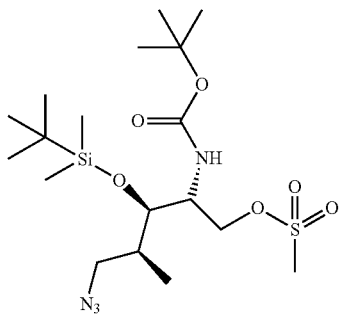

To a solution of tert-butyl [(1R,2R,3S)-4-azido-2-{[tert-butyl(dimethyl)silyl]oxy}-1-(hydroxymethyl)-3-methylbutyl]carbamate (5.80 g, 14.9 mmol) in pyridine (75 mL) at 0° C. was added methanesulfonyl chloride (1.50 mL, 19.4 mmol) and DMAP (0.36 g, 3.0 mmol). The mixture was stirred at 0° C. for 1 h. The solution was diluted with EtOAc, washed with saturated aq. NaHCO$_3$ solution, concentrated under reduced pressure, and purified by chromatography on silica gel (0-25% EtOAc/Hexane) to give 4.8 g (69% yield) of the sub-title compound as a colorless oil. LCMS calc. for $C_{13}H_{31}N_4O_4SSi$ (M+H-Boc)$^+$: m/z=367.2; found: 367.2.

Step 9. tert-butyl ((3R,4R,5S)-4-{[tert-butyl(dimethyl)silyl]oxy}-5-methylpiperidin-3-yl)carbamate

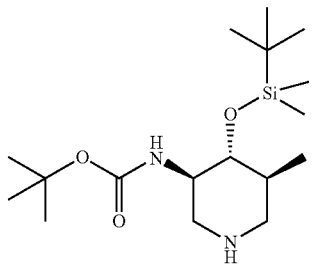 [SMILES: C[C@H]1CNC[C@@H](NC(=O)OC(C)(C)C)[C@@H]1O[Si](C)(C)C(C)(C)C]

A solution of (2R,3R,4S)-5-azido-2-[(tert-butoxycarbonyl)amino]-3-{[tert-butyl(dimethyl)silyl]oxy}-4-methyl-pentyl methanesulfonate (4.25 g, 9.11 mmol) in MeOH (100 mL) (0.09M) was deoxygenated with a stream of N$_2$ for 20 min. DIPEA (4.0 mL, 23 mmol) was added, followed by mixture of 10% Pd on carbon (0.97 g, 0.91 mmol). The reaction mixture was stirred under a balloon containing H$_2$ for 2 h. The solution was filtered through a pad of diatoma-ceous earth and rinsed with MeOH. The filtrate was concentrated under reduced pressure to give 2.10 g (66% yield) of the sub-title compound as a white solid. LCMS calc. for $C_{17}H_{37}N_2O_3Si$ (M+H)$^+$: m/z=345.3; found: 345.1.

Step 10. tert-butyl [(3R,4R,5S)-4-{[tert-butyl(dimethyl)silyl]oxy}-5-methyl-1-(3-nitropyridin-4-yl)piperidin-3-yl]carbamate

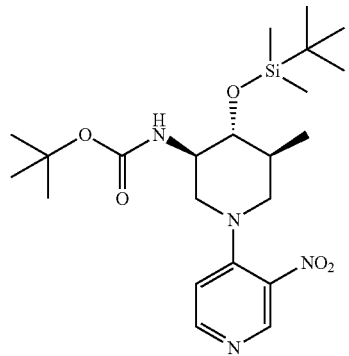 [SMILES: C[C@H]1CN(c2ccncc2[N+](=O)[O-])C[C@@H](NC(=O)OC(C)(C)C)[C@@H]1O[Si](C)(C)C(C)(C)C]

A mixture of 4-chloro-3-nitropyridine (from Aldrich, 150.0 mg, 0.9461 mmol) and tert-butyl ((3R,4R,5S)-4-{[tert-butyl(dimethyl)silyl]oxy}-5-methylpiperidin-3-yl)carbamate (300.0 mg, 0.8707 mmol) and TEA (0.3763 mL, 2.700 mmol) in IPA (10.0 mL) was stirred at 60° C. for 2 h. The reaction mixture was concentrated under reduced pressure and the residue was purified by column chromatography on silica gel using CombiFlash® apparatus (eluting with 0 to 30% EtOAc in hexane) to give 100 mg (24% yield) of the sub-title compound. LCMS calc. for $C_{22}H_{39}N_4O_5Si$ (M+H)$^+$: m/z=467.3; found: 467.1.

Step 11. tert-butyl ((3R,4R,5S)-1-(3-aminopyridin-4-yl)-4-{[tert-butyl(dimethyl)silyl]oxy}-5-methylpiperidin-3-yl)carbamate

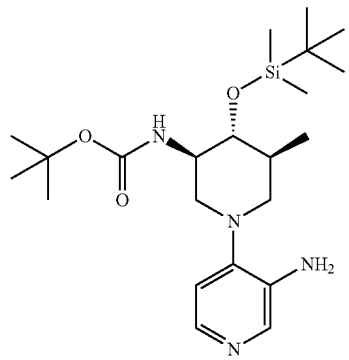

A mixture of tert-butyl [(3R,4R,5S)-4-{[tert-butyl(dimethyl)silyl]oxy}-5-methyl-1-(3-nitropyridin-4-yl)piperidin-3-yl]carbamate (100.00 mg, 0.27858 mmol), AcOH (10.00 mL) and iron powder (558.4 mg, 9.999 mmol) was stirred at ambient temperature for 2 h. The mixture was diluted with 30 mL of EtOAc and filtered through a pad of diatomaceous earth. The combined organic filtrate was concentrated under reduced pressure. The residue was diluted with EtOAc and washed with aq. Na$_2$CO$_3$ solution and 0.2M NaOH. The organic phase was concentrated under reduced pressure to give 50 mg (47% yield) of the title compound. LCMS calc. for C$_{22}$H$_{41}$N$_4$O$_3$Si (M+H)$^+$: m/z=437.3; found: 437.1.

Step 12. tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate tert-Butyl ((3R,4R,5S)-1-(3-aminopyridin-4-yl)-4-{[tert-butyl(dimethyl)silyl]oxy}-5-methylpiperidin-3-yl)carbamate (350 mg, 0.80 mmol) and 6-bromo-5-fluoropyridine-2-carbaldehyde (Prepared in Step 2, 188 mg, 0.922 mmol) were dissolved in toluene (6.0 mL). Then catalytic amount of acetic acid was added and the reaction mixture was heated at 100° C. for 2 h. After imine formation was complete as determined by LCMS, the reaction was cooled to room temperature and toluene was evaporated under reduced pressure. The resulting intermediate imine was dissolved in methanol (5.0 mL) and the resulting reaction mixture was cooled to 0° C. Then sodium tetrahydroborate (61 mg, 1.6 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (400 mg, 80%). LCMS calc. for C$_{28}$H$_{44}$BrFN$_5$O$_3$Si (M+H)$^+$ m/z=624.2; found: 624.2.

Intermediate 2 tert-Butyl [(3S,5R)-1-(3-{[(6-bromo-5-fluoropyridin-2-yl)methyl]amino}pyridin-4-yl)-5-methylpiperidin-3-yl]carbamate

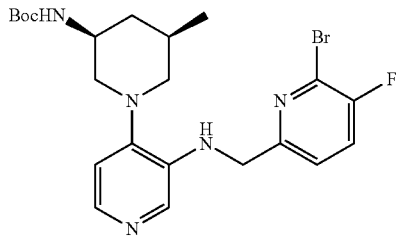 [SMILES: C[C@@H]1C[C@H](NC(=O)OC(C)(C)C)CN(c2ccncc2NCc2ccc(F)c(Br)n2)C1]

Step 1. 1-tert-butyl 2-methyl (2S,4R)-4-methyl-5-oxopyrrolidine-1,2-dicarboxylate

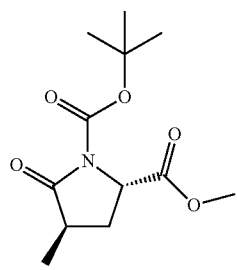 [SMILES: COC(=O)[C@@H]1C[C@@H](C)C(=O)N1C(=O)OC(C)(C)C]

A solution of 1-tert-butyl 2-methyl (2S)-5-oxopyrrolidine-1,2-dicarboxylate (16.1 g, 66.2 mmol) in THF (100 mL) was cooled to −78° C. LiHMDS in THF (1.0M, 68.2 mL, 68.2 mmol) was added dropwise over 5 min. The resulting mixture was stirred at −78° C. for 35 min., then MeI (10.0 mL, 160 mmol) was added. The reaction mixture was allowed to warm to room temperature slowly overnight. The reaction was quenched with AcOH (7.5 mL, 130 mmol) and water (5 mL) and then concentrated under reduced pressure. The concentrated residue was further diluted with water and extracted with EtOAc (3 times). The combined extracts were washed with water and brine, dried over Na$_2$SO$_4$, filtered, and concentrated under reduced pressure. The residue was purified by silica gel column and eluted with 0-50% EtOAc/Hexanes over 45 min. Fractions were checked by TLC (MoSO$_4$ stain) and LCMS. 6.1 g (35% yield) of the sub-title compound was obtained. LCMS calc. for C$_7$H$_{12}$NO$_3$ (M+H-Boc+H)$^+$: m/z=158.1; found: 158.1.

Step 2. tert-butyl [(1S,3R)-4-hydroxy-1-(hydroxymethyl)-3-methylbutyl]carbamate

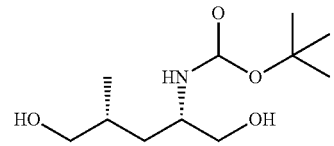 [SMILES: C[C@@H](CO)C[C@@H](CO)NC(O)OC(C)(C)C]

A solution of 1-tert-butyl 2-methyl (2S,4R)-4-methyl-5-oxopyrrolidine-1,2-dicarboxylate (11.0 g, 42.8 mmol) in THF (100 mL) was cooled to 0° C. then LiBH$_4$ (2.8 g, 130 mmol) and then EtOH (22 mL) were added. The mixture was slowly warmed to room temperature and stirred for 4 h. The reaction was quenched with water then extracted with EtOAc (3 times). The combined extracts were dried over Na$_2$SO$_4$, filtered, and concentrated under reduced pressure to give 4.5 g (45% yield) of the crude sub-title compound. The crude product was used without further purification.

Step 3. tert-butyl [(3S,5R)-1-benzyl-5-methylpiperidin-3-yl]carbamate

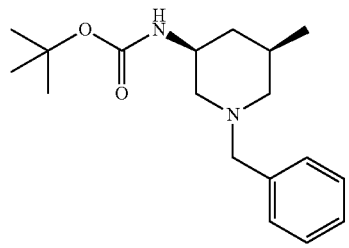 [SMILES: C[C@@H]1C[C@H](NC(=O)OC(C)(C)C)CN(Cc2ccccc2)C1]

A solution of tert-butyl [(1S,3R)-4-hydroxy-1-(hydroxymethyl)-3-methylbutyl]carbamate (9.50 g, 40.7 mmol) in DCM (200 mL) was cooled to 0° C. TEA (23 mL, 160 mmol) was added followed by dropwise addition of methanesulfonyl chloride (9.4 mL, 120 mmol). The clear solution became cloudy and yellow and the mixture was stirred at 0° C. for 1 h. The mixture was diluted with DCM and washed with saturated aq. NaHCO$_3$ and water. The organic layer was dried over Na$_2$SO$_4$, filtered, and concentrated under reduced pressure to give an intermediate mesylate as a yellow oil that was used immediately for the next step.

The intermediate mesylate and benzylamine (90 mL, 800 mmol) were combined in microwave vial, sealed and heated at 70° C. overnight. After 18 h, the mixture was quenched with 10% aq. NaOH. The mixture was then extracted with hexanes (3 times). The combined extracts were washed with brine, dried over MgSO$_4$, filtered, and concentrated under reduced pressure. The residue was purified on a silica gel column and eluted with 0-40% EtOAc/hexane over 34 min. to give 6.0 g (49% yield) of the sub-title compound as a white solid. LCMS calc. for $C_{18}H_{29}N_2O_2$ (M+H)$^+$: m/z=305.2; found: 305.1.

Step 4. tert-butyl [(3S,5R)-5-methylpiperidin-3-yl]carbamate

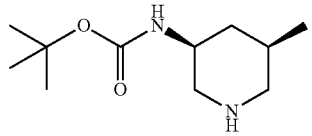

A mixture of tert-butyl [(3S,5R)-1-benzyl-5-methylpiperidin-3-yl]carbamate (4.5 g, 15 mmol), AcOH (2.0 mL, 35 mmol) and 10% Pd on carbon (1.6 g, 1.5 mmol) in EtOH (100 mL) was stirred in a Par-shaker under H$_2$ (50 psi) overnight. The mixture was filtered through a pad of diatomaceous earth and concentrated under reduced pressure. The residue was diluted with DCM (500 mL) and washed with saturated aq. NaHCO$_3$ solution. The aqueous layer was extracted twice with DCM. The combined DCM extract was dried over Na$_2$SO$_4$, and concentrated under reduced pressure to give 2.2 g (67% yield) of the sub-title compound as a white solid. LCMS calc. for $C_{11}H_{23}N_2O_2$ (M+H)$^+$: m/z=: 215.2; found: 215.1.

Step 5. tert-butyl [(3S,5R)-5-methyl-1-(3-nitropyridin-4-yl)piperidin-3-yl]carbamate

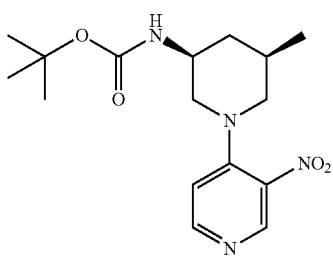 [SMILES: C[C@@H]1C[C@H](NC(=O)OC(C)(C)C)CN(c2ccncc2[N+](=O)[O-])C1]

A mixture of 4-chloro-3-nitropyridine (740 mg, 4.7 mmol), tert-butyl [(3S,5R)-5-methylpiperidin-3-yl]carbamate (1000.0 mg, 4.67 mmol) and DIPEA (2.4 mL, 14 mmol) was irradiated in a microwave oven for 1 h at 130° C. The reaction mixture was concentrated under reduced pressure and the residue was purified by column chromatography on silica gel using a CombiFlash® apparatus eluting with EtOAc/hexane (10-60%). The purification gave 1.21 g (80% yield) of the sub-title compound as a colorless oil. LCMS calc. for $C_{16}H_{25}N_4O_4$ (M+H)$^+$: m/z=337.2; found: 337.1.

Step 6. tert-butyl [(3S,5R)-1-(3-aminopyridin-4-yl)-5-methylpiperidin-3-yl]carbamate

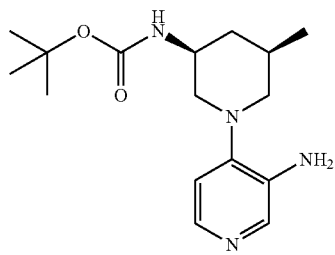 [SMILES: C[C@@H]1C[C@H](NC(=O)OC(C)(C)C)CN(c2ccncc2N)C1]

A mixture of tert-butyl [(3S,5R)-5-methyl-1-(3-nitropyridin-4-yl)piperidin-3-yl]carbamate (100 mg, 0.3 mmol), iron powder (0.072 g, 1.3 mmol), AcOH (2.0 mL, 35 mmol) and water (0.2 mL, 10 mmol) was stirred at room temperature for 60 min. When the reaction was complete, the reaction mixture was concentrated under reduced pressure, diluted with EtOAc, filtered through a pad of diatomaceous earth, washed with aqueous NaHCO$_3$ solution, washed with water and brine, dried over Na$_2$SO$_4$, and concentrated under reduced pressure to give 60 mg (60% yield) of the title compound as a brown solid. LCMS calc. for $C_{16}H_{27}N_4O_2$ (M+H)$^+$: m/z=307.1; found: 307.1.

Step 7. tert-Butyl [(3S,5R)-1-(3-{[(6-bromo-5-fluoropyridin-2-yl)methyl]amino}pyridin-4-yl)-5-methylpiperidin-3-yl]carbamate tert-Butyl [(3S,5R)-1-(3-aminopyridin-4-yl)-5-methylpiperidin-3-yl]carbamate (388 mg, 1.27 mmol) and 6-bromo-5-fluoropyridine-2-carbaldehyde (Prepared in Intermediate 1, Step 2; 340 mg, 1.6 mmol) were dissolved in toluene (11.0 mL). Then catalytic amount of acetic acid was added and the reaction mixture was heated at 100° C. for 2 h. After imine formation was complete as determined by LCMS, the reaction mixture was cooled to room temperature and toluene was evaporated under reduced pressure. The resulting intermediate imine was dissolved in methanol (7.0 mL) and resulting reaction mixture was cooled to 0° C. Then sodium tetrahydroborate (120 mg, 3.2 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (526 mg, 84%). LCMS calc. for $C_{22}H_{30}BrFN_5O_2$ (M+H)$^+$ m/z=494.2; found: 494.1.

Intermediate 3 tert-Butyl ((3S,5R)-1-(3-(((6-bromo-5-fluoropyridin-2-yl)methyl)amino)pyridin-4-yl)-5-(trifluoromethyl)piperidin-3-yl)carbamate

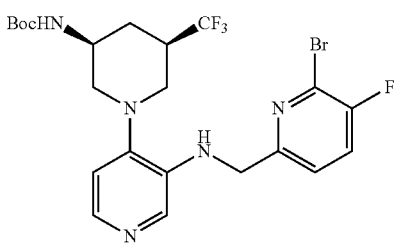 [SMILES: CC(C)(C)OC(=O)N[C@H]1C[C@@H](C(F)(F)F)CN(c2ccncc2NCc2ccc(F)c(Br)n2)C1]

Step 1. Benzyl (3S,5R)-3-[(tert-butoxycarbonyl)amino]-5-(trifluoromethyl)piperidine-1-carboxylate

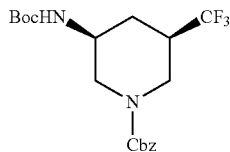 [SMILES: CC(C)(C)OC(=O)N[C@H]1C[C@@H](C(F)(F)F)CN(C(=O)OCc2ccccc2)C1]

To a round bottom flask containing cis-3-(Boc-amino)-5-(trifluoromethyl)piperidine (Molbridge, 10.00 g, 37.27 mmol) and NaHCO$_3$ (18.8 g, 224 mmol), THF (200 mL) was added, followed by water (200 mL). Benzyl chloroformate (20.1, g, 112 mmol) was then added dropwise over a period of 30 min. via a syringe pump. The mixture was stirred at room temperature for 2 h. The mixture was then diluted with EtOAc and water. The layers were separated and the organic layer was washed with brine, dried over Na$_2$SO$_4$, filtered, and concentrated under reduced pressure. The resulting residue was purified by flash chromatography on silica gel (340 g, 15% EtOAc in hexanes) to give a white foamy solid which was subjected to chiral HPLC separation (Phenomenex Lux Cellulose C-1, 5 μm, 21.2×250 mm column, eluting with 15% EtOH in hexanes, at flow rate of 18 mL/min., with a loading of 100 mg in 1000 μL at 220 nm wavelength) to give the sub-title compound (retention time: 9.1 min.) as a white foamy solid (6.51 g, 43%). LCMS calc. for C$_{19}$H$_{25}$F$_3$N$_2$NaO$_4$ (M+Na)$^+$: m/z=425.2; found: 425.2. The sub-title compound is assigned as the (3S,5R) isomer. The alternative (3R,5S) isomer can be obtained from the same separation.

Step 2. tert-Butyl [(3S,5R)-5-(trifluoromethyl)piperidin-3-yl]carbamate

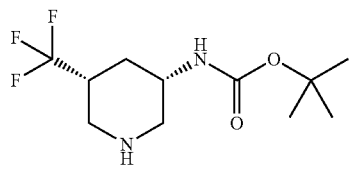 [SMILES: CC(C)(C)OC(=O)N[C@@H]1CNC[C@H](C(F)(F)F)C1]

A mixture of benzyl (3S,5R)-3-[(tert-butoxycarbonyl)amino]-5-(trifluoromethyl)piperidine-1-carboxylate (3.86 g, 9.59 mmol) in MeOH (50 mL) was hydrogenated in the presence of 10% Pd on carbon (0.30 g) under 25 psi of hydrogen for 2 h. The reaction mixture was filtered and the filtrate was concentrated under reduced pressure to give the sub-title compound (2.6 g, 100%). LCMS calc. for C$_{11}$H$_{20}$F$_3$N$_2$O$_2$ (M+H)$^+$: m/z=269.1; found: 269.2.

Step 3: tert-Butyl [(3S,5R)-1-(3-nitropyridin-4-yl)-5-(trifluoromethyl)piperidin-3-yl]carbamate

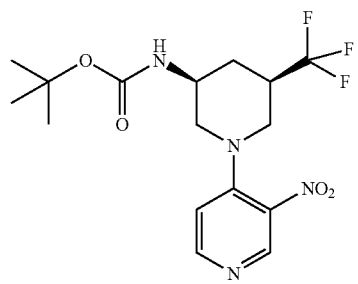 [SMILES: CC(C)(C)OC(=O)N[C@H]1C[C@@H](C(F)(F)F)CN(c2ccncc2[N+](=O)[O-])C1]

A mixture of 4-chloro-3-nitropyridine (580 mg, 3.6 mmol), tert-butyl [(3S,5R)-5-(trifluoromethyl)piperidin-3-yl]carbamate (800 mg, 3 mmol), isopropyl alcohol (5.0 mL) and DIPEA (1.0 mL, 6.0 mmol) was stirred at 80° C. overnight. The reaction mixture was concentrated under reduced pressure and the residue was purified by column chromatography on silica gel using CombiFlash® apparatus eluting with 50-100% EtOAc/hexanes. The purification gave 1.0 g (80% yield) of the sub-title compound as a yellow solid. LCMS calc. for C$_{16}$H$_{22}$F$_3$N$_4$O$_4$ (M+H)$^+$: m/z=: 391.2; found: 391.1.

Step 4: tert-Butyl [(3S,5R)-1-(3-aminopyridin-4-yl)-5-(trifluoromethyl)piperidin-3-yl]carbamate

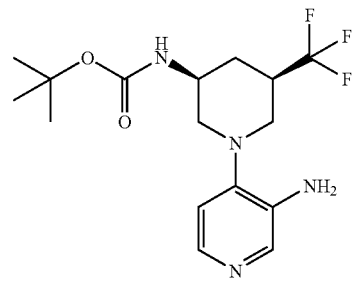 [SMILES: CC(C)(C)OC(=O)N[C@H]1C[C@@H](C(F)(F)F)CN(c2ccncc2N)C1]

A mixture of tert-butyl [(3S,5R)-1-(3-nitropyridin-4-yl)-5-(trifluoromethyl)piperidin-3-yl]carbamate (1 g, 2 mmol), iron powder (0.57 g, 10 mmol), AcOH (16 mL) and water (2 mL) was stirred at room temperature for 1 h. The mixture was allowed to cool to room temperature, concentrated under reduced pressure and the resulting residue was diluted with EtOAc. The resulting mixture was filtered through a diatomaceous earth pad. The filtrate was concentrated under reduced pressure, and the residue was dissolved in 1M NaOH aqueous solution and extracted with EtOAc (100 mL×3). The combined organic layers were washed with water and brine, dried over Na$_2$SO$_4$, filtered and concentrated under reduced pressure to give 0.9 g (100% yield) of the sub-title compound as a brown solid. LCMS calc. for $C_{16}H_{24}F_3N_4O_2$ (M+H)$^+$: m/z=: 361.2; found: 361.1.

Step 5. tert-butyl ((3S,5R)-1-(3-(((6-bromo-5-fluoropyridin-2-yl)methyl)amino)pyridin-4-yl)-5-(trifluoromethyl)piperidin-3-yl)carbamate tert-Butyl (3S,5R)-1-(3-aminopyridin-4-yl)-5-(trifluoromethyl)piperidin-3-ylcarbamate (457 mg, 1.27 mmol) and 6-bromo-5-fluoropyridine-2-carbaldehyde (Prepared in Intermediate 1, Step 2; 340 mg, 1.6 mmol) were dissolved in toluene (11.0 mL). Then catalytic amount of acetic acid was added and the reaction mixture was heated at 100° C. for 2 h. After imine formation was complete as determined by LCMS, the reaction mixture was cooled to room temperature and toluene was evaporated under reduced pressure. The resulting intermediate imine was dissolved in methanol (7.0 mL) and resulting reaction mixture was cooled to 0° C. Then sodium tetrahydroborate (120 mg, 3.2 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (536 mg, 77%). LCMS calc. for $C_{22}H_{27}BrF_4N_5O_2$ (M+H)$^+$ m/z=548.1; found: 548.1.

Intermediate 4 tert-Butyl ((3R,4R,5S)-1-(3-{[(3-bromofuro[3,2-b]pyridin-5-yl)methyl]amino}pyridin-4-yl)-4-{[tert-butyl(dimethyl)silyl]oxy}-5-methylpiperidin-3-yl)carbamate

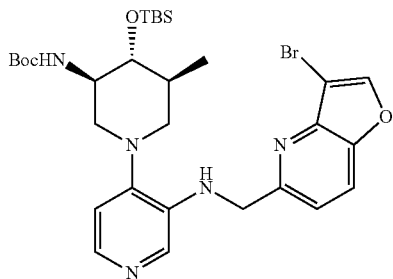 [SMILES: C[C@H]1CN(c2ccncc2NCc2ccc3occ(Br)c3n2)C[C@@H](NC(=O)OC(C)(C)C)[C@@H]1O[Si](C)(C)C(C)(C)C]

Step 1. Methyl 5-hydroxypyridine-2-carboxylate

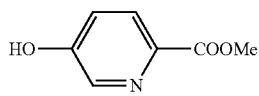 [SMILES: COC(=O)c1ccc(O)cn1]

Methanol (70 mL) was added to 5-hydroxypyridine-2-carboxylic acid (Combi-Blocks, 5.01 g, 36.0 mmol). Then sulfuric acid (5.8 mL, 110 mmol) was carefully added to the reaction mixture. Reaction mixture was stirred at 75° C. overnight. After this time the solvent was evaporated and the product was dissolved in EtOAc. To the resultant solution was added saturated aq. NaHCO$_3$ to pH 3. Formed precipitate was collected by filtration and dried under vacuum. The rest of the product was extracted with EtOAc. Collected organic fractions were washed with brine, dried over Na$_2$SO$_4$ and the solvent was evaporated under reduced pressure. Obtained solid product (5.3 g, 96%) was used in the next step without further purification. LCMS calc. for $C_7H_8NO_3$ (M+H)$^+$ m/z=154.1; found: 154.1.

Step 2. Methyl 5-hydroxy-6-iodopyridine-2-carboxylate

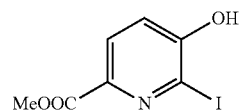 [SMILES: COC(=O)c1ccc(O)c(I)n1]

Iodine (3.331 g, 13.12 mmol) was added to the mixture of sodium carbonate (3.034 g, 28.63 mmol) and methyl 5-hydroxypyridine-2-carboxylate (2.0 g, 13 mmol) in water (60 mL). The reaction mixture was stirred at room temperature overnight. After this time reaction was acidified to pH 5 by the addition of 1M solution of HCl and the desired product was extracted with EtOAc. Collected organic fractions were washed with brine, dried over Na$_2$SO$_4$ and the solvent evaporated under reduced pressure to give the product as white solid (3.4 g, 93%). Obtained product was used in the next step without further purification. LCMS calc. for $C_7H_{71}NO_3$ (M+H)$^+$ m/z=280.0; found: 279.9.

Step 3. Methyl 2-(trimethylsilyl)furo[3,2-b]pyridine-5-carboxylate

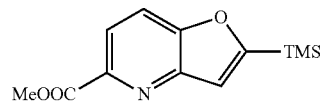 [SMILES: COC(=O)c1ccc2oc([Si](C)(C)C)cc2n1]

Methyl 5-hydroxy-6-iodopyridine-2-carboxylate, copper (I)iodide (360 mg, 1.9 mmol) and dichloro[bis(triphenylphosphonio)]palladate (1.1 g, 1.6 mmol) were placed in a vial. The vial was then evacuated and backfilled with nitrogen three times. After this 1,4-dioxane (120 mL) and triethylamine (5.69 mL, 40.8 mmol) were added to the reaction mixture. Reaction mixture was stirred at room temperature for 5 min. Then (trimethylsilyl)acetylene (4.62 mL, 32.7 mmol) was added and the reaction mixture was stirred at 60° C. for 3 h. After this time reaction mixture was quenched by the addition of water and the product was extracted with EtOAc. Collected organic fractions were washed with brine, dried over Na$_2$SO$_4$ and the solvents were evaporated under reduced pressure. The crude product was purified by Biotage Isolera to give the desired compound as brown oil (4.2 g, 62%). LCMS calc. for $C_{12}H_{16}NO_3Si$ (M+H)$^+$ m/z=250.1; found: 250.0.

Step 4. Methyl furo[3,2-b]pyridine-5-carboxylate

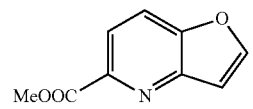 [SMILES: COC(=O)c1ccc2occc2n1]

Potassium carbonate (7.0 g, 50 mmol) was added to a solution of methyl 2-(trimethylsilyl)furo[3,2-b]pyridine-5-carboxylate (4.2 g, 17 mmol) in methanol (50 mL). Reaction mixture was stirred at room temperature for 2 h. Then water was added and the product was extracted with EtOAc. Collected organic fractions were washed with brine, dried over $Na_2SO_4$ and the solvents were evaporated under reduced pressure. Obtained product was used in the next step without further purification (2.1 g, 72%). LCMS calc. for $C_9H_8NO_3$ $(M+H)^+$ m/z=178.1; found: 178.1.

Step 5. Methyl 2,3-dibromo-2,3-dihydrofuro[3,2-b]pyridine-5-carboxylate

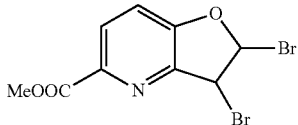 [SMILES: COC(=O)c1ccc2c(n1)C(Br)C(Br)O2]

Bromine (3.1 mL, 60. mmol) was slowly added to a solution of methyl furo[3,2-b]pyridine-5-carboxylate (2.138 g, 12.07 mmol) in DCM (50 mL) and the reaction mixture was stirred at room temperature for 3 h. Then excess of bromine was carefully quenched by the addition of the saturated solution of $Na_2S_2O_3$. The product was extracted with DCM. Collected organic fractions were washed with brine, dried over $Na_2SO_4$ and the solvents were evaporated under reduced pressure. Obtained crude product was purified by Biotage Isolera to give the desired compound (1.65 g, 41%). LCMS calc. for $C_9H_8Br_2NO_3$ $(M+H)^+$ m/z=337.9; found: 337.9.

Step 6. 3-Bromofuro[3,2-b]pyridine-5-carboxylic acid

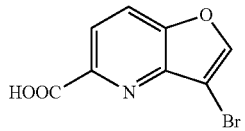 [SMILES: O=C(O)c1ccc2occ(Br)c2n1]

1.0M Solution of potassium hydroxide in ethanol (15 mL, 15 mmol) was added to a solution of methyl 2,3-dibromo-2,3-dihydrofuro[3,2-b]pyridine-5-carboxylate (1.65 g, 4.90 mmol) in tetrahydrofuran (15 mL). The reaction mixture was stirred at room temperature for 20 min. After this time, it was diluted with EtOAc and water was added. The reaction was neutralized by the addition of the 1M solution of HCl in water and the desired product was extracted with EtOAc. Collected organic fractions were washed with brine, dried over $Na_2SO_4$ and solvents were evaporated under reduced pressure to give the desired compound (0.94 g, 79%), which was used in the next step without further purification. LCMS calc. for $C_8H_5BrNO_3$ $(M+H)^+$ m/z=242.0; found: 241.

Step 7. (3-Bromofuro[3,2-b]pyridin-5-yl)methanol

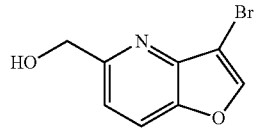 [SMILES: OCc1ccc2occ(Br)c2n1]

To a solution of 3-bromofuro[3,2-b]pyridine-5-carboxylic acid (334 mg, 1.38 mmol) and triethylamine (202 µL, 1.45 mmol) in tetrahydrofuran (10 mL) was slowly added isobutyl chloroformate (0.188 mL, 1.45 mmol). Reaction was stirred at room temperature for 1 h. The formed precipitate was filtered and to obtained clear solution was slowly added solution of sodium tetrahydroborate (100 mg, 3.2 mmol) in water (1 mL). Reaction mixture was stirred at room temperature for 30 min. Then water was added and the product was extracted with EtOAc. Combined organic fractions were washed with brine and dried with $Na_2SO_4$. After evaporation of the solvents under reduced pressure, obtained product was used in the next step without further purification (310 mg, 99%). LCMS calc. for $C_8H_7BrNO_2$ $(M+H)^+$ m/z=228.0; found 228.0.

Step 8. 3-Bromofuro[3,2-b]pyridine-5-carbaldehyde

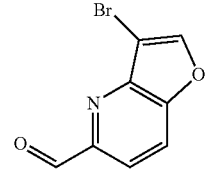 [SMILES: O=Cc1ccc2occ(Br)c2n1]

To a stirred solution of (3-bromofuro[3,2-b]pyridin-5-yl)methanol (360 mg, 1.6 mmol) in DCM (10 mL) at 0° C. were added pyridine (0.15 mL, 1.9 mmol) and Dess-Martin periodinane (0.703 g, 1.66 mmol). The reaction mixture was stirred at room temperature for 3 h. Then saturated solutions of $NaHCO_3$ in water (10 mL) and $Na_2S_2O_3$ in water (5 mL) were added and the reaction mixture was stirred for 30 min. Then product was extracted with DCM. Combined organic fractions were washed with brine, dried over $Na_2SO_4$ and solvents were evaporated under reduced pressure. The crude product was purified by Biotage Isolera to give the desired compound (280 mg, 78%). LCMS calc. for $C_8H_5BrNO_2$ $(M+H)^+$ m/z=226.0; found: 226.0.

Step 9. tert-Butyl ((3R,4R,5S)-1-(3-{[(3-bromofuro[3,2-b]pyridin-5-yl)methyl]amino}pyridin-4-yl)-4-{[tert-butyl(dimethyl)silyl]oxy}-5-methylpiperidin-3-yl)carbamate tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 120 mg, 0.27 mmol) and 3-bromofuro[3,2-b]pyridine-5-carbaldehyde (68 mg, 0.30 mmol) were dissolved in toluene (6.0 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (5.0 mL) and resulting reaction mixture was cooled to 0° C. Then sodium tetrahydroborate (26 mg, 0.69 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (420 mg, 68%). LCMS calc. for C$_{30}$H$_{45}$BrN$_5$O$_4$Si (M+H)$^+$ m/z=646.2; found: 646.2.

Intermediate 5 tert-Butyl [(3S,5R)-1-(3-{[(3-bromofuro[3,2-b]pyridin-5-yl)methyl]amino}pyridin-4-yl)-5-methylpiperidin-3-yl]carbamate

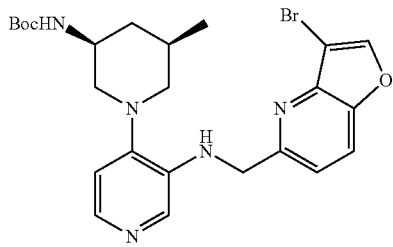 [SMILES: C[C@@H]1C[C@H](NC(=O)OC(C)(C)C)CN(c2ccncc2NCc2ccc3occ(Br)c3n2)C1]

tert-Butyl [(3S,5R)-1-(3-aminopyridin-4-yl)-5-methylpiperidin-3-yl]carbamate (Prepared in Intermediate 2, Step 6; 84 mg, 0.27 mmol) and 3-bromofuro[3,2-b]pyridine-5-carbaldehyde (Prepared in Intermediate 4, Step 8; 68 mg, 0.30 mmol) were dissolved in toluene (5 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (5 mL) and resulting reaction mixture was cooled to 0° C. Then sodium tetrahydroborate (26 mg, 0.69 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (82 mg, 58%). LCMS calc. for C$_{24}$H$_{31}$BrN$_5$O$_3$ (M+H)$^+$ m/z=516.2; found: 516.1.

Intermediate 6 tert-Butyl [(1S,3R,5S)-3-(3-aminopyridin-4-yl)-5-methylcyclohexyl]carbamate and tert-butyl [(1R,3S,5R)-3-(3-aminopyridin-4-yl)-5-methylcyclohexyl]carbamate

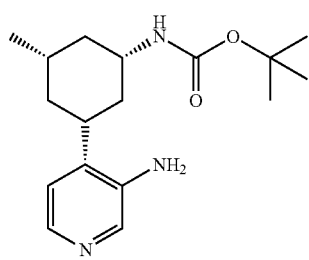

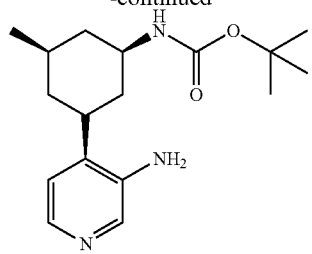

Step 1. 5-Methyl-3-oxocyclohex-1-en-1-yl trifluoromethanesulfonate

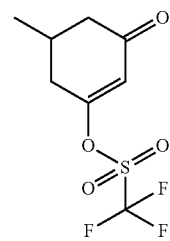

To a solution of 5-methylcyclohexane-1,3-dione (50.1 g, 397 mmol) in DCM (700 mL) was added Na$_2$CO$_3$ (46.3 g, 437 mmol) and the resulting mixture was cooled to 0° C. A solution of trifluoromethanesulfonic anhydride (66.8 mL, 397 mmol) in DCM (600 mL) was added dropwise over 1 h at 0° C. The reaction mixture was stirred at room temperature for 2 h. The solution was filtered and the filtrate was quenched by careful addition of saturated aq. NaHCO$_3$ to pH=7. The organic layer was washed with water, brine, dried over Na$_2$SO$_4$ and concentrated under reduced pressure to give the sub-title product as light yellow oil, which was used for next step without further purification. LCMS calc. for C$_8$H$_{10}$F$_3$O$_4$S (M+H)$^+$: m/z=259.0; Found: 259.1.

Step 2. 5-Methyl-3-(4,4,5,5-tetramethyl-1,3,2-dioxaborolan-2-yl)cyclohex-2-en-1-one

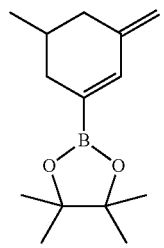

To a mixture of 4,4,5,5,4',4',5',5'-octamethyl-[2,2']bi[[1,3,2]dioxaborolanyl] (77.6 g, 306 mmol), potassium acetate (77.1 g, 785 mmol) and [1,1'-bis(diphenylphosphino)ferrocene]dichloropalladium(II), complex with DCM (1:1) (8.6 g, 10.0 mmol) under N$_2$ was added a solution of 5-methyl-3-oxocyclohex-1-en-1-yl trifluoromethanesulfonate (67.6 g, 262 mmol) in 1,4-dioxane (420 mL). The reaction mixture was degassed with N$_2$ and the mixture was stirred at 80° C. overnight. After cooling to room temperature, the mixture was filtered through a pad of diatomaceous earth (eluted with EtOAc). The filtrate was concentrated under reduced pressure, and the crude product was used in next step without further purification.

Step 3. 5-Methyl-3-(3-nitropyridin-4-yl)cyclohex-2-en-1-one

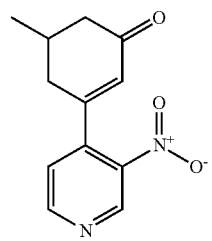 [SMILES: CC1CC(=O)C=C(c2ccncc2[N+](=O)[O-])C1]

A solution of 5-methyl-3-(4,4,5,5-tetramethyl-1,3,2-dioxaborolan-2-yl)cyclohex-2-en-1-one (20.0 g, 84.7 mmol) in 1,4-dioxane (120 mL), 4-chloro-3-nitropyridine (10.0 g, 63.1 mmol), 2.0M $Na_2Co_3$ in water (63.1 mL, 126 mmol) and [1,1'-bis(diphenylphosphino)ferrocene]dichloropalladium(II), complex with DCM (1:1) (2.58 g, 3.15 mmol) was refluxed under a $N_2$ atmosphere for 1 h. The reaction mixture was diluted with EtOAc and water, then filtered through a pad of diatomaceous earth, and washed with EtOAc. The two layers were separated, and the aqueous layer was extracted with EtOAc (2×). The combined organic phases were washed with water and brine, and dried over $Na_2SO_4$. The crude residue was purified by flash chromatography (eluting with a gradient 0-60% EtOAc in hexanes) to give the sub-title product as an orange oil (6.6 g, 45%). LCMS calc. for $C_{12}H_{13}N_2O_3$ $(M+H)^+$: m/z=233.1; Found: 233.1.

Step 4. cis-(+/−)-5-Methyl-3-(3-nitropyridin-4-yl)cyclohex-2-en-1-ol

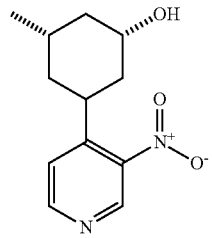 [SMILES: C[C@H]1CC(c2ccncc2[N+](=O)[O-])C[C@@H](O)C1]

To a solution of 5-methyl-3-(3-nitropyridin-4-yl)cyclohex-2-en-1-one (6.6 g, 28 mmol) in EtOH (93 mL) was added $CeCl_3 \cdot 7H_2O$ (12.7 g, 34.1 mmol), The resulting mixture was cooled to 0° C. and $NaBH_4$ (1.29 g, 34.1 mmol) was added portion-wise. After stirring at 0° C. for 1 h, the reaction was quenched with water and concentrated under reduced pressure to remove the EtOH. The residue was then extracted with EtOAc. The organic layer was washed with brine, dried over $Na_2SO_4$, filtered, and concentrated. The crude product was purified by flash chromatography (gradient elution with 20-90% EtOAc in hexanes) to give the sub-title product as a racemic mixture (6.4 g, 96%). LCMS calc. for $C_{12}H_{15}N_2O_3$ $(M+H)^+$: m/z=235.1; Found: 235.1.

Step 5. 4-(3-(tert-Butyldimethylsilyloxy)-5-methyl-cyclohex-1-enyl)3-nitropyridine

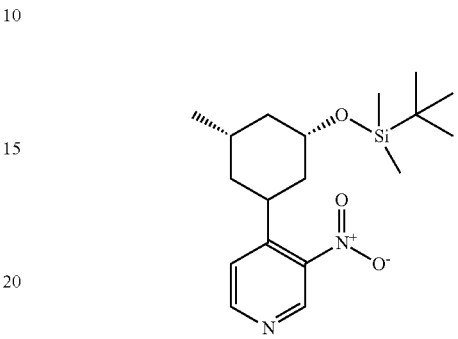

A solution of cis(+/−)-5-methyl-3-(3-nitropyridin-4-yl)cyclohex-2-en-1-ol (6.4 g, 27 mmol) in DMF (51 mL) was added 1H-imidazole (3.7 g, 55 mmol) and tert-butyldimethylsilyl chloride (5.8 g, 38 mmol). The resulting mixture was stirred at room temperature overnight. The reaction solution was diluted with water and EtOAc. The organic layer was washed with water (2×), brine, dried over $Na_2SO_4$ and concentrated under reduced pressure to give product as an orange oil. LCMS calc. for $C_{18}H_{29}N_2O_3Si$ $(M+H)^+$: m/z=349.2; Found: 349.2.

Step 6. 4-(3-(tert-Butyldimethylsilyloxy)-5-methyl-cyclohex-1-enyl)pyridin-3-amine

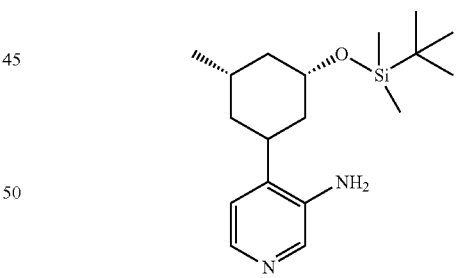

A mixture of 4-(3-(tert-butyldimethylsilyloxy)-5-methyl-cyclohex-1-enyl)3-nitropyridine (9.3 g, 27 mmol), iron (8.9 g, 160 mmol) and AcOH (67 mL) was stirred at room temperature for 2 h. The reaction mixture was filtered through a pad of diatomaceous earth, washed with MeOH. The filtrate was concentrated under reduced pressure to remove the volatiles, the residue was dissolved in EtOAc, washed with saturated aq. $Na_2CO_3$, washed with brine, dried over $Na_2SO_4$, filtered, and concentrated under reduced pressure to give the sub-title product as a yellow oil (7.7 g, 90%). LCMS calc. for $C_{18}H_{31}N_2OSi$ $(M+H)^+$: m/z=319.2; Found: 319.2.

Step 7. 4-(3-(tert-Butyldimethylsilyloxy)-5-methylcyclohexyl)pyridin-3-amine

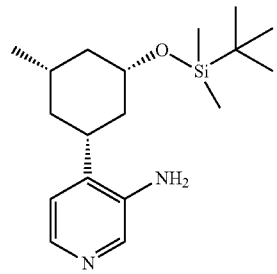 [SMILES: C[C@@H]1C[C@H](O[Si](C)(C)C(C)(C)C)C[C@H](c2ccncc2N)C1]

To a suspension of 4-(3-(tert-butyldimethylsilyloxy)-5-methylcyclohex-1-enyl)pyridin-3-amine (7.7 g, 24 mmol) in MeOH (203 mL) under $N_2$ was added 10% Pd on carbon (2.64 g). The mixture was purged with $H_2$ and stirred under a $H_2$ balloon for 3 h. The mixture was filtered through a pad of diatomaceous earth and eluted with MeOH. The filtrate was concentrated under reduced pressure to give the crude product as an off-white foamy solid (7.3 g, 93%). The crude product was used directly in the next step without further purification. LCMS calc. for $C_{18}H_{33}N_2OSi$ $(M+H)^+$: m/z=321.2; Found: 321.3.

Step 8. cis (+/−) Benzyl 4-3-(tert-butyldimethylsilyloxy)-5-methylcyclohexylpyridin-3-ylcarbamate

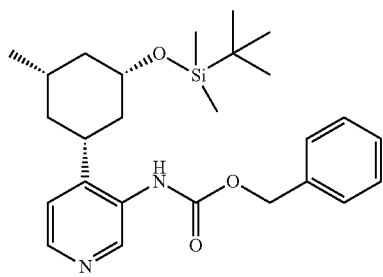 [SMILES: C[C@@H]1C[C@H](O[Si](C)(C)C(C)(C)C)C[C@H](c2ccncc2NC(=O)OCc2ccccc2)C1]

To a solution of 4-(3-(tert-butyldimethylsilyloxy)-5-methylcyclohexyl)pyridin-3-amine (7.3 g, 23 mmol) in DCM (50 mL) was added N-(benzyloxycarbonyloxy)succinimide (6.5 g, 26 mmol) and DMAP (0.14 g, 1.2 mmol). After stirring for 16 h, another portion of N-(benzyloxycarbonyloxy) succinimide (3.1 g, 12 mmol) was added, followed by DMAP. The reaction mixture was stirred overnight. The reaction solution was partitioned between EtOAc and saturated aq. $Na_2CO_3$ solution. The organic layer was washed with saturated aq. $Na_2CO_3$ solution and brine, dried over $Na_2SO_4$, filtered and concentrated. The residue was purified by flash chromatography (gradient elution with 0-40% EtOAc in hexanes) to give the sub-title product as a brown oil. LCMS calc. for $C_{26}H_{39}N_2O_3Si$ $(M+H)^+$: m/z=455.3; Found: 455.2.

Step 9. cis-(+/−)Benzyl 4-(-3-hydroxy-5-methylcyclohexyl)pyridin-3-ylcarbamate

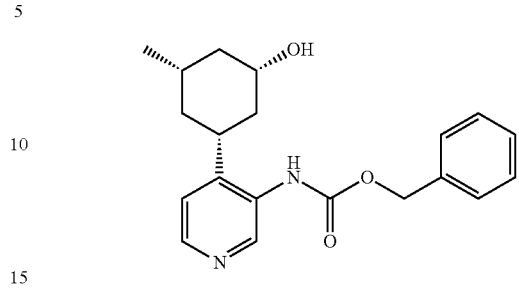

To a solution of cis (+/−) benzyl 4-3-(tert-butyldimethylsilyloxy)-5-methylcyclohexylpyridin-3-ylcarbamate (7.0 g, 15 mmol) in MeOH (100.0 mL) was added 6.0M HCl in water (50.0 mL, 300 mmol). The resulting mixture was stirred at room temperature for 6 h. The pH was then adjusted to pH=7 by addition of 6N NaOH and the volatiles were removed under reduced pressure. The aqueous layer was extracted with EtOAc and the organic was washed with brine, dried over $MgSO_4$, filtered and concentrated under reduced pressure to give the crude product which was used in next step without purification (4.8 g, 92%). LCMS calc. for $C_{20}H_{25}N_2O_3$ $(M+H)^+$: m/z=341.2; Found: 341.1.

Step 10. cis-(+/−)-Benzyl 4-(3-methyl-5-oxocyclohexyl)pyridin-3-ylcarbamate

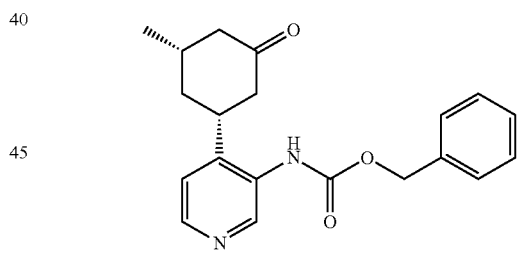

To a solution of cis-(+/−)benzyl 4-(-3-hydroxy-5-methylcyclohexyl)pyridin-3-ylcarbamate (4.8 g, 14 mmol) in DCM (90 mL) was added Dess-Martin periodinane (8.97 g, 21.2 mmol). The reaction mixture was stirred at room temperature for 2 h. The reaction mixture was diluted with $Et_2O$ and saturated aq. $NaHCO_3$ solution and stirred for 30 min. The organic layer was separated and washed with brine, dried over $Na_2SO_4$, filtered and concentrated. The crude product was purified by flash chromatography (gradient elution with 0-50% EtOAc in hexanes) to give the sub-title product (2.5 g, 52%). LCMS calc. for $C_{20}H_{23}N_2O_3$ $(M+H)^+$: m/z=339.2; Found: 339.1.

Step 11. cis-(+/−)-Benzyl 4-(3-(benzylamino)-5-methylcyclohexyl)pyridin-3-ylcarbamate

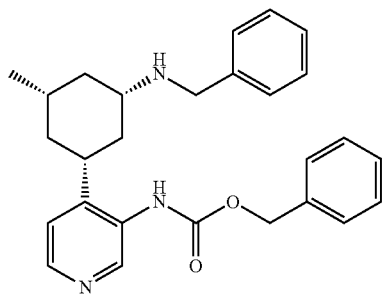 [SMILES: C[C@@H]1C[C@H](NCc2ccccc2)C[C@H](c2ccncc2NC(=O)OCc2ccccc2)C1]

To a solution of cis-(+/−)-benzyl 4-(3-methyl-5-oxocyclohexyl)pyridin-3-ylcarbamate (2.50 g, 7.39 mmol) in MeOH (30 mL) was added benzylamine (2.42 mL, 22.2 mmol). The resulting mixture was stirred at room temperature for 2 h. After cooling to −78° C., 2.0M LiBH$_4$ in THF (4.1 mL, 8.1 mmol) was added. The reaction mixture was warmed to room temperature and stirred overnight. The solution was partitioned between EtOAc and saturated aq. NaHCO$_3$, then the resulting layers were separated. The organic layer was washed with additional saturated aq. NaHCO$_3$ and brine, dried over MgSO$_4$, filtered, and concentrated. The crude product was used in the next step without purification (3.1 g, 98%). LCMS calc. for $C_{27}H_{32}N_3O_2$ (M+H)$^+$: m/z=430.2; Found: 430.2.

Step 12. tert-Butyl [(1S,3R,5S)-3-(3-aminopyridin-4-yl)-5-methylcyclohexyl]carbamate and tert-Butyl [(1R,3S,5R)-3-(3-aminopyridin-4-yl)-5-methylcyclohexyl]carbamate To a solution of cis-(+/−)-benzyl 4-(3-(benzylamino)-5-methylcyclohexyl)pyridin-3-ylcarbamate (3.10 g, 7.22 mmol) in MeOH (100 mL) was added 20% palladium hydroxide on carbon (1.0 g, 1.4 mmol). The resulting heterogeneous solution was put under an atmosphere of H$_2$ and was stirred for 14 h, at which time the reaction mixture was purged with N$_2$, di-tert-butyldicarbonate (1.6 g, 7.2 mmol) was added and the solution was stirred for 7 h. Additional di-tert-butyldicarbonate (1.6 g, 7.2 mmol) was added and the solution was stirred overnight. The solvent was removed under reduced pressure and the residue was purified by flash chromatography (gradient elution with 20-100% EtOAc in hexanes) to give the racemic product. The racemic mixture was separated by chiral column (CHIRALPAK® IA column eluting with 15% EtOH/85% Hexanes, 12 mL/min) to give two peaks.

Peak 1 retention time 14.3 min., LCMS calc. for $C_{17}H_{28}N_3O_2$ (M+H)$^+$: m/z=306.2; Found: 306.2.

Peak 2 retention time 18.6 min., LCMS calc. for $C_{17}H_{28}N_3O_2$ (M+H)$^+$: m/z=306.2; Found: 306.2.

Peak 1 is tentatively identified as tert-butyl [(1R,3S,5R)-3-(3-aminopyridin-4-yl)-5-methylcyclohexyl]carbamate.

Peak 2 is tentatively identified as tert-butyl [(1S,3R,5S)-3-(3-aminopyridin-4-yl)-5-methylcyclohexyl]carbamate.

Example 1

(3R,4R,5S)-3-Amino-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-4-ol

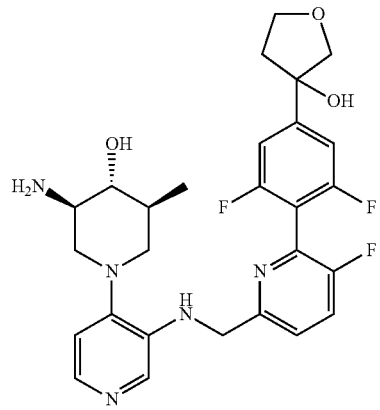 [SMILES: C[C@H]1CN(c2ccncc2NCc2ccc(F)c(-c3c(F)cc(C4(O)CCOC4)cc3F)n2)C[C@@H](N)[C@@H]1O]

Step 1. 3-(3,5-Difluorophenyl)tetrahydrofuran-3-ol

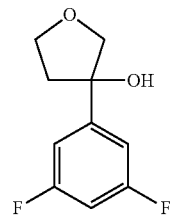 [SMILES: OC1(c2cc(F)cc(F)c2)CCOC1]

Dihydrofuran-3(2H)-one (340 mg, 4.0 mmol) and a magnet bar were placed in a vial. The vial was evacuated and backfilled with nitrogen three times. After addition of tetrahydrofuran (6.0 mL), the reaction mixture was cooled to 0° C. Then 0.5M solution of (3,5-difluorophenyl)magnesium bromide in THF (from Aldrich, 8.8 mL, 4.4 mmol) was slowly added and the reaction mixture was stirred at room temperature for 16 h. After this time it was carefully quenched by the addition of the saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (448 mg, 56%).

Step 2. 3-[3,5-Difluoro-4-(4,4,5,5-tetramethyl-1,3,2-dioxaborolan-2-yl)phenyl]tetrahydrofuran-3-ol

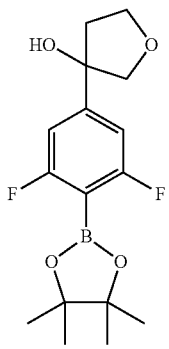

3-(3,5-Difluorophenyl)tetrahydrofuran-3-ol (448 mg, 2.24 mmol) and a magnet bar were placed in a vial. The vial was evacuated and backfilled with nitrogen three times. After addition of tetrahydrofuran (9.0 mL), the reaction mixture was cooled to −78° C. Then 2.5M solution of n-butyllithium in hexanes (2.2 mL, 5.6 mmol) was slowly added and the reaction mixture was stirred at −78° C. for 1 h. After this time 2-isopropoxy-4,4,5,5-tetramethyl-1,3,2-dioxaborolane (from Aldrich, 1.37 mL, 6.71 mmol) was slowly added. After stirring at −78° C. for 5 min more, the reaction mixture was allowed to warm to room temperature and the reaction mixture was stirred at room temperature for 1 h. After this time it was carefully quenched by the addition of the saturated solution of ammonium chloride. The product was extracted with EtOAc. Combined organic fractions were washed with brine, dried over $Na_2SO_4$ and solvents were evaporated under reduced pressure. The resulting product was used in the next step without further purification (610 mg, 84%).

Step 3. tert-Butyl ((3R,4R,5S)-4-{[tert-butyl(dimethyl)silyl]oxy}-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-3-yl)carbamate

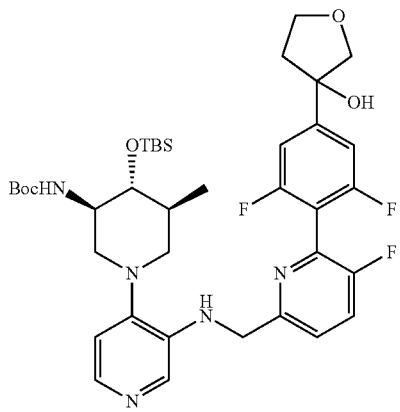 [SMILES: C[C@H]1CN(c2ccncc2NCc2ccc(F)c(-c3c(F)cc(C4(O)CCOC4)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 3-[3,5-difluoro-4-(4,4,5,5-tetramethyl-1,3,2-dioxaborolan-2-yl)phenyl]tetrahydrofuran-3-ol (17 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{38}H_{53}F_3N_5O_5Si$ $(M+H)^+$ m/z=744.4; found: 744.4.

Step 4. (3R,4R,5S)-3-Amino-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-3-yl)carbamate (24 mg, 0.032 mmol) was dissolved in methanol (2 mL). Then 4.0M solution of HCl in dioxane (1 mL, 4 mmol) was added to the reaction mixture to the reaction mixture. The resultant reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{27}H_{31}F_3N_5O_3$ $(M+H)^+$ m/z=530.2; found: 530.2. $^1H$ NMR (400 MHz, DMSO-d6) δ 7.91 (t, J=9.0 Hz, 1H), 7.81 (d, J=5.1 Hz, 1H), 7.77 (s, 1H), 7.58 (dd, J=8.7, 3.9 Hz, 1H), 7.38 (d, J=9.3 Hz, 2H), 6.83 (d, J=5.1 Hz, 1H), 5.74 (br, 1H), 5.65 (t, J=5.7 Hz, 1H), 4.83 (br, 1H), 4.53 (t, J=6.1 Hz, 2H), 4.04 (dd, J=9.0, 5.0 Hz, 2H), 3.88-3.77 (m, 2H), 3.27-3.11 (m, 2H), 2.80-2.64 (m, 2H), 2.43-2.30 (m, 4H), 2.27-2.13 (m, 2H), 0.85 (d, J=6.5 Hz, 3H) ppm.

Example 2

(3R,4R,5S)-3-Amino-1-(3-(((6-(2,6-difluoro-4-(1-hydroxycyclobutyl)phenyl)-5-fluoropyridin-2-yl)methyl)amino)pyridin-4-yl)-5-methylpiperidin-4-ol

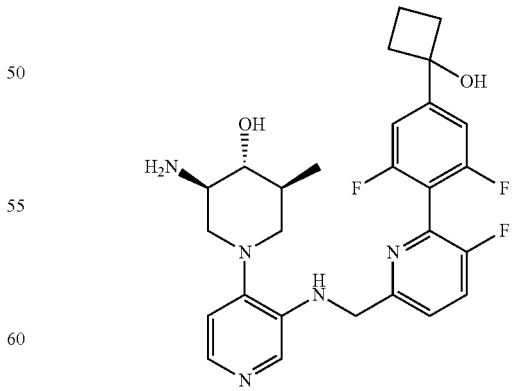

This compound was synthesized using similar procedures as described in Example 1, using cyclobutanone to replace dihydrofuran-3(2H)-one in Step 1. LCMS calc. for $C_{27}H_{31}F_3N_5O_2$ $(M+H)^+$ m/z=514.2; found: 514.2. $^1H$ NMR (400 MHz, DMSO-d6) δ 7.91 (t, J=9.0 Hz, 1H), 7.81 (d, J=5.1 Hz, 1H), 7.76 (s, 1H), 7.57 (dd, J=8.6, 3.9 Hz, 1H), 7.34 (d, J=9.3 Hz, 2H), 6.83 (d, J=5.1 Hz, 1H), 5.84 (s, 1H), 5.62 (t, J=5.6 Hz, 1H), 4.76 (d, J=4.7 Hz, 1H), 4.53 (t, J=5.3 Hz, 2H), 3.27-3.13 (m, 3H), 2.80-2.62 (m, 3H), 2.48-2.41 (m, 2H), 2.38-2.27 (m, 3H), 2.22 (t, J=11.5 Hz, 1H), 2.04-1.91 (m, 1H), 1.85-1.61 (m, 2H), 0.86 (d, J=6.6 Hz, 3H) ppm.

Example 3

(3R,4R,5S)-3-Amino-1-(3-(((6-(2,6-difluoro-4-(4-hydroxytetrahydro-2H-pyran-4-yl)phenyl)-5-fluoro-pyridin-2-yl)methyl)amino)pyridin-4-yl)-5-methylpiperidin-4-ol

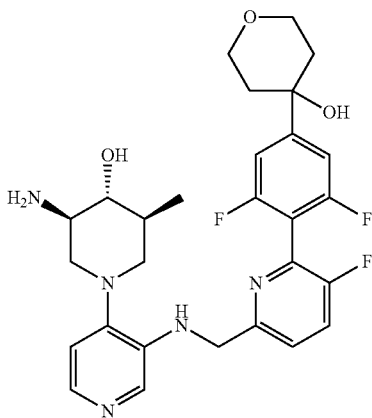 [SMILES: C[C@H]1CN(c2ccncc2NCc2ccc(F)c(-c3c(F)cc(C4(O)CCOCC4)cc3F)n2)C[C@@H](N)[C@@H]1O]

This compound was synthesized using similar procedures as described in Example 1, using dihydro-2H-pyran-4(3H)-one to replace dihydrofuran-3(2H)-one in Step 1. LCMS calc. for $C_{28}H_{33}F_3N_5O_3$ (M+H)$^+$ m/z=544.3; found: 544.3. $^1$H NMR (400 MHz, DMSO-d6) δ 7.91 (t, J=9.0 Hz, 1H), 7.81 (d, J=5.1 Hz, 1H), 7.77 (s, 1H), 7.57 (dd, J=8.7, 3.8 Hz, 1H), 7.37 (d, J=9.5 Hz, 2H), 6.83 (d, J=5.1 Hz, 1H), 5.63 (t, J=5.7 Hz, 1H), 5.37 (s, 1H), 4.79 (d, J=4.6 Hz, 1H), 4.53 (t, J=5.5 Hz, 2H), 3.86-3.69 (m, 3H), 3.20 (t, J=14.0 Hz, 1H), 2.79-2.63 (m, 2H), 2.39-2.30 (m, 2H), 2.22 (t, J=11.5 Hz, 2H), 2.13-1.99 (m, 2H), 1.79-1.65 (m, 1H), 1.57 (d, J=13.2 Hz, 2H), 0.86 (d, J=6.6 Hz, 3H) ppm.

Example 4

3-(4-{6-[({4-[(3S,5R)-3-Amino-5-methylpiperidin-1-yl]pyridin-3-yl}amino)methyl]-3-fluoropyridin-2-yl}-3,5-difluorophenyl)tetrahydrofuran-3-ol

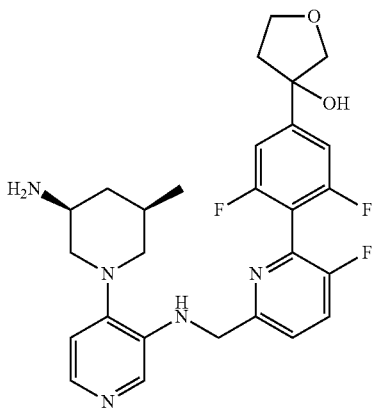 [SMILES: C[C@@H]1C[C@H](N)CN(c2ccncc2NCc2ccc(F)c(-c3c(F)cc(C4(O)CCOC4)cc3F)n2)C1]

Step 1. tert-Butyl ((3S,5R)-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-3-yl)carbamate

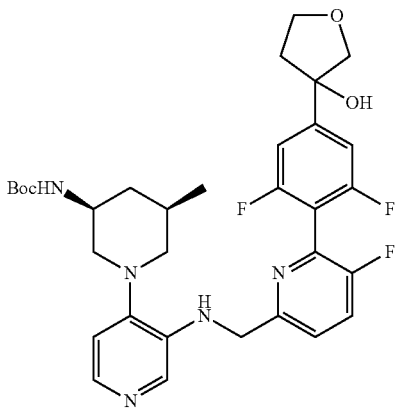 [SMILES: C[C@@H]1C[C@H](NC(=O)OC(C)(C)C)CN(c2ccncc2NCc2ccc(F)c(-c3c(F)cc(C4(O)CCOC4)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 3-[3,5-difluoro-4-(4,4,5,5-tetramethyl-1,3,2-dioxaborolan-2-yl)phenyl]tetrahydrofuran-3-ol (Example 1, Step 2; 17 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for $C_{32}H_{39}F_3N_5O_4$ (M+H)$^+$ m/z=614.3; found: 614.3.

Step 2. 3-(4-{6-[({4-[(3S,5R)-3-Amino-5-methylpiperidin-1-yl]pyridin-3-yl}amino)methyl]-3-fluoropyridin-2-yl}-3,5-difluorophenyl)tetrahydrofuran-3-ol tert-Butyl ((3S,5R)-1-{3-[({6-[2,6-difluoro-4-(3-hydroxytetrahydrofuran-3-yl)phenyl]-5-fluoropyridin-2-yl}methyl)amino]pyridin-4-yl}-5-methylpiperidin-3-yl)carbamate (20 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for $C_{27}H_{31}F_3N_5O_2$ (M+H)$^+$ m/z=514.2; found: 514.2. $^1$H NMR (400 MHz, DMSO-d6) δ 7.93 (t, J=8.9 Hz, 1H), 7.85 (d, J=5.0 Hz, 1H), 7.81 (s, 1H), 7.61 (dd, J=8.7, 3.9 Hz, 1H), 7.41 (d, J=9.4 Hz, 2H), 6.86 (d, J=5.1 Hz, 1H), 5.83-5.73 (m, 2H), 4.63-4.45 (m, 2H), 4.06 (dd, J=8.9, 5.0 Hz, 3H), 3.87-3.80 (m, 1H), 3.20-3.09 (m, 1H), 2.43-2.28 (m, 3H), 2.24-2.13 (m, 1H), 2.06 (t, J=11.2

Hz, 2H), 1.98-1.87 (m, 1H), 1.85-1.72 (m, 1H), 0.94 (q, J=11.7 Hz, 1H), 0.79 (d, J=6.5 Hz, 3H) ppm.

Example 5

1-(4-(6-((4-((3S,5R)-3-Amino-5-methylpiperidin-1-yl)pyridin-3-ylamino)methyl)-3-fluoropyridin-2-yl)-3,5-difluorophenyl)cyclobutanol

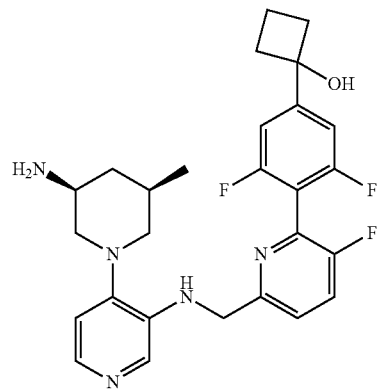 [SMILES: C[C@@H]1C[C@H](N)CN(c2ccncc2NCc2ccc(F)c(-c3c(F)cc(C4(O)CCC4)cc3F)n2)C1]

This compound was synthesized using similar procedures as described in Example 4, using 0.5M solution of (3,5-difluorophenyl)magnesium bromide in THF and cyclobutanone. LCMS calc. for $C_{27}H_{31}F_3N_5O$ (M+H)$^+$ m/z=498.3; found: 498.2. $^1$H NMR (400 MHz, DMSO-d6) δ 7.93 (t, J=8.9 Hz, 1H), 7.82 (d, J=5.0 Hz, 1H), 7.81 (s, 1H), 7.60 (dd, J=8.7, 3.9 Hz, 1H), 7.36 (d, J=9.4 Hz, 2H), 6.82 (d, J=5.1 Hz, 1H), 6.00-5.84 (m, 1H), 5.73 (t, J=5.3 Hz, 1H), 4.52 (qd, J=16.4, 5.2 Hz, 2H), 3.22-3.08 (m, 2H), 2.84-2.71 (m, 1H), 2.49-2.41 (m, 2H), 2.38-2.27 (m, 3H), 2.13 (t, J=10.6 Hz, 1H), 2.03-1.92 (m, 2H), 1.86-1.58 (m, 3H), 0.78-0.65 (m, 4H) ppm.

Example 6

4-(4-(6-((4-((3S,5R)-3-Amino-5-methylpiperidin-1-yl)pyridin-3-ylamino)methyl)-3-fluoropyridin-2-yl)-3,5-difluorophenyl)tetrahydro-2H-pyran-4-ol

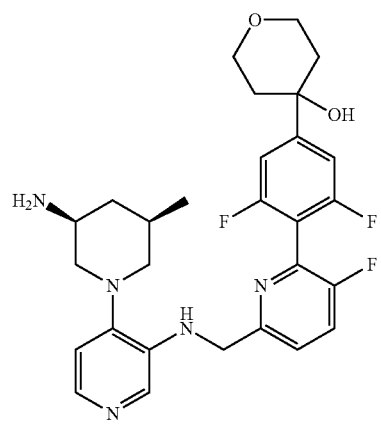

This compound was synthesized using similar procedures as described in Example 4, using 0.5M solution of (3,5-difluorophenyl)magnesium bromide in THF and dihydro-2H-pyran-4(3H)-one. LCMS calc. for $C_{28}H_{33}F_3N_5O_2$ (M+H)$^+$ m/z=528.3; found: 528.3. $^1$H NMR (400 MHz, DMSO-d6) δ 7.93 (t, J=8.9 Hz, 1H), 7.83 (d, J=5.0 Hz, 1H), 7.81 (s, 1H), 7.60 (dd, J=8.7, 3.8 Hz, 1H), 7.39 (d, J=9.5 Hz, 2H), 6.82 (d, J=5.1 Hz, 1H), 5.73 (t, J=5.3 Hz, 2H), 5.45 (s, 1H), 4.52 (qd, J=16.3, 4.9 Hz, 2H), 3.88-3.69 (m, 4H), 3.24-3.09 (m, 2H), 2.91-2.75 (m, 1H), 2.17 (t, J=10.5 Hz, 2H), 2.14-2.00 (m, 1H), 1.96 (t, J=11.2 Hz, 1H), 1.85-1.67 (m, 2H), 1.57 (d, J=13.1 Hz, 2H), 0.74 (d, J=6.5 Hz, 3H) ppm.

Example 7

1-(4-{6-[({4-[(3S,5R)-3-Amino-5-(trifluoromethyl)piperidin-1-yl]pyridin-3-yl}amino)methyl]-3-fluoropyridin-2-yl}-3,5-difluorophenyl)cyclobutanol

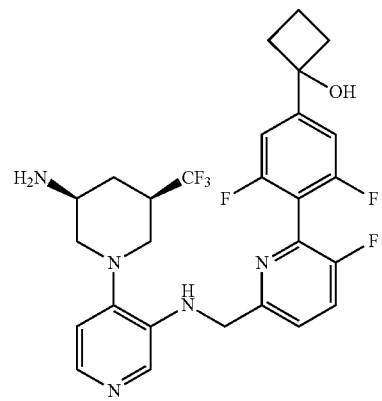 [SMILES: N[C@H]1C[C@@H](C(F)(F)F)CN(c2ccncc2NCc2ccc(F)c(-c3c(F)cc(C4(O)CCC4)cc3F)n2)C1]

Step 1. 1-(3,5-Difluorophenyl)cyclobutanol

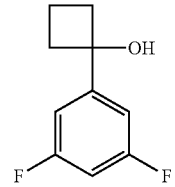 [SMILES: OC1(c2cc(F)cc(F)c2)CCC1]

Cyclobutanone (280 mg, 4.0 mmol) and a magnet bar were placed in a vial. The vial was evacuated and backfilled with nitrogen three times. After addition of tetrahydrofuran (6.0 mL), the reaction mixture was cooled to 0° C. Then 0.5M solution of (3,5-difluorophenyl)magnesium bromide in THF (8.8 mL, 4.4 mmol) was slowly added and the reaction mixture was stirred at room temperature for 16 h. After this time it was carefully quenched by the addition of saturated solution of ammonium chloride. The product was extracted with EtOAc. Combined organic fractions were washed with brine, dried over $Na_2SO_4$ and solvents were evaporated under reduced pressure. The resulting product was used in the next step without further purification (643 mg, 87%).

Step 2. 1-[3,5-Difluoro-4-(4,4,5,5-tetramethyl-1,3,2-dioxaborolan-2-yl)phenyl]cyclobutanol

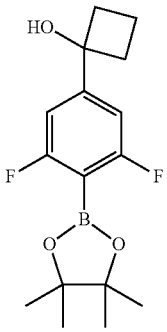

1-(3,5-difluorophenyl)cyclobutanol (643 mg, 3.49 mmol) and a magnet bar were placed in a vial. The vial was evacuated and backfilled with nitrogen three times. After addition of tetrahydrofuran (14 mL), the reaction mixture was cooled to −78° C. Then 2.5M solution of n-butyllithium in hexanes (3.5 mL, 8.7 mmol) was slowly added and the reaction was stirred at −78° C. for 1 h. After this time 2-isopropoxy-4,4,5,5-tetramethyl-1,3,2-dioxaborolane (2.14 mL, 10.5 mmol) was slowly added. After stirring at −78° C. for 5 min more, the reaction mixture was allowed to warm to room temperature and it was stirred at room temperature for 1 h. After this time it was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (660 mg, 61%).

Step 3. tert-Butyl [(3S,5R)-1-{3-[({6-[2,6-difluoro-4-(1-hydroxycyclobutyl)phenyl]-5-fluoropyridin-2-yl}methyl)amino]pyridin-4-yl}-5-(trifluoromethyl)piperidin-3-yl]carbamate

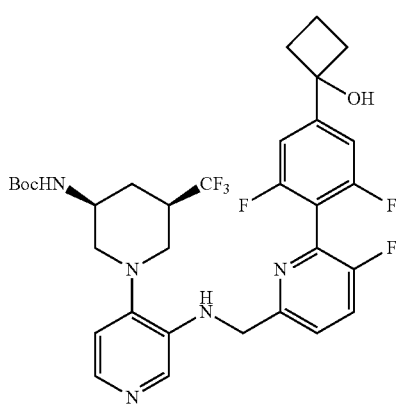 [SMILES: CC(C)(C)OC(=O)N[C@H]1C[C@@H](C(F)(F)F)CN(c2ccncc2NCc2ccc(F)c(-c3c(F)cc(C4(O)CCC4)cc3F)n2)C1]

tert-butyl ((3S,5R)-1-(3-(((6-bromo-5-fluoropyridin-2-yl)methyl)amino)pyridin-4-yl)-5-(trifluoromethyl)piperidin-3-yl)carbamate (intermediate 3, 18 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 1-[3,5-Difluoro-4-(4,4,5,5-tetramethyl-1,3,2-dioxaborolan-2-yl)phenyl]cyclobutanol (16 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{32}$H$_{36}$F$_6$N$_5$O$_3$ (M+H)$^+$ m/z=652.3; found: 652.3.

Step 4. 1-(4-{6-[({4-[(3S,5R)-3-Amino-5-(trifluoromethyl)piperidin-1-yl]pyridin-3-yl}amino)methyl]-3-fluoropyridin-2-yl}-3,5-difluorophenyl)cyclobutanol tert-Butyl [(3S,5R)-1-{3-[({6-[2,6-difluoro-4-(1-hydroxycyclobutyl)phenyl]-5-fluoropyridin-2-yl}methyl)amino]pyridin-4-yl}-5-(trifluoromethyl)piperidin-3-yl]carbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{27}$H$_{28}$F$_6$N$_5$O (M+H)$^+$ m/z=552.2; found: 552.3. $^1$H NMR (400 MHz, DMSO-d6) δ 7.93 (t, J=9.0 Hz, 1H), 7.85 (d, J=5.0 Hz, 1H), 7.83 (s, 1H), 7.58 (dd, J=8.7, 3.9 Hz, 1H), 7.35 (d, J=9.3 Hz, 2H), 6.91 (d, J=5.1 Hz, 1H), 5.86 (dd, J=12.4, 6.8 Hz, 2H), 4.62-4.41 (m, 2H), 3.46-3.34 (m, 2H), 3.19 (dd, J=10.9, 4.0 Hz, 2H), 2.91-2.78 (m, 1H), 2.78-2.64 (m, 1H), 2.49-2.40 (m, 2H), 2.40-2.26 (m, 3H), 2.06-1.92 (m, 2H), 1.79 (dq, J=9.7, 8.2, 7.5 Hz, 1H), 1.75-1.60 (m, 1H), 1.14 (q, J=12.2 Hz, 1H) ppm.

Example 8

(3R,4R,5S)-3-Amino-1-{3-[({6-[2,6-difluoro-4-(1-hydroxycyclopropyl)phenyl]-5-fluoropyridin-2-yl}methyl)amino]pyridin-4-yl}-5-methylpiperidin-4-ol

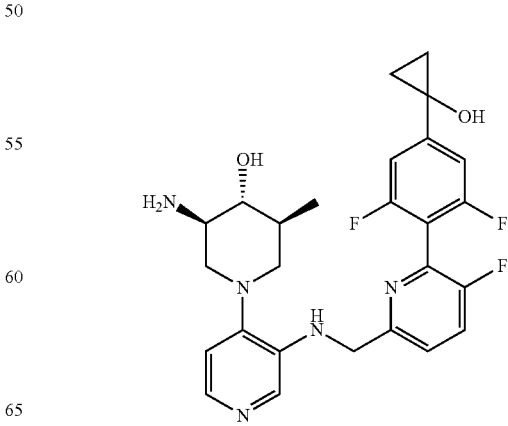

Step 1. {[1-(3,5-Difluorophenyl)vinyl]oxy}(trimethyl)silane

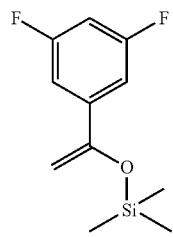

To a solution of 1-(3,5-difluorophenyl)ethanone (Matrix Scientific, 500 mg, 3.2 mmol) in DCM (13 mL) was added triethylamine (890 µL, 6.4 mmol). Then trimethylsilyl trifluoromethanesulfonate (from Aldrich, 640 µL, 3.5 mmol) was slowly added at 0° C. to the resulting mixture. The reaction mixture was stirred at 0° C. for 15 min before it was carefully quenched by the addition saturated aq. NaHCO₃. The product was extracted with EtOAc. Combined organic fractions were washed with brine, dried over Na₂SO₄ and solvents were evaporated under reduced pressure. The resulting product was used in the next step without further purification (664 mg, 91%).

Step 2. {[1-(3,5-Difluorophenyl)cyclopropyl]oxy}(trimethyl)silane

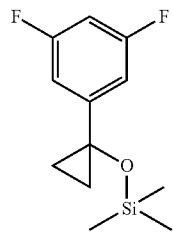 [SMILES: C[Si](C)(C)OC1(c2cc(F)cc(F)c2)CC1]

To a solution of diiodomethane (2.5 g, 9.3 mmol) in DCM (30 mL) was slowly added 1.2M solution of diethyl zinc in toluene (7.8 mL, 9.3 mmol) at 0° C. After stirring for 20 min at 0° C., {[1-(3,5-difluorophenyl)vinyl]oxy}(trimethyl)silane (664 mg, 2.91 mmol) was added dropwise and the reaction mixture was stirred at room temperature overnight. After this time it was carefully quenched by the addition of the saturated solution of ammonium chloride. The product was extracted with DCM. Combined organic fractions were washed with brine, dried over Na₂SO₄ and solvents were evaporated under reduced pressure. The resulting product was used in the next step without further purification (656 mg, 93%).

Step 3. 1-(3,5-Difluoro-4-(4,4,5,5-tetramethyl-1,3,2-dioxaborolan-2-yl)phenyl)cyclopropanol

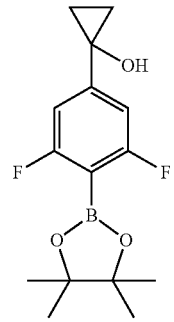 [SMILES: CC1(C)OB(c2c(F)cc(C3(O)CC3)cc2F)OC1(C)C]

{[1-(3,5-Difluorophenyl)cyclopropyl]oxy}(trimethyl)silane (656 mg, 2.71 mmol) and a magnet bar were placed in a vial. The vial was evacuated and backfilled with nitrogen three times. After addition of tetrahydrofuran (12 mL), the reaction mixture was cooled to −78° C. Then 2.5M solution of n-butyllithium in hexanes (2.7 mL, 6.8 mmol) was slowly added and the reaction mixture was stirred at −78° C. for 1 h. After this time 2-isopropoxy-4,4,5,5-tetramethyl-1,3,2-dioxaborolane (1.66 mL, 8.12 mmol) was slowly added. After stirring at −78° C. for 5 min, the reaction was allowed to warm to room temperature and it was stirred at room temperature for 1 h. After this time the reaction mixture was carefully quenched by the addition of the saturated solution of ammonium chloride. The product was extracted with EtOAc. Combined organic fractions were washed with brine, dried over Na₂SO₄ and solvents were evaporated under reduced pressure. The resulting product was used in the next step without further purification (420 mg, 52%). LCMS calc. for $C_{15}H_{20}BF_2O_3$ (M+H)⁺ m/z=297.1; found: 297.1.

Step 4. tert-Butyl ((3R,4R,5S)-4-{[tert-butyl(dimethyl)silyl]oxy}-1-{3-[({6-[2,6-difluoro-4-(1-hydroxycyclopropyl)phenyl]-5-fluoropyridin-2-yl}methyl)amino]pyridin-4-yl}-5-methylpiperidin-3-yl)carbamate

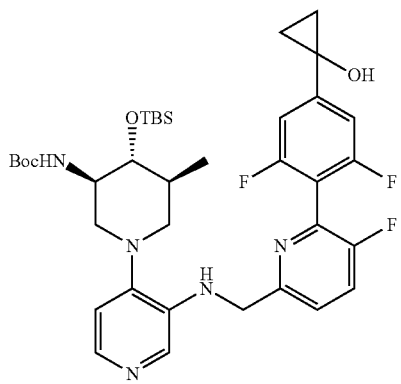 [SMILES: C[C@H]1CN(c2ccncc2NCc2ccc(F)c(-c3c(F)cc(C4(O)CC4)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 1-[3,5-difluoro-4-(4,4,5,5-tetramethyl-1,3,2-dioxaborolan-2-yl)phenyl]cyclopropanol (15 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{37}H_{51}F_3N_5O_4Si$ (M+H)$^+$ m/z=714.4; found: 714.3.

Step 5. (3R,4R,5S)-3-Amino-1-{3-[({6-[2,6-difluoro-4-(1-hydroxycyclopropyl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(1-hydroxycyclopropyl)phenyl]-5-fluoropyridin-2-yl}methyl)amino]pyridin-4-yl}-5-methylpiperidin-3-yl)carbamate (23 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for $C_{26}H_{29}F_3N_5O_2$ (M+H)$^+$ m/z=500.2; found: 500.2.

Example 9

(3R,4R,5S)-3-Amino-1-(3-(((6-(2,6-difluoro-3-(1-hydroxycyclopropyl)phenyl)-5-fluoropyridin-2-yl)methyl)amino)pyridin-4-yl)-5-methylpiperidin-4-ol

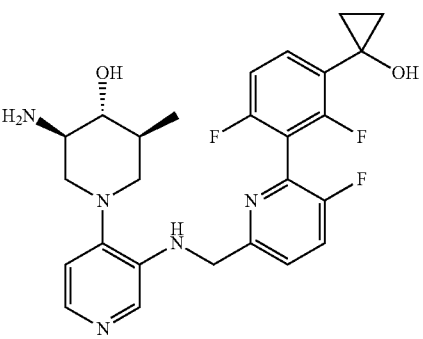 [SMILES: C[C@H]1CN(c2ccncc2NCc2ccc(F)c(-c3c(F)ccc(C4(O)CC4)c3F)n2)C[C@@H](N)[C@@H]1O]

This compound was synthesized according to the procedures described in Example 8, using 1-(2,4-difluorophenyl)ethanone to replace 1-(3,5-difluorophenyl)ethanone in Step 1. LCMS calc. for $C_{26}H_{29}F_3N_5O_2$ (M+H)$^+$ m/z=500.2; found: 500.2.

Example 10

1-(4-{6-[({4-[(3S,5R)-3-Amino-5-methylpiperidin-1-yl]pyridin-3-yl}amino)methyl]-3-fluoropyridin-2-yl}-3,5-difluorophenyl)cyclopropanol

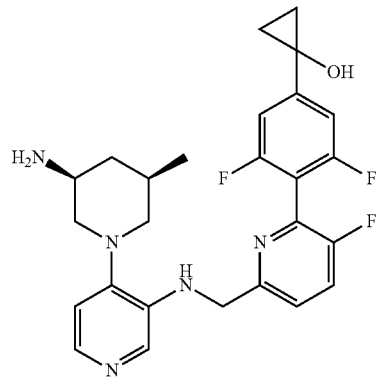 [SMILES: C[C@@H]1C[C@H](N)CN(c2ccncc2NCc2ccc(F)c(-c3c(F)cc(C4(O)CC4)cc3F)n2)C1]

Step 1. tert-Butyl ((3S,5R)-1-{3-[({6-[2,6-difluoro-4-(1-hydroxycyclopropyl)phenyl]-5-fluoropyridin-2-yl}methyl)amino]pyridin-4-yl}-5-methylpiperidin-3-yl)carbamate

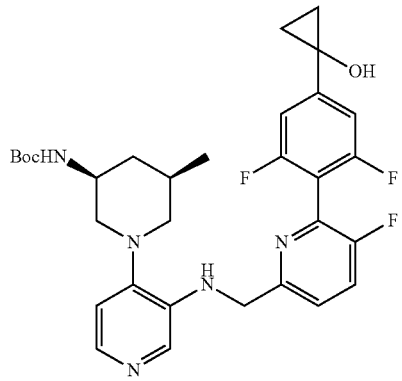 [SMILES: C[C@@H]1C[C@H](NC(=O)OC(C)(C)C)CN(c2ccncc2NCc2ccc(F)c(-c3c(F)cc(C4(O)CC4)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (Intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 1-[3,5-difluoro-4-(4,4,5,5-tetramethyl-1,3,2-dioxaborolan-2-yl)phenyl]cyclopropanol (Example 8, Step 3; 15 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{31}H_{37}F_3N_5O_3$ (M+H)$^+$ m/z=584.3; found: 584.2.

Step 2. 1-(4-{6-[({4-[(3S,5R)-3-Amino-5-methylpiperidin-1-yl]pyridin-3-yl}amino)methyl]-3-fluoropyridin-2-yl}-3,5-difluorophenyl)cyclopropanol tert-Butyl ((3S,5R)-1-{3-[({6-[2,6-difluoro-4-(1-hydroxycyclopropyl)phenyl]-5-fluoropyridin-2-yl}methyl)

amino]pyridin-4-yl}-5-methylpiperidin-3-yl)carbamate (19 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{26}$H$_{29}$F$_3$N$_5$O (M+H)$^+$ m/z=484.2; found: 484.2. $^1$H NMR (400 MHz, DMSO-d6) δ 7.91 (t, J=9.0 Hz, 1H), 7.84 (d, J=5.0 Hz, 1H), 7.80 (s, 1H), 7.58 (dd, J=8.7, 3.8 Hz, 1H), 7.10 (d, J=9.6 Hz, 2H), 6.85 (d, J=5.1 Hz, 1H), 5.76 (t, J=5.3 Hz, 2H), 4.62-4.45 (m, 3H), 3.21-3.05 (m, 1H), 2.32 (t, J=10.8 Hz, 1H), 2.06 (t, J=11.3 Hz, 1H), 1.98-1.87 (m, 1H), 1.79 (br, 1H), 1.30-1.20 (m, 2H), 1.19-1.09 (m, 2H), 0.92 (q, J=11.8 Hz, 1H), 0.80 (d, J=6.6 Hz, 3H) ppm.

Example 11

1-(3-(6-((4-((3S,5R)-3-Amino-5-methylpiperidin-1-yl)pyridin-3-ylamino)methyl)-3-fluoropyridin-2-yl)-2,4-difluorophenyl)cyclopropanol

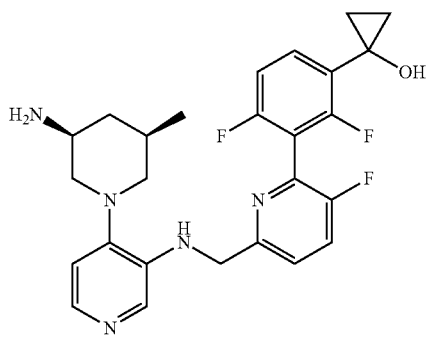 [SMILES: C[C@@H]1C[C@H](N)CN(c2ccncc2NCc2ccc(F)c(-c3c(F)ccc(C4(O)CC4)c3F)n2)C1]

This compound was synthesized according to the procedures described in Example 10, using 1-(2,4-difluorophenyl)ethanone. LCMS calc. for C$_{26}$H$_{29}$F$_3$N$_5$O (M+H)$^+$ m/z=484.2; found: 484.2.

Example 12

(3R,4R,5S)-3-Amino-1-{3-[({6-[2,6-difluoro-4-(2-hydroxy-2-methylpropyl)phenyl]-5-fluoropyridin-2-yl}methyl)amino]pyridin-4-yl}-5-methylpiperidin-4-ol

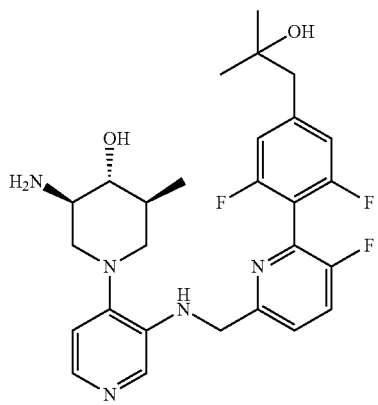 [SMILES: C[C@H]1CN(c2ccncc2NCc2ccc(F)c(-c3c(F)cc(CC(C)(C)O)cc3F)n2)C[C@@H](N)[C@@H]1O]

Step 1. Methyl (3,5-difluorophenyl)acetate

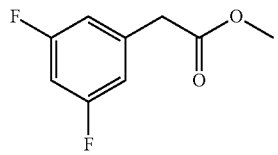

(3,5-Difluorophenyl)acetic acid (Sigma-Aldrich, 690 mg, 4.0 mmol) and potassium carbonate (1.1 g, 8.0 mmol) were added to DMF (12 mL). After subsequent addition of methyl iodide (750 μL, 12 mmol), the resultant reaction mixture was stirred at room temperature for 6 h. After this time, water was added to the reaction mixture and the product was extracted with EtOAc. Combined organic fractions were washed with brine, dried over Na$_2$SO$_4$ and solvents were evaporated under reduced pressure. The crude product was purified by Biotage Isolera to give the desired compound (670 mg, 90%).

Step 2. 1-(3,5-Difluorophenyl)-2-methylpropan-2-ol

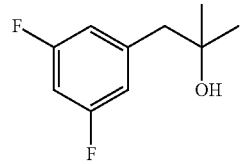

Methyl (3,5-difluorophenyl)acetate (670 mg, 3.6 mmol) and a magnet bar were placed in a vial. The vial was evacuated and backfilled with nitrogen three times. After addition of tetrahydrofuran (10 mL), the reaction mixture was cooled to 0° C. Then 3.0M solution of methylmagnesium bromide in ether (3.6 mL, 11 mmol) was slowly added and the reaction mixture was stirred at room temperature for 16 h. After this time the reaction mixture was carefully quenched by the addition of the saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (301 mg, 45%).

Step 3. 1-[3,5-Difluoro-4-(4,4,5,5-tetramethyl-1,3,2-dioxaborolan-2-yl)phenyl]-2-methylpropan-2-ol

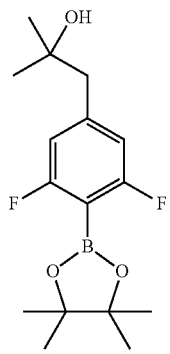 [SMILES: CC(C)(O)Cc1cc(F)c(B2OC(C)(C)C(C)(C)O2)c(F)c1]

1-(3,5-Difluorophenyl)-2-methylpropan-2-ol (301 mg, 1.62 mmol) and a magnet bar were placed in a vial. The vial was evacuated and backfilled with nitrogen three times. After addition of tetrahydrofuran (6.0 mL), the reaction mixture was cooled to −78° C. Then 2.5M solution of n-butyllithium in hexanes (1.6 mL, 4.0 mmol) was slowly added and the reaction was stirred at −78° C. for 1 h. After this time 2-isopropoxy-4,4,5,5-tetramethyl-1,3,2-dioxaborolane (989 μL, 4.85 mmol) was slowly added. After stirring at −78° C. for 5 min, the reaction mixture was allowed to warm to room temperature and it was stirred at room temperature for 1 h. After this time the reaction mixture was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (343 mg, 68%).

Step 4. tert-Butyl ((3R,4R,5S)-4-{[tert-butyl(dimethyl)silyl]oxy}-1-{3-[({6-[2,6-difluoro-4-(2-hydroxy-2-methylpropyl)phenyl]-5-fluoropyridin-2-yl}methyl)amino]pyridin-4-yl}-5-methylpiperidin-3-yl)carbamate

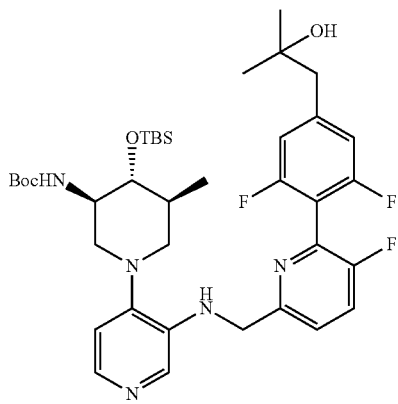 [SMILES: C[C@H]1CN(c2ccncc2NCc2ccc(F)c(-c3c(F)cc(CC(C)(C)O)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 1-[3,5-difluoro-4-(4,4,5,5-tetramethyl-1,3,2-dioxaborolan-2-yl)phenyl]-2-methylpropan-2-ol (16 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{38}$H$_{55}$F$_3$N$_5$O$_4$Si (M+H)$^+$ m/z=730.4; found: 730.4.

Step 5. (3R,4R,5S)-3-Amino-1-{3-[({6-[2,6-difluoro-4-(2-hydroxy-2-methylpropyl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(2-hydroxy-2-methylpropyl)phenyl]-5-fluoropyridin-2-yl}methyl)amino]pyridin-4-yl}-5-methylpiperidin-3-yl)carbamate (23 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{27}$H$_{33}$F$_3$N$_5$O$_2$ (M+H)$^+$ m/z=516.3; found: 516.3. $^1$H NMR (400 MHz, DMSO-d6) δ 8.07 (d, J=6.1 Hz, 1H), 7.92 (t, J=8.9 Hz, 1H), 7.84 (s, 1H), 7.61 (dd, J=8.6, 3.8 Hz, 1H), 7.13 (s, 2H), 7.00 (s, 1H), 6.35 (s, 1H), 5.77 (s, 1H), 4.61 (ddd, J=37.2, 16.7, 5.9 Hz, 3H), 3.91-3.77 (m, 1H), 3.58-3.45 (m, 1H), 3.22-3.10 (m, 1H), 2.82-2.71 (m, 4H), 2.63-2.54 (m, 2H), 1.83 (s, 1H), 1.13 (s, 6H), 0.95 (d, J=6.5 Hz, 3H) ppm.

Example 13

1-(4-{6-[({4-[(3S,5R)-3-Amino-5-methylpiperidin-1-yl]pyridin-3-yl}amino)methyl]-3-fluoropyridin-2-yl}-3,5-difluorophenyl)-2-methylpropan-2-ol

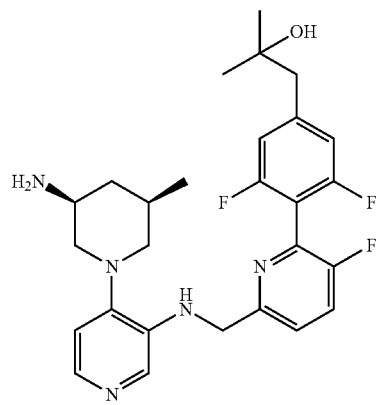 [SMILES: C[C@@H]1C[C@H](N)CN(c2ccncc2NCc2ccc(F)c(-c3c(F)cc(CC(C)(C)O)cc3F)n2)C1]

Step 1. tert-Butyl ((3S,5R)-1-{3-[({6-[2,6-difluoro-4-(2-hydroxy-2-methylpropyl)phenyl]-5-fluoropyridin-2-yl}methyl)amino]pyridin-4-yl}-5-methylpiperidin-3-yl)carbamate

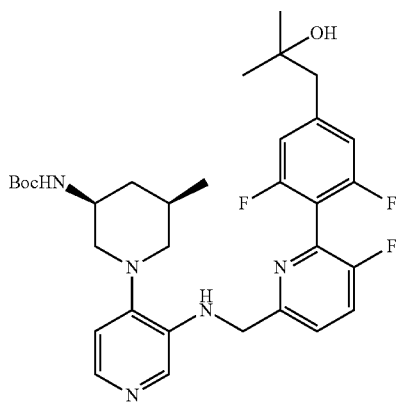 [SMILES: C[C@@H]1C[C@H](NC(=O)OC(C)(C)C)CN(c2ccncc2NCc2ccc(F)c(-c3c(F)cc(CC(C)(C)O)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (Intermediate 2; 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 1-[3,5-difluoro-4-(4,4,5,5-tetramethyl-1,3,2-dioxaborolan-2-yl)phenyl]-2-methylpropan-2-ol (Example 12, Step 3; 16 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{32}H_{41}F_3N_5O_3$ (M+H)$^+$ m/z=600.3; found: 600.3.

Step 2. 1-(4-{6-[({4-[(3S,5R)-3-Amino-5-methylpiperidin-1-yl]pyridin-3-yl}amino)methyl]-3-fluoropyridin-2-yl}-3,5-difluorophenyl)-2-methylpropan-2-ol tert-Butyl ((3S,5R)-1-{3-[({6-[2,6-difluoro-4-(2-hydroxy-2-methylpropyl)phenyl]-5-fluoropyridin-2-yl}methyl)amino]pyridin-4-yl}-5-methylpiperidin-3-yl)carbamate (19 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{27}H_{33}F_3N_5O$ (M+H)$^+$ m/z=500.3; found: 500.3. $^1$H NMR (400 MHz, DMSO-d6) δ 8.07 (d, J=6.2 Hz, 1H), 7.94 (t, J=8.9 Hz, 1H), 7.87 (s, 1H), 7.62 (dd, J=8.6, 3.8 Hz, 1H), 7.23 (s, 2H), 7.14 (d, J=9.2 Hz, 1H), 6.24 (s, 1H), 4.73-4.48 (m, 3H), 3.73 (d, J=10.7 Hz, 1H), 3.47 (d, J=12.1 Hz, 1H), 2.77 (s, 2H), 2.64 (t, J=11.3 Hz, 2H), 2.39-2.26 (m, 2H), 2.06 (d, J=12.1 Hz, 1H), 1.87 (s, 1H), 1.14 (d, J=2.5 Hz, 6H), 0.85 (d, J=6.6 Hz, 3H) ppm.

Example 14

(3R,4R,5S)-3-Amino-1-[3-({[6-(2,6-difluorophenyl)-5-fluoropyridin-2-yl]methyl}amino)pyridin-4-yl]-5-methylpiperidin-4-ol

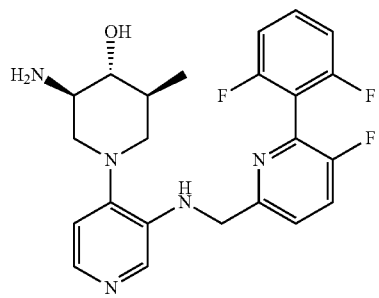

Step 1. tert-Butyl {(3R,4R,5S)-4-{[tert-butyl(dimethyl)silyl]oxy}-1-[3-({[6-(2,6-difluorophenyl)-5-fluoropyridin-2-yl]methyl}amino)pyridin-4-yl]-5-methylpiperidin-3-yl}carbamate

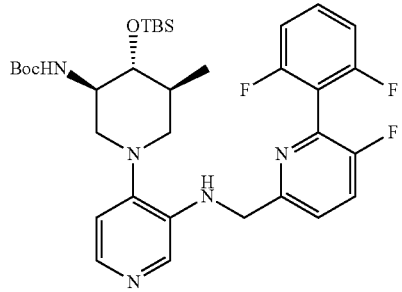

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 2-(2,6-difluorophenyl)-4,4,5,5-tetramethyl-1,3,2-dioxaborolane (from Combi-Blocks, 13 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{34}H_{47}F_3N_5O_3Si$ (M+H)$^+$ m/z=658.3; found: 658.3.

Step 2. (3R,4R,5S)-3-Amino-1-[3-({[6-(2,6-difluorophenyl)-5-fluoropyridin-2-yl]methyl}amino)pyridin-4-yl]-5-methylpiperidin-4-ol tert-Butyl {(3R,4R,5S)-4-{[tert-butyl(dimethyl)silyl]oxy}-1-[3-({[6-(2,6-difluorophenyl)-5-fluoropyridin-2-yl]methyl}amino)pyridin-4-yl]-5-methylpiperidin-3-yl}carbamate (21 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for $C_{23}H_{25}F_3N_5O$ (M+H)$^+$ m/z=444.2; found: 444.2. $^1$H NMR (400 MHz, DMSO-d6) δ 7.89 (t, J=9.0 Hz, 1H), 7.79 (d, J=5.1 Hz, 1H), 7.74 (s, 1H), 7.70-7.58 (m, 1H), 7.56 (dd, J=8.7, 3.9 Hz, 1H), 7.34-7.23 (m, 2H), 6.82 (d, J=5.1 Hz, 1H), 5.63 (t, J=5.8 Hz, 1H), 4.61-4.45 (m, 3H), 3.29-3.22 (m, 1H), 3.21-3.12 (m, 1H), 2.89-2.69 (m, 2H), 2.36 (t, J=10.7 Hz, 1H), 2.23 (t, J=11.6 Hz, 1H), 1.79-1.63 (m, 1H), 0.87 (d, J=6.6 Hz, 3H) ppm.

Example 15

(3R,4R,5S)-3-Amino-1-(3-(((5-fluoro-6-(2-fluoro-6-methoxyphenyl)pyridin-2-yl)methyl)amino)pyridin-4-yl)-5-methylpiperidin-4-ol

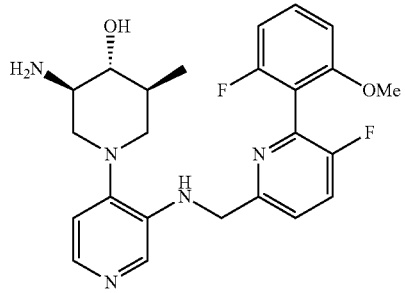 [SMILES: COc1cccc(F)c1-c1nc(CNc2cnccc2N2C[C@@H](N)[C@H](O)[C@@H](C)C2)ccc1F]

This compound was synthesized according to the procedures described in Example 14, using 2-fluoro-6-methoxyphenylboronic acid (from Combi-Blocks) to replace 2-(2,6-difluorophenyl)-4,4,5,5-tetramethyl-1,3,2-dioxaborolane in Step 1. LCMS calc. for $C_{24}H_{28}F_2N_5O_2$ (M+H)$^+$ m/z=456.2; found: 456.4.

Example 16

(3R,4R,5S)-3-Amino-5-methyl-1-(3-(((3,3',5'-trifluoro-[2,4'-bipyridin]-6-yl)methyl)amino)pyridin-4-yl)piperidin-4-ol

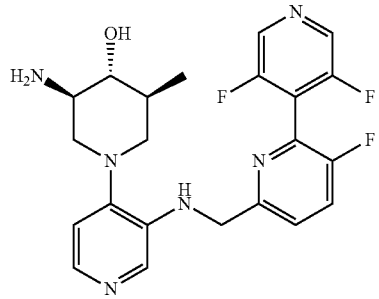 [SMILES: C[C@H]1CN(c2ccncc2NCc2ccc(F)c(-c3c(F)cncc3F)n2)C[C@@H](N)[C@@H]1O]

This compound was synthesized according to the procedures described in Example 14, using 3,5-difluoropyridin-4-ylboronic acid (from Ark Pharm) to replace 2-(2,6-difluorophenyl)-4,4,5,5-tetramethyl-1,3,2-dioxaborolane. LCMS calc. for $C_{22}H_{24}F_3N_6O$ (M+H)$^+$ m/z=445.2; found: 445.2.

Example 17

2-(6-((4-((3R,4R,5S)-3-Amino-4-hydroxy-5-methylpiperidin-1-yl)pyridin-3-ylamino)methyl)-3-fluoropyridin-2-yl)-3-fluorobenzonitrile

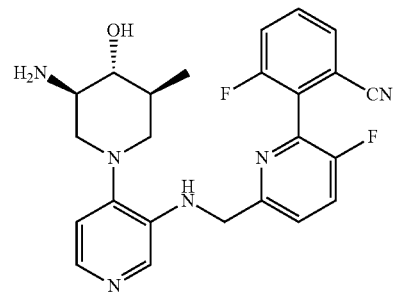 [SMILES: C[C@H]1CN(c2ccncc2NCc2ccc(F)c(-c3c(F)cccc3C#N)n2)C[C@@H](N)[C@@H]1O]

This compound was synthesized using similar procedures as described in Example 14, using 2-cyano-6-fluorophenylboronic acid (from Combi-Blocks) to replace 2-(2,6-difluorophenyl)-4,4,5,5-tetramethyl-1,3,2-dioxaborolane. LCMS calc. for $C_{24}H_{25}F_2N_6O$ (M+H)+m/z=451.2; found: 451.2.

Example 18

(3R,4R,5S)-3-Amino-1-(3-(((5-fluoro-6-(2-fluorophenyl)pyridin-2-yl)methyl)amino)pyridin-4-yl)-5-methylpiperidin-4-ol

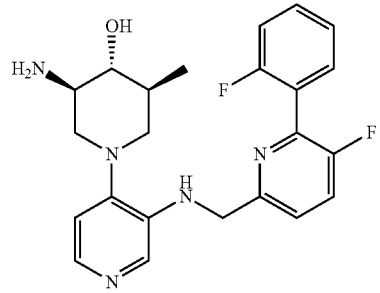 [SMILES: C[C@H]1CN(c2ccncc2NCc2ccc(F)c(-c3ccccc3F)n2)C[C@@H](N)[C@@H]1O]

This compound was synthesized using similar procedures as described in Example 14, using 2-fluorophenylboronic acid (from Aldrich) to replace 2-(2,6-difluorophenyl)-4,4,5,5-tetramethyl-1,3,2-dioxaborolane. LCMS calc. for $C_{23}H_{26}F_2N_5O$ (M+H)$^+$ m/z=426.2; found: 426.3.

Example 19

4-[(3S,5R)-3-Amino-5-methylpiperidin-1-yl]-N-{[6-(2,6-difluorophenyl)-5-fluoropyridin-2-yl]methyl}pyridin-3-amine

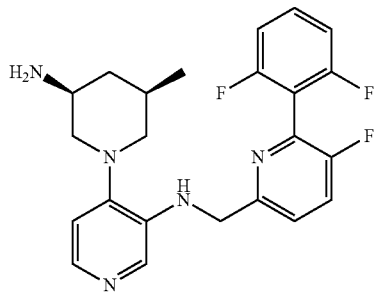

Step 1. tert-Butyl {(3S,5R)-1-[3-({[6-(2,6-difluorophenyl)-5-fluoropyridin-2-yl]methyl}amino)pyridin-4-yl]-5-methylpiperidin-3-yl}carbamate

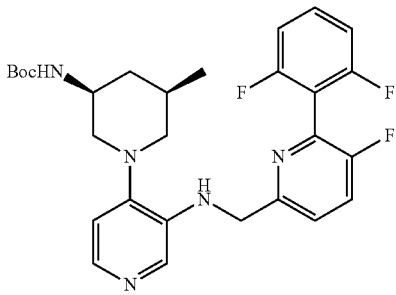

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 2-(2,6-difluorophenyl)-4,4,5,5-tetramethyl-1,3,2-dioxaborolane (13 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{28}H_{33}F_3N_5O_2$ $(M+H)^+$ m/z=528.3; found: 528.3.

Step 2. 4-[(3S,5R)-3-amino-5-methylpiperidin-1-yl]-N-{[6-(2,6-difluorophenyl)-5-fluoropyridin-2-yl]methyl}pyridin-3-amine tert-Butyl {(3S,5R)-1-[3-({[6-(2,6-difluorophenyl)-5-fluoropyridin-2-yl]methyl}amino)pyridin-4-yl]-5-methylpiperidin-3-yl}carbamate (17 mg, 0.032 mmol) was dissolved in methanol (2 mL). Then 4.0M solution of HCl in dioxane (1 mL, 4 mmol) was added to the reaction mixture.

The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{23}H_{25}F_3N_5$ $(M+H)^+$ m/z=428.2; found: 428.2.

Example 20

4-((3S,5R)-3-Amino-5-methylpiperidin-1-yl)-N-((5-fluoro-6-(2-fluoro-6-methoxyphenyl)pyridin-2-yl)methyl)pyridin-3-amine

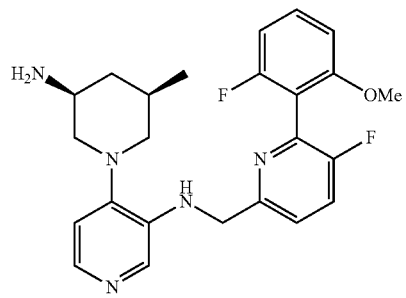 [SMILES: COc1cccc(F)c1-c1nc(CNc2cnccc2N2C[C@H](C)C[C@H](N)C2)ccc1F]

This compound was synthesized using similar procedures as described in Example 19, using 2-fluoro-6-methoxyphenylboronic acid (from Combi-Blocks) to replace 2-(2,6-difluorophenyl)-4,4,5,5-tetramethyl-1,3,2-dioxaborolane. LCMS calc. for $C_{24}H_{28}F_2N_5O$ (M+H)+m/z=440.2; found: 440.2.

Example 21

4-((3S,5R)-3-Amino-5-methylpiperidin-1-yl)-N-((3,3',5'-trifluoro-2,4'-bipyridin-6-yl)methyl)pyridin-3-amine

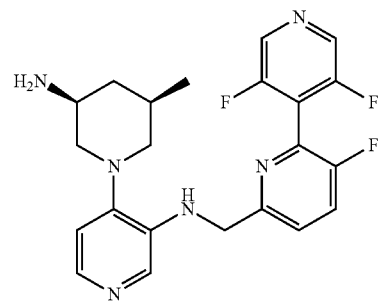 [SMILES: C[C@@H]1C[C@H](N)CN(c2ccncc2NCc2ccc(F)c(-c3c(F)cncc3F)n2)C1]

This compound was synthesized using similar procedures as described in Example 19, using 3,5-difluoropyridin-4-ylboronic acid (from Ark Pharm) to replace 2-(2,6-difluorophenyl)-4,4,5,5-tetramethyl-1,3,2-dioxaborolane. LCMS calc. for $C_{22}H_{24}F_3N_6$ (M+H)$^+$ m/z=429.2; found: 429.2.

Example 22

2-(6-((4-((3S,5R)-3-Amino-5-methylpiperidin-1-yl)pyridin-3-ylamino)methyl)-3-fluoropyridin-2-yl)-3-fluorobenzonitrile

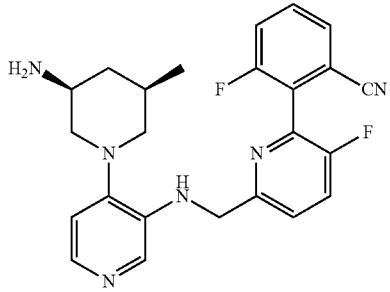 [SMILES: C[C@@H]1C[C@H](N)CN(c2ccncc2NCc2ccc(F)c(-c3c(F)cccc3C#N)n2)C1]

This compound was synthesized using similar procedures as described in Example 19, using 2-cyano-6-fluorophenylboronic acid (from Combi-Blocks) to replace 2-(2,6-difluorophenyl)-4,4,5,5-tetramethyl-1,3,2-dioxaborolane. LCMS calc. for $C_{24}H_{25}F_2N_6$ (M+H)+m/z=435.2; found: 435.1.

Example 23

4-((3S,5R)-3-Amino-5-methylpiperidin-1-yl)-N-((5-fluoro-6-(2-fluorophenyl)pyridin-2-yl)methyl)pyridin-3-amine

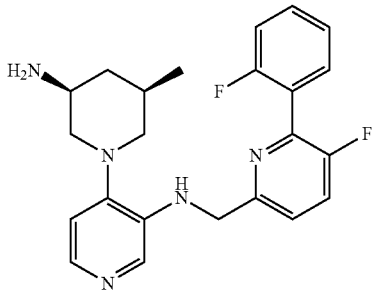 [SMILES: C[C@@H]1C[C@H](N)CN(c2ccncc2NCc2ccc(F)c(-c3ccccc3F)n2)C1]

This compound was synthesized using similar procedures as described in Example 19, using 2-fluorophenylboronic acid to replace 2-(2,6-difluorophenyl)-4,4,5,5-tetramethyl-1,3,2-dioxaborolane. LCMS calc. for $C_{23}H_{26}F_2N_5$ (M+H)$^+$ m/z=410.2; found: 410.2.

Example 24

2-(4-{6-[({4-[(3R,4R,5S)-3-Amino-4-hydroxy-5-methylpiperidin-1-yl]pyridin-3-yl}amino)methyl]-3-fluoropyridin-2-yl}-3,5-difluorophenyl)-2-methylpropanenitrile

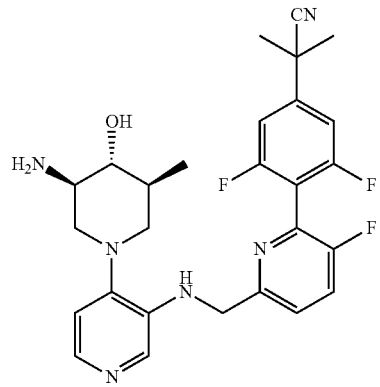 [SMILES: C[C@H]1CN(c2ccncc2NCc2ccc(F)c(-c3c(F)cc(C(C)(C)C#N)cc3F)n2)C[C@@H](N)[C@@H]1O]

Step 1.
2-(3,5-Difluorophenyl)-2-methylpropanenitrile

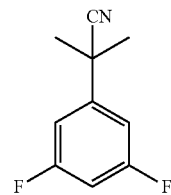

3,5-Difluorophenylacetonitrile (Sigma-Aldrich, 413 mg, 2.70 mmol) was dissolved in DMF (8.0 mL) and the reaction mixture was cooled to 0° C. Then NaH in mineral oil (60%, 240 mg, 5.9 mmol) was slowly added to the reaction mixture. After addition was complete, the reaction mixture was stirred at 0° C. for 30 min. Then methyl iodide (670 μL, 11 mmol) was slowly added to the reaction mixture and the reaction mixture was stirred at room temperature overnight. After this time, water was added to the reaction mixture and the product was extracted with EtOAc. Combined organic fractions were washed with brine, dried over $Na_2SO_4$ and solvents were evaporated under reduced pressure. The crude product was purified by Biotage Isolera to give the desired compound (343 mg, 70%).

Step 2. 2-[3,5-Difluoro-4-(4,4,5,5-tetramethyl-1,3,2-dioxaborolan-2-yl)phenyl]-2-methylpropanenitrile

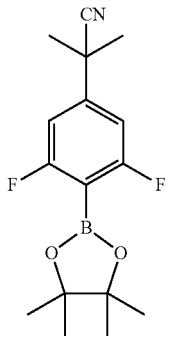 [SMILES: CC(C)(C#N)c1cc(F)c(B2OC(C)(C)C(C)(C)O2)c(F)c1]

2-(3,5-Difluorophenyl)-2-methylpropanenitrile (343 mg, 1.89 mmol) and a magnet bar were placed in a vial. The vial was evacuated and backfilled with nitrogen three times. After addition of tetrahydrofuran (6.0 mL), the reaction mixture was cooled to −78° C. Then 2.5M solution of n-butyllithium in hexanes (1.5 mL, 3.8 mmol) was slowly added to the reaction mixture and the reaction mixture was stirred at −78° C. for 1 h. After this time 2-isopropoxy-4,4,5,5-tetramethyl-1,3,2-dioxaborolane (960 μL, 4.7 mmol) was slowly added. After stirring at −78° C. for 5 min, the reaction mixture was allowed to warm to room temperature and was stirred at room temperature for 1 h. After this time the reaction mixture was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification.

Step 3. tert-Butyl ((3R,4R,5S)-4-{[tert-butyl(dimethyl)silyl]oxy}-1-{3-[({6-[4-(1-cyano-1-methylethyl)-2,6-difluorophenyl]-5-fluoropyridin-2-yl}methyl)amino]pyridin-4-yl}-5-methylpiperidin-3-yl)carbamate

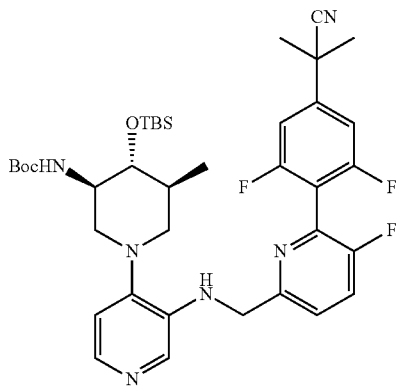 [SMILES: C[C@H]1CN(c2ccncc2NCc2ccc(F)c(-c3c(F)cc(C(C)(C)C#N)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), bis(tri-t-butylphosphine)palladium (1.6 mg, 0.0031 mmol) and magnet bar were placed in a vial with septum. The vial was then evacuated and backfilled with nitrogen three times. 1,4-Dioxane (2.5 mL), DIPEA (11 μL, 0.062 mmol) and degassed water (0.3 mL) were added to the reaction mixture to the reaction mixture. Finally 2-[3,5-difluoro-4-(4,4,5,5-tetramethyl-1,3,2-dioxaborolan-2-yl)phenyl]-2-methylpropanenitrile (15 mg, 0.050 mmol) was added and the reaction mixture was stirred at 70° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{38}$H$_{52}$F$_3$N$_6$O$_3$Si (M+H)$^+$ m/z=725.4; found: 725.3.

Step 4. 2-(4-{6-[({4-[(3R,4R,5S)-3-Amino-4-hydroxy-5-methylpiperidin-1-yl]pyridin-3-yl}amino)methyl]-3-fluoropyridin-2-yl}-3,5-difluorophenyl)-2-methylpropanenitrile tert-Butyl ((3R,4R,5S)-4-{[tert-butyl(dimethyl)silyl]oxy}-1-{3-[({6-[4-(1-cyano-1-methylethyl)-2,6-difluorophenyl]-5-fluoropyridin-2-yl}methyl)amino]pyridin-4-yl}-5-methylpiperidin-3-yl)carbamate (23 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{27}$H$_{30}$F$_3$N$_6$O (M+H)$^+$ m/z=511.2; found: 511.3. $^1$H NMR (400 MHz, DMSO-d6) δ 7.95 (t, J=9.0 Hz, 1H), 7.81 (d, J=5.1 Hz, 1H), 7.78 (s, 1H), 7.61 (dd, J=8.7, 3.9 Hz, 1H), 7.48 (d, J=9.0 Hz, 2H), 6.83 (d, J=5.1 Hz, 1H), 5.66 (t, J=5.6 Hz, 1H), 4.76 (d, J=4.3 Hz, 1H), 4.62-4.44 (m, 3H), 3.23-3.13 (m, 2H), 2.66 (d, J=6.5 Hz, 2H), 2.40-2.30 (m, 1H), 2.20 (t, J=11.6 Hz, 1H), 1.78 (s, 6H), 1.66 (s, 1H), 0.83 (d, J=6.6 Hz, 3H) ppm.

Example 24A 2-(4-{6-[({4-[(3S,5R)-3-Amino-5-methylpiperidin-1-yl]pyridin-3-yl}amino)methyl]-3-fluoropyridin-2-yl}-3,5-difluorophenyl)-2-methylpropanenitrile

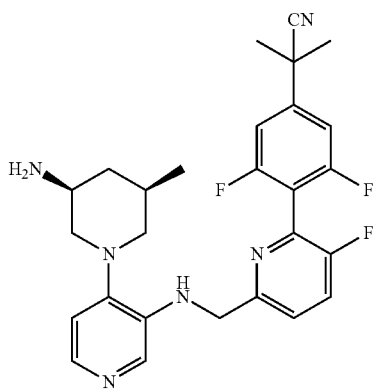

103

Step 1. tert-Butyl ((3S,5R)-1-{3-[({6-[4-(1-cyano-1-methylethyl)-2,6-difluorophenyl]-5-fluoropyridin-2-yl}methyl)amino]pyridin-4-yl}-5-methylpiperidin-3-yl)carbamate

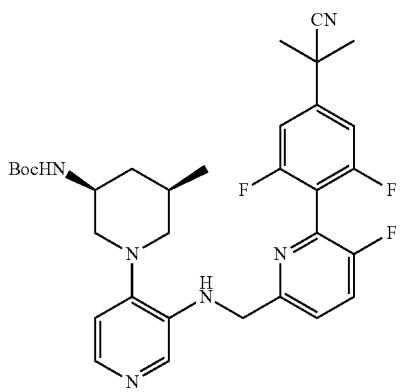 [SMILES: C[C@@H]1C[C@H](NC(=O)OC(C)(C)C)CN(c2ccncc2NCc2ccc(F)c(-c3c(F)cc(C(C)(C)C#N)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.3 mg, 0.0310 mmol), bis(tri-t-butylphosphine)palladium (1.6 mg, 0.0031 mmol) and magnet bar were placed in a vial with septum. The vial was then evacuated and backfilled with nitrogen three times. 1,4-Dioxane (2.5 mL), DIPEA (11 μL, 0.062 mmol) and degassed water (0.3 mL) were added to the reaction mixture to the reaction mixture. Finally 2-[3,5-difluoro-4-(4,4,5,5-tetramethyl-1,3,2-dioxaborolan-2-yl)phenyl]-2-methylpropanenitrile (Example 24, Step 2; 15 mg, 0.050 mmol) was added to the reaction mixture and the reaction mixture was stirred at 70° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{32}$H$_{38}$F$_3$N$_6$O$_2$ (M+H)$^+$ m/z=595.3; found: 595.4.

Step 2. 2-(4-{6-[({4-[(3S,5R)-3-Amino-5-methylpiperidin-1-yl]pyridin-3-yl}amino)methyl]-3-fluoropyridin-2-yl}-3,5-difluorophenyl)-2-methylpropanenitrile tert-Butyl ((3S,5R)-1-{3-[({6-[4-(1-cyano-1-methylethyl)-2,6-difluorophenyl]-5-fluoropyridin-2-yl}methyl)amino]pyridin-4-yl}-5-methylpiperidin-3-yl)carbamate (19 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{27}$H$_{30}$F$_3$N$_6$ (M+H)$^+$ m/z=495.3; found: 495.3. $^1$H NMR (400 MHz, DMSO-d6) δ 7.96 (t, J=9.0 Hz, 1H), 7.83 (d, J=5.0 Hz, 1H), 7.81 (s, 1H), 7.63 (dd, J=8.7, 3.9 Hz, 1H), 7.51 (d, J=9.1 Hz, 2H), 6.82 (d, J=5.1 Hz, 1H), 5.74 (t, J=5.3 Hz, 1H), 4.61-4.43 (m, 3H), 3.23-3.05 (m, 2H), 2.77 (ddt, J=14.9, 8.5, 4.1 Hz, 2H), 2.14 (t, J=10.5 Hz, 2H), 1.96 (t, J=11.1 Hz, 2H), 1.79 (d, J=1.6 Hz, 6H), 1.70 (s, 1H), 0.78-0.71 (m, 3H) ppm.

104

Example 24B (3R,4R,5S)-3-Amino-5-methyl-1-(3-{[(2',6,6'-trifluorobiphenyl-3-yl)methyl]amino}pyridin-4-yl)piperidin-4-ol

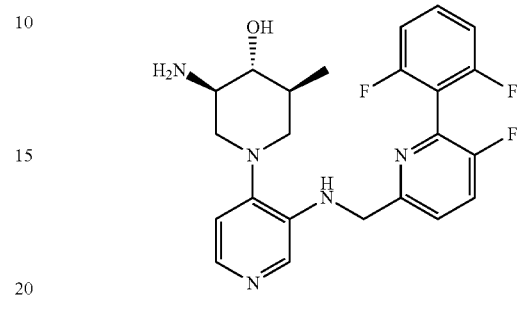

Step 1. tert-Butyl ((3R,4R,5S)-4-{[tert-butyl(dimethyl)silyl]oxy}-1-{3-[(3-chloro-4-fluorobenzyl)amino]pyridin-4-yl}-5-methylpiperidin-3-yl)carbamate

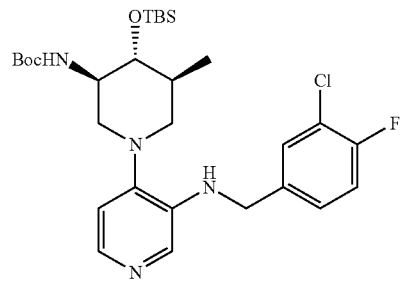 [SMILES: C[C@H]1CN(c2ccncc2NCc2ccc(F)c(Cl)c2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 30.0 mg, 0.0687 mmol) and 3-chloro-4-fluorobenzaldehyde (from Aldrich, 14 mg, 0.089 mmol) were added to toluene (3.0 mL). Then catalytic amount of acetic acid was added to the reaction mixture and the reaction mixture was heated at 100° C. for 2 h. After this time, the reaction mixture was cooled to room temperature and toluene was evaporated under reduced pressure. The resulting intermediate imine was dissolved in methanol (5.0 mL) and the solution was cooled to 0° C. Then sodium tetrahydroborate (6.5 mg, 0.17 mmol) was slowly added to the reaction mixture and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (40 mg, 99%). LCMS calc. for C$_{29}$H$_{45}$ClFN$_4$O$_3$Si (M+H)$^+$ m/z=579.3; found: 579.3.

Step 2. tert-Butyl [(3R,4R,5S)-4-{[tert-butyl(dimethyl)silyl]oxy}-5-methyl-1-(3-{[(2',6,6'-trifluorobiphenyl-3-yl)methyl]amino}pyridin-4-yl)piperidin-3-yl]carbamate

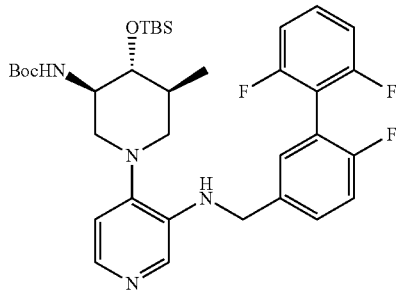 [SMILES: C[C@H]1CN(c2ccncc2NCc2ccc(F)c(-c3c(F)cccc3F)c2)C[C@@H](NC(=O)OC(C)(C)C)[C@@H]1O[Si](C)(C)C(C)(C)C]

tert-Butyl ((3R,4R,5S)-4-{[tert-butyl(dimethyl)silyl]oxy}-1-{3-[(3-chloro-4-fluorobenzyl)amino]pyridin-4-yl}-5-methylpiperidin-3-yl)carbamate (40.0 mg, 0.0690 mmol), chloro(2-dicyclohexylphosphino-2',4',6'-triisopropyl-1,1'-biphenyl)[2-(2'-amino-1,1'-biphenyl)]palladium(II) (Pd XPhos G2) (5.0 mg, 0.0064 mmol), potassium phosphate (40 mg, 0.192 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 2-(2,6-difluorophenyl)-4,4,5,5-tetramethyl-1,3,2-dioxaborolane (26 mg, 0.11 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{35}$H$_{48}$F$_3$N$_4$O$_3$Si (M+H)$^+$ m/z=657.3; found: 657.3.

Step 3. (3R,4R,5S)-3-Amino-5-methyl-1-(3-{[(2',6,6'-trifluorobiphenyl-3-yl)methyl]amino}pyridin-4-yl)piperidin-4-ol tert-Butyl [(3R,4R,5S)-4-{[tert-butyl(dimethyl)silyl]oxy}-5-methyl-1-(3-{[(2',6,6'-trifluorobiphenyl-3-yl)methyl]amino}pyridin-4-yl)piperidin-3-yl]carbamate (21 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{24}$H$_{26}$F$_3$N$_4$O (M+H)$^+$ m/z=443.2; found: 443.2.

Example 25

4-[(3S,5R)-3-Amino-5-methylpiperidin-1-yl]-N-[(2',6,6'-trifluorobiphenyl-3-yl)methyl]pyridin-3-amine

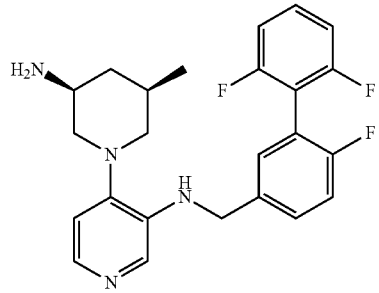 [SMILES: C[C@@H]1C[C@H](N)CN(c2ccncc2NCc2ccc(F)c(-c3c(F)cccc3F)c2)C1]

Step 1. tert-Butyl ((3S,5R)-1-{3-[(3-chloro-4-fluorobenzyl)amino]pyridin-4-yl}-5-methylpiperidin-3-yl)carbamate

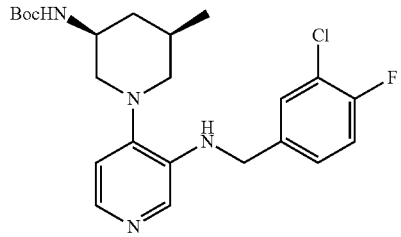 [SMILES: C[C@@H]1C[C@H](NC(=O)OC(C)(C)C)CN(c2ccncc2NCc2ccc(F)c(Cl)c2)C1]

tert-Butyl [(3S,5R)-1-(3-aminopyridin-4-yl)-5-methylpiperidin-3-yl]carbamate (Prepared in Intermediate 2, Step 6; 21.0 mg, 0.0687 mmol) and 3-chloro-4-fluorobenzaldehyde (14 mg, 0.089 mmol) were added to toluene (3 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (3.0 mL) and the solution was cooled to 0° C. Then sodium tetrahydroborate (6.5 mg, 0.17 mmol) was slowly added to the reaction mixture and the resultant reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The crude product was purified by Biotage Isolera to give the desired compound (30 mg, 99%). LCMS calc. for C$_{23}$H$_{31}$ClFN$_4$O$_2$ (M+H)$^+$ m/z=449.2; found: 449.2.

107

Step 2. tert-Butyl [(3S,5R)-5-methyl-1-(3-{[(2',6,6'-trifluorobiphenyl-3-yl)methyl]amino}pyridin-4-yl)piperidin-3-yl]carbamate

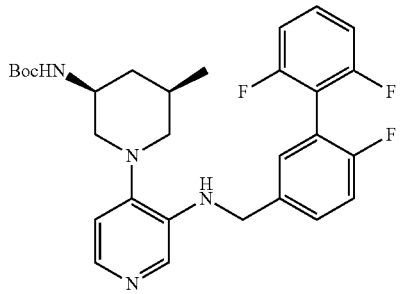 [SMILES: C[C@@H]1C[C@H](NC(=O)OC(C)(C)C)CN(c2ccncc2NCc2ccc(F)c(-c3c(F)cccc3F)c2)C1]

tert-Butyl ((3S,5R)-1-{3-[(3-chloro-4-fluorobenzyl)amino]pyridin-4-yl}-5-methylpiperidin-3-yl)carbamate (31.0 mg, 0.0690 mmol), chloro(2-dicyclohexylphosphino-2',4',6'-triisopropyl-1,1'-biphenyl)[2-(2'-amino-1,1'-biphenyl)]palladium(II) (Pd XPhos G2) (5.0 mg, 0.0064 mmol), potassium phosphate (40 mg, 0.192 mmol) and magnet bar were placed in a vial with septum. the vial was then evacuated and backfilled with nitrogen three times. 1,4-Dioxane (2.5 mL) and degassed water (0.3 mL) were added to the reaction mixture to the reaction mixture. Finally 2-(2,6-difluorophenyl)-4,4,5,5-tetramethyl-1,3,2-dioxaborolane (26 mg, 0.11 mmol) was added to the reaction mixture and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{29}$H$_{34}$F$_3$N$_4$O$_2$ (M+H)$^+$ m/z=527.3; found: 527.3.

Step 3. 4-[(3S,5R)-3-Amino-5-methylpiperidin-1-yl]-N-[(2',6,6'-trifluorobiphenyl-3-yl)methyl]pyridin-3-amine tert-Butyl [(3S,5R)-5-methyl-1-(3-{[(2',6,6'-trifluorobiphenyl-3-yl)methyl]amino}pyridin-4-yl)piperidin-3-yl]carbamate (17 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 µm particle size, gradient elution with acetonitrile/water containing 0.1% NH$_4$OH, at flow rate of 60 mL/min). LCMS calc. for C$_{24}$H$_{26}$F$_3$N$_4$ (M+H)$^+$ m/z=427.2; found: 427.2.

108

Example 26

1-(5'-((4-((3S,5R)-3-Amino-5-methylpiperidin-1-yl)pyridin-3-ylamino)methyl)-2,2',6-trifluorobiphenyl-4-yl)cyclobutanol

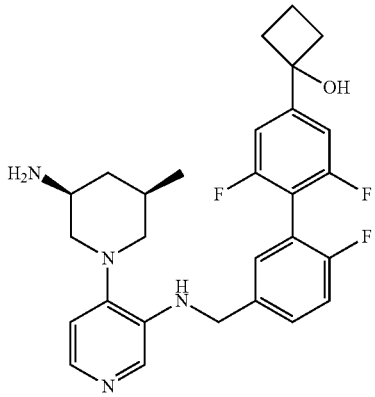 [SMILES: C[C@@H]1C[C@H](N)CN(c2ccncc2NCc2ccc(F)c(-c3c(F)cc(C4(O)CCC4)cc3F)c2)C1]

This compound was synthesized using similar procedures as described in Example 25, using 1-(3,5-difluoro-4-(4,4,5,5-tetramethyl-1,3,2-dioxaborolan-2-yl)phenyl)cyclobutanol (from Example 7, Step 2) to replace 2-(2,6-difluorophenyl)-4,4,5,5-tetramethyl-1,3,2-dioxaborolane in Step 2. LCMS calc. for C$_{28}$H$_{32}$F$_3$N$_4$O (M+H)$^+$ m/z=497.3; found: 497.2. $^1$H NMR (400 MHz, DMSO-d6) δ 7.78 (d, J=5.1 Hz, 1H), 7.75 (s, 1H), 7.57-7.49 (m, 1H), 7.47 (d, J=6.9 Hz, 1H), 7.35 (d, J=9.6 Hz, 1H), 7.30 (d, J=9.6 Hz, 2H), 6.81 (d, J=5.1 Hz, 1H), 5.82 (s, 1H), 5.36 (t, J=6.2 Hz, 1H), 4.44 (d, J=5.9 Hz, 2H), 3.18 (dd, J=31.1, 8.1 Hz, 1H), 3.00-2.84 (m, 1H), 2.43 (ddd, J=12.4, 8.9, 5.4 Hz, 3H), 2.34-2.24 (m, 3H), 2.10 (t, J=10.6 Hz, 1H), 2.07-1.65 (m, 6H), 0.86 (d, J=6.4 Hz, 3H), 0.76 (q, J=12.0 Hz, 1H) ppm.

Example 27

4-(5'-((4-((3S,5R)-3-Amino-5-methylpiperidin-1-yl)pyridin-3-ylamino)methyl)-2,2',6-trifluorobiphenyl-4-yl)tetrahydro-2H-pyran-4-ol

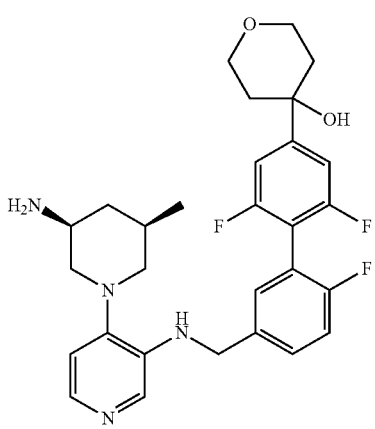 [SMILES: C[C@@H]1C[C@H](N)CN(c2ccncc2NCc2ccc(F)c(-c3c(F)cc(C4(O)CCOCC4)cc3F)c2)C1]

This compound was synthesized using similar procedures as described in Example 25, using 4-(3,5-difluoro-4-(4,4,5, 5-tetramethyl-1,3,2-dioxaborolan-2-yl)phenyl)tetrahydro-2H-pyran-4-ol (Prepared by an analogous route to that described in Example 3) to replace 2-(2,6-difluorophenyl)-4,4,5,5-tetramethyl-1,3,2-dioxaborolane in Step 2. LCMS calc. for $C_{29}H_{34}F_3N_4O_2$ (M+H)$^+$ m/z=527.3; found: 527.3.

Example 28

(3R,4R,5S)-3-Amino-1-[3-({[6-(2,6-difluorophenyl)pyridin-2-yl]methyl}amino)pyridin-4-yl]-5-methyl-piperidin-4-ol

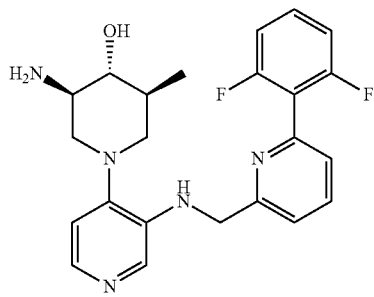 [SMILES: C[C@H]1CN(c2ccncc2NCc2cccc(-c3c(F)cccc3F)n2)C[C@@H](N)[C@@H]1O]

Step 1. Methyl 6-(2,6-difluorophenyl)pyridine-2-carboxylate

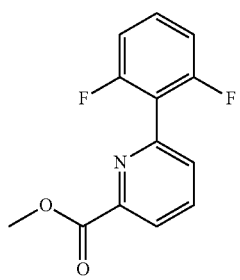 [SMILES: COC(=O)c1cccc(-c2c(F)cccc2F)n1]

Methyl 6-bromopyridine-2-carboxylate (from Aldrich, 300 mg, 1.39 mmol), chloro(2-dicyclohexylphosphino-2',4',6'-triisopropyl-1,1'-biphenyl)[2-(2'-amino-1,1'-biphenyl)] palladium(II) (Pd XPhos G2) (110 mg, 0.14 mmol), potassium phosphate (880 mg, 4.2 mmol) and magnet bar were placed in a vial with septum. The vial was then evacuated and backfilled with nitrogen three times. 1,4-Dioxane (10 mL) and degassed water (2 mL) were added to the reaction mixture. Finally 2-(2,6-difluorophenyl)-4,4,5,5-tetramethyl-1,3,2-dioxaborolane (583 mg, 2.43 mmol) was added and the reaction mixture was stirred at 65° C. for 1 h. Then the reaction mixture was diluted with EtOAc. The resulting solution was washed with brine, dried over $Na_2SO_4$ and solvent evaporated. The crude product was purified by Biotage Isolera to give the desired compound (284 mg, 82%). LCMS calc. for $C_{13}H_{10}F_2NO_2$ (M+H)$^+$ m/z=250.1; found: 250.1.

Step 2. 6-(2,6-Difluorophenyl)pyridine-2-carboxylic acid

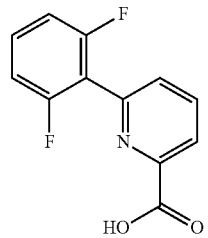 [SMILES: O=C(O)c1cccc(-c2c(F)cccc2F)n1]

6-(2,6-Difluorophenyl)pyridine-2-carboxylate (284 mg, 1.14 mmol) was dissolved in tetrahydrofuran (6 mL). Then methanol (4 mL) and 1.0M solution of sodium hydroxide in water (2 mL, 2 mmol) were added and reaction mixture was stirred at room temperature for 30 min. After this time pH was adjusted to 5 by addition of the 1M solution of HCl. The product was then extracted with EtOAc and organic phase was washed with brine and dried over $Na_2SO_4$. The solvents were evaporated under reduced pressure. Obtained solid product was used in the next step without further purification (260 mg, 96%). LCMS calc. for $C_{12}H_8F_2NO_2$ (M+H)$^+$ m/z=236.1; found 236.0.

Step 3. [6-(2,6-Difluorophenyl)pyridin-2-yl]methanol

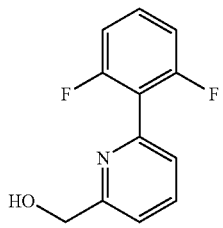 [SMILES: OCc1cccc(-c2c(F)cccc2F)n1]

To a solution of 6-(2,6-difluorophenyl)pyridine-2-carboxylic acid (260 mg, 1.1 mmol) and triethylamine (162 µL, 1.16 mmol) in tetrahydrofuran (3 mL) was slowly added isobutyl chloroformate (0.15 mL, 1.16 mmol). The reaction mixture was stirred at room temperature for 1 h. The formed precipitate was filtered off and to obtained clear solution was slowly added the solution of sodium tetrahydroborate (84 mg, 2.2 mmol) in water (1 mL). Reaction mixture was stirred at room temperature for 30 min. Then water was added and the product was extracted with EtOAc. Combined organic fractions were washed with brine and dried over $Na_2SO_4$. After evaporation of the solvents under reduced pressure, obtained product was used in the next step without further purification (116 mg, 48%). LCMS calc. for $C_{12}H_{10}F_2NO$ (M+H)$^+$ m/z=222.1; found 222.1.

Step 4.
6-(2,6-Difluorophenyl)pyridine-2-carbaldehyde

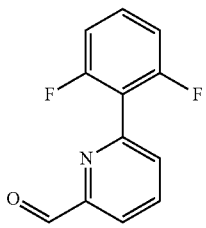 [SMILES: O=Cc1cccc(-c2c(F)cccc2F)n1]

To a stirred solution of [6-(2,6-difluorophenyl)pyridin-2-yl]methanol (116 mg, 0.524 mmol) in DCM (4 mL) at 0° C. were added pyridine (51 μL, 0.63 mmol) and Dess-Martin periodinane (234 mg, 0.551 mmol). The reaction mixture was stirred at room temperature for 3 h. Then saturated solutions of NaHCO$_3$ in water (10 mL) and Na$_2$S$_2$O$_3$ in water (5 mL) were added and the reaction mixture was stirred for 30 min. Then the product was extracted with DCM. Combined organic fractions were washed with brine, dried over Na$_2$SO$_4$ and solvents were evaporated under reduced pressure. The crude product was purified by Biotage Isolera to give the desired compound (95 mg, 83%). LCMS calc. for C$_{12}$H$_8$F$_2$NO (M+H)$^+$ m/z=220.1; found: 220.1.

Step 5. tert-Butyl {(3R,4R,4R,5S)-4-{[tert-butyl(dimethyl)silyl]oxy}-1-[3-({[6-(2,6-difluorophenyl)pyridin-2-yl]methyl}amino)pyridin-4-yl]-5-methylpiperidin-3-yl}carbamate

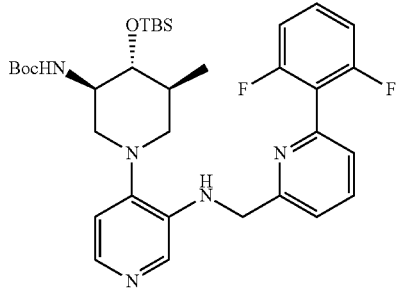 [SMILES: C[C@H]1CN(c2ccncc2NCc2cccc(-c3c(F)cccc3F)n2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 20.0 mg, 0.0458 mmol) and 6-(2,6-difluorophenyl)pyridine-2-carbaldehyde (12 mg, 0.055 mmol) were dissolved in toluene (2.0 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (2.0 mL) and resulting solution was cooled to 0° C. Then sodium tetrahydroborate (3.5 mg, 0.092 mmol) was slowly added and the reaction mixture was stirred at room temperature for 30 min. After this time, water was added to the reaction mixture and product was extracted with EtOAc. Combined organic fractions were washed with brine, dried over Na$_2$SO$_4$ and solvents were evaporated under reduced pressure. The resulting crude product was used in the next step without further purification. LCMS calc. for C$_{34}$H$_{48}$F$_2$N$_5$O$_3$Si (M+H)$^+$ m/z=640.4; found: 640.3.

Step 6. (3R,4R,5S)-3-Amino-1-[3-({[6-(2,6-difluorophenyl)pyridin-2-yl]methyl}amino)pyridin-4-yl]-5-methylpiperidin-4-ol tert-Butyl {(3R,4R,5S)-4-{[tert-butyl(dimethyl)silyl]oxy}-1-[3-({[6-(2,6-difluorophenyl)pyridin-2-yl]methyl}amino)pyridin-4-yl]-5-methylpiperidin-3-yl}carbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{23}$H$_{26}$F$_2$N$_5$O (M+H)$^+$ m/z=426.2; found: 426.2.

Example 29

4-[(3S,5R)-3-Amino-5-methylpiperidin-1-yl]-N-{[6-(2,6-difluorophenyl)pyridin-2-yl]methyl}pyridin-3-amine

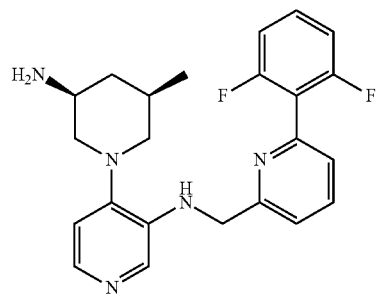 [SMILES: C[C@@H]1C[C@H](N)CN(c2ccncc2NCc2cccc(-c3c(F)cccc3F)n2)C1]

Step 1. tert-Butyl {(3S,5R)-1-[3-({[6-(2,6-difluorophenyl)pyridin-2-yl]methyl}amino)pyridin-4-yl]-5-methylpiperidin-3-yl}carbamate

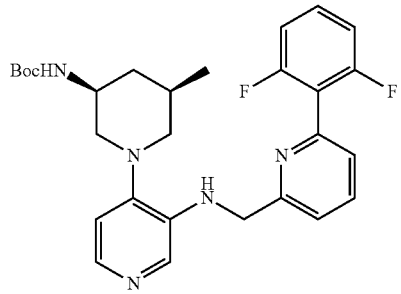 [SMILES: C[C@@H]1C[C@H](NC(=O)OC(C)(C)C)CN(c2ccncc2NCc2cccc(-c3c(F)cccc3F)n2)C1]

tert-Butyl [(3S,5R)-1-(3-aminopyridin-4-yl)-5-methylpiperidin-3-yl]carbamate (Prepared in Intermediate 2, Step 6; 14.0 mg, 0.0458 mmol) and 6-(2,6-difluorophenyl)pyridine-2-carbaldehyde (Prepared in Example 28, Step 4; 12 mg, 0.055 mmol) were dissolved in toluene (2 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (1 mL) and resulting solution was cooled to 0° C. Then sodium tetrahydroborate (3.5 mg, 0.092 mmol) was slowly added and the reaction mixture was stirred at room temperature for 30 min. After this time, water was added to the reaction mixture and product was extracted with EtOAc. Combined organic fractions were washed with brine, dried over $Na_2SO_4$ and solvents were evaporated under reduced pressure. The resulting crude product was used in the next step without further purification. LCMS calc. for $C_{28}H_{34}F_2N_5O_2$ $(M+H)^+$ m/z=510.3; found: 510.3.

Step 2. 4-[(3S,5R)-3-Amino-5-methylpiperidin-1-yl]-N-{[6-(2,6-difluorophenyl)pyridin-2-yl]methyl}pyridin-3-amine tert-Butyl {(3S,5R)-1-[3-({[6-(2,6-difluorophenyl)pyridin-2-yl]methyl}amino)pyridin-4-yl]-5-methylpiperidin-3-yl}carbamate (16 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 µm particle size, gradient elution with acetonitrile/water containing 0.1% $NH_4OH$, at flow rate of 60 mL/min). LCMS calc. for $C_{23}H_{26}F_2N_5$ $(M+H)^+$ m/z=410.2; found: 410.1.

Example 30

(3R,4R,5S)-3-Amino-1-[3-({[2-(2,6-difluorophenyl)pyrimidin-4-yl]methyl}amino)pyridin-4-yl]-5-methylpiperidin-4-ol

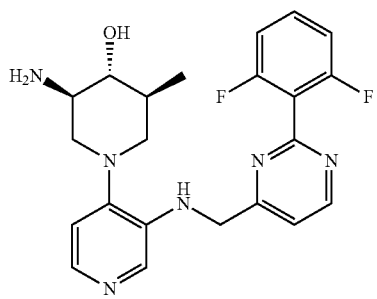

Step 1. (2-Chloropyrimidin-4-yl)methanol

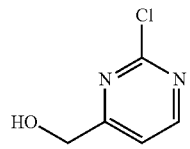

To a solution of 2-chloropyrimidine-4-carboxylic acid (from Combi-Blocks, 250 mg, 1.6 mmol) and triethylamine (231 µL, 1.66 mmol) in tetrahydrofuran (5 mL) was slowly added isobutyl chloroformate (0.22 mL, 1.66 mmol). Reaction mixture was stirred at room temperature for 1 h. The formed precipitate was filtered off and to obtained clear solution was slowly added solution of sodium tetrahydroborate (120 mg, 3.2 mmol) in water (1 mL). Reaction mixture was stirred at room temperature for 30 min. Then water was added and the product was extracted with EtOAc. Combined organic fractions were washed with brine and dried with $Na_2SO_4$. After evaporation of the solvents under reduced pressure, obtained product was used in the next step without further purification (223 mg, 96%). LCMS calc. for $C_5H_6ClN_2O$ $(M+H)^+$ m/z=145.0; found 145.0.

Step 2. [2-(2,6-Difluorophenyl)pyrimidin-4-yl]methanol

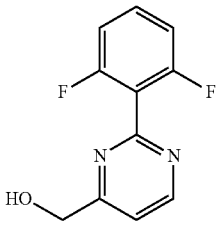 [SMILES: OCc1ccnc(-c2c(F)cccc2F)n1]

(2-Chloropyrimidin-4-yl)methanol (223 mg, 1.54 mmol), chloro(2-dicyclohexylphosphino-2',4',6'-triisopropyl-1,1'-biphenyl)[2-(2'-amino-1,1'-biphenyl)]palladium(II) (Pd XPhos G2) (120 mg, 0.15 mmol), potassium phosphate (980 mg, 4.6 mmol) and magnet bar were placed in a vial with septum. The vial was then evacuated and backfilled with nitrogen three times. 1,4-Dioxane (12 mL) and degassed water (2 mL) were added. Finally 2-(2,6-difluorophenyl)-4,4,5,5-tetramethyl-1,3,2-dioxaborolane (590 mg, 2.5 mmol) was added and the reaction mixture was stirred at 65° C. for 1 h. Then the reaction mixture was diluted with EtOAc. The resulting solution was washed with brine, dried over $Na_2SO_4$ and solvent evaporated. The crude product was purified by Biotage Isolera to give the desired compound (321 mg, 94%). LCMS calc. for $C_{11}H_9F_2N_2O$ $(M+H)^+$ m/z=223.1; found: 223.1.

Step 3. 2-(2,6-Difluorophenyl)pyrimidine-4-carbaldehyde

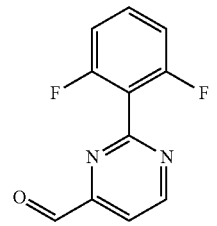 [SMILES: O=Cc1ccnc(-c2c(F)cccc2F)n1]

To a stirred solution of [2-(2,6-difluorophenyl)pyrimidin-4-yl]methanol (321 mg, 1.44 mmol) in DCM (10 mL) at 0° C. were added pyridine (140 µL, 1.7 mmol) and Dess-Martin periodinane (643 mg, 1.52 mmol). The reaction mixture was stirred at room temperature for 3 h. Then saturated solutions of $NaHCO_3$ in water (10 mL) and $Na_2S_2O_3$ in water (5 mL) were added and the reaction mixture was stirred for 30 min.

Then product was extracted with DCM. Combined organic fractions were washed with brine, dried over Na₂SO₄ and solvents were evaporated under reduced pressure. The crude product was purified by Biotage Isolera to give the desired compound (244 mg, 77%). LCMS calc. for $C_{11}H_7F_2N_2O$ (M+H)⁺ m/z=221.1; found: 221.0.

Step 4. tert-Butyl {(3R,4R,5S)-4-{[tert-butyl(dimethyl)silyl]oxy}-1-[3-({[2-(2,6-difluorophenyl)pyrimidin-4-yl]methyl}amino)pyridin-4-yl]-5-methylpiperidin-3-yl}carbamate

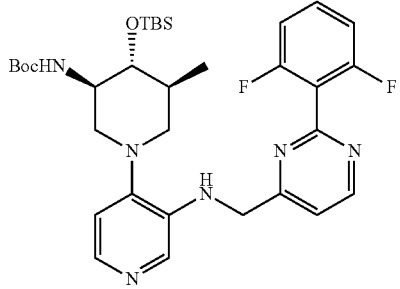 [SMILES: C[C@H]1CN(c2ccncc2NCc2ccnc(-c3c(F)cccc3F)n2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 20.0 mg, 0.0458 mmol) and 2-(2,6-difluorophenyl)pyrimidine-4-carbaldehyde (12 mg, 0.055 mmol) were dissolved in toluene (2.0 mL). Then catalytic amount of acetic acid was added and the reaction mixture was heated at 100° C. for 2 h. After this time, the reaction mixture was cooled to room temperature and toluene was evaporated under reduced pressure. The resulting intermediate imine was dissolved in methanol (2.0 mL) and resulting solution was cooled to 0° C. Then sodium tetrahydroborate (3.5 mg, 0.092 mmol) was slowly added and the reaction mixture was stirred at room temperature for 30 min. After this time, water was added to the reaction mixture and product was extracted with EtOAc. Combined organic fractions were washed with brine, dried over Na₂SO₄ and solvents were evaporated under reduced pressure. The resulting crude product was used in the next step without further purification. LCMS calc. for $C_{33}H_{47}F_2N_6O_3Si$ (M+H)⁺ m/z=641.3; found: 641.4.

Step 5. (3R,4R,5S)-3-Amino-1-[3-({[2-(2,6-difluorophenyl)pyrimidin-4-yl]methyl}amino)pyridin-4-yl]-5-methylpiperidin-4-ol tert-Butyl {(3R,4R,5S)-4-{[tert-butyl(dimethyl)silyl]oxy}-1-[3-({[2-(2,6-difluorophenyl)pyrimidin-4-yl]methyl}amino)pyridin-4-yl]-5-methylpiperidin-3-yl}carbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH₄OH, at flow rate of 60 mL/min). LCMS calc. for $C_{22}H_{25}F_2N_6O$ (M+H)⁺ m/z=427.2; found: 427.2.

Example 31

4-[(3S,5R)-3-Amino-5-methylpiperidin-1-yl]-N-{[2-(2,6-difluorophenyl)pyrimidin-4-yl]methyl}pyridin-3-amine

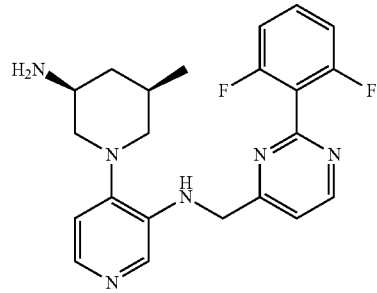

Step 1. tert-Butyl {(3S,5R)-1-[3-({[2-(2,6-difluorophenyl)pyrimidin-4-yl]methyl}amino)pyridin-4-yl]-5-methylpiperidin-3-yl}carbamate

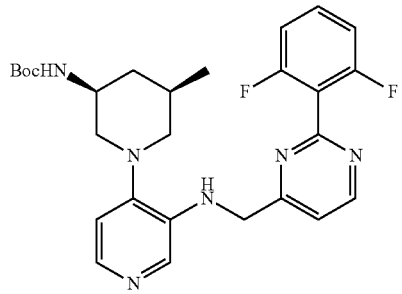

tert-Butyl [(3S,5R)-1-(3-aminopyridin-4-yl)-5-methylpiperidin-3-yl]carbamate (Prepared in Intermediate 2, Step 6; 14.0 mg, 0.0458 mmol) and 2-(2,6-difluorophenyl)pyrimidine-4-carbaldehyde (Prepared in Example 30, Step 3; 12 mg, 0.055 mmol) were dissolved in toluene (2 mL). Then catalytic amount of acetic acid was added and the reaction was heated at 100° C. for 2 h. After this time, the reaction mixture was cooled to room temperature and toluene was evaporated under reduced pressure. The resulting intermediate imine was dissolved in methanol (1 mL) and resulting solution was cooled to 0° C. Then sodium tetrahydroborate (3.5 mg, 0.092 mmol) was slowly added and the reaction mixture was stirred at room temperature for 30 min. After this time, water was added to the reaction mixture and product was extracted with EtOAc. Combined organic fractions were washed with brine, dried over Na₂SO₄ and solvents were evaporated under reduced pressure. The resulting crude product was used in the next step without further purification. LCMS calc. for $C_{27}H_{33}F_2N_6O_2$ (M+H)⁺ m/z=511.3; found: 511.2.

Step 2. 4-[(3S,5R)-3-Amino-5-methylpiperidin-1-yl]-N-{[2-(2,6-difluorophenyl)pyrimidin-4-yl]methyl}pyridin-3-amine tert-Butyl {(3S,5R)-1-[3-({[2-(2,6-difluorophenyl)pyrimidin-4-yl]methyl}amino)pyridin-4-yl]-5-methylpiperidin-3-yl}carbamate (16 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{22}$H$_{25}$F$_2$N$_6$ (M+H)$^+$ m/z=411.2; found: 411.2.

Example 32

(3R,4R,5S)-3-Amino-1-(3-(((6-(2,6-difluoro-4-morpholinophenyl)-5-fluoropyridin-2-yl)methyl)amino)pyridin-4-yl)-5-methylpiperidin-4-ol

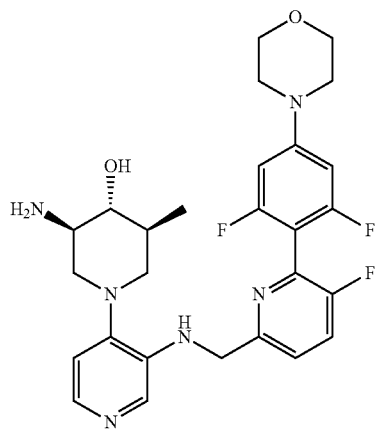 [SMILES: C[C@H]1CN(c2ccncc2NCc2ccc(F)c(-c3c(F)cc(N4CCOCC4)cc3F)n2)C[C@@H](N)[C@@H]1O]

Step 1. 4-(3,5-Difluorophenyl)morpholine

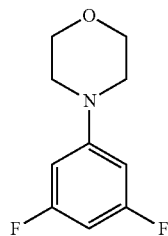

1-Bromo-3,5-difluorobenzene (Sigma-Aldrich, 600 μL, 5.2 mmol), cesium carbonate (4.2 g, 13 mmol) and chloro(2-dicyclohexylphosphino-2',6'-diisopropoxy-1,1'-biphenyl)[2-(2'-amino-1,1'-biphenyl)]palladium (210 mg, 0.26 mmol) were placed in a vial. The vial was then evacuated and backfilled with nitrogen three times. After this 1,4-dioxane (8 mL) and morpholine (900 μL, 10 mmol) were added to the reaction mixture. The reaction mixture was stirred at 110° C. overnight. After this time the reaction was quenched by the addition of water and the product was extracted with EtOAc. Combined organic fractions were washed with brine, dried over Na$_2$SO$_4$ and the solvents were evaporated under reduced pressure. The crude product was purified by Biotage Isolera to give the desired compound (450 mg, 45%). LCMS calc. for C$_{10}$H$_{12}$F$_2$NO (M+H)$^+$ m/z=200.1; found: 200.0.

Step 2. 4-[3,5-Difluoro-4-(4,4,5,5-tetramethyl-1,3,2-dioxaborolan-2-yl)phenyl]morpholine

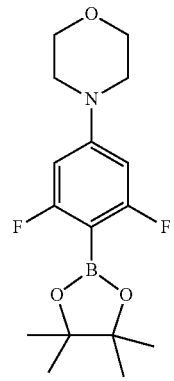 [SMILES: CC1(C)OB(c2c(F)cc(N3CCOCC3)cc2F)OC1(C)C]

4-(3,5-Difluorophenyl)morpholine (250 mg, 1.26 mmol) and a magnet bar were placed in a vial. The vial was evacuated and backfilled with nitrogen three times. After addition of tetrahydrofuran (6.0 mL), the reaction mixture was cooled to −78° C. Then 1.6M solution of n-butyllithium in hexanes (780 μL, 1.2 mmol) was slowly added and the reaction mixture was stirred at −78° C. for 1 h. After this time 2-isopropoxy-4,4,5,5-tetramethyl-1,3,2-dioxaborolane (510 μL, 2.5 mmol) was slowly added to the reaction mixture. After stirring at −78° C. for 5 min, the reaction mixture was allowed to warm to room temperature and was stirred at room temperature for 1 h. After this time the reaction was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (305 mg, 75%). LCMS calc. for C$_{16}$H$_{23}$BF$_2$NO$_3$ (M+H)$^+$ m/z=326.2; found: 326.1.

Step 3. tert-Butyl ((3R,4R,5S)-4-((tert-butyldimethylsilyl)oxy)-1-(3-(((6-(2,6-difluoro-4-morpholinophenyl)-5-fluoropyridin-2-yl)methyl)amino)pyridin-4-yl)-5-methylpiperidin-3-yl)carbamate

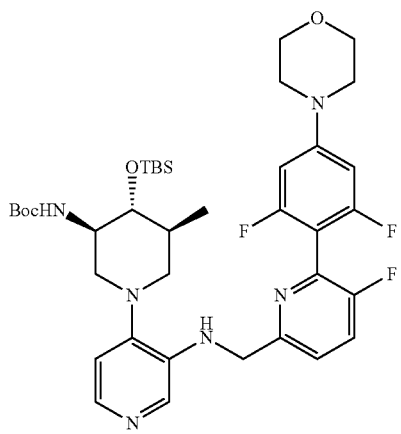 [SMILES: C[C@H]1CN(c2ccncc2NCc2ccc(F)c(-c3c(F)cc(N4CCOCC4)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (Intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 4-[3,5-difluoro-4-(4,4,5,5-tetramethyl-1,3,2-dioxaborolan-2-yl)phenyl]morpholine (Prepared in Example 32, Step 2; 17 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{38}H_{54}F_3N_6O_4Si$ $(M+H)^+$ m/z=743.4; found: 743.4.

Step 4. (3R,4R,5S)-3-Amino-1-(3-(((6-(2,6-difluoro-4-morpholinophenyl)-5-fluoropyridin-2-yl)methyl)amino)pyridin-4-yl)-5-methylpiperidin-4-ol tert-Butyl ((3R,4R,5S)-4-((tert-butyldimethylsilyl)oxy)-1-(3-(((6-(2,6-difluoro-4-morpholinophenyl)-5-fluoropyridin-2-yl)methyl)amino)pyridin-4-yl)-5-methylpiperidin-3-yl)carbamate (24 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{27}H_{32}F_3N_6O_2$ $(M+H)^+$ m/z=529.3; found: 529.3.

Example 33

4-((3S,5R)-3-Amino-5-methylpiperidin-1-yl)-N-((6-(2,6-difluoro-4-morpholinophenyl)-5-fluoropyridin-2-yl)methyl)pyridin-3-amine

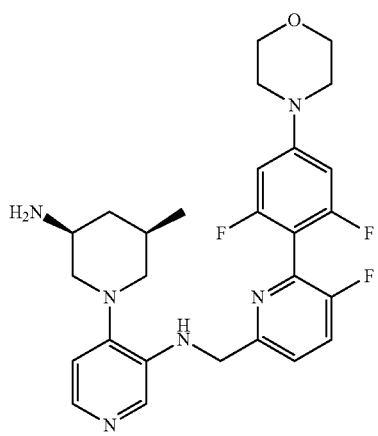 [SMILES: C[C@@H]1C[C@H](N)CN(c2ccncc2NCc2ccc(F)c(-c3c(F)cc(N4CCOCC4)cc3F)n2)C1]

Step 1. tert-butyl ((3S,5R)-1-(3-(((6-(2,6-difluoro-4-morpholinophenyl)-5-fluoropyridin-2-yl)methyl)amino)pyridin-4-yl)-5-methylpiperidin-3-yl)carbamate

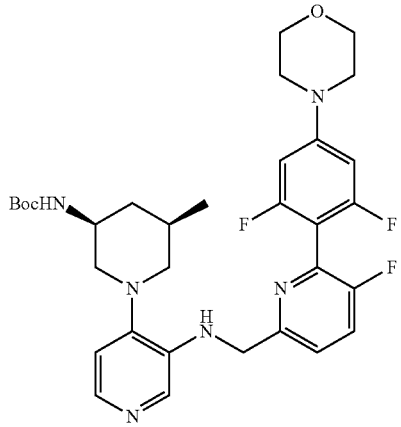 [SMILES: C[C@@H]1C[C@H](NC(=O)OC(C)(C)C)CN(c2ccncc2NCc2ccc(F)c(-c3c(F)cc(N4CCOCC4)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture to the reaction mixture. Finally 4-[3,5-Difluoro-4-(4,4,5,5-tetramethyl-1,3,2-dioxaborolan-2-yl)phenyl]morpholine (Prepared in Example 32, Step 2; 17 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{32}H_{40}F_3N_6O_3$ $(M+H)^+$ m/z=613.3; found: 613.3.

Step 2. 4-((3S,5R)-3-Amino-5-methylpiperidin-1-yl)-N-((6-(2,6-difluoro-4-morpholinophenyl)-5-fluoropyridin-2-yl)methyl)pyridin-3-amine tert-Butyl (3S,5R)-1-(3-((6-(2,6-difluoro-4-morpholinophenyl)-5-fluoropyridin-2-yl)methylamino)pyridin-4-yl)-5-methylpiperidin-3-ylcarbamate (20 mg, 0.032 mmol) was dissolved in methanol (2 mL). Then 4.0M solution of HCl in dioxane (1 mL, 4 mmol) was added to the reaction mixture to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{27}H_{32}F_3N_6O$ $(M+H)^+$ m/z=513.3; found: 513.2. $^1H$ NMR (400 MHz, DMSO-d6) δ 7.88-7.81 (m, 2H), 7.79 (s, 1H), 7.52 (dd, J=8.6, 3.8 Hz, 1H), 6.87-6.77 (m, 3H), 5.73 (t, J=5.4 Hz, 1H), 4.58-4.40 (m, 3H), 3.81-3.71 (m, 4H), 3.30-3.26 (m, 4H), 3.26-3.11 (m, 2H), 2.91 (d, J=10.8 Hz, 1H), 2.20 (t, J=10.6 Hz, 1H), 2.00 (t, J=11.1 Hz, 1H), 1.86 (d, J=12.1 Hz, 1H), 1.77 (d, J=10.8 Hz, 1H), 0.87-0.74 (m, 4H) ppm.

Example 34

4-((3S, 5R)-3-Amino-5-(trifluoromethyl)piperidin-1-yl)-N-((6-(2,6-difluoro-4-morpholinophenyl)-5-fluoropyridin-2-yl)methyl)pyridin-3-amine

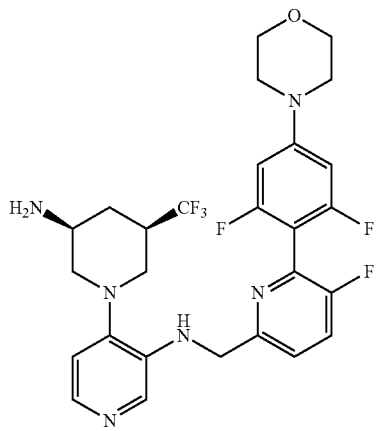 [SMILES: N[C@H]1C[C@@H](C(F)(F)F)CN(c2ccncc2NCc2ccc(F)c(-c3c(F)cc(N4CCOCC4)cc3F)n2)C1]

Step 1. tert-butyl ((3S,5R)-1-(3-(((6-(2,6-difluoro-4-morpholinophenyl)-5-fluoropyridin-2-yl)methyl)amino)pyridin-4-yl)-5-(trifluoromethyl)piperidin-3-yl)carbamate

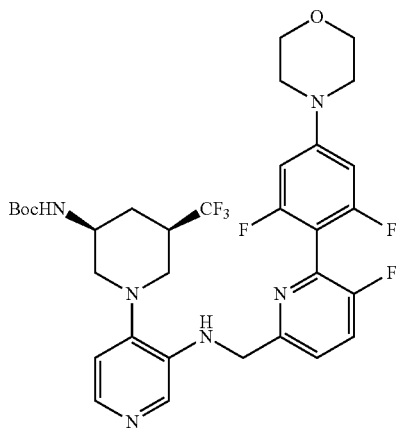 [SMILES: CC(C)(C)OC(=O)N[C@H]1C[C@@H](C(F)(F)F)CN(c2ccncc2NCc2ccc(F)c(-c3c(F)cc(N4CCOCC4)cc3F)n2)C1]

tert-Butyl ((3S,5R)-1-(3-(((6-bromo-5-fluoropyridin-2-yl)methyl)amino)pyridin-4-yl)-5-(trifluoromethyl)piperidin-3-yl)carbamate (intermediate 3, 17.5 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally, 4-[3,5-difluoro-4-(4,4,5,5-tetramethyl-1,3,2-dioxaborolan-2-yl)phenyl]morpholine (Prepared in Example 32, Step 2; 17 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{32}H_{37}F_6N_6O_3$ $(M+H)^+$ m/z=667.3; found: 667.3.

Step 2. 4-((3S,5R)-3-amino-5-(trifluoromethyl)piperidin-1-yl)-N-((6-(2,6-difluoro-4-morpholinophenyl)-5-fluoropyridin-2-yl)methyl)pyridin-3-amine tert-Butyl (3S,5R)-1-(3-((6-(2,6-difluoro-4-morpholinophenyl)-5-fluoropyridin-2-yl)methylamino)pyridin-4-yl)-5-(trifluoromethyl)piperidin-3-ylcarbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{27}H_{29}F_6N_6O$ $(M+H)^+$ m/z=567.2; found: 567.2. $^1H$ NMR (400 MHz, DMSO-d6) δ 7.89-7.80 (m, 3H), 7.50 (dd, J=8.6, 3.8 Hz, 1H), 6.91 (d, J=5.1 Hz, 1H), 6.80 (d, J=11.8 Hz, 1H), 5.86 (t, J=5.5 Hz, 1H), 4.60-4.44 (m, 2H), 3.80-3.69 (m, 4H), 3.45-3.35 (m, 1H), 3.30-3.26 (m, 4H), 3.24-3.15 (m, 2H), 2.97-2.83 (m, 1H), 2.80-2.66 (m, 1H), 2.43-2.26 (m, 2H), 2.01 (d, J=12.0 Hz, 1H), 1.70 (br, 1H), 1.16 (q, J=12.3 Hz, 1H) ppm.

Example 35

(3R,4R,5S)-3-Amino-1-{3-[({6-[2,6-difluoro-4-(hydroxymethyl)phenyl]-5-fluoropyridin-2-yl}methyl)amino]pyridin-4-yl}-5-methylpiperidin-4-ol

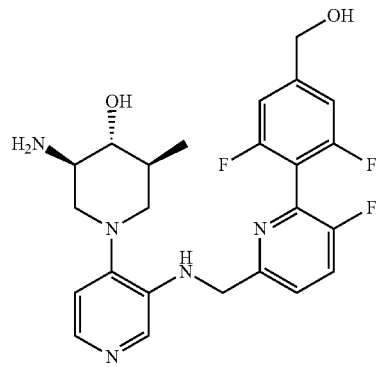 [SMILES: C[C@H]1CN(c2ccncc2NCc2ccc(F)c(-c3c(F)cc(CO)cc3F)n2)C[C@@H](N)[C@@H]1O]

Step 1. [3,5-Difluoro-4-(4,4,5,5-tetramethyl-1,3,2-dioxaborolan-2-yl)phenyl]methanol

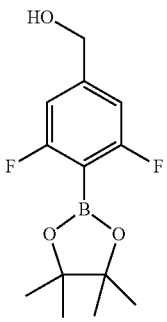

To a solution of 3,5-difluoro-4-(4,4,5,5-tetramethyl-1,3,2-dioxaborolan-2-yl)benzaldehyde (Sigma-Aldrich, 500.0 mg, 1.865 mmol) in methanol (10 mL) was slowly added sodium tetrahydroborate (150 mg, 3.9 mmol) at 0° C. Reaction mixture was stirred at room temperature for 1 h. Then the reaction mixture was diluted with EtOAc. The resulting solution was washed with brine, dried over Na$_2$SO$_4$ and solvents were evaporated under reduced pressure. The resulting crude product was used in the next step without further purification.

Step 2. tert-Butyl ((3R,4R,5S)-4-{[tert-butyl(dimethyl)silyl]oxy}-1-{3-[({6-[2,6-difluoro-4-(hydroxymethyl)phenyl]-5-fluoropyridin-2-yl}methyl)amino]pyridin-4-yl}-5-methylpiperidin-3-yl)carbamate

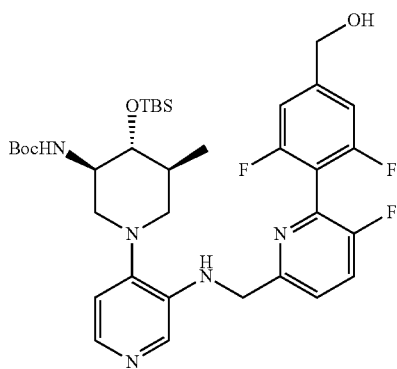 [SMILES: C[C@H]1CN(c2ccncc2NCc2ccc(F)c(-c3c(F)cc(CO)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally [3,5-difluoro-4-(4,4,5,5-tetramethyl-1,3,2-dioxaborolan-2-yl)phenyl]methanol (14 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{35}$H$_{49}$F$_3$N$_5$O$_4$Si (M+H)$^+$ m/z=688.4; found: 688.4.

Step 3. (3R,4R,5S)-3-Amino-1-{3-[({6-[2,6-difluoro-4-(hydroxymethyl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(hydroxymethyl)phenyl]-5-fluoropyridin-2-yl}methyl)amino]pyridin-4-yl}-5-methylpiperidin-3-yl)carbamate (22 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{24}$H$_{27}$F$_3$N$_5$O$_2$ (M+H)$^+$ m/z=474.2; found: 474.2. $^1$H NMR (400 MHz, DMSO-d6) δ 7.90 (t, J=9.0 Hz, 1H), 7.80 (d, J=5.1 Hz, 1H), 7.75 (s, 1H), 7.56 (dd, J=8.7, 3.9 Hz, 1H), 7.20 (d, J=8.6 Hz, 2H), 6.83 (d, J=5.1 Hz, 1H), 5.61 (t, J=5.8 Hz, 1H), 5.53 (br, 1H), 4.75 (d, J=4.5 Hz, 1H), 4.61 (d, J=4.3 Hz, 2H), 4.57-4.50 (m, 2H), 3.26-3.15 (m, 2H), 2.77-2.63 (m, 2H), 2.33 (t, J=10.6 Hz, 1H), 2.23 (t, J=11.5 Hz, 1H), 1.80-1.65 (m, 1H), 1.57 (br, 1H), 0.88 (d, J=6.6 Hz, 3H) ppm.

Example 36

(4-{6-[({4-[(3S,5R)-3-Amino-5-methylpiperidin-1-yl]pyridin-3-yl}amino)methyl]-3-fluoropyridin-2-yl}-3,5-difluorophenyl)methanol

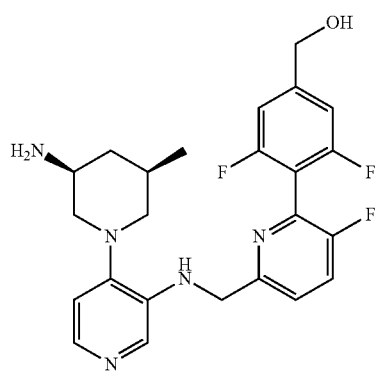 [SMILES: C[C@@H]1C[C@H](N)CN(c2ccncc2NCc2ccc(F)c(-c3c(F)cc(CO)cc3F)n2)C1]

Step 1. tert-Butyl ((3S,5R)-1-{3-[({6-[2,6-difluoro-4-(hydroxymethyl)phenyl]-5-fluoropyridin-2-yl}methyl)amino]pyridin-4-yl}-5-methylpiperidin-3-yl)carbamate

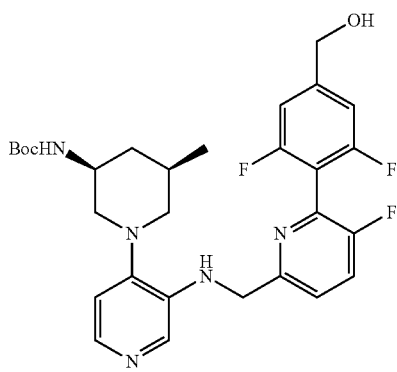 [SMILES: C[C@@H]1C[C@H](NC(=O)OC(C)(C)C)CN(c2ccncc2NCc2ccc(F)c(-c3c(F)cc(CO)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally [3,5-difluoro-4-(4,4,5,5-tetramethyl-1,3,2-dioxaborolan-2-yl)phenyl]methanol (14 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{29}$H$_{35}$F$_3$N$_5$O$_3$ (M+H)$^+$ m/z=558.3; found: 558.2.

Step 2. (4-{6-[({4-[(3S,5R)-3-Amino-5-methylpiperidin-1-yl]pyridin-3-yl}amino)methyl]-3-fluoropyridin-2-yl}-3,5-difluorophenyl)methanol tert-Butyl ((3S,5R)-1-{3-[({6-[2,6-difluoro-4-(hydroxymethyl)phenyl]-5-fluoropyridin-2-yl}methyl)amino]pyridin-4-yl}-5-methylpiperidin-3-yl)carbamate (18 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{24}$H$_{27}$F$_3$N$_5$O (M+H)$^+$ m/z=458.2; found: 458.2.
$^1$H NMR (400 MHz, DMSO-d6) δ 7.92 (t, J=9.0 Hz, 1H), 7.82 (d, J=5.0 Hz, 1H), 7.79 (s, 1H), 7.59 (dd, J=8.7, 3.9 Hz, 1H), 7.22 (d, J=8.7 Hz, 2H), 6.82 (d, J=5.1 Hz, 1H), 5.70 (t, J=5.5 Hz, 1H), 4.62 (s, 2H), 4.52 (qd, J=16.4, 5.4 Hz, 3H), 3.20-3.10 (m, 2H), 2.77 (dq, J=10.5, 5.4, 3.9 Hz, 2H), 2.13 (t, J=10.5 Hz, 1H), 1.97 (t, J=11.1 Hz, 1H), 1.86-1.71 (m, 1H), 1.61 (s, 1H), 0.77 (d, J=6.5 Hz, 3H), 0.74-0.67 (m, 1H) ppm.

Example 37

(3R,4R,5S)-3-Amino-1-[3-({[6-(5,7-difluoroquinolin-6-yl)-5-fluoropyridin-2-yl]methyl}amino)pyridin-4-yl]-5-methylpiperidin-4-ol

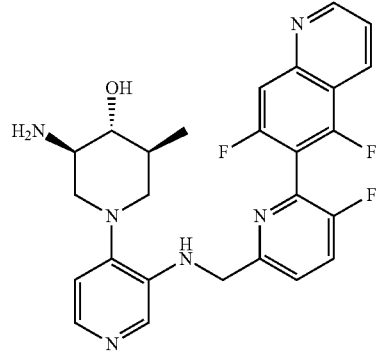 [SMILES: C[C@H]1CN(c2ccncc2NCc2ccc(F)c(-c3c(F)cc4ncccc4c3F)n2)C[C@@H](N)[C@@H]1O]

Step 1. 5,7-Difluoro-6-(4,4,5,5-tetramethyl-1,3,2-dioxaborolan-2-yl)quinoline

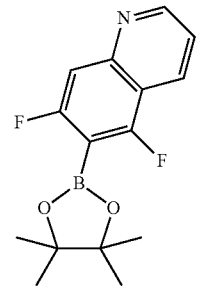

6-Bromo-5,7-difluoroquinoline (Sigma-Aldrich, 500.0 mg, 2.049 mmol), 4,4,5,5,4',4',5',5'-octamethyl-[2,2']bi[[1,3,2]dioxaborolanyl] (from Aldrich, 780 mg, 3.07 mmol), [1,1'-bis(diphenylphosphino)ferrocene]dichloropalladium (II), complex with DCM (1:1) (170 mg, 0.20 mmol), potassium acetate (600 mg, 6.1 mmol) and magnet bar were placed in a vial with septum. The vial was then evacuated and backfilled with nitrogen three times. 1,4-Dioxane (9 mL) was added and the reaction mixture was stirred at 100° C. overnight. Then the reaction mixture was diluted with EtOAc. The resulting solution was washed with brine, dried over Na$_2$SO$_4$ and solvents were evaporated under reduced pressure. The resulting crude product was used in the next step without further purification. LCMS calc. for C$_9$H$_7$BF$_2$NO$_2$ (pinacol ester hydrolyzed to acid on HPLC, M-C$_6$H$_{12}$+H)$^+$ m/z=210.1; found: 210.1.

Step 2. tert-Butyl {(3R,4R,5S)-4-{[tert-butyl(dimethyl)silyl]oxy}-1-[3-({[6-(5,7-difluoroquinolin-6-yl)-5-fluoropyridin-2-yl]methyl}amino)pyridin-4-yl]-5-methylpiperidin-3-yl}carbamate

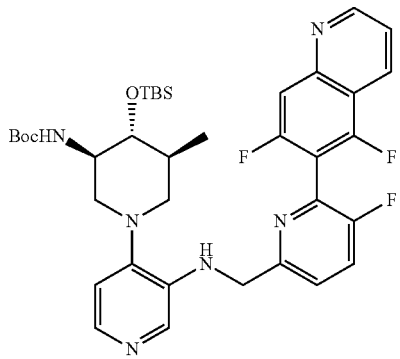 [SMILES: C[C@H]1CN(c2ccncc2NCc2ccc(F)c(-c3c(F)cc4ncccc4c3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 5,7-difluoro-6-(4,4,5,5-tetramethyl-1,3,2-dioxaborolan-2-yl)quinoline (15 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{37}H_{48}F_3N_6O_3Si$ $(M+H)^+$ m/z=709.4; found: 709.4.

Step 3. (3R,4R,5S)-3-Amino-1-[3-({[6-(5,7-difluoroquinolin-6-yl)-5-fluoropyridin-2-yl]methyl}amino)pyridin-4-yl]-5-methylpiperidin-4-ol tert-Butyl {(3R,4R,5S)-4-{[tert-butyl(dimethyl)silyl]oxy}-1-[3-({[6-(5,7-difluoroquinolin-6-yl)-5-fluoropyridin-2-yl]methyl}amino)pyridin-4-yl]-5-methylpiperidin-3-yl}carbamate (23 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{26}H_{26}F_3N_6O$ $(M+H)^+$ m/z=495.2; found: 495.2.

Example 38

4-[(3S,5R)-3-Amino-5-methylpiperidin-1-yl]-N-{[6-(5,7-difluoroquinolin-6-yl)-5-fluoropyridin-2-yl]methyl}pyridin-3-amine

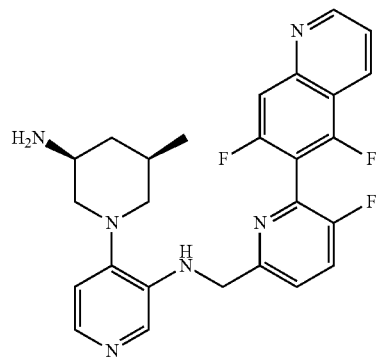 [SMILES: C[C@@H]1C[C@H](N)CN(c2ccncc2NCc2ccc(F)c(-c3c(F)cc4ncccc4c3F)n2)C1]

Step 1. tert-Butyl {(3S,5R)-1-[3-({[6-(5,7-difluoroquinolin-6-yl)-5-fluoropyridin-2-yl]methyl}amino)pyridin-4-yl]-5-methylpiperidin-3-yl}carbamate

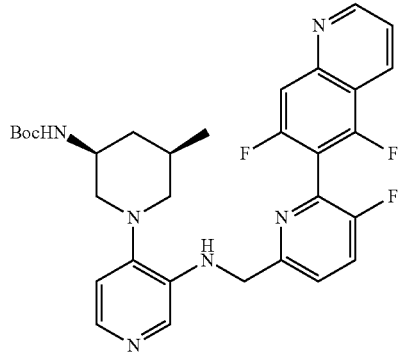 [SMILES: C[C@@H]1C[C@H](NC(=O)OC(C)(C)C)CN(c2ccncc2NCc2ccc(F)c(-c3c(F)cc4ncccc4c3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 5,7-difluoro-6-(4,4,5,5-tetramethyl-1,3,2-dioxaborolan-2-yl)quinoline (15 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{31}H_{34}F_3N_6O_2$ $(M+H)^+$ m/z=579.3; found: 579.2.

Step 2. 4-[(3S,5R)-3-Amino-5-methylpiperidin-1-yl]-N-{[6-(5,7-difluoroquinolin-6-yl)-5-fluoropyridin-2-yl]methyl}pyridin-3-amine tert-Butyl {(3S,5R)-1-[3-({[6-(5,7-difluoroquinolin-6-yl)-5-fluoropyridin-2-yl]methyl}amino)pyridin-4-yl]-5- methylpiperidin-3-yl}carbamate (18 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{26}$H$_{26}$F$_3$N$_6$ (M+H)$^+$ m/z=479.2; found: 479.1.

Example 39

(3R,4R,5S)-3-Amino-1-{3-[({6-[2,6-difluoro-4-(morpholin-4-ylmethyl)phenyl]-5-fluoropyridin-2-yl}methyl)amino]pyridin-4-yl}-5-methylpiperidin-4-ol

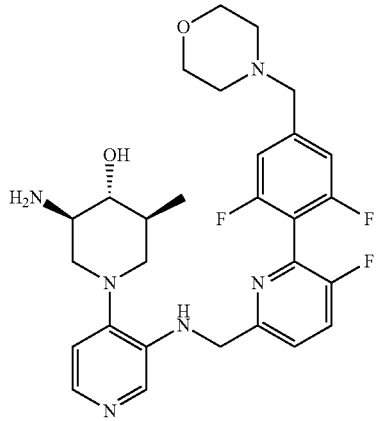 [SMILES: C[C@H]1CN(c2ccncc2NCc2ccc(F)c(-c3c(F)cc(CN4CCOCC4)cc3F)n2)C[C@@H](N)[C@@H]1O]

Step 1. 4-[3,5-Difluoro-4-(4,4,5,5-tetramethyl-1,3,2-dioxaborolan-2-yl)benzyl]morpholine

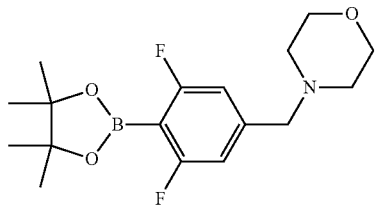 [SMILES: CC1(C)OB(c2c(F)cc(CN3CCOCC3)cc2F)OC1(C)C]

To a solution of 3,5-difluoro-4-(4,4,5,5-tetramethyl-1,3,2-dioxaborolan-2-yl)benzaldehyde (Sigma-Aldrich, 220 mg, 0.81 mmol) in DCM (3 mL) was added morpholine (92.0 μL, 1.05 mmol), followed by the addition of acetic acid (117 μL, 2.06 mmol). The resulting reaction mixture was stirred at room temperature for 1 h. Then sodium triacetoxyborohydride (598 mg, 2.82 mmol) was added in one portion. The resulting reaction mixture was stirred at room temperature for 2 h. After this time, the reaction mixture was diluted with DCM and washed with saturated aq. NaHCO$_3$ and brine. The organic layer was dried over Na$_2$SO$_4$, filtered and concentrated under reduced pressure to afford the crude desired product which was directly used in the next step without further purification (160 mg, 59%). LCMS calc. for C$_{11}$H$_{15}$BF$_2$NO$_3$ (pinacol ester hydrolyzed to boronic acid on HPLC, M-C$_6$H$_{12}$+H)$^+$ m/z=258.1; found: 258.1.

Step 2. tert-Butyl ((3R,4R,5S)-4-{[tert-butyl(dimethyl)silyl]oxy}-1-{3-[({6-[2,6-difluoro-4-(morpholin-4-ylmethyl)phenyl]-5-fluoropyridin-2-yl}methyl)amino]pyridin-4-yl}-5-methylpiperidin-3-yl)carbamate

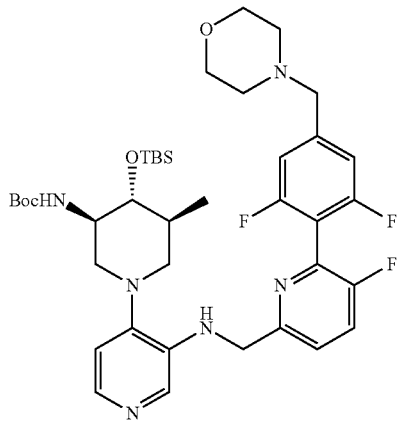 [SMILES: C[C@H]1CN(c2ccncc2NCc2ccc(F)c(-c3c(F)cc(CN4CCOCC4)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 4-[3,5-difluoro-4-(4,4,5,5-tetramethyl-1,3,2-dioxaborolan-2-yl)benzyl]morpholine (17 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{39}$H$_{56}$F$_3$N$_6$O$_4$Si (M+H)$^+$ m/z=757.4; found: 757.3.

Step 3. (3R,4R,5S)-3-Amino-1-{3-[({6-[2,6-difluoro-4-(morpholin-4-ylmethyl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(morpholin-4-ylmethyl)phenyl]-5-fluoropyridin-2-yl}methyl)amino]pyridin-4-yl}-5-methylpiperidin-3-yl)carbamate (24 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{28}$H$_{34}$F$_3$N$_6$O$_2$ (M+H)$^+$ m/z=543.3; found: 543.2. $^1$H NMR (400 MHz, DMSO-d6) δ 7.91 (t, J=9.0 Hz, 1H), 7.81 (d, J=5.1 Hz, 1H), 7.76 (s, 1H), 7.57 (dd, J=8.7, 3.9 Hz, 1H), 7.23 (d, J=8.6 Hz, 2H), 6.83 (d, J=5.1 Hz, 1H), 5.62 (t, J=5.7 Hz, 1H), 4.74 (d, J=4.3 Hz, 1H), 4.60-4.43 (m, 2H), 3.68-3.59 (m, 4H), 3.58 (s, 2H), 3.24-3.13 (m, 2H), 2.75-2.64 (m, 2H), 2.49-2.40 (m, 4H), 2.34 (t, J=10.5 Hz, 1H), 2.21 (t, J=11.6 Hz, 1H), 1.68 (s, 1H), 1.61 (s, 1H), 0.86 (d, J=6.6 Hz, 3H) ppm.

Example 40

(3R,4R,5S)-3-Amino-1-(3-(((6-(2,6-difluoro-4-((methylamino)methyl)phenyl)-5-fluoropyridin-2-yl)methyl)amino)pyridin-4-yl)-5-methylpiperidin-4-ol

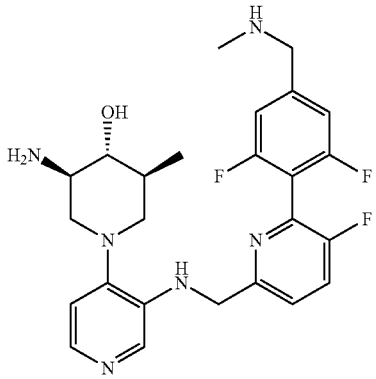 [SMILES: CNCc1cc(F)c(-c2nc(CNc3cnccc3N3C[C@@H](N)[C@H](O)[C@@H](C)C3)ccc2F)c(F)c1]

This compound was synthesized according to the procedures described in Example 39, using 2.0M solution of methanamine in THF to replace morpholine in Step 1. LCMS calc. for $C_{25}H_{30}F_3N_6O$ (M+H)$^+$ m/z=487.2; found: 487.2.

Example 41

(3R,4R,5S)-3-Amino-1-(3-(((6-(4-(azetidin-1-ylmethyl)-2,6-difluorophenyl)-5-fluoropyridin-2-yl)methyl)amino)pyridin-4-yl)-5-methylpiperidin-4-ol

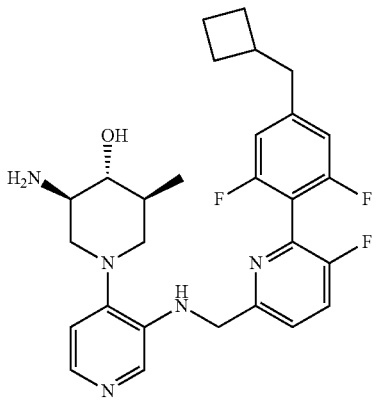 [SMILES: C[C@H]1CN(c2ccncc2NCc2ccc(F)c(-c3c(F)cc(CC4CCC4)cc3F)n2)C[C@@H](N)[C@@H]1O]

This compound was synthesized using similar procedures as described in Example 39, using azetidine to replace morpholine in Step 1. LCMS calc. for $C_{27}H_{32}F_3N_6O$ (M+H)$^+$ m/z=513.3; found: 513.3. $^1$H NMR (400 MHz, DMSO-d6) δ 7.90 (t, J=9.0 Hz, 1H), 7.80 (d, J=5.1 Hz, 1H), 7.75 (s, 1H), 7.56 (dd, J=8.7, 3.9 Hz, 1H), 7.16 (d, J=8.6 Hz, 2H), 6.83 (d, J=5.1 Hz, 1H), 5.61 (t, J=5.7 Hz, 1H), 4.74 (s, 1H), 4.58-4.46 (m, 3H), 3.63 (s, 2H), 3.21 (t, J=7.0 Hz, 6H), 2.76-2.63 (m, 2H), 2.33 (t, J=10.5 Hz, 1H), 2.22 (t, J=11.5 Hz, 1H), 2.03 (p, J=7.0 Hz, 2H), 1.69 (s, 1H), 1.60 (s, 1H), 0.86 (d, J=6.5 Hz, 3H) ppm.

Example 42

(3R,4R,5S)-3-Amino-1-(3-(((6-(2,6-difluoro-4-(((R)-3-hydroxypyrrolidin-1-yl)methyl)phenyl)-5-fluoropyridin-2-yl)methyl)amino)pyridin-4-yl)-5-methylpiperidin-4-ol

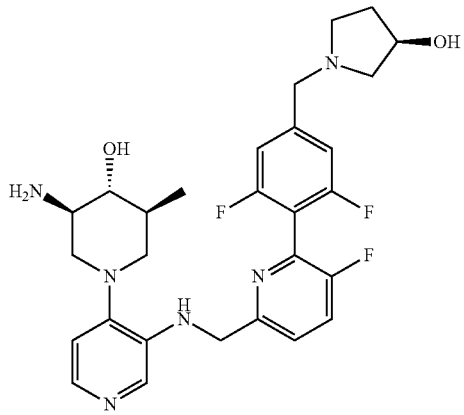 [SMILES: C[C@H]1CN(c2ccncc2NCc2ccc(F)c(-c3c(F)cc(CN4CC[C@@H](O)C4)cc3F)n2)C[C@@H](N)[C@@H]1O]

This compound was synthesized according to the procedures described in Example 39, using (R)-pyrrolidin-3-ol (from Aldrich) to replace morpholine in Step 1. LCMS calc. for $C_{28}H_{34}F_3N_6O_2$ (M+H)$^+$ m/z=543.3; found: 543.3. $^1$H NMR (400 MHz, DMSO-d6) δ 7.90 (t, J=9.0 Hz, 1H), 7.80 (d, J=5.1 Hz, 1H), 7.75 (s, 1H), 7.57 (dd, J=8.7, 3.9 Hz, 1H), 7.22 (d, J=8.6 Hz, 2H), 6.83 (d, J=5.1 Hz, 1H), 5.62 (t, J=5.8 Hz, 1H), 4.74 (s, 1H), 4.57-4.47 (m, 2H), 4.23 (s, 1H), 3.68 (q, J=14.1 Hz, 2H), 3.27-3.15 (m, 2H), 2.78-2.62 (m, 5H), 2.50-2.44 (m, 1H), 2.40 (dd, J=9.6, 3.6 Hz, 1H), 2.34 (t, J=10.6 Hz, 1H), 2.22 (t, J=11.5 Hz, 1H), 2.04 (dq, J=14.2, 7.6 Hz, 1H), 1.70 (s, 1H), 1.65-1.55 (m, 1H), 0.87 (d, J=6.5 Hz, 3H) ppm.

Example 43

(3R,4R,5S)-3-Amino-1-(3-(((6-(2,6-difluoro-4-(((S)-3-hydroxypyrrolidin-1-yl)methyl)phenyl)-5-fluoropyridin-2-yl)methyl)amino)pyridin-4-yl)-5-methylpiperidin-4-ol

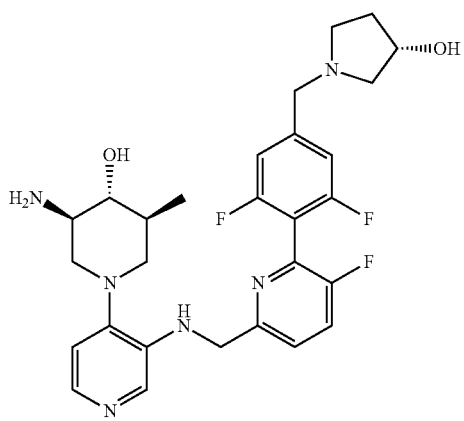 [SMILES: C[C@H]1CN(c2ccncc2NCc2ccc(F)c(-c3c(F)cc(CN4CC[C@H](O)C4)cc3F)n2)C[C@@H](N)[C@@H]1O]

This compound was synthesized according to the procedures described in Example 39, using (S)-pyrrolidin-3-ol (from Aldrich) to replace morpholine in Step 1. LCMS calc. for $C_{28}H_{34}F_3N_6O_2$ (M+H)$^+$ m/z=543.3; found: 543.3. $^1$H NMR (400 MHz, DMSO-d6) δ 7.90 (t, J=9.0 Hz, 1H), 7.80 (d, J=5.1 Hz, 1H), 7.76 (s, 1H), 7.57 (dd, J=8.7, 3.9 Hz, 1H), 7.22 (d, J=8.6 Hz, 2H), 6.83 (d, J=5.1 Hz, 1H), 5.62 (t, J=5.8 Hz, 1H), 4.74 (d, J=4.4 Hz, 1H), 4.58-4.49 (m, 2H), 4.23 (s, 1H), 3.76-3.59 (m, 2H), 3.25-3.12 (m, 1H), 2.76-2.61 (m, 5H), 2.49-2.43 (m, 2H), 2.40 (dd, J=9.7, 3.5 Hz, 1H), 2.34 (t, J=10.6 Hz, 1H), 2.22 (t, J=11.5 Hz, 1H), 2.10-1.98 (m, 2H), 1.70 (s, 1H), 1.65-1.55 (m, 1H), 0.87 (d, J=6.5 Hz, 3H) ppm.

Example 44

(R)-1-(4-(6-((4-((3R,4R,5S)-3-Amino-4-hydroxy-5-methylpiperidin-1-yl)pyridin-3-ylamino)methyl)-3-fluoropyridin-2-yl)-3,5-difluorobenzyl)pyrrolidine-3-carbonitrile

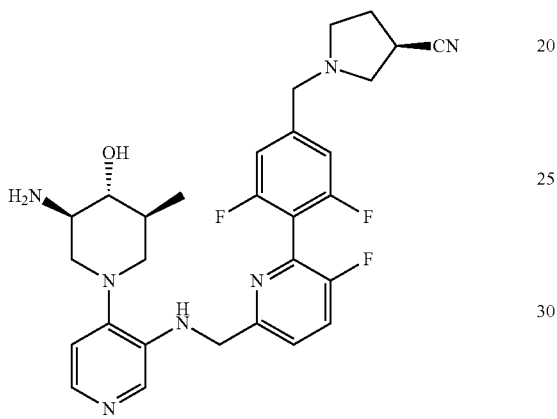

This compound was synthesized according to the procedures described in Example 39, using (R)-pyrrolidine-3-carbonitrile (from Tyger) to replace morpholine in Step 1. LCMS calc. for $C_{29}H_{33}F_3N_7O$ (M+H)$^+$ m/z=552.3; found: 552.3. $^1$H NMR (400 MHz, DMSO-d6) δ 7.91 (t, J=9.0 Hz, 1H), 7.81 (d, J=5.1 Hz, 1H), 7.76 (s, 1H), 7.57 (dd, J=8.6, 3.9 Hz, 1H), 7.23 (d, J=8.5 Hz, 2H), 6.83 (d, J=5.1 Hz, 1H), 5.63 (t, J=5.6 Hz, 1H), 4.77 (s, 1H), 4.61-4.46 (m, 2H), 3.74 (s, 2H), 3.26-3.12 (m, 2H), 2.88-2.64 (m, 5H), 2.62-2.53 (m, 1H), 2.39-2.28 (m, 2H), 2.30-2.16 (m, 3H), 2.05-1.94 (m, 2H), 1.70 (s, 1H), 0.87 (d, J=6.5 Hz, 3H) ppm.

Example 45

(S)-1-(4-(6-((4-((3R,4R,5S)-3-Amino-4-hydroxy-5-methylpiperidin-1-yl)pyridin-3-ylamino)methyl)-3-fluoropyridin-2-yl)-3,5-difluorobenzyl)pyrrolidine-3-carbonitrile

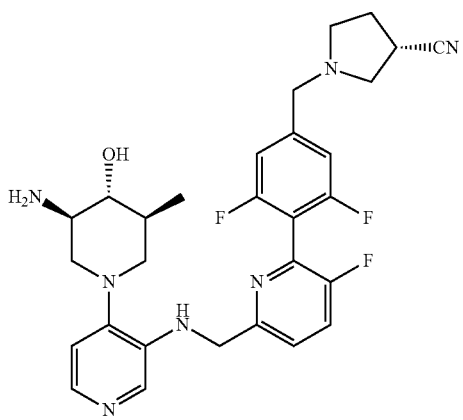 [SMILES: C[C@H]1CN(c2ccncc2NCc2ccc(F)c(-c3c(F)cc(CN4CC[C@H](C#N)C4)cc3F)n2)C[C@@H](N)[C@@H]1O]

This compound was synthesized according to the procedures described in Example 39, using (S)-pyrrolidine-3-carbonitrile (from Tyger) to replace morpholine in Step 1. LCMS calc. for $C_{29}H_{33}F_3N_7O$ (M+H)$^+$ m/z=552.3; found: 552.3. $^1$H NMR (400 MHz, DMSO-d6) δ 7.91 (t, J=9.0 Hz, 1H), 7.81 (d, J=5.1 Hz, 1H), 7.76 (s, 1H), 7.57 (dd, J=8.6, 3.9 Hz, 1H), 7.23 (d, J=8.6 Hz, 2H), 6.83 (d, J=5.1 Hz, 1H), 5.63 (t, J=5.8 Hz, 1H), 4.77 (d, J=4.0 Hz, 1H), 4.62-4.45 (m, 2H), 3.74 (s, 2H), 3.26-3.14 (m, 2H), 2.88-2.64 (m, 5H), 2.59-2.52 (m, 2H), 2.38-2.30 (m, 2H), 2.29-2.18 (m, 3H), 2.06-1.95 (m, 1H), 1.69 (s, 1H), 0.87 (d, J=6.6 Hz, 3H) ppm.

Example 46

(3R,4R,5S)-3-amino-1-(3-(((6-(2,6-difluoro-4-(((R)-3-fluoropyrrolidin-1-yl)methyl)phenyl)-5-fluoropyridin-2-yl)methyl)amino)pyridin-4-yl)-5-methylpiperidin-4-ol

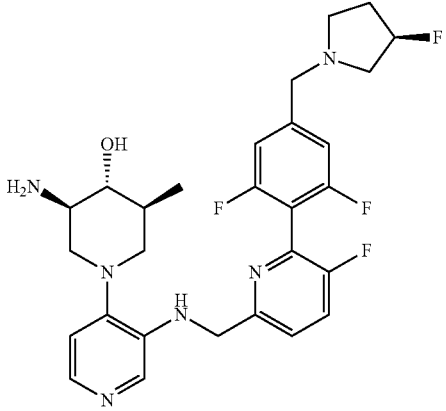 [SMILES: C[C@H]1CN(c2ccncc2NCc2ccc(F)c(-c3c(F)cc(CN4CC[C@@H](F)C4)cc3F)n2)C[C@@H](N)[C@@H]1O]

This compound was synthesized using similar procedures as described in Example 39, using (R)-3-fluoropyrrolidine (from Aldrich) to replace morpholine in Step 1. LCMS calc. for $C_{28}H_{33}F_4N_6O$ (M+H)$^+$ m/z=545.3; found: 545.2. $^1$H NMR (400 MHz, DMSO-d6) δ 7.91 (t, J=9.0 Hz, 1H), 7.81 (d, J=5.1 Hz, 1H), 7.76 (s, 1H), 7.57 (dd, J=8.6, 3.9 Hz, 1H), 7.23 (d, J=8.6 Hz, 2H), 6.83 (d, J=5.1 Hz, 1H), 5.62 (t, J=5.7 Hz, 1H), 5.34-5.29 (m, 1H), 5.21-5.15 (m, 1H), 4.76 (d, J=4.3 Hz, 1H), 4.59-4.44 (m, 2H), 3.81-3.69 (m, 2H), 3.26-3.14 (m, 2H), 2.95-2.79 (m, 2H), 2.79-2.64 (m, 4H), 2.47-2.38 (m, 1H), 2.34 (t, J=10.6 Hz, 1H), 2.29-2.09 (m, 2H), 2.02-1.81 (m, 1H), 1.69 (br, 1H), 0.91-0.83 (m, 3H) ppm.

Example 47

(3R,4R,5S)-3-amino-1-(3-(((6-(2,6-difluoro-4-(((S)-3-fluoropyrrolidin-1-yl)methyl)phenyl)-5-fluoropyridin-2-yl)methyl)amino)pyridin-4-yl)-5-methylpiperidin-4-ol

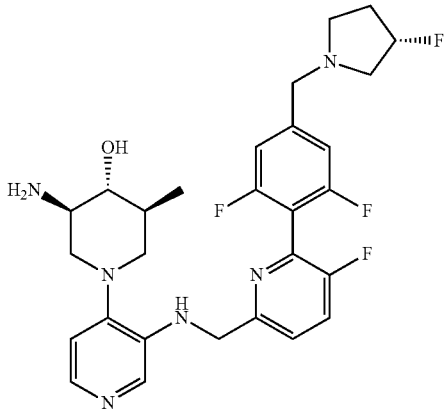 [SMILES: C[C@H]1CN(c2ccncc2NCc2ccc(F)c(-c3c(F)cc(CN4CC[C@H](F)C4)cc3F)n2)C[C@@H](N)[C@@H]1O]

This compound was synthesized according to the procedures described in Example 39, using (S)-3-fluoropyrrolidine (from Aldrich) to replace morpholine in Step 1. LCMS calc. for $C_{28}H_{33}F_4N_6O$ (M+H)$^+$ m/z=545.3; found: 545.2.

Example 48

4-[(3S,5R)-3-Amino-5-methylpiperidin-1-yl]-N-({6-[2,6-difluoro-4-(morpholin-4-ylmethyl)phenyl]-5-fluoropyridin-2-yl}methyl)pyridin-3-amine

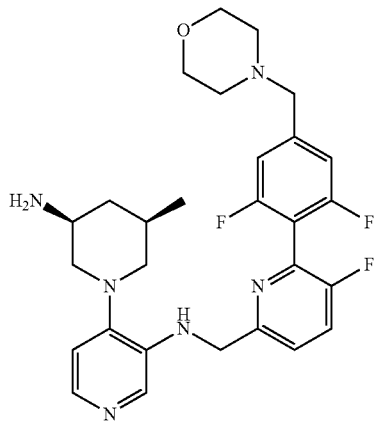 [SMILES: C[C@@H]1C[C@H](N)CN(c2ccncc2NCc2ccc(F)c(-c3c(F)cc(CN4CCOCC4)cc3F)n2)C1]

Step 1. tert-Butyl ((3S,5R)-1-{3-[({6-[2,6-difluoro-4-(morpholin-4-ylmethyl)phenyl]-5-fluoropyridin-2-yl}methyl)amino]pyridin-4-yl}-5-methylpiperidin-3-yl)carbamate

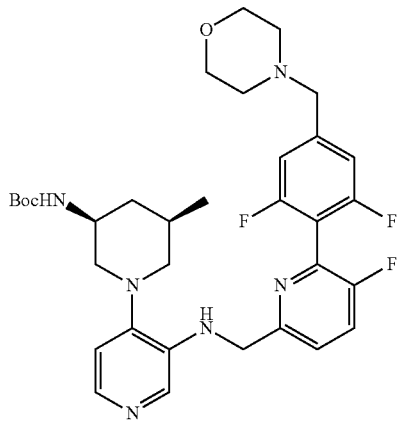 [SMILES: C[C@@H]1C[C@H](NC(=O)OC(C)(C)C)CN(c2ccncc2NCc2ccc(F)c(-c3c(F)cc(CN4CCOCC4)cc3F)n2)C1]

tert-Butyl [(3S,5R)-1-(3-{[[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 4-[3,5-difluoro-4-(4,4,5,5-tetramethyl-1,3,2-dioxaborolan-2-yl)benzyl]morpholine (17 mg, 0.051 mmol) was added and the reaction mixture was stirred at 65° C. for 1 h. Then the reaction mixture was diluted with EtOAc. The resulting solution was washed with brine, dried over $Na_2SO_4$ and the solvent was evaporated. The resulting crude product was used in the next step without further purification. LCMS calc. for $C_{33}H_{42}F_3N_6O_3$ (M+H)$^+$ m/z=627.3; found: 627.3.

Step 2. 4-[(3S,5R)-3-Amino-5-methylpiperidin-1-yl]-N-({6-[2,6-difluoro-4-(morpholin-4-ylmethyl)phenyl]-5-fluoropyridin-2-yl}methyl)pyridin-3-amine tert-Butyl ((3S,5R)-1-{3-[({6-[2,6-difluoro-4-(morpholin-4-ylmethyl)phenyl]-5-fluoropyridin-2-yl}methyl)amino]pyridin-4-yl}-5-methylpiperidin-3-yl)carbamate (20 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{28}H_{34}F_3N_6O$ (M+H)$^+$ m/z=527.3; found: 527.3. $^1$H NMR (400 MHz, DMSO-d6) δ 7.93 (t, J=9.0 Hz, 1H), 7.82 (d, J=5.0 Hz, 1H), 7.80 (s, 1H), 7.60 (dd, J=8.7, 3.9 Hz, 1H), 7.25 (d, J=8.6 Hz, 2H), 6.82 (d, J=5.1 Hz, 1H), 5.69 (t, J=5.5 Hz, 1H), 4.52 (qd, J=16.3, 5.3 Hz, 3H), 3.68-3.60 (m, 4H), 3.60 (s, 2H), 3.15 (t, J=12.5 Hz, 2H), 2.76 (t, J=10.7 Hz, 1H), 2.47-2.38 (m, 4H), 2.13 (t, J=10.5

Hz, 1H), 1.96 (t, J=11.0 Hz, 1H), 1.86-1.57 (m, 2H), 0.76 (d, J=6.4 Hz, 3H), 0.74-0.65 (m, 1H) ppm.

Example 49

4-((3S,5R)-3-Amino-5-methylpiperidin-1-yl)-N-((6-(2,6-difluoro-4-((methylamino)methyl)phenyl)-5-fluoropyridin-2-yl)methyl)pyridin-3-amine

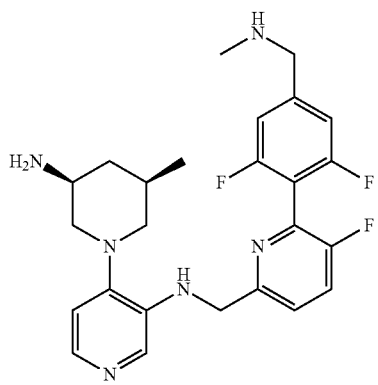

This compound was synthesized according to the procedures described in Example 48 and Example 39, using 2.0M solution of methanamine in THF to replace morpholine in Step 1 of Example 39. LCMS calc. for $C_{25}H_{30}F_3N_6$ (M+H)$^+$ m/z=471.3; found: 471.2.

Example 50

4-((3S,5R)-3-Amino-5-methylpiperidin-1-yl)-N-((6-(4-(azetidin-1-ylmethyl)-2,6-difluorophenyl)-5-fluoropyridin-2-yl)methyl)pyridin-3-amine

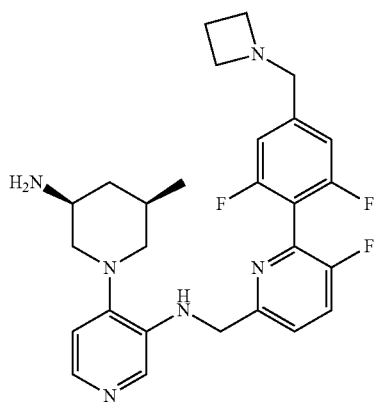 [SMILES: C[C@@H]1C[C@H](N)CN(c2ccncc2NCc2ccc(F)c(-c3c(F)cc(CN4CCC4)cc3F)n2)C1]

This compound was synthesized according to the procedures as described in Example 48 and Example 39, using azetidine to replace morpholine in Step 1 of Example 39. LCMS calc. for $C_{27}H_{32}F_3N_6$ (M+H)$^+$ m/z=497.3; found: 497.3. $^1$H NMR (400 MHz, DMSO-d6) δ 7.92 (t, J=9.0 Hz, 1H), 7.82 (d, J=5.0 Hz, 1H), 7.79 (s, 1H), 7.59 (dd, J=8.6, 3.9 Hz, 1H), 7.18 (d, J=8.7 Hz, 2H), 6.82 (d, J=5.1 Hz, 1H), 5.69 (t, J=5.4 Hz, 1H), 4.52 (qd, J=16.4, 5.6 Hz, 3H), 3.64 (s, 2H), 3.21 (t, J=7.0 Hz, 4H), 3.18-3.10 (m, 2H), 2.84-2.72 (m, 1H), 2.13 (t, J=10.5 Hz, 1H), 2.04 (p, J=7.0 Hz, 2H), 1.95 (t, J=11.0 Hz, 1H), 1.85-1.66 (m, 2H), 0.75 (d, J=6.5 Hz, 3H), 0.73-0.66 (m, 1H) ppm.

Example 51

(R)-1-(4-(6-((4-((3S,5R)-3-Amino-5-methylpiperidin-1-yl)pyridin-3-ylamino)methyl)-3-fluoropyridin-2-yl)-3,5-difluorobenzyl)pyrrolidin-3-ol

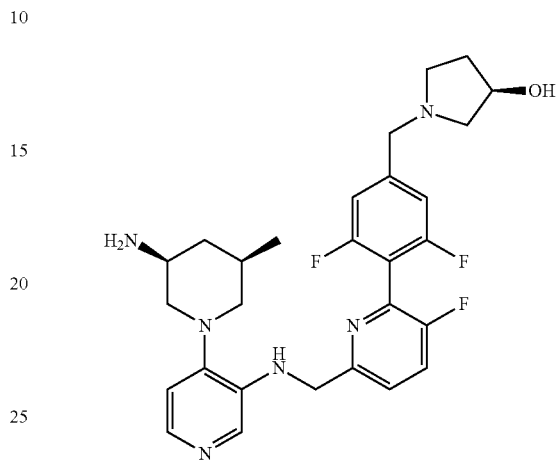

This compound was synthesized according to the procedures described in Example 48 and Example 39, using (R)-pyrrolidin-3-ol to replace morpholine in Step 1 of Example 39. LCMS calc. for $C_{28}H_{34}F_3N_6O$ (M+H)$^+$ m/z=527.3; found: 527.3. $^1$H NMR (400 MHz, DMSO-d6) δ 7.93 (t, J=8.9 Hz, 1H), 7.82 (d, J=5.0 Hz, 1H), 7.80 (s, 1H), 7.60 (dd, J=8.7, 3.8 Hz, 1H), 7.24 (d, J=8.6 Hz, 2H), 6.82 (d, J=5.1 Hz, 1H), 5.70 (t, J=5.4 Hz, 1H), 4.61-4.45 (m, 3H), 4.30-4.19 (m, 2H), 3.78-3.59 (m, 2H), 3.15 (t, J=11.1 Hz, 1H), 2.82-2.62 (m, 4H), 2.49-2.44 (m, 1H), 2.40 (dd, J=9.6, 3.5 Hz, 1H), 2.14 (t, J=10.5 Hz, 1H), 2.10-2.00 (m, 2H), 1.95 (t, J=11.1 Hz, 1H), 1.86-1.66 (m, 1H), 1.64-1.53 (m, 1H), 0.76 (d, J=6.5 Hz, 3H), 0.75-0.67 (m, 1H) ppm.

Example 52

(S)-1-(4-(6-((4-((3S,5R)-3-Amino-5-methylpiperidin-1-yl)pyridin-3-ylamino)methyl)-3-fluoropyridin-2-yl)-3,5-difluorobenzyl)pyrrolidin-3-ol

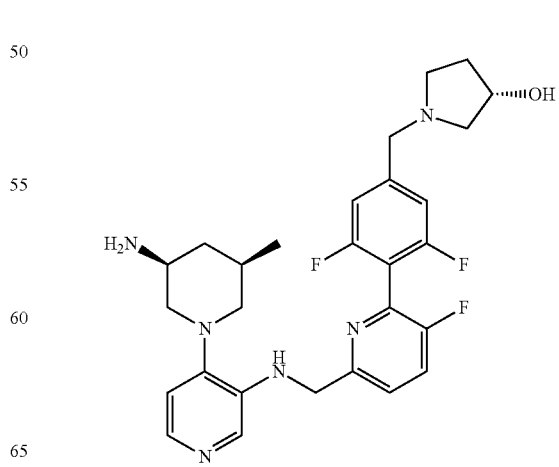

This compound was synthesized according to the procedures described in Example 48 and Example 39, using (S)-pyrrolidin-3-ol to replace morpholine in Step 1 of Example 39. LCMS calc. for $C_{28}H_{34}F_3N_6O$ (M+H)$^+$ m/z=527.3; found: 527.3. $^1$H NMR (400 MHz, DMSO-d6) δ 7.93 (t, J=8.9 Hz, 1H), 7.83 (d, J=5.0 Hz, 1H), 7.81 (s, 1H), 7.60 (dd, J=8.7, 3.9 Hz, 1H), 7.24 (d, J=8.6 Hz, 2H), 6.82 (d, J=5.1 Hz, 1H), 5.71 (t, J=5.3 Hz, 1H), 4.64-4.41 (m, 3H), 4.31-4.18 (m, 1H), 3.81-3.57 (m, 2H), 3.24-3.09 (m, 2H), 2.83-2.60 (m, 4H), 2.49-2.44 (m, 1H), 2.39 (dd, J=9.6, 3.6 Hz, 1H), 2.14 (t, J=10.6 Hz, 1H), 2.04 (dq, J=14.3, 7.7 Hz, 2H), 1.94 (t, J=11.1 Hz, 1H), 1.86-1.66 (m, 1H), 1.66-1.54 (m, 1H), 0.76 (d, J=6.5 Hz, 3H), 0.74-0.66 (m, 1H) ppm.

Example 53

(R)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidine-3-carbonitrile

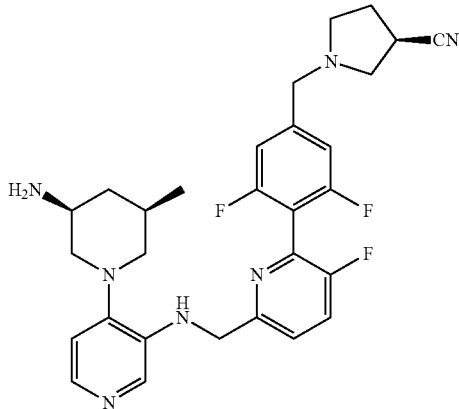 [SMILES: C[C@@H]1C[C@H](N)CN(c2ccncc2NCc2ccc(F)c(-c3c(F)cc(CN4CC[C@@H](O)C4)cc3F)n2)C1]

This compound was synthesized according to the procedures described in Example 48 and Example 39, using (R)-pyrrolidine-3-carbonitrile to replace morpholine in Step 1 of Example 39. LCMS calc. for $C_{29}H_{33}F_3N_7$ (M+H)$^+$ m/z=536.3; found: 536.3. $^1$H NMR (400 MHz, DMSO-d6) δ 7.93 (t, J=9.0 Hz, 1H), 7.82 (d, J=5.1 Hz, 1H), 7.80 (s, 1H), 7.60 (dd, J=8.7, 3.9 Hz, 1H), 7.25 (d, J=8.5 Hz, 2H), 6.82 (d, J=5.1 Hz, 1H), 5.70 (t, J=5.3 Hz, 1H), 4.69-4.45 (m, 3H), 3.76 (s, 2H), 3.16 (dd, J=19.2, 10.3 Hz, 1H), 2.86-2.69 (m, 4H), 2.59-2.52 (m, 1H), 2.30-2.17 (m, 2H), 2.14 (t, J=10.6 Hz, 1H), 2.06-1.93 (m, 3H), 1.85-1.64 (m, 2H), 0.77 (d, J=6.5 Hz, 3H), 0.76-0.68 (m, 1H) ppm.

Example 54

(S)-1-(4-(6-((4-((3S,5R)-3-amino-5-methylpiperidin-1-yl)pyridin-3-ylamino)methyl)-3-fluoropyridin-2-yl)-3,5-difluorobenzyl)pyrrolidine-3-carbonitrile

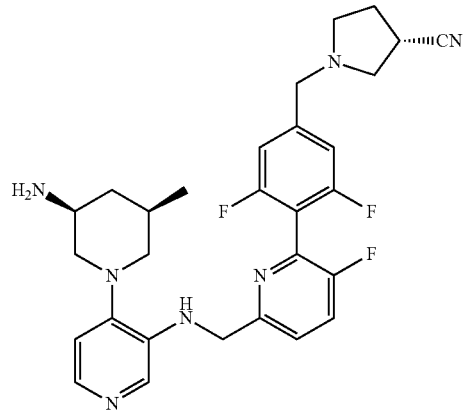 [SMILES: C[C@@H]1C[C@H](N)CN(c2ccncc2NCc2ccc(F)c(-c3c(F)cc(CN4CC[C@H](C#N)C4)cc3F)n2)C1]

This compound was synthesized according to the procedures described in Example 48 and Example 39, using (S)-pyrrolidine-3-carbonitrile to replace morpholine in Step 1 of Example 39. LCMS calc. for $C_{29}H_{33}F_3N_7$ (M+H)$^+$ m/z=536.3; found: 536.3. $^1$H NMR (400 MHz, DMSO-d6) δ 7.93 (t, J=9.0 Hz, 1H), 7.83 (d, J=5.0 Hz, 1H), 7.80 (s, 1H), 7.60 (dd, J=8.7, 3.9 Hz, 1H), 7.25 (d, J=8.6 Hz, 2H), 6.83 (d, J=5.1 Hz, 1H), 5.70 (t, J=5.4 Hz, 1H), 4.53 (qd, J=16.4, 5.5 Hz, 3H), 3.76 (s, 2H), 3.17 (dd, J=26.0, 8.3 Hz, 1H), 2.79 (tdd, J=14.2, 11.4, 5.2 Hz, 5H), 2.59-2.52 (m, 1H), 2.29-2.19 (m, 2H), 2.16 (t, J=10.6 Hz, 1H), 2.05-1.93 (m, 3H), 1.78 (dd, J=22.4, 12.1 Hz, 2H), 0.78 (d, J=6.5 Hz, 3H), 0.75-0.71 (m, 1H) ppmS.

Example 55

4-((3S,5R)-3-amino-5-methylpiperidin-1-yl)-N-((6-(2,6-difluoro-4-(((R)-3-fluoropyrrolidin-1-yl)methyl)phenyl)-5-fluoropyridin-2-yl)methyl)pyridin-3-amine

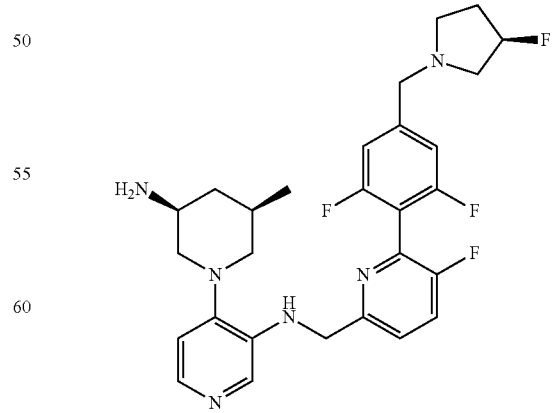

This compound was synthesized according to the procedures described in Example 48 and Example 39, using (R)-3-fluoropyrrolidine to replace morpholine in Step 1 of Example 39. LCMS calc. for $C_{28}H_{33}F_4N_6$ $(M+H)^+$ m/z=529.3; found: 529.2.

Example 56

4-((3S,5R)-3-amino-5-methylpiperidin-1-yl)-N-((6-(2,6-difluoro-4-(((S)-3-fluoropyrrolidin-1-yl)methyl)phenyl)-5-fluoropyridin-2-yl)methyl)pyridin-3-amine

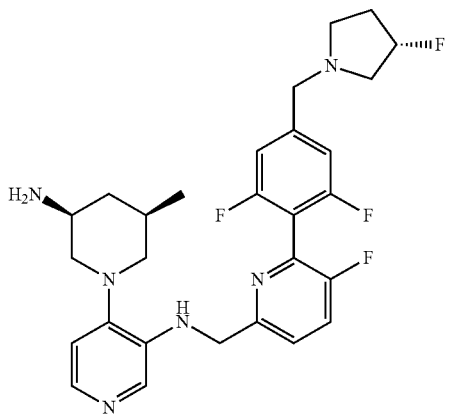 [SMILES: C[C@@H]1C[C@H](N)CN(c2ccncc2NCc2ccc(F)c(-c3c(F)cc(CN4CC[C@H](F)C4)cc3F)n2)C1]

This compound was synthesized according to the procedures described in Example 48 and Example 39, using (S)-3-fluoropyrrolidine to replace morpholine in Step 1 of Example 39. LCMS calc. for $C_{28}H_{33}F_4N_6$ $(M+H)^+$ m/z=529.3; found: 529.2.

Example 57

(3R,4R,5S)-3-Amino-1-(3-{[(6-cyclohex-1-en-1-yl-5-fluoropyridin-2-yl)methyl]amino})pyridin-4-yl)-5-methylpiperidin-4-ol

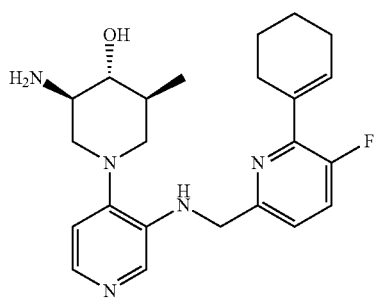 [SMILES: C[C@H]1CN(c2ccncc2NCc2ccc(F)c(C3=CCCCC3)n2)C[C@@H](N)[C@@H]1O]

Step 1. tert-Butyl [(3R,4R,5S)-4-{[tert-butyl(dimethyl)silyl]oxy}-1-(3-{[(6-cyclohex-1-en-1-yl-5-fluoropyridin-2-yl)methyl]amino}pyridin-4-yl)-5-methylpiperidin-3-yl]carbamate

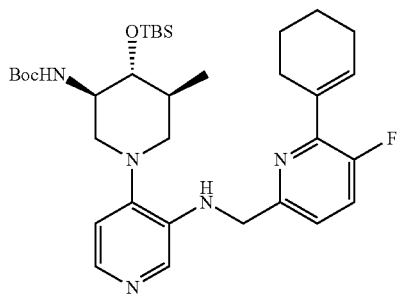 [SMILES: C[C@H]1CN(c2ccncc2NCc2ccc(F)c(C3=CCCCC3)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally, 2-cyclohex-1-en-1-yl-4,4,5,5-tetramethyl-1,3,2-dioxaborolane (from Aldrich, 11 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{34}H_{53}FN_5O_3Si$ $(M+H)^+$ m/z=626.4; found: 626.4.

Step 2. (3R,4R,5S)-3-Amino-1-(3-{[(6-cyclohex-1-en-1-yl-5-fluoropyridin-2-yl)methyl]amino}pyridin-4-yl)-5-methylpiperidin-4-ol tert-Butyl [(3R,4R,5S)-4-{[tert-butyl(dimethyl)silyl]oxy}-1-(3-{[(6-cyclohex-1-en-1-yl-5-fluoropyridin-2-yl)methyl]amino}pyridin-4-yl)-5-methylpiperidin-3-yl]carbamate (20 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{23}H_{31}FN_5O$ $(M+H)^+$ m/z=412.3; found: 412.3.

Example 58

4-[(3S,5R)-3-Amino-5-methylpiperidin-1-yl]-N-[(6-cyclohexyl-5-fluoropyridin-2-yl)methyl]pyridin-3-amine

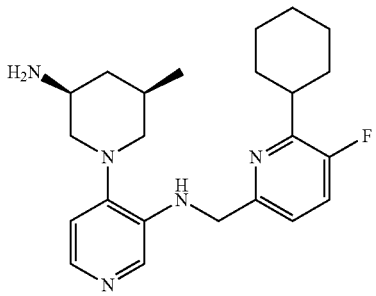 [SMILES: C[C@@H]1C[C@H](N)CN(c2ccncc2NCc2ccc(F)c(C3CCCCC3)n2)C1]

Step 1. tert-Butyl [(3S,5R)-1-(3-{[(6-cyclohex-1-en-1-yl-5-fluoropyridin-2-yl)methyl]amino}pyridin-4-yl)-5-methylpiperidin-3-yl]carbamate

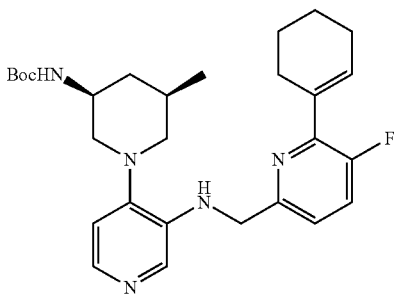 [SMILES: C[C@@H]1C[C@H](NC(=O)OC(C)(C)C)CN(c2ccncc2NCc2ccc(F)c(C3=CCCCC3)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (Intermediate 2; 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-cyclohex-1-en-1-yl-4,4,5,5-tetramethyl-1,3,2-dioxaborolane (11 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{28}H_{39}FN_5O_2$ $(M+H)^+$ m/z=496.3; found: 496.3.

Step 2. tert-Butyl [(3S,5R)-1-(3-{[(6-cyclohexyl-5-fluoropyridin-2-yl)methyl]amino}pyridin-4-yl)-5-methylpiperidin-3-yl]carbamate

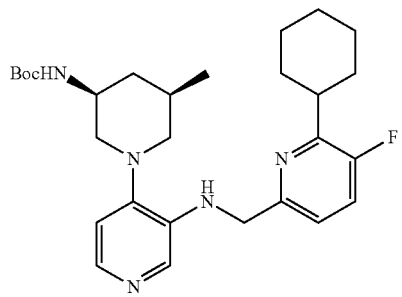 [SMILES: C[C@@H]1C[C@H](NC(=O)OC(C)(C)C)CN(c2ccncc2NCc2ccc(F)c(C3CCCCC3)n2)C1]

To a stirred solution of tert-butyl [(3S,5R)-1-(3-{[(6-cyclohex-1-en-1-yl-5-fluoropyridin-2-yl)methyl]amino}pyridin-4-yl)-5-methylpiperidin-3-yl]carbamate (16 mg, 0.032 mmol) in methanol (1.5 mL) was added 5 w % of Pd on carbon (3.1 mg, 0.0015 mmol). The vial containing reaction mixture was closed with septum and was connected to a balloon with hydrogen. After stirring at room temperature overnight, reaction mixture was filtered through a pad of diatomaceous earth and the solvent was evaporated under reduced pressure. The resulting crude product was used in the next step without further purification. LCMS calc. for $C_{28}H_{41}FN_5O_2$ $(M+H)^+$ m/z=498.3; found: 498.3.

Step 3. 4-[(3S,5R)-3-Amino-5-methylpiperidin-1-yl]-N-[(6-cyclohexyl-5-fluoropyridin-2-yl)methyl]pyridin-3-amine tert-Butyl [(3S,5R)-1-(3-{[(6-cyclohexyl-5-fluoropyridin-2-yl)methyl]amino}pyridin-4-yl)-5-methylpiperidin-3-yl]carbamate (16 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 µm particle size, gradient elution with acetonitrile/water containing 0.1% $NH_4OH$, at flow rate of 60 mL/min). LCMS calc. for $C_{23}H_{33}FN_5$ $(M+H)^+$ m/z=398.3; found: 398.2.

Example 59

(3R,4R,5S)-3-Amino-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-4-ol

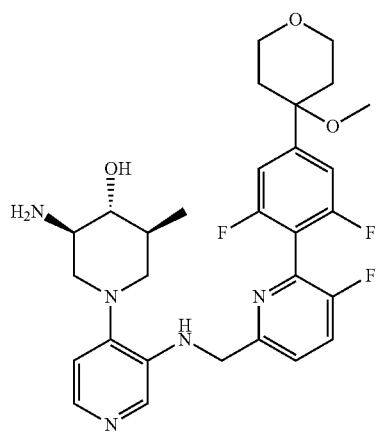 [SMILES: COC1(c2cc(F)c(-c3nc(CNc4cnccc4N4C[C@@H](N)[C@H](O)[C@@H](C)C4)ccc3F)c(F)c2)CCOCC1]

Step 1.
4-(3,5-Difluorophenyl)tetrahydro-2H-pyran-4-ol

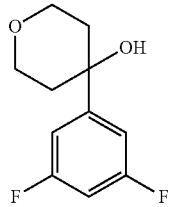 [SMILES: OC1(c2cc(F)cc(F)c2)CCOCC1]

Tetrahydro-4H-pyran-4-one (from Aldrich, 1.00 g, 9.99 mmol) and a magnet bar were placed in a vial. The vial was evacuated and backfilled with nitrogen three times. After addition of tetrahydrofuran (15 mL), the reaction mixture was cooled to 0° C. Then 0.5M solution of (3,5-difluorophenyl)magnesium bromide in THF (22 mL, 11 mmol) was slowly added and the reaction mixture was stirred at room temperature for 16 h. After this time the reaction mixture was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification (1.2 g, 56%).

Step 2. 4-(3,5-Difluorophenyl)-4-methoxytetrahydro-2H-pyran

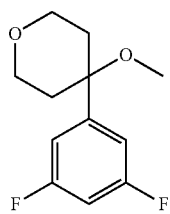 [SMILES: COC1(c2cc(F)cc(F)c2)CCOCC1]

4-(3,5-Difluorophenyl)tetrahydro-2H-pyran-4-ol (400.0 mg, 1.867 mmol) was added to DMF (6.0 mL) and the reaction mixture was cooled to 0° C. Then NaH in mineral oil (60%, 90 mg, 2.2 mmol) was slowly added to the reaction mixture. After addition was complete, the reaction mixture was stirred at 0° C. for 30 min. Then methyl iodide (350 µL, 5.6 mmol) was slowly added and the reaction mixture was stirred at room temperature overnight. After this time, water was added to the reaction and the product was extracted with EtOAc. Combined organic fractions were washed with brine, dried over Na$_2$SO$_4$ and the solvents were evaporated under reduced pressure. The crude product was purified by Biotage Isolera to give the desired compound (183 mg, 43%).

Step 3. 4-[3,5-Difluoro-4-(4,4,5,5-tetramethyl-1,3,2-dioxaborolan-2-yl)phenyl]-4-methoxytetrahydro-2H-pyran

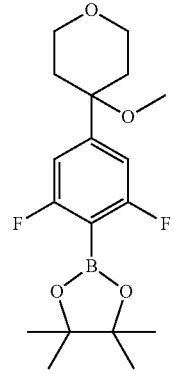 [SMILES: COC1(c2cc(F)c(B3OC(C)(C)C(C)(C)O3)c(F)c2)CCOCC1]

4-(3,5-Difluorophenyl)-4-methoxytetrahydro-2H-pyran (183 mg, 0.802 mmol) and a magnet bar were placed in a vial. The vial was evacuated and backfilled with nitrogen three times. After addition of tetrahydrofuran (3.0 mL), the reaction mixture was cooled to −78° C. Then 2.5M solution of n-butyllithium in hexanes (640 µL, 1.6 mmol) was slowly added and the reaction mixture was stirred at −78° C. for 1 h. After this time 2-isopropoxy-4,4,5,5-tetramethyl-1,3,2-dioxaborolane (410 µL, 2.0 mmol) was slowly added. After stirring at −78° C. for 5 min, the reaction mixture was allowed to warm to room temperature and was stirred at room temperature for 1 h. After this time the reaction mixture was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification.

Step 4. tert-Butyl ((3R,4R,5S)-4-{[tert-butyl(dimethyl)silyl]oxy}-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-3-yl)carbamate

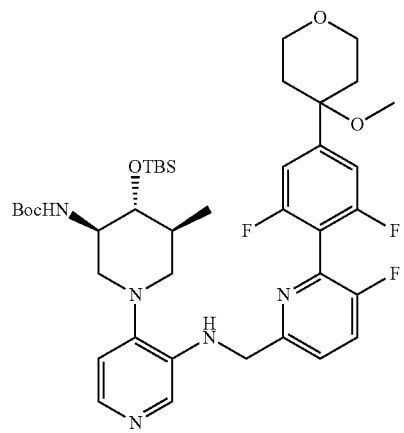 [SMILES: COC1(c2cc(F)c(-c3nc(CNc4cnccc4N4C[C@H](C)[C@@H](O[Si](C)(C)C(C)(C)C)[C@H](NC(=O)OC(C)(C)C)C4)ccc3F)c(F)c2)CCOCC1]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally, 4-[3,5-difluoro-4-(4,4,5,5-tetramethyl-1,3,2-dioxaborolan-2-yl)phenyl]-4-methoxytetrahydro-2H-pyran (18 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{40}H_{57}F_3N_5O_5Si$ $(M+H)^+$ m/z=772.4; found: 772.3.

Step 5. (3R,4R,5S)-3-Amino-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-3-yl)carbamate (25 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{29}H_{35}F_3N_5O_3$ $(M+H)^+$ m/z=558.3; found: 558.2.

Example 60

4-[(3S,5R)-3-Amino-5-methylpiperidin-1-yl]-N-({6-[2,6-difluoro-4-(4-methoxytetrahydro-2H-pyran-4-yl)phenyl]-5-fluoropyridin-2-yl}methyl)pyridin-3-amine

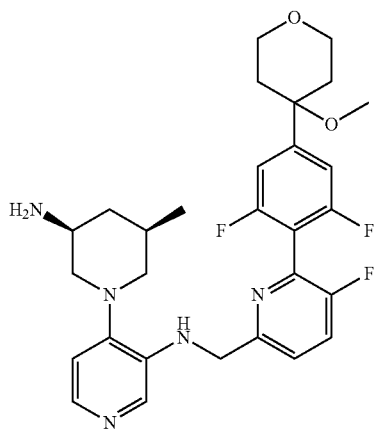 [SMILES: COC1(c2cc(F)c(-c3nc(CNc4cnccc4N4C[C@H](C)C[C@H](N)C4)ccc3F)c(F)c2)CCOCC1]

Step 1. tert-Butyl ((3S,5R)-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-3-yl)carbamate

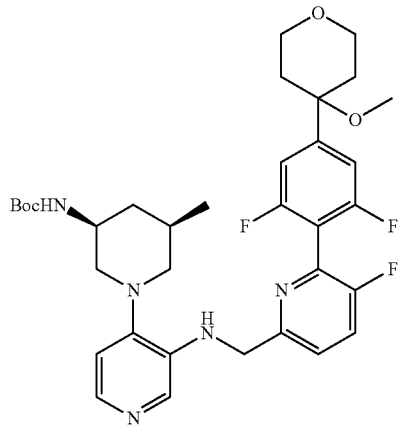 [SMILES: COC1(c2cc(F)c(-c3nc(CNc4cnccc4N4C[C@H](C)C[C@H](NC(=O)OC(C)(C)C)C4)ccc3F)c(F)c2)CCOCC1]

tert-Butyl [(3S,5R)-1-(3-{[(6-bromo-5-fluoropyridin-2-yl)methyl]amino}pyridin-4-yl)-5-methylpiperidin-3-yl]carbamate (Intermediate 2; 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 4-[3,5-difluoro-4-(4,4,5,5-tetramethyl-1,3,2-dioxaborolan-2-yl)phenyl]-4-methoxytetrahydro-2H-pyran (18 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{34}H_{43}F_3N_5O_4$ $(M+H)^+$ m/z=642.3; found: 642.4.

Step 2. 4-[(3S,5R)-3-Amino-5-methylpiperidin-1-yl]-N-({6-[2,6-difluoro-4-(4-methoxytetrahydro-2H-pyran-4-yl)phenyl]-5-fluoropyridin-2-yl}methyl)pyridin-3-amine tert-Butyl ((3S,5R)-1-{3-[({6-[2,6-difluoro-4-(4-methoxytetrahydro-2H-pyran-4-yl)phenyl]-5-fluoropyridin-2-yl}methyl)amino]pyridin-4-yl}-5-methylpiperidin-3-yl)carbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{29}H_{35}F_3N_5O_2$ $(M+H)^+$ m/z=542.3; found: 542.2.

Example 61

(3R,4R,5S)-3-Amino-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-4-ol

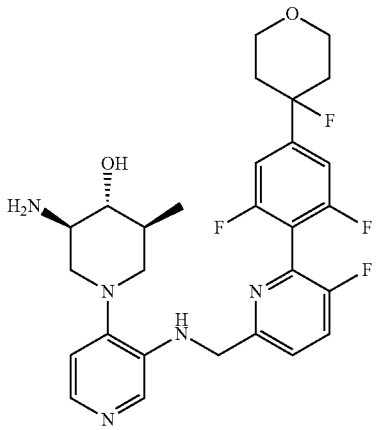 [SMILES: C[C@H]1CN(c2ccncc2NCc2ccc(F)c(-c3c(F)cc(C4(F)CCOCC4)cc3F)n2)C[C@@H](N)[C@@H]1O]

Step 1.
4-(3,5-Difluorophenyl)-4-fluorotetrahydro-2H-pyran

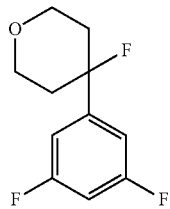 [SMILES: Fc1cc(F)cc(C2(F)CCOCC2)c1]

To a solution of 4-(3,5-difluorophenyl)tetrahydro-2H-pyran-4-ol (Prepared in Example 59, Step 1; 400.0 mg, 1.867 mmol) in DCM (5.0 mL) was slowly added diethylaminosulfur trifluoride (270 µL, 2.0 mmol). After stirring at room temperature for 1 h the solvent was evaporated under reduced pressure and the crude product was purified by Biotage Isolera to give the desired compound (208 mg, 52%).

Step 2. 4-[3,5-Difluoro-4-(4,4,5,5-tetramethyl-1,3,2-dioxaborolan-2-yl)phenyl]-4-fluorotetrahydro-2H-pyran

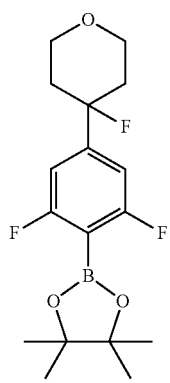 [SMILES: CC1(C)OB(c2c(F)cc(C3(F)CCOCC3)cc2F)OC1(C)C]

4-(3,5-Difluorophenyl)-4-fluorotetrahydro-2H-pyran (208 mg, 0.962 mmol) and a magnet bar were placed in a vial. The vial was evacuated and backfilled with nitrogen three times. After addition of tetrahydrofuran (3.0 mL), the reaction mixture was cooled to −78° C. Then 2.5M solution of n-butyllithium in hexanes (770 µL, 1.9 mmol) was slowly added and the reaction was stirred at −78° C. for 1 h. After this time 2-isopropoxy-4,4,5,5-tetramethyl-1,3,2-dioxaborolane (490 µL, 2.4 mmol) was slowly added to the reaction mixture. After stirring at −78° C. for 5 min more, the reaction was allowed to warm to room temperature and was stirred at room temperature for 1 h. After this time the reaction mixture was carefully quenched by the addition of saturated solution of ammonium chloride. The product was extracted with EtOAc. Combined organic fractions were washed with brine, dried over $Na_2SO_4$ and solvents were evaporated under reduced pressure. The resulting product was used in the next step without further purification.

Step 3. tert-Butyl ((3R,4R,5S)-4-{[tert-butyl(dimethyl)silyl]oxy}-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-3-yl)carbamate

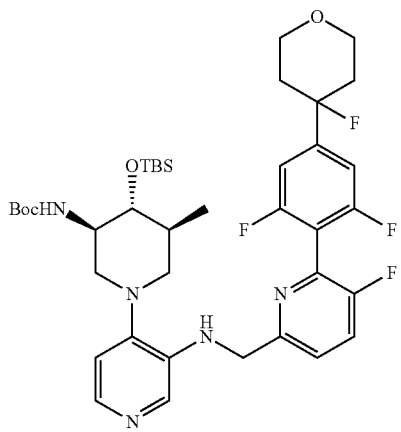 [SMILES: C[C@H]1CN(c2ccncc2NCc2ccc(F)c(-c3c(F)cc(C4(F)CCOCC4)cc3F)n2)C[C@@H](NC(=O)OC(C)(C)C)[C@@H]1O[Si](C)(C)C(C)(C)C]

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (Intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 4-[3,5-difluoro-4-(4,4,5,5-tetramethyl-1,3,2-dioxaborolan-2-yl)phenyl]-4-fluorotetrahydro-2H-pyran (18 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{39}H_{54}F_4N_5O_4Si$ $(M+H)^+$ m/z=760.4; found: 760.4.

Step 4. (3R,4R,5S)-3-Amino-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-3-yl)carbamate (24 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{28}$H$_{32}$F$_4$N$_5$O$_2$ (M+H)$^+$ m/z=546.3; found: 546.3. $^1$H NMR (400 MHz, DMSO-d6) δ 7.93 (t, J=9.0 Hz, 1H), 7.82 (d, J=5.1 Hz, 1H), 7.79 (s, 1H), 7.60 (dd, J=8.7, 3.9 Hz, 1H), 7.40 (d, J=8.8 Hz, 2H), 6.85 (d, J=5.1 Hz, 1H), 5.73 (t, J=5.6 Hz, 1H), 5.21 (d, J=4.4 Hz, 2H), 4.64-4.43 (m, 3H), 3.90 (dd, J=11.1, 5.0 Hz, 2H), 3.71 (t, J=11.0 Hz, 2H), 3.19 (d, J=10.7 Hz, 1H), 2.95 (td, J=10.1, 4.4 Hz, 1H), 2.91-2.83 (m, 1H), 2.49-2.41 (m, 1H), 2.38-2.12 (m, 4H), 1.91 (t, J=11.8 Hz, 2H), 1.80-1.64 (m, 1H), 0.86 (d, J=6.6 Hz, 3H) ppm.

Example 62

4-[(3S,5R)-3-Amino-5-methylpiperidin-1-yl]-N-({6-[2,6-difluoro-4-(4-fluorotetrahydro-2H-pyran-4-yl)phenyl]-5-fluoropyridin-2-yl}methyl)pyridin-3-amine

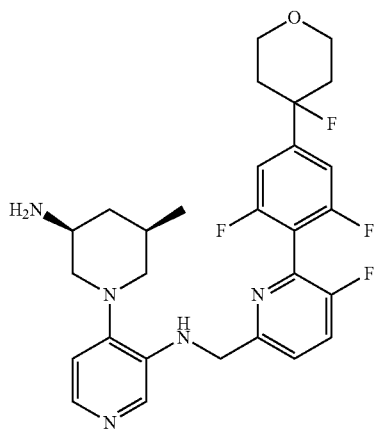 [SMILES: C[C@@H]1C[C@H](N)CN(c2ccncc2NCc2ccc(F)c(-c3c(F)cc(C4(F)CCOCC4)cc3F)n2)C1]

Step 1. tert-Butyl ((3S,5R)-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-3-yl)carbamate

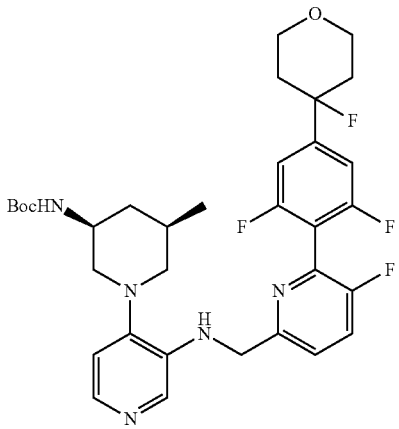 [SMILES: C[C@@H]1C[C@H](NC(=O)OC(C)(C)C)CN(c2ccncc2NCc2ccc(F)c(-c3c(F)cc(C4(F)CCOCC4)cc3F)n2)C1]

tert-Butyl [(3S,5R)-1-(3-{[(6-bromo-5-fluoropyridin-2-yl)methyl]amino}pyridin-4-yl)-5-methylpiperidin-3-yl]carbamate (intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 4-[3,5-difluoro-4-(4,4,5,5-tetramethyl-1,3,2-dioxaborolan-2-yl)phenyl]-4-fluorotetrahydro-2H-pyran (Prepared in Example 61, Step 2; 18 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{33}$H$_{40}$F$_4$N$_5$O$_3$ (M+H)$^+$ m/z=630.3; found: 630.3.

Step 2. 4-[(3S,5R)-3-Amino-5-methylpiperidin-1-yl]-N-({6-[2,6-difluoro-4-(4-fluorotetrahydro-2H-pyran-4-yl)phenyl]-5-fluoropyridin-2-yl}methyl)pyridin-3-amine tert-Butyl ((3S,5R)-1-{3-[({6-[2,6-difluoro-4-(4-fluorotetrahydro-2H-pyran-4-yl)phenyl]-5-fluoropyridin-2-yl}methyl)amino]pyridin-4-yl}-5-methylpiperidin-3-yl)carbamate (20 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{28}$H$_{32}$F$_4$N$_5$O (M+H)$^+$ m/z=530.3; found: 530.2.

Example 63

(3R,4R,5S)-3-Amino-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-4-ol

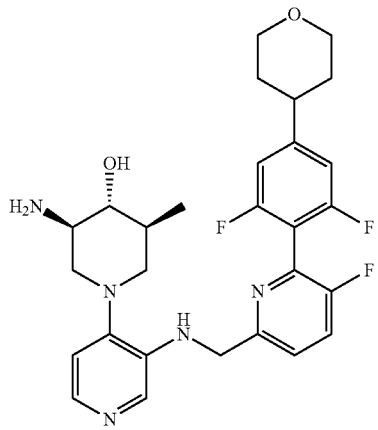 [SMILES: C[C@H]1CN(c2ccncc2NCc2ccc(F)c(-c3c(F)cc(C4CCOCC4)cc3F)n2)C[C@@H](N)[C@@H]1O]

Step 1. 4-(3,5-Difluorophenyl)-3,6-dihydro-2H-pyran

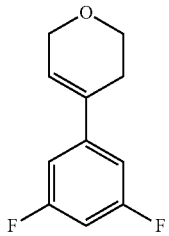 [SMILES: Fc1cc(F)cc(C2=CCOCC2)c1]

1-Bromo-3,5-difluorobenzene (0.80 g, 4.14 mmol), chloro(2-dicyclohexylphosphino-2',4',6'-triisopropyl-1,1'-biphenyl)[2-(2'-amino-1,1'-biphenyl)]palladium(II) (Pd XPhos G2) (326 mg, 0.414 mmol), potassium phosphate (2.59 g, 12.4 mmol) and magnet bar were placed in a vial with septum. The vial was then evacuated and backfilled with nitrogen three times. 1,4-Dioxane (10 mL) and degassed water (1 mL) were added. Finally, 4-(4,4,5,5-tetramethyl-1,3,2-dioxaborolan-2-yl)-3,6-dihydro-2H-pyran (Sigma-Aldrich, 1.05 g, 4.99 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The crude product was purified by Biotage Isolera to give the desired compound (700 mg, 86%).

Step 2. 4-(3,5-Difluorophenyl)tetrahydro-2H-pyran

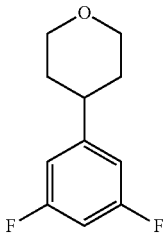 [SMILES: Fc1cc(F)cc(C2CCOCC2)c1]

To a stirred solution of 4-(3,5-difluorophenyl)-3,6-dihydro-2H-pyran (0.700 g, 3.57 mmol) in methanol (10 mL) was added 5 w % of Pd on carbon (31 mg, 0.015 mmol). Vial containing the reaction mixture was closed with septum and was connected to a balloon with hydrogen. After stirring at room temperature overnight, the reaction was filtered through a pad of diatomaceous earth and the solvent was evaporated under reduced pressure. The resulting crude product was used in the next step without further purification (700 mg, 99%).

Step 3. 2-(2,6-Difluoro-4-(tetrahydro-2H-pyran-4-yl)phenyl)-4,4,5,5-tetramethyl-1,3,2-dioxaborolane

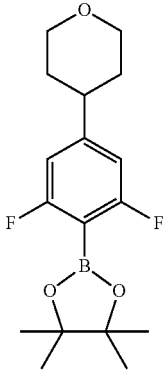 [SMILES: CC1(C)OB(c2c(F)cc(C3CCOCC3)cc2F)OC1(C)C]

4-(3,5-Difluorophenyl)tetrahydro-2H-pyran (700 mg, 2.2 mmol) and a magnet bar were placed in a vial. The vial was evacuated and backfilled with nitrogen three times. After addition of tetrahydrofuran (8 mL), the reaction mixture was cooled to −78° C. Then 2.5M solution of n-butyllithium in hexanes (1.22 mL, 3.0 mmol) was slowly added and the reaction mixture was stirred at −78° C. for 1 h. After this time 2-isopropoxy-4,4,5,5-tetramethyl-1,3,2-dioxaborolane (715 μL, 3.5 mmol) was slowly added to the reaction mixture. After stirring at −78° C. for 5 min more, the reaction was allowed to warm to room temperature and was stirred at room temperature for 1 h. After this time the reaction mixture was carefully quenched by the addition of saturated solution of ammonium chloride. The product was extracted with EtOAc. Combined organic fractions were washed with brine, dried over Na$_2$SO$_4$ and solvents were evaporated under reduced pressure. The resulting product was used in the next step without further purification.

Step 4. tert-Butyl ((3R,4R,5S)-4-{[tert-butyl(dimethyl)silyl]oxy}-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-3-yl)carbamate

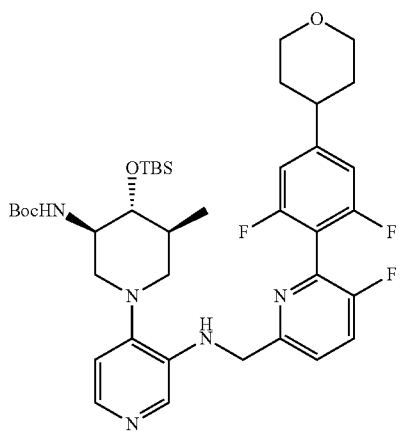

tert-Butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (intermediate 1, 20.0 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-(2,6-Difluoro-4-(tetrahydro-2H-pyran-4-yl)phenyl)-4,4,5,5-tetramethyl-1,3,2-dioxaborolane (17 mg, 0.051 mmol) was added and the reaction mixture was stirred at 65° C. for 1 h. Then the reaction mixture was diluted with EtOAc. The resulting solution was washed with brine, dried over $Na_2SO_4$ and solvent evaporated. The resulting crude product was used in the next step without further purification. LCMS calc. for $C_{39}H_{55}F_3N_5O_4Si$ $(M+H)^+$ m/z=742.4; found: 742.3.

Step 5. (3R,4R,5S)-3-Amino-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-3-yl)carbamate (24 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{28}H_{33}F_3N_5O_2$ $(M+H)^+$ m/z=528.3; found: 528.3. $^1H$ NMR (400 MHz, DMSO-d6) δ 7.90 (t, J=9.0 Hz, 1H), 7.80 (d, J=5.1 Hz, 1H), 7.77 (s, 1H), 7.57 (dd, J=8.6, 3.8 Hz, 1H), 7.21 (d, J=9.0 Hz, 2H), 6.83 (d, J=5.1 Hz, 1H), 5.63 (t, J=5.9 Hz, 1H), 4.74 (d, J=4.6 Hz, 1H), 4.61-4.45 (m, 2H), 4.02-3.92 (m, 2H), 3.52-3.40 (m, 2H), 3.19 (td, J=9.5, 3.0 Hz, 2H), 2.92 (t, J=11.4 Hz, 1H), 2.76-2.62 (m, 2H), 2.34 (t, J=10.8 Hz, 1H), 2.21 (t, J=11.6 Hz, 1H), 1.87-1.52 (m, 7H), 0.84 (d, J=6.6 Hz, 3H) ppm.

Example 64

4-[(3S,5R)-3-Amino-5-methylpiperidin-1-yl]-N-({6-[2,6-difluoro-4-(tetrahydro-2H-pyran-4-yl)phenyl]-5-fluoropyridin-2-yl}methyl)pyridin-3-amine

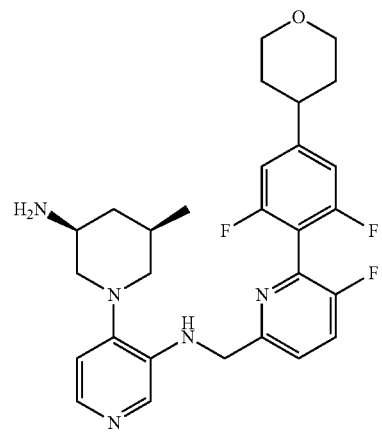

Step 1. tert-Butyl ((3S,5R)-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-3-yl)carbamate

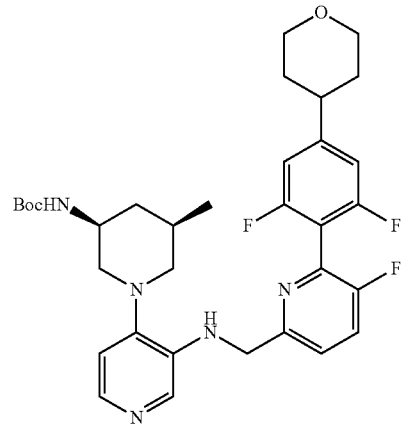

tert-Butyl [(3S,5R)-1-(3-{[(6-bromo-5-fluoropyridin-2-yl)methyl]amino}pyridin-4-yl)-5-methylpiperidin-3-yl]carbamate (Intermediate 2, 15.8 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-(2,6-

Difluoro-4-(tetrahydro-2H-pyran-4-yl)phenyl)-4,4,5,5-tetramethyl-1,3,2-dioxaborolane (Prepared in Example 63, Step 3; 17 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{33}$H$_{41}$F$_3$N$_5$O$_3$ (M+H)$^+$ m/z=612.3; found: 612.3.

Step 2. 4-[(3S,5R)-3-Amino-5-methylpiperidin-1-yl]-N-({6-[2,6-difluoro-4-(tetrahydro-2H-pyran-4-yl)phenyl]-5-fluoropyridin-2-yl}methyl)pyridin-3-amine tert-Butyl ((3S,5R)-1-{3-[({6-[2,6-difluoro-4-(tetrahydro-2H-pyran-4-yl)phenyl]-5-fluoropyridin-2-yl}methyl)amino]pyridin-4-yl}-5-methylpiperidin-3-yl)carbamate (20 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{28}$H$_{33}$F$_3$N$_5$O (M+H)$^+$ m/z=512.3; found: 512.3. $^1$H NMR (400 MHz, DMSO-d6) δ 7.93 (t, J=8.9 Hz, 1H), 7.82 (d, J=5.0 Hz, 1H), 7.80 (s, 1H), 7.60 (dd, J=8.7, 3.9 Hz, 1H), 7.24 (d, J=9.2 Hz, 2H), 6.81 (d, J=5.1 Hz, 1H), 5.73 (t, J=5.4 Hz, 1H), 4.52 (qd, J=16.4, 5.3 Hz, 2H), 3.99 (d, J=10.6 Hz, 2H), 3.46 (td, J=11.2, 3.4 Hz, 2H), 3.21-3.07 (m, 2H), 2.94 (dq, J=10.2, 5.3 Hz, 1H), 2.83-2.71 (m, 1H), 2.14 (t, J=10.5 Hz, 1H), 1.94 (t, J=11.1 Hz, 1H), 1.86-1.56 (m, 7H), 0.79-0.66 (m, 4H) ppm.

Example 65

4-((3S,5R)-3-Amino-5-(trifluoromethyl)piperidin-1-yl)-N-((6-(2,6-difluoro-4-(tetrahydro-2H-pyran-4-yl)phenyl)-5-fluoropyridin-2-yl)methyl)pyridin-3-amine

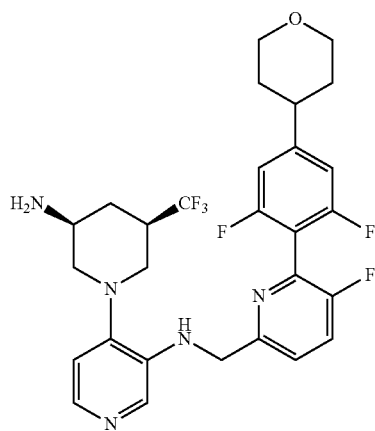 [SMILES: N[C@H]1C[C@@H](C(F)(F)F)CN(c2ccncc2NCc2ccc(F)c(-c3c(F)cc(C4CCOCC4)cc3F)n2)C1]

Step 1. tert-butyl ((3S,5R)-1-(3-(((6-(2,6-difluoro-4-(tetrahydro-2H-pyran-4-yl)phenyl)-5-fluoropyridin-2-yl)methyl)amino)pyridin-4-yl)-5-(trifluoromethyl)piperidin-3-yl)carbamate

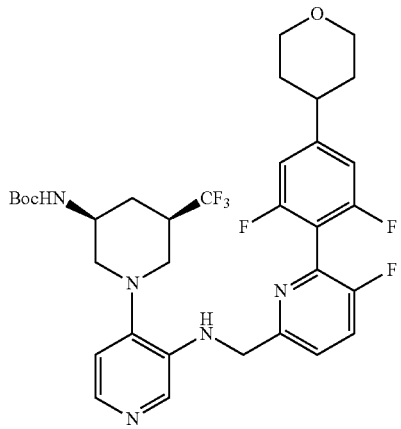 [SMILES: CC(C)(C)OC(=O)N[C@H]1C[C@@H](C(F)(F)F)CN(c2ccncc2NCc2ccc(F)c(-c3c(F)cc(C4CCOCC4)cc3F)n2)C1]

tert-butyl ((3S,5R)-1-(3-(((6-bromo-5-fluoropyridin-2-yl)methyl)amino)pyridin-4-yl)-5-(trifluoromethyl)piperidin-3-yl)carbamate (intermediate 3, 17.5 mg, 0.0320 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-(2,6-Difluoro-4-(tetrahydro-2H-pyran-4-yl)phenyl)-4,4,5,5-tetramethyl-1,3,2-dioxaborolane (Prepared in Example 63, Step 3; 17 mg, 0.051 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The resulting crude product was used in the next step without further purification. LCMS calc. for C$_{33}$H$_{38}$F$_6$N$_5$O$_3$ (M+H)$^+$ m/z=666.3; found: 666.2.

Step 2. 4-((3S,5R)-3-Amino-5-(trifluoromethyl)piperidin-1-yl)-N-((6-(2,6-difluoro-4-(tetrahydro-2H-pyran-4-yl)phenyl)-5-fluoropyridin-2-yl)methyl)pyridin-3-amine tert-Butyl ((3S,5R)-1-(3-(((6-(2,6-difluoro-4-(tetrahydro-2H-pyran-4-yl)phenyl)-5-fluoropyridin-2-yl)methyl)amino)pyridin-4-yl)-5-(trifluoromethyl)piperidin-3-yl)carbamate (21 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% NH$_4$OH, at flow rate of 60 mL/min). LCMS calc. for C$_{28}$H$_{30}$F$_6$N$_5$O (M+H)$^+$ m/z=566.2; found: 566.2.

Example 66

4-[(1R,3S,5S)-3-Amino-5-methylcyclohexyl]-N-{[6-(2,6-difluorophenyl)-5-fluoropyridin-2-yl]methyl}pyridin-3-amine

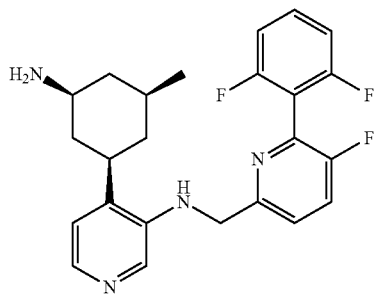 [SMILES: C[C@@H]1C[C@H](N)C[C@H](c2ccncc2NCc2ccc(F)c(-c3c(F)cccc3F)n2)C1]

Step 1. Methyl 6-(2,6-difluorophenyl)-5-fluoropyridine-2-carboxylate

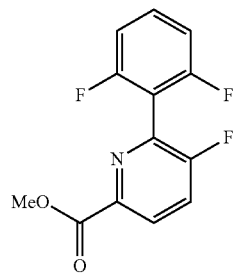 [SMILES: COC(=O)c1ccc(F)c(-c2c(F)cccc2F)n1]

To a screw-cap vial equipped with a magnetic stir bar, methyl 6-bromo-5-fluoropyridine-2-carboxylate (Frontier Scientific, 200.2 mg, 0.8555 mmol) was added followed by the addition of 2-(2,6-difluorophenyl)-4,4,5,5-tetramethyl-1,3,2-dioxaborolane (Combi-Blocks, 310.2 mg, 1.292 mmol), and bis(tri-tert-butylphosphine)palladium (87.5 mg, 0.171 mmol). The vial was sealed with a PTFE-lined septum, evacuated and backfilled with nitrogen three times. 1,4-Dioxane (3.0 mL) was added via a syringe, followed by the addition of DIPEA (0.30 mL, 1.7 mmol) and deoxygenated water (0.1 mL). The reaction mixture was heated at 100° C. for 2 h and was then allowed to cool to room temperature. The reaction mixture was diluted with EtOAc (40 mL), washed with water (40 mL) and brine (40 mL), then dried over Na$_2$SO$_4$, and concentrated under reduced pressure. The resulting residue was purified by chromatography on silica gel (gradient elution with 0-50% EtOAc in hexanes) to give the sub-title compound as a white solid (210.2 mg, 92%). LCMS calc. for C$_{13}$H$_9$F$_3$NO$_2$ (M+H)$^+$: m/z=268.1; found 268.0.

Step 2. 6-(2,6-Difluorophenyl)-5-fluoropyridine-2-carboxylic acid

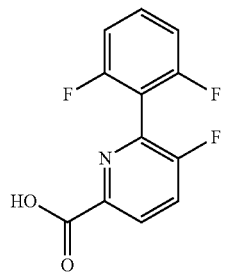 [SMILES: O=C(O)c1ccc(F)c(-c2c(F)cccc2F)n1]

To a mixture of methyl 6-(2,6-difluorophenyl)-5-fluoropyridine-2-carboxylate (210.2 mg, 0.7867 mmol) and lithium hydroxide, monohydrate (162 mg, 3.86 mmol), THF (3.0 mL) was added followed by the addition of water (1.0 mL). The reaction mixture was heated at 50° C. for 3 h. The reaction mixture was then cooled to 0° C., and 1M HCl was added slowly until the pH reached 2. The reaction mixture was then diluted with water (20 mL), extracted with EtOAc (3×20 mL) and the combined organic layers were washed with brine (30 mL), dried over Na$_2$SO$_4$, and concentrated under reduced pressure to yield the sub-title compound as a white solid (162.1 mg, 81%). LCMS calc. for C$_{12}$H$_7$F$_3$NO$_2$ (M+H)$^+$: m/z=254.0; found 254.0.

Step 3: [6-(2,6-Difluorophenyl)-5-fluoropyridin-2-yl]methanol

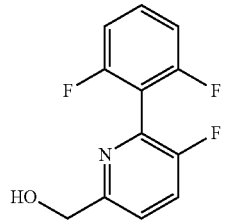 [SMILES: OCc1ccc(F)c(-c2c(F)cccc2F)n1]

To a mixture of 6-(2,6-difluorophenyl)-5-fluoropyridine-2-carboxylic acid (2.00 g, 7.9 mmol) and triethylamine (1.16 mL, 8.3 mmol) in tetrahydrofuran (38.4 mL) was slowly added isobutyl chloroformate (1.08 mL, 8.3 mmol). The reaction mixture was stirred at room temperature for 1 h. The precipitate was then collected by filtration. The filtrate was cooled in an ice bath and a solution of sodium borohydride (0.60 g, 2.0 mmol) in water (10.0 mL) was added dropwise. The reaction mixture was stirred for 1 h at room temperature, and then quenched with NaHCO$_3$ solution, extracted with EtOAc, washed with brine. The combined organic layers were filtered, dried over Na$_2$SO$_4$ and concentrated to give the desired product as white powders (1.82 g, 96%). LCMS calc. for C$_{12}$H$_9$F$_3$NO (M+H)$^+$: m/z=240.2. Found: 240.1.

Step 4: 6-(2,6-Difluorophenyl)-5-fluoropyridine-2-carbaldehyde

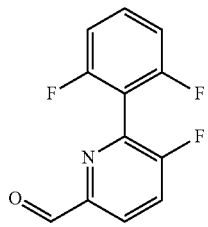 [SMILES: O=Cc1ccc(F)c(-c2c(F)cccc2F)n1]

To a stirred solution of [6-(2,6-difluorophenyl)-5-fluoropyridin-2-yl]methanol (945 mg, 3.95 mmol) in DCM (25.3 mL) at 0° C. were added pyridine (0.38 mL, 4.7 mmol) and Dess-Martin periodinane (1.76 g, 4.15 mmol). The reaction mixture was stirred for 16 h at room temperature, at which time full conversion of the starting material to the aldehyde product was detected by LCMS. NaHCO$_3$ and Na$_2$S$_2$O$_3$ aqueous solutions were added and the resulting mixture was stirred for 30 min. The reaction mixture was extracted with DCM, dried and purified by Biotage column to give the desired product (675 mg, 72%) as white powders. LCMS calc. for C$_{12}$H$_7$F$_3$NO (M+H)$^+$: m/z=238.0. Found: 238.2.

Step 5. tert-Butyl {(1S,3R,5S)-3-[3-({[6-(2,6-difluorophenyl)-5-fluoropyridin-2-yl]methyl}amino)pyridin-4-yl]-5-methylcyclohexyl}carbamate

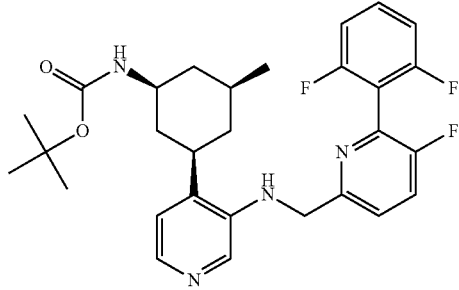 [SMILES: C[C@@H]1C[C@H](NC(=O)OC(C)(C)C)C[C@H](c2ccncc2NCc2ccc(F)c(-c3c(F)cccc3F)n2)C1]

tert-Butyl [(1S,3R,5S)-3-(3-aminopyridin-4-yl)-5-methylcyclohexyl]carbamate (Intermediate 6, peak 2; 69.4 mg, 0.227 mmol) and 6-(2,6-difluorophenyl)-5-fluoropyridine-2-carbaldehyde (62.0 mg, 0.261 mmol) were dissolved in toluene (1.4 mL) and 1 drop of acetic acid was added. The reaction mixture was heated at 100° C. for 2 h. After cooling to room temperature, the solvent was evaporated under reduced pressure and methanol (1.4 mL) was added. To the reaction mixture was added sodium tetrahydroborate (17 mg, 0.45 mmol) and the resulting reaction mixture was stirred for 30 min. The reaction mixture was quenched with water and NaHCO3. The layers were separated and the aqueous layer was extracted with EtOAc. The combined organic phases were washed with brine, dried over Na$_2$SO$_4$, filtered and concentrated. The crude was used in the next step without further purification.

Step 6. 4-[(1R,3S,5S)-3-Amino-5-methylcyclohexyl]-N-{[6-(2,6-difluorophenyl)-5-fluoropyridin-2-yl]methyl}pyridin-3-amine tert-Butyl {(1 S,3R,5 S)-3-[3-({[6-(2,6-difluorophenyl)-5-fluoropyridin-2-yl]methyl}amino)pyridin-4-yl]-5-methylcyclohexyl}carbamate (140 mg, 0.266 mmol) was dissolved in DCM (6 mL) and trifluoroacetic acid (6 mL) was added. The reaction mixture was stirred for 1 h. After removing the solvent under reduced pressure, the residue was dissolved in methanol and purified with prep-LCMS (XBridge C18 column, gradient elution with acetonitrile/water containing 0.1% ammonium hydroxide, at flow rate of 60 mL/min) to give the desired product as white solid (10.5 mg, 9%). LCMS calc. for C$_{24}$H$_{26}$F$_3$N$_4$ (M+H)$^+$: m/z=427.2; Found: 427.1.

Example 67

1-(4-{6-[({4-[(1R,3S,5S)-3-Amino-5-methylcyclohexyl]pyridin-3-yl}amino)methyl]-3-fluoropyridin-2-yl}-3,5-difluorophenyl)cyclobutanol

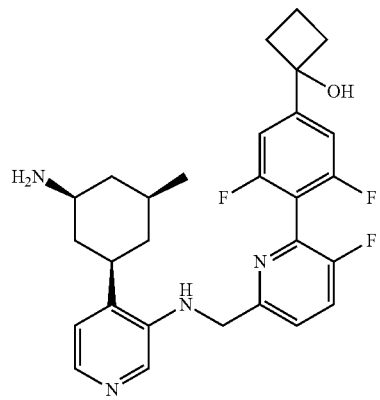 [SMILES: C[C@@H]1C[C@H](N)C[C@H](c2ccncc2NCc2ccc(F)c(-c3c(F)cc(C4(O)CCC4)cc3F)n2)C1]

Step 1. tert-Butyl ((1S,3R,5S)-3-{3-[({6-[2,6-difluoro-4-(1-hydroxycyclobutyl)phenyl]-5-fluoropyridin-2-yl}methyl)amino]pyridin-4-yl}-5-methylcyclohexyl)carbamate

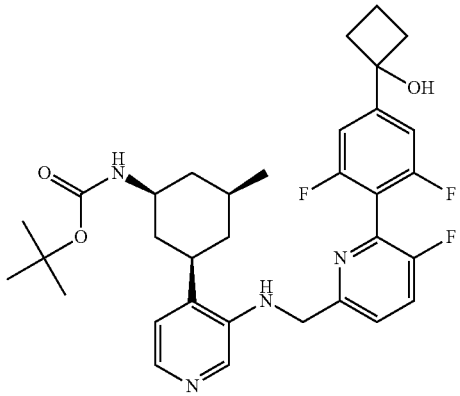 [SMILES: C[C@@H]1C[C@H](NC(=O)OC(C)(C)C)C[C@H](c2ccncc2NCc2ccc(F)c(-c3c(F)cc(C4(O)CCC4)cc3F)n2)C1]

tert-Butyl [(1S,3R,5S)-3-(3-aminopyridin-4-yl)-5-methylcyclohexyl]carbamate (Intermediate 6, peak 2; 37.2 mg, 0.122 mmol) and 6-[2,6-difluoro-4-(1-hydroxycyclobutyl)phenyl]-5-fluoropyridine-2-carbaldehyde (Prepared in Example 2; 43.0 mg, 0.140 mmol) were dissolved in toluene (0.75 mL) and a drop of acetic acid was added. The reaction mixture was heated at 100° C. for 2 h. After cooling to room temperature, the solvent was evaporated under reduced pressure and methanol (0.8 mL) was added. To the reaction mixture was added sodium tetrahydroborate (9.2 mg, 0.24 mmol) and the resulting reaction mixture was stirred for 30 min. The reaction was quenched with water and NaHCO$_3$. The layers were separated and the aqueous layer was extracted with EtOAc. The combined organic layers were washed with brine, dried over Na₂SO₄, filtered and concentrated. The crude residue was used in the next step without further purification.

Step 2. 1-(4-{6-[({4-[(1R,3S,5S)-3-Amino-5-methylcyclohexyl]pyridin-3-yl}amino)methyl]-3-fluoropyridin-2-yl}-3,5-difluorophenyl)cyclobutanol The crude residue from last step was treated with 1:1 TFA/DCM (2 mL) for 1 h. The solvent was evaporated under reduced pressure and the resultant residue was dissolved in methanol and purified with prep-LCMS (XBridge C18 column, gradient elution with acetonitrile/water containing 0.1% ammonium hydroxide, at flow rate of 60 mL/min) to give the desired product as white solid (25 mg, 41%). LCMS calc. for $C_{28}H_{32}F_3N_4O$ (M+H)⁺: m/z=497.2; Found: 497.2.

Example 68

4-[(1R,3S,5S)-3-Amino-5-methylcyclohexyl]-N-{[6-(2,6-difluoro-4-morpholin-4-ylphenyl)-5-fluoropyridin-2-yl]methyl}pyridin-3-amine

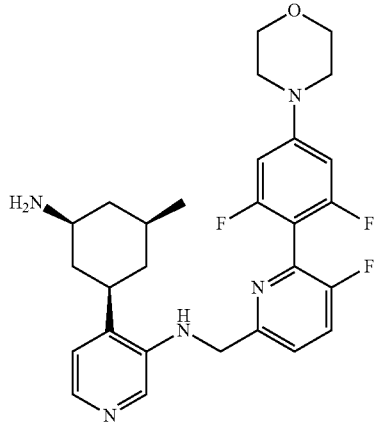 [SMILES: C[C@@H]1C[C@H](N)C[C@H](c2ccncc2NCc2ccc(F)c(-c3c(F)cc(N4CCOCC4)cc3F)n2)C1]

Step 1. Methyl 6-(2,6-difluoro-4-morpholin-4-ylphenyl)-5-fluoropyridine-2-carboxylate

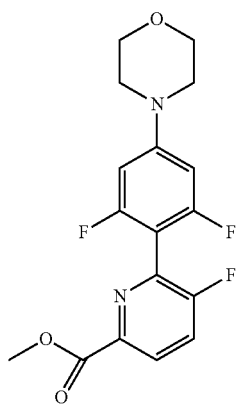 [SMILES: COC(=O)c1ccc(F)c(-c2c(F)cc(N3CCOCC3)cc2F)n1]

Methyl 6-bromo-5-fluoropyridine-2-carboxylate (250 mg, 1.1 mmol), dicyclohexyl(2',4',6'-triisopropylbiphenyl-2-yl)phosphine-(2'-aminobiphenyl-2-yl)(chloro)palladium (1:1) (84 mg, 0.11 mmol) and K₃PO₄ (680 mg, 3.2 mmol) were placed in a vial with septum. The vial was then evacuated and backfilled with nitrogen three times. 1,4-Dioxane (8.1 mL) and degassed water (3 mL) were added, followed by 4-[3,5-difluoro-4-(4,4,5,5-tetramethyl-1,3,2-dioxaborolan-2-yl)phenyl]morpholine (Prepared in Example 32, Step 2, 450 mg, 1.4 mmol). The reaction was stirred at 55° C. for 1 h. The reaction mixture was diluted with EtOAc and washed with brine, dried over Na₂SO₄, filtered and concentrated. The residue was purified by silica gel column to give the desired product (0.27 g, 72%). LCMS calc. for $C_{17}H_{16}F_3N_2O_3$ (M+H)⁺: m/z=353.1; Found: 353.1.

Step 2. 6-(2,6-Difluoro-4-morpholin-4-ylphenyl)-5-fluoropyridine-2-carboxylic acid

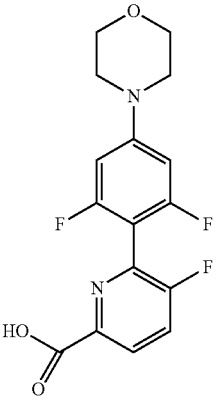 [SMILES: O=C(O)c1ccc(F)c(-c2c(F)cc(N3CCOCC3)cc2F)n1]

A mixture of methyl 6-(2,6-difluoro-4-morpholin-4-ylphenyl)-5-fluoropyridine-2-carboxylate (272 mg, 0.772 mmol), 1.0M sodium hydroxide in water (3.1 mL, 3.1 mmol) in THF (8 mL)/methanol (6 mL) was stirred at r.t. for 1 h. The reaction mixture was acidified by the addition of 1M HCl. The aqueous layer was extracted with EtOAc. The combined organic layers were washed with brined, dried and concentrated to give the desired product which was used in the next step without further purification. LCMS calc. for $C_{16}H_{14}F_3N_2O_3$ (M+H)⁺: m/z=339.1; Found: 339.0.

Step 3. [6-(2,6-Difluoro-4-morpholin-4-ylphenyl)-5-fluoropyridin-2-yl]methanol

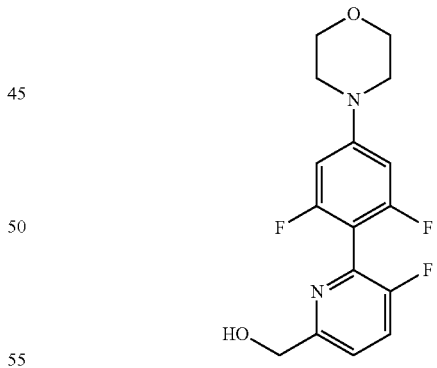

To a mixture of 6-(2,6-difluoro-4-morpholin-4-ylphenyl)-5-fluoropyridine-2-carboxylic acid (242 mg, 0.715 mmol) and triethylamine (105 μL, 0.751 mmol) was slowly added isobutyl chloroformate (97 μL, 0.75 mmol). The reaction mixture was stirred at room temperature for 1 h. The precipitate was then collected by filtration. The filtrate was cooled in an ice bath and a solution of sodium borohydride (54 mg, 1.4 mmol) in water (0.3 mL) was added dropwise. The reaction mixture was stirred for 1 h at room temperature, and then quenched with NaHCO₃ solution, extracted with EtOAc. The combined organic layers were washed with brine, dried over Na$_2$SO$_4$ and concentrated to give the desired product which was used in the next step without further purification. LCMS calc. for C$_{16}$H$_{16}$F$_3$N$_2$O$_2$ (M+H)$^+$: m/z=325.1; Found: 325.1.

Step 4. 6-(2,6-Difluoro-4-morpholin-4-ylphenyl)-5-fluoropyridine-2-carbaldehyde

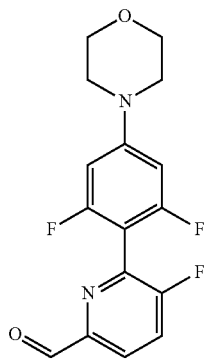 [SMILES: O=Cc1ccc(F)c(-c2c(F)cc(N3CCOCC3)cc2F)n1]

To a stirred solution of [6-(2,6-difluoro-4-morpholin-4-ylphenyl)-5-fluoropyridin-2-yl]methanol (226 mg, 0.697 mmol) in DCM (5 mL) at 0° C. were added pyridine (68 μL, 0.84 mmol) and Dess-Martin periodinane (310 mg, 0.732 mmol). The reaction mixture was stirred for 16 h at r.t. The reaction mixture was diluted with ether and solution of NaHCO$_3$ and Na$_2$S$_2$O$_3$ and the resulting mixture was stirred for 30 min. The layers were separated and the aqueous layer was extracted with ether. The extracts were combined, dried and concentrated. The residue was purified by flashchromatography to give the desired product (0.19 g, 86%). LCMS calc. for C$_{16}$H$_{14}$F$_3$N$_2$O$_2$ (M+H)$^+$: m/z=323.1; Found: 323.1.

Step 5. tert-Butyl {(S, 3R,5S)-3-[3-({[6-(2,6-difluoro-4-morpholin-4-ylphenyl)-5-fluoropyridin-2-yl]methyl}amino)pyridin-4-yl]-5-methylcyclohexyl}carbamate

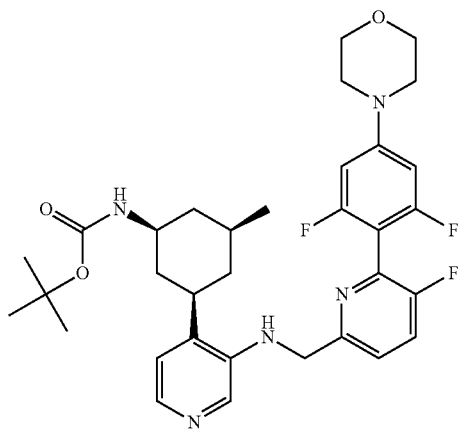 [SMILES: C[C@@H]1C[C@H](NC(=O)OC(C)(C)C)C[C@H](c2ccncc2NCc2ccc(F)c(-c3c(F)cc(N4CCOCC4)cc3F)n2)C1]

tert-Butyl [(1S,3R,5S)-3-(3-aminopyridin-4-yl)-5-methylcyclohexyl]carbamate (Intermediate 6, peak 2; 16.5 mg, 0.054 mmol) and 6-(2,6-difluoro-4-morpholin-4-ylphenyl)-5-fluoropyridine-2-carbaldehyde (20.0 mg, 0.062 mmol) were dissolved in toluene (0.4 mL) and a drop of AcOH was added. The reaction mixture was heated at 100° C. for 2 h. After cooling to room temperature, the solvent was evaporated under reduced pressure and methanol (0.4 mL) was added. To the reaction mixture was added sodium tetrahydroborate (4.1 mg, 0.11 mmol) and the resulting reaction mixture was stirred for 30 min. The reaction was quenched with water and NaHCO$_3$. The layers were separated and the aqueous layer was extracted with EtOAc. The combined organic phases were washed with brine, dried over Na$_2$SO$_4$, filtered and concentrated. The crude residue was used in the next step without further purification.

Step 6. 4-[(1R,3S,5S)-3-Amino-5-methylcyclohexyl]-N-{[6-(2,6-difluoro-4-morpholin-4-ylphenyl)-5-fluoropyridin-2-yl]methyl}pyridin-3-amine The crude product from last step was treated with 1:1 TFA/DCM (2 mL) for 1 h. The solvent was evaporated under reduced pressure and the residue was dissolved in methanol and purified with prep-LCMS (XBridge C18 column, gradient elution with acetonitrile/water containing 0.1% ammonium hydroxide, at flow rate of 60 mL/min) to give the desired product as white solid (11 mg, 40%). LCMS calc. for C$_{28}$H$_{33}$F$_3$N$_5$O (M+H)$^+$: m/z=512.3; Found: 512.2.

Example 69

N-{[5-Amino-2-(2,6-difluorophenyl)-1,3-thiazol-4-yl]methyl}-4-[(3S,5R)-3-amino-5-methylpiperidin-1-yl]pyridin-3-amine

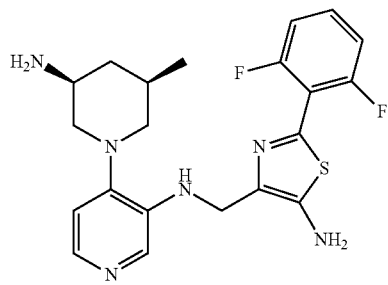 [SMILES: C[C@@H]1C[C@H](N)CN(c2ccncc2NCc2nc(-c3c(F)cccc3F)sc2N)C1]

Step 1. (3S,5R)-5-Methyl-1-(3-nitropyridin-4-yl)piperidin-3-amine

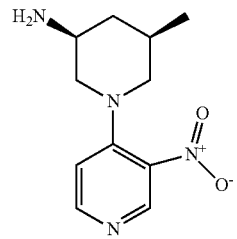 [SMILES: C[C@@H]1C[C@H](N)CN(c2ccncc2[N+](=O)[O-])C1]

To a solution of tert-butyl [(3S,5R)-5-methyl-1-(3-nitropyridin-4-yl)piperidin-3-yl]carbamate (Prepared in Intermediate 2, Step 5; 2.10 g, 6.24 mmol) in DCM (28 mL) was added 4.0M hydrogen chloride in dioxane (12.5 mL, 49.9 mmol). The resulting mixture was stirred at room temperature for 4 h. The solvent was removed under reduced pressure and the solid was used in the next step. LCMS calc. for $C_{11}H_{17}N_4O_2$ (M+H)⁺: m/z=237.1; Found: 237.2.

Step 2. Benzyl [(3S,5R)-1-(3-aminopyridin-4-yl)-5-methylpiperidin-3-yl]carbamate

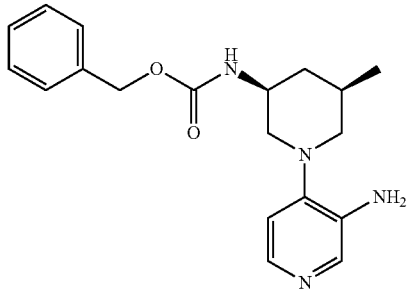 [SMILES: C[C@@H]1C[C@H](NC(=O)OCc2ccccc2)CN(c2ccncc2N)C1]

To a solution of (3S,5R)-5-methyl-1-(3-nitropyridin-4-yl) piperidin-3-amine (1.47 g, 6.22 mmol) in DCM (20 mL) was added DIPEA (3.25 mL, 18.7 mmol), followed by benzyl chloroformate (1.33 mL, 9.33 mmol) at 0° C. After stirring for 1 h, the solution was diluted with water. The organic phase was separated and concentrated under reduced pressure. The residue was dissolved in acetic acid (20 mL) and iron (2.8 g, 50 mmol) was added to the resultant reaction mixture. The reaction mixture was heated at 60° C. for 2 h. The reaction mixture was filtered through a pad of diatomaceous earth and washed with EtOAc. The solvent was removed under reduced pressure and the residue was dissolved in methanol and purified with prep-LCMS (XBridge C18 column, gradient elution with acetonitrile/water containing 0.05% TFA, at flow rate of 60 mL/min) give the desired product (0.32 g, 15%) as an orange oil. LCMS calc. for $C_{19}H_{25}N_4O_2$ (M+H)⁺: m/z=341.2; Found: 341.2.

Step 3. Methyl 5-amino-2-bromo-1,3-thiazole-4-carboxylate

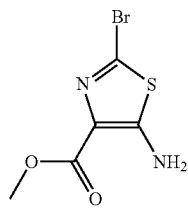

To a solution of methyl 5-amino-1,3-thiazole-4-carboxylate (J & W PharmLab, 10.0 g, 63.2 mmol) in THF (100 mL), N-bromosuccinimide (12.0 g, 67.4 mmol) was added portion-wise. After stirring at room temperature for 1 h, the reaction mixture was filtered to give a first crop of product as a pink solid (9.8 g). The filtrate was concentrated under reduced pressure. The resulting residue was triturated with EtOAc (15 mL) and filtered to give a second crop of product as a pink solid (5.0 g, total yield: 99%). LCMS calc. for $C_5H_6BrN_2O_2S$ (M+H)⁺: m/z=236.9; found 237.0.

Step 4. Methyl 2-bromo-5-[(tert-butoxycarbonyl) amino]-1,3-thiazole-4-carboxylate

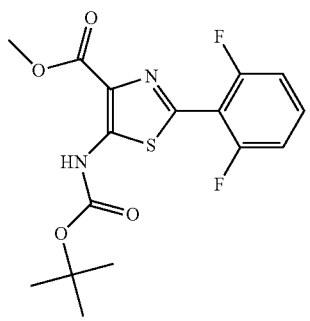 [SMILES: COC(=O)c1nc(-c2c(F)cccc2F)sc1NC(=O)OC(C)(C)C]

To a solution of methyl 5-amino-2-bromo-1,3-thiazole-4-carboxylate (14.8 g, 62.4 mmol) in THF (100 mL), di-tert-butyl dicarbonate (18.0 g, 82.2 mmol), DMAP (1.5 g, 13 mmol) and triethylamine (17.6 mL, 126 mmol) were added. After stirring at room temperature for 16 h, the reaction mixture was diluted with EtOAc (400 mL) and washed with water (2×250 mL). The organic layer was washed with brine (250 mL), dried over $Na_2SO_4$, and concentrated under reduced pressure. The resulting residue was purified by chromatography on silica gel (gradient elution with 0-50% EtOAc in hexanes) to give the sub-title compound as a white solid (15.1 g, 72%). LCMS calc. for $C_{10}H_{14}BrN_2O_4S$ (M+H)⁺: m/z=337.0; found 337.0.

Step 5. Methyl 5-[(tert-butoxycarbonyl)amino]-2-(2,6-difluorophenyl)-1,3-thiazole-4-carboxylate To a round bottom flask equipped with a magnetic stir bar, methyl 2-bromo-5-[(tert-butoxycarbonyl)amino]-1,3-thiazole-4-carboxylate (9.60 g, 28.5 mmol) was added, followed by the addition of 2-(2,6-difluorophenyl)-4,4,5,5-tetramethyl-1,3,2-dioxaborolane (Combi-Blocks, 8.88 g, 37.0 mmol) and bis(tri-tert-butylphosphine)palladium (2.30 g, 4.50 mmol). The flask was sealed with a rubber septum, and evacuated and backfilled with nitrogen three times. 1,4-Dioxane (40.0 mL) was added via a syringe, followed by the addition of DIPEA (9.6 mL, 55 mmol) and deoxygenated water (2.0 mL). The resulting reaction mixture was heated at 100° C. for 1 h. After cooling to room temperature, the reaction mixture was diluted with EtOAc (200 mL) and washed with water (100 mL) and brine (200 mL), then dried over $Na_2SO_4$, and concentrated under reduced pressure. The resulting residue was purified by chromatography on silica gel (0-100% EtOAc in hexanes) to give the sub-title compound as a white solid (9.80 g, 93%). LCMS calc. for $C_{16}H_{17}F_2N_2O_4S$ (M+H)⁺: m/z=371.1; found 371.0.

Step 6. 5-[(tert-Butoxycarbonyl)amino]-2-(2,6-difluorophenyl)-1,3-thiazole-4-carboxylic acid

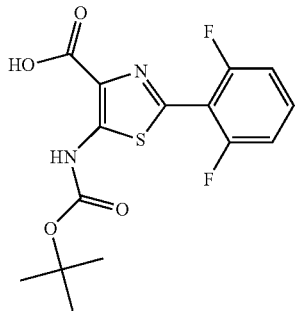 [SMILES: CC(C)(C)OC(=O)Nc1sc(-c2c(F)cccc2F)nc1C(=O)O]

To a suspension of methyl 5-[(tert-butoxycarbonyl)amino]-2-(2,6-difluorophenyl)-1,3-thiazole-4-carboxylate (6.99 g, 18.9 mmol) in MeOH (50.0 mL), lithium hydroxide monohydrate (5.24 g, 125 mmol) was added, followed by water (50.0 mL). The reaction mixture was heated at 60° C. for 5 h. The reaction mixture was then cooled to 0° C., and 6M HCl was added slowly until the pH reached 2. The resulting solid was collected by filtration and the filter cake was washed with water (50 mL) and MeOH/water (1:1, 50 mL) to provide the sub-title compound as a yellow solid (6.59 g, 98%). LCMS calc. for $C_{15}H_{15}F_2N_2O_4S$ (M+H)$^+$: m/z=357.1; found 357.0.

Step 7. tert-Butyl (2-(2,6-difluorophenyl)-4-{[methoxy(methyl)amino]carbonyl}-1,3-thiazol-5-yl)carbamate

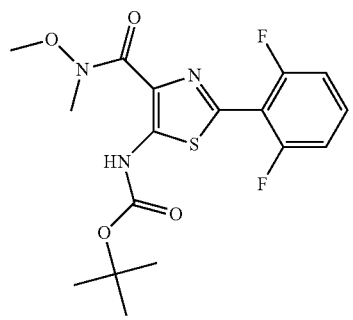 [SMILES: CON(C)C(=O)c1nc(-c2c(F)cccc2F)sc1NC(=O)OC(C)(C)C]

To a solution of 5-[(tert-butoxycarbonyl)amino]-2-(2,6-difluorophenyl)-1,3-thiazole-4-carboxylic acid (2.51 g, 7.04 mmol) and N, O-dimethylhydroxylamine hydrochloride (0.656 g, 6.73 mmol) in DMF (20 mL) was added N,N,N',N'-tetramethyl-O-(7-azabenzotriazol-1-yl)uronium hexafluorophosphate (3.12 g, 8.22 mmol) and DIPEA (3.8 mL, 22 mmol). The reaction mixture was stirred at room temperature overnight, and then diluted with water, extracted with DCM. The combined organic layers were dried over Na$_2$SO$_4$, filtered and concentrated. The residue was purified with flash chromatography (gradient elution with 0-30% EtOAc in hexanes) to give the desired product (2.14 g, 80%). LCMS calc. for $C_{17}H_{20}F_2N_3O_4S$ (M+H)$^+$: m/z=400.1; Found: 400.1.

Step 8. tert-Butyl [2-(2,6-difluorophenyl)-4-formyl-1,3-thiazol-5-yl]carbamate

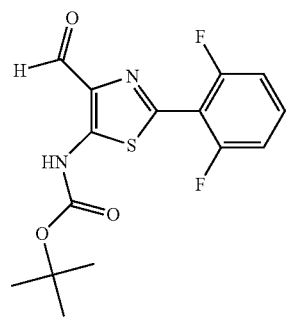 [SMILES: CC(C)(C)OC(=O)Nc1sc(-c2c(F)cccc2F)nc1C=O]

A solution of tert-butyl (2-(2,6-difluorophenyl)-4-{[methoxy(methyl)amino]carbonyl}-1,3-thiazol-5-yl)carbamate (322 mg, 0.806 mmol) in THF (2.6 mL) was slowly added to 1.0M lithium tetrahydroaluminate in THF (0.846 mL, 0.846 mmol) at 0° C. The reaction mixture was allowed to warm to room temperature, and then stirred at room temperature for 1 hour. The reaction was carefully quenched with saturated aqueous Na$_2$SO$_4$ solution, and then extracted with EtOAc. The combined organic layers were washed with brine, dried and concentrated. The residue was purified with flash chromatography to give the desired product as white solid (0.19 g, 69%). LCMS calc. for $C_{15}H_{15}F_2N_2O_3S$ (M+H)$^+$: m/z=341.1; Found: 341.0.

Step 5. 5-Amino-2-(2,6-difluorophenyl)-1,3-thiazole-4-carbaldehyde

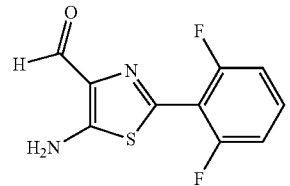 [SMILES: Nc1sc(-c2c(F)cccc2F)nc1C=O]

To a stirred solution of tert-butyl [2-(2,6-difluorophenyl)-4-formyl-1,3-thiazol-5-yl]carbamate (190 mg, 0.56 mmol) in DCM (0.5 mL) was added trifluoroacetic acid (0.5 mL, 6 mmol). The resulting red solution was stirred at room temperature for 1 h. The reaction mixture was concentrated, and the resultant residue was diluted with methanol and purified with prep-LCMS (XBridge C18 column, gradient elution with acetonitrile/water containing 0.1% ammonium hydroxide, at flow rate of 60 mL/min) to give the desired product as white solid (25 mg, 19%). LCMS calc. for $C_{10}H_7F_2N_2OS$ (M+H)$^+$: m/z=241.0; Found: 241.0.

Step 6. Benzyl {(3S,5R)-1-[3-({[5-amino-2-(2,6-difluorophenyl)-1,3-thiazol-4-yl]methyl}amino)pyridin-4-yl]-5-methylpiperidin-3-yl}carbamate

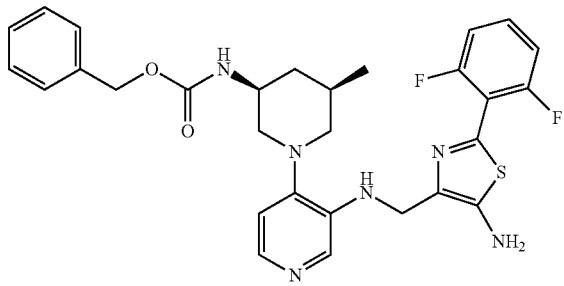 [SMILES: C[C@@H]1C[C@H](NC(=O)OCc2ccccc2)CN(c2ccncc2NCc2nc(-c3c(F)cccc3F)sc2N)C1]

Benzyl [(3S,5R)-1-(3-aminopyridin-4-yl)-5-methylpiperidin-3-yl]carbamate (101 mg, 0.297 mmol) and 5-amino-2-(2,6-difluorophenyl)-1,3-thiazole-4-carbaldehyde (82.0 mg, 0.341 mmol) were dissolved in toluene (1.8 mL) and a drop of acetic acid was added. The reaction mixture was heated at 100° C. for 2 h. Then solvent was evaporated and methanol (1.8 mL) was added. After addition of sodium tetrahydroborate (22 mg, 0.59 mmol), the reaction mixture was stirred for 30 min. The reaction solution was diluted with methanol and purified by prep-LCMS (XBridge C18 column, gradient elution with acetonitrile/water containing 0.1% ammonium hydroxide, at flow rate of 60 mL/min) to give the desired product as white solid (10.5 mg, 6%). LCMS calc. for $C_{29}H_{31}F_2N_6O_2S$ (M+H)$^+$: m/z=565.2; Found: 565.2.

Step 7. N-{[5-Amino-2-(2,6-difluorophenyl)-1,3-thiazol-4-yl]methyl}-4-[(3S,5R)-3-amino-5-methylpiperidin-1-yl]pyridin-3-amine To a solution of benzyl {(3S,5R)-1-[3-({[5-amino-2-(2,6-difluorophenyl)-1,3-thiazol-4-yl]methyl}amino)pyridin-4-yl]-5-methylpiperidin-3-yl}carbamate (10.5 mg, 0.018 mm0l) in methanol (1 mL) was added 10% palladium on carbon (10 mg). The mixture was stirred under positive pressure of H$_2$ overnight. The reaction mixture was filtered and the filtrate was purified with preparative LCMS (XBridge C18 column, gradient elution with acetonitrile/water containing 0.1% ammonium hydroxide, at flow rate of 60 mL/min) to give the desired product as white solid (4.5 mg, 40%). LCMS calc. for $C_{21}H_{25}F_2N_6S$ (M+H)$^+$: m/z=431.2; Found: 431.2.

Example 70

4-[(3S,5R)-3-Amino-5-methylpiperidin-1-yl]-N-[(6-{2,6-difluoro-4-[(3R)-3-fluoropyrrolidin-1-yl]phenyl}-5-fluoropyridin-2-yl)methyl]pyridin-3-amine

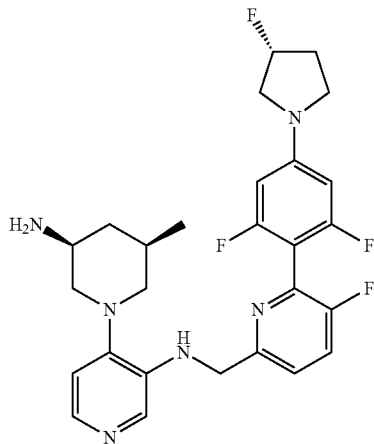 [SMILES: C[C@@H]1C[C@H](N)CN(c2ccncc2NCc2ccc(F)c(-c3c(F)cc(N4CC[C@@H](F)C4)cc3F)n2)C1]

Step 1. (3R)-1-(3,5-Difluorophenyl)-3-fluoropyrrolidine

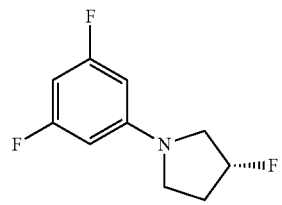 [SMILES: Fc1cc(F)cc(N2CC[C@@H](F)C2)c1]

To a vial dicyclohexyl(2',6'-diisopropoxybiphenyl-2-yl)phosphine-(2'-aminobiphenyl-2-yl)(chloro)palladium (1:1) (325.4 mg, 0.4190 mmol), (3R)-3-fluoropyrrolidine hydrochloride (from Aldrich, 0.27 g, 2.2 mmol) and cesium carbonate (2.261 g, 6.939 mmol) were added. The vial was sealed with a Teflon screw-cap, evacuated and backfilled with nitrogen (this process was repeated a total of three times). Anhydrous tert-butyl alcohol (11.9 mL) was added, followed by the addition of 1-bromo-3,5-difluorobenzene (190 μL, 1.6 mmol). The reaction mixture was heated at 90° C. for 6 h. The reaction mixture was cooled to room temperature, and diluted with EtOAc, filtered through a pad of diatomaceous earth (eluted with EtOAc). The filtrate was concentrated, and the residue was purified by flash chromatography (gradient elution with 0-30% EtOAc in hexanes) to give the desired product as a yellow solid (0.27 g, 81%). LCMS calc. for $C_{10}H_{11}F_3N$ (M+H)$^+$: m/z=202.1; Found: 202.1.

Step 2. (3R)-1-[3,5-Difluoro-4-(4,4,5,5-tetramethyl-1,3,2-dioxaborolan-2-yl)phenyl]-3-fluoropyrrolidine

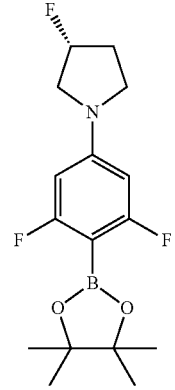 [SMILES: CC1(C)OB(c2c(F)cc(N3CC[C@@H](F)C3)cc2F)OC1(C)C]

To a solution of (3R)-1-(3,5-difluorophenyl)-3-fluoropyrrolidine (271 mg, 1.35 mmol) in THF (3.6 mL) was slowly added 2.5M n-butyllithium in hexanes (1.1 mL, 2.7 mmol) at −78° C. After stirring at −78° C. for 1 h, 2-isopropoxy-4,4,5,5-tetramethyl-1,3,2-dioxaborolane (690 μL, 3.4 mmol) was added to the reaction mixture in one portion. The reaction mixture was allowed to warm to room temperature and stirred at room temperature for 1 h. The mixture was diluted with EtOAc and NaHCO$_3$ solution. The organic layer was separated and washed with brine, dried over Na$_2$SO$_4$, and concentrated. The residue was purified with flash chromatography (gradient elution with 0-30% EtOAc in Step 3. 4-[(3S,5R)-3-Amino-5-methylpiperidin-1-yl]-N-[(6-{2,6-difluoro-4-[(3R)-3-fluoropyrrolidin-1-yl]phenyl}-5-fluoropyridin-2-yl)methyl]pyridin-3-amine A mixture of tert-butyl [(3S,5R)-1-(3-{[(6-bromo-5-fluoropyridin-2-yl)methyl]amino}pyridin-4-yl)-5-methylpiperidin-3-yl]carbamate (Intermediate 2; 28.1 mg, 0.0568 mmol), (3R)-1-[3,5-difluoro-4-(4,4,5,5-tetramethyl-1,3,2-dioxaborolan-2-yl)phenyl]-3-fluoropyrrolidine (29.7 mg, 0.0908 mmol), dicyclohexyl(2',4',6'-triisopropylbiphenyl-2-yl)phosphine-(2'-aminobiphenyl-2-yl)(chloro)palladium (1:1) (3.9 mg, 0.0050 mmol) and tripotassium phosphate hydrate (28.8 mg, 0.125 mmol) in 1,4-dioxane (0.61 mL)/water (0.20 mL) was degassed and stirred at 80° C. for 1.5 h. The reaction mixture was diluted with DCM and washed with water. Layers were separated and the organic layer was dried and filtered. The filtrate was concentrated. The residue was treated with 1:1 DCM/TFA (2 mL) for 2 h. The volatile was removed under reduced pressure and the residue was dissolved in methanol and purified with prep-LCMS (XBridge C18 column, gradient elution with acetonitrile/water containing 0.1% ammonium hydroxide, at flow rate of 60 mL/min) to give the desired product as a white solid (8.9 mg, 30%). LCMS calc. for $C_{27}H_{31}F_4N_6$ (M+H)$^+$: m/z=515.3; Found: 515.3.

Example 71

4-[(3S,5R)-3-Amino-5-methylpiperidin-1-yl]-N-({6-[2,6-difluoro-4-(3-fluoropiperidin-1-yl)phenyl]-5-fluoropyridin-2-yl}methyl)pyridin-3-amine

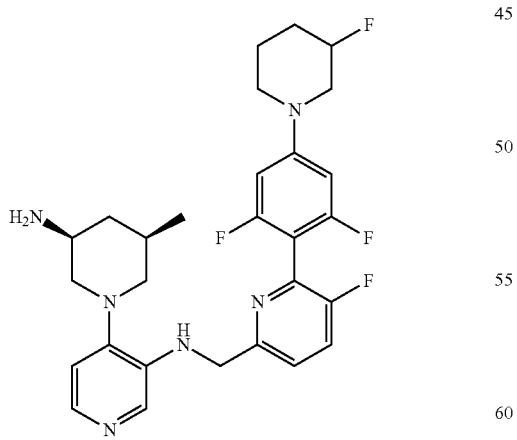

This compound was synthesized according to the procedures described in Example 70, using 3-fluoropiperidine hydrochloride to replace (3R)-3-fluoropyrrolidine hydrochloride in Step 1. LCMS calc. for $C_{28}H_{33}F_4N_6$ (M+H)$^+$: m/z=529.3; Found: 529.3.

Example 72

1-(4-{6-[({4-[(3S,5R)-3-Amino-5-methylpiperidin-1-yl]pyridin-3-yl}amino)methyl]-3-fluoropyridin-2-yl}-3,5-difluorophenyl)-3-methylazetidin-3-ol

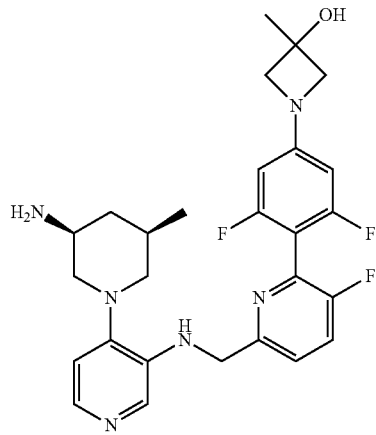 [SMILES: C[C@@H]1C[C@H](N)CN(c2ccncc2NCc2ccc(F)c(-c3c(F)cc(N4CC(C)(O)C4)cc3F)n2)C1]

Step 1.
1-(3,5-Difluorophenyl)-3-methylazetidin-3-ol

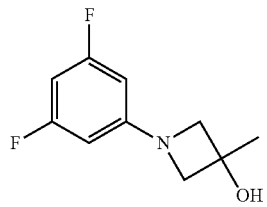

This compound was synthesized according to the procedures described in Example 70, using 3-methylazetidin-3-ol hydrochloride to replace (3R)-3-fluoropyrrolidine hydrochloride in Step 1. LCMS calc. for $C_{27}H_{32}F_3N_6O$ (M+H)$^+$: m/z=513.3; Found: 513.3.

Example 73

(3R,4R,5S)-3-Amino-1-(3-{[(6-{2,6-difluoro-4-[(3R)-tetrahydrofuran-3-yloxy]phenyl}-5-fluoropyridin-2-yl)methyl]amino}pyridin-4-yl)-5-methylpiperidin-4-ol

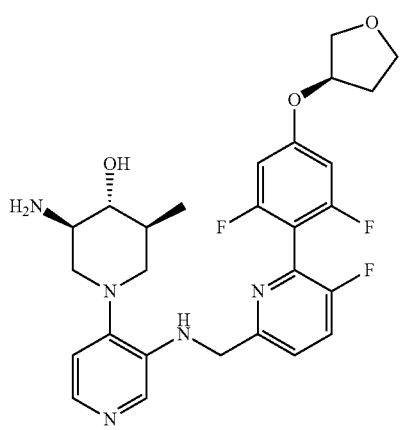 [SMILES: C[C@H]1CN(c2ccncc2NCc2ccc(F)c(-c3c(F)cc(O[C@@H]4CCOC4)cc3F)n2)C[C@@H](N)[C@@H]1O]

Step 1: Methyl 6-(2,6-difluoro-4-hydroxyphenyl)-5-fluoropyridine-2-carboxylate

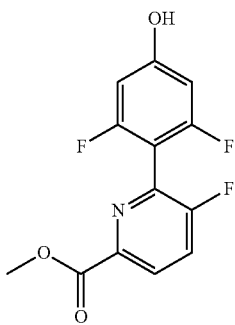 [SMILES: COC(=O)c1ccc(F)c(-c2c(F)cc(O)cc2F)n1]

A mixture of methyl 6-chloro-5-fluoropyridine-2-carboxylate (from Frontier Scientific, Inc., 1.90 g, 10.0 mmol), (2,6-difluoro-4-hydroxyphenyl)boronic acid (2.00 g, 11.5 mmol), N,N-diisopropylethylamine (3.4 mL, 20. mmol) in 1,4-dioxane (17 mL) and water (1.0 mL) was purged with nitrogen, followed by addition of bis(tri-t-butylphosphine) palladium (0.51 g, 1.0 mmol). The reaction mixture was degassed and re-charged with nitrogen for three cycles, and then heated at 120° C. with stirring for 2 h. The reaction mixture was allowed to cool to room temperature and concentrated under reduced pressure. The residue was purified by flash chromatography on a silica gel column with EtOAc in hexanes (gradient: 0-50%) to afford the desired product (1.34 g, 47%). LCMS calc. for $C_{13}H_9F_3NO_3$ (M+H)$^+$: 284.1; Found: 284.0.

Step 2: Methyl 6-{2,6-difluoro-4-[(3R)-tetrahydrofuran-3-yloxy]phenyl}-5-fluoropyridine-2-carboxylate

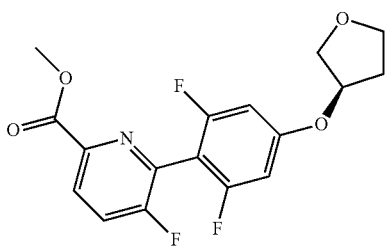 [SMILES: COC(=O)c1ccc(F)c(-c2c(F)cc(O[C@@H]3CCOC3)cc2F)n1]

To a mixture of methyl 6-(2,6-difluoro-4-hydroxyphenyl)-5-fluoropyridine-2-carboxylate (283 mg, 1.00 mmol) and (3S)-tetrahydrofuran-3-ol (88.1 mg, 1.00 mmol) in THF (2.0 mL) was added a solution of triphenylphosphine (524 mg, 2.00 mmol) in THF (1.0 mL), and solution of diethyl azodicarboxylate (315 μL, 2.00 mmol) in THF (1.0 mL). The mixture was stirred at room temperature for 2 h. The volatiles were removed under reduced pressure. The residue was purified by flash chromatography on a silica gel column with EtOAc in hexanes (gradient: 0-60%) to afford the desired product (0.34 g, 96%). LCMS calc. for $C_{17}H_{15}F_3NO_4$ (M+H)$^+$: 354.1; Found: 354.1.

Step 3: 6-{2,6-Difluoro-4-[(3R)-tetrahydrofuran-3-yloxy]phenyl}-5-fluoropyridine-2-carboxylic acid

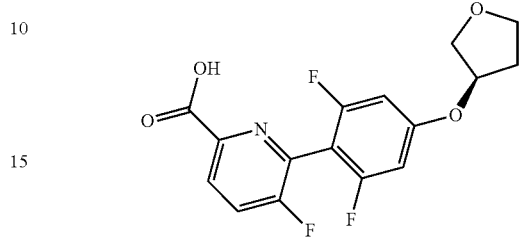

To a solution of methyl 6-{2,6-difluoro-4-[(3R)-tetrahydrofuran-3-yloxy]phenyl}-5-fluoropyridine-2-carboxylate (0.353 g, 1.00 mmol) in tetrahydrofuran (1.0 mL) and methanol (1.0 mL) was added lithium hydroxide monohydrate (0.0839 g, 2.00 mmol) in water (1 mL). The mixture was stirred at room temperature for 1 h., and then neutralized with 1.0N HCl aqueous solution (2.0 mL). The mixture was extracted with EtOAc. The combined organic layers were dried over Na$_2$SO$_4$, filtered and concentrated under reduced pressure to afford the desired product which was directly used in the next step reaction without further purification. LCMS calc. for $C_{16}H_{13}F_3NO_4$ (M+H)$^+$: 340.1; Found: 340.1.

Step 4: (6-{2,6-Difluoro-4-[(3R)-tetrahydrofuran-3-yloxy]phenyl}-5-fluoropyridin-2-yl)methanol

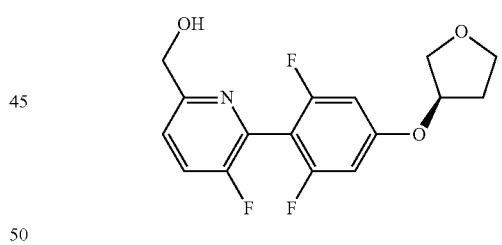

To a mixture of 6-{2,6-difluoro-4-[(3R)-tetrahydrofuran-3-yloxy]phenyl}-5-fluoropyridine-2-carboxylic acid (0.319 g, 0.940 mmol) and triethylamine (151 μL, 1.08 mmol) in tetrahydrofuran (5 mL) cooled in an ice bath was added isobutyl chloroformate (140 uL, 1.08 mmol). The mixture was stirred for 30 min. and then sodium tetrahydroborate (76 mg, 2.0 mmol) in water (0.5 mL, 30 mmol) was added dropwise. The mixture was stirred for 1 h, quenched with aq. sat. NaHCO$_3$ solution, and extracted with EtOAc. The combined organic layers were washed with brine, dried over MgSO$_4$, filtered and concentrated to give the title compound of Step 4, which was directly used in the next step reaction without further purification. LCMS calc. for $C_{16}H_{15}F_3NO_3$ (M+H)$^+$: 326.1; Found: 326.1.

Step 5: 6-{2,6-Difluoro-4-[(3R)-tetrahydrofuran-3-yloxy]phenyl}-5-fluoropyridine-2-carbaldehyde

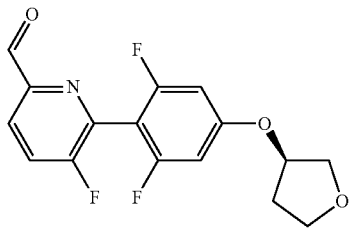 [SMILES: O=Cc1ccc(F)c(-c2c(F)cc(O[C@@H]3CCOC3)cc2F)n1]

To a mixture of (6-{2,6-difluoro-4-[(3R)-tetrahydrofuran-3-yloxy]phenyl}-5-fluoropyridin-2-yl)methanol (the crude product from previous step) in DCM (8 mL) was added Dess-Martin periodinane (0.439 g, 1.03 mmol). The reaction mixture was stirred at room temperature overnight. NaHCO$_3$ solution (7.5%, 2 mL) and Na$_2$S$_2$O$_3$ solution (2 mL) was added and the resulting reaction mixture was stirred for 30 min. The product was extracted with DCM, dried over Na$_2$SO$_4$, filtered and concentrated under reduced pressure. The residue was purified by flash chromatography on a silica gel column with EtOAc in hexanes (gradient: 0-50%) to afford the desired product (0.23 g, 76% in 2 step 2). LCMS calc. for C$_{16}$H$_{13}$F$_3$NO$_3$ (M+H)$^+$: 324.1; Found: 324.2.

Step 6: (3R,4R,5S)-3-Amino-1-(3-{[(6-{2,6-difluoro-4-[(3R)-tetrahydrofuran-3-yloxy]phenyl}-5-fluoropyridin-2-yl)methyl]amino}pyridin-4-yl)-5-methylpiperidin-4-ol tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 20. mg, 0.046 mmol) and 6-{2,6-difluoro-4-[(3R)-tetrahydrofuran-3-yloxy]phenyl}-5-fluoropyridine-2-carbaldehyde (16 mg, 0.050 mmol) were dissolved in toluene (2.0 mL) and AcOH (3 uL) was added. The mixture was heated at 100° C. for 2 h. The solvent was evaporated and methanol (2.0 mL) was added.

After addition of sodium tetrahydroborate (4.3 mg, 0.11 mmol), the resulting mixture was stirred for 30 min. To the reaction mixture was added 4N HCl in dioxane (1.0 mL), and stirring was continued at room temperature for 1 h. The mixture was diluted with methanol, and purified by RP-HPLC (XBridge C18 column, gradient elution with acetonitrile/water containing 0.05% TFA, at flow rate of 60 mL/min) to afford the desired product as a TFA salt. LCMS calc. for C$_{27}$H$_{31}$F$_3$N$_5$O$_3$ (M+H)$^+$:530.2; Found: 530.3.

Example 74

4-[(3S,5R)-3-Amino-5-methylpiperidin-1-yl]-N-[(6-{2,6-difluoro-4-[(3R)-tetrahydrofuran-3-yloxy]phenyl}-5-fluoropyridin-2-yl)methyl]pyridin-3-amine

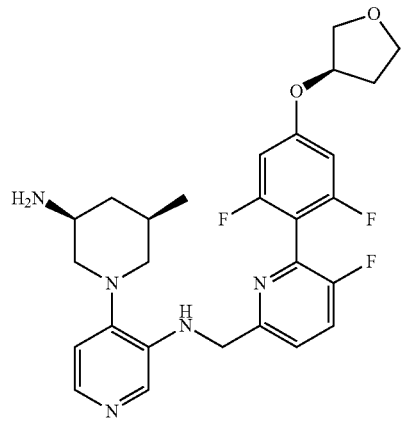 [SMILES: C[C@@H]1C[C@H](N)CN(c2ccncc2NCc2ccc(F)c(-c3c(F)cc(O[C@@H]4CCOC4)cc3F)n2)C1]

This compound was prepared as a TFA salt by using procedures analogous to those described for the synthesis of Example 73, Step 6, starting from tert-butyl [(3S,5R)-1-(3-aminopyridin-4-yl)-5-methylpiperidin-3-yl]carbamate (Prepared in Intermediate 2, Step 6) and 6-{2,6-difluoro-4-[(3R)-tetrahydrofuran-3-yloxy]phenyl}-5-fluoropyridine-2-carbaldehyde (Prepared in Example 73, Step 5). LCMS calc. for C$_{27}$H$_{31}$F$_3$N$_5$O$_2$ (M+H)$^+$: 514.2; Found: 514.2.

Example 75

(3R,4R,5S)-3-Amino-1-(3-{[(6-{2,6-difluoro-4-[(3S)-tetrahydrofuran-3-yloxy]phenyl}-5-fluoropyridin-2-yl)methyl]amino}pyridin-4-yl)-5-methylpiperidin-4-ol

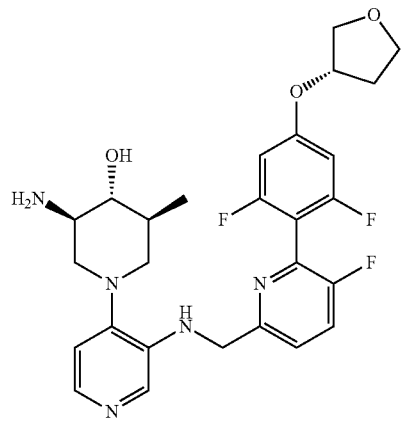 [SMILES: C[C@H]1CN(c2ccncc2NCc2ccc(F)c(-c3c(F)cc(O[C@H]4CCOC4)cc3F)n2)C[C@@H](N)[C@@H]1O]

Step 1: 6-{2,6-Difluoro-4-[(3S)-tetrahydrofuran-3-yloxy]phenyl}-5-fluoropyridine-2-carbaldehyde

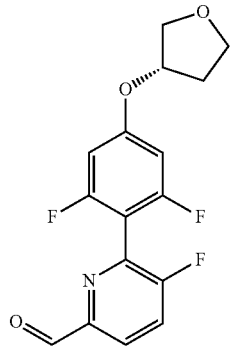 [SMILES: O=Cc1ccc(F)c(-c2c(F)cc(O[C@H]3CCOC3)cc2F)n1]

This compound was prepared by using procedures analogous to those described for the synthesis of Example 73, Step 1 to 5, using (3R)-tetrahydrofuran-3-ol instead of (3S)-tetrahydrofuran-3-ol. LCMS calc. for $C_{16}H_{13}F_3NO_3$ (M+H)$^+$: 324.1; Found: 324.1.

Step 2: (3R,4R,5S)-3-Amino-1-(3-{[(6-{2,6-difluoro-4-[(3S)-tetrahydrofuran-3-yloxy]phenyl}-5-fluoropyridin-2-yl)methyl]amino}pyridin-4-yl)-5-methylpiperidin-4-ol This compound was prepared as a TFA salt by using procedures analogous to those described for the synthesis of Example 73, Step 6 starting from tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11) and 6-{2,6-difluoro-4-[(3S)-tetrahydrofuran-3-yloxy]phenyl}-5-fluoropyridine-2-carbaldehyde. LCMS calc. for $C_{27}H_{31}F_3N_5O_3$ (M+H)$^+$: 530.2; Found: 530.2.

Example 76

4-[(3S,5R)-3-Amino-5-methylpiperidin-1-yl]-N-[(6-{2,6-difluoro-4-[(3S)-tetrahydrofuran-3-yloxy]phenyl}-5-fluoropyridin-2-yl)methyl]pyridin-3-amine

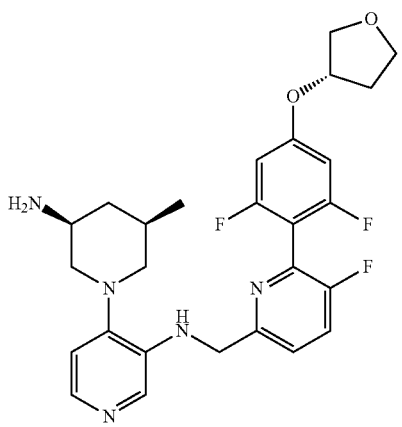 [SMILES: C[C@@H]1C[C@H](N)CN(c2ccncc2NCc2ccc(F)c(-c3c(F)cc(O[C@H]4CCOC4)cc3F)n2)C1]

This compound was prepared as a TFA salt by using procedures analogous to those described for the synthesis of Example 73, Step 6 starting from tert-butyl [(3S,5R)-1-(3-aminopyridin-4-yl)-5-methylpiperidin-3-yl]carbamate (Prepared in Intermediate 2, Step 6) and 6-{2,6-difluoro-4-[(3S)-tetrahydrofuran-3-yloxy]phenyl}-5-fluoropyridine-2-carbaldehyde (Prepared in Example 75, Step 1). LCMS calc. for $C_{27}H_{31}F_3N_5O_2$ (M+H)$^+$: 514.2; Found: 514.2.

Example 77

(3R,4R,5S)-3-Amino-1-{3-[({6-[2,6-difluoro-4-(tetrahydro-2H-pyran-4-yloxy)phenyl]-5-fluoropyridin-2-yl}methyl)amino]pyridin-4-yl}-5-methylpiperidin-4-ol

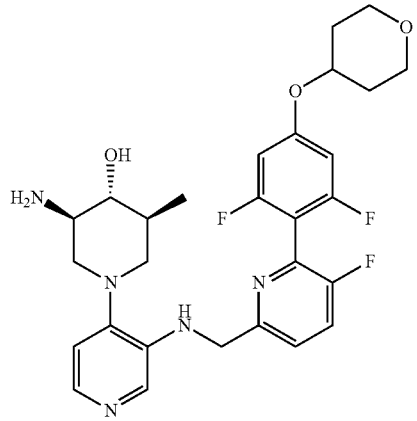 [SMILES: C[C@H]1CN(c2ccncc2NCc2ccc(F)c(-c3c(F)cc(OC4CCOCC4)cc3F)n2)C[C@@H](N)[C@@H]1O]

Step 1: 6-[2,6-difluoro-4-(tetrahydro-2H-pyran-4-yloxy)phenyl]-5-fluoropyridine-2-carbaldehyde

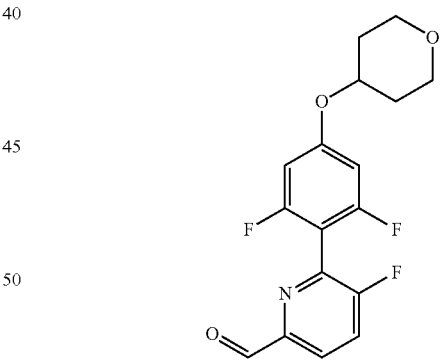

This compound was prepared by using procedures analogous to those described for the synthesis of Example 73, Step 1 to 5, using tetrahydropyran-4-ol (from Aldrich) instead of (3S)-tetrahydrofuran-3-ol. LCMS calc. for $C_{17}H_{15}F_3NO_3$ (M+H)$^+$: 338.1; Found: 338.1.

Step 2: (3R,4R,5S)-3-amino-1-{3-[({6-[2,6-difluoro-4-(tetrahydro-2H-pyran-4-yloxy)phenyl]-5-fluoropyridin-2-yl}methyl)amino]pyridin-4-yl}-5-methylpiperidin-4-ol This compound was prepared as a TFA salt by using procedures analogous to those described for the synthesis of Example 73, Step 6 starting from tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11) and 6-[2,6-difluoro-4-(tetrahydro-2H-pyran-4-yloxy)phenyl]-5-fluoropyridine-2-carbaldehyde. LCMS calc. for $C_{28}H_{33}F_3N_5O_3$ (M+H)$^+$: 544.3; Found: 544.2.

Example 78

4-[(3S,5R)-3-Amino-5-methylpiperidin-1-yl]-N-({6-[2,6-difluoro-4-(tetrahydro-2H-pyran-4-yloxy)phenyl]-5-fluoropyridin-2-yl}methyl)pyridin-3-amine

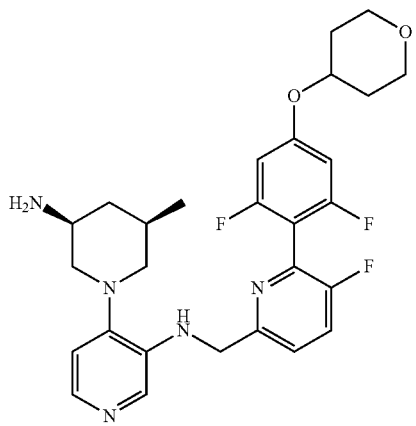 [SMILES: C[C@@H]1C[C@H](N)CN(c2ccncc2NCc2ccc(F)c(-c3c(F)cc(OC4CCOCC4)cc3F)n2)C1]

This compound was prepared as a TFA salt by using procedures analogous to those described for the synthesis of Example 73, Step 6 starting from tert-butyl [(3S,5R)-1-(3-aminopyridin-4-yl)-5-methylpiperidin-3-yl]carbamate (Prepared in Intermediate 2, Step 6) and 6-[2,6-difluoro-4-(tetrahydro-2H-pyran-4-yloxy)phenyl]-5-fluoropyridine-2-carbaldehyde (Prepared in Example 77, Step 1). LCMS calc. for $C_{28}H_{33}F_3N_5O_2$ (M+H)$^+$: 528.3; Found: 528.2.

Example 79

4-[(3S,5R)-3-Amino-5-methylpiperidin-1-yl]-N-[(6-{2,6-difluoro-4-[(1-methylpiperidin-4-yl)oxy]phenyl}-5-fluoropyridin-2-yl)methyl]pyridin-3-amine

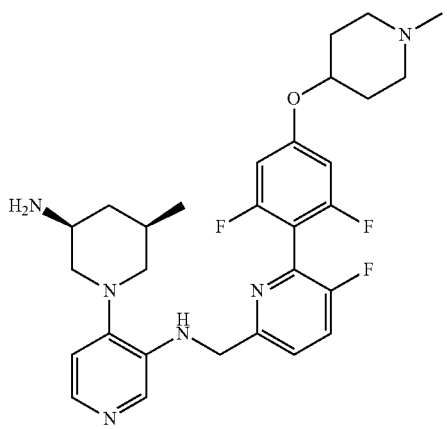 [SMILES: C[C@@H]1C[C@H](N)CN(c2ccncc2NCc2ccc(F)c(-c3c(F)cc(OC4CCN(C)CC4)cc3F)n2)C1]

Step 1: 6-{2,6-Difluoro-4-[(1-methylpiperidin-4-yl)oxy]phenyl}-5-fluoropyridine-2-carbaldehyde

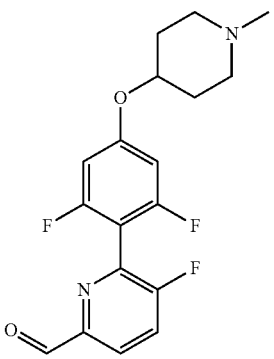 [SMILES: CN1CCC(Oc2cc(F)c(-c3nc(C=O)ccc3F)c(F)c2)CC1]

This compound was prepared by using procedures analogous to those described for the synthesis of Example 73, Steps 1 to 5, using 1-methylpiperidin-4-ol (from Aldrich) instead of (3S)-tetrahydrofuran-3-ol. LCMS calc. for $C_{18}H_{18}F_3N_2O_2$ (M+H)$^+$: 351.1; Found: 351.1.

Step 2: 4-[(3S,5R)-3-Amino-5-methylpiperidin-1-yl]-N-[(6-{2,6-difluoro-4-[(1-methylpiperidin-4-yl)oxy]phenyl}-5-fluoropyridin-2-yl)methyl]pyridin-3-amine This compound was prepared as a TFA salt by using procedures analogous to those described for the synthesis of Example 73, Step 6 starting from tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11) and 6-{2,6-difluoro-4-[(1-methylpiperidin-4-yl)oxy]phenyl}-5-fluoropyridine-2-carbaldehyde. LCMS calc. for $C_{29}H_{36}F_3N_6O$ (M+H)$^+$: 541.3; Found: 541.3.

Example 80

(3R,4R,5S)-3-Amino-1-(3-{[(6-{4-[(3,3-difluorocyclobutyl)oxy]-2,6-difluorophenyl}-5-fluoropyridin-2-yl)methyl]amino}pyridin-4-yl)-5-methylpiperidin-4-ol

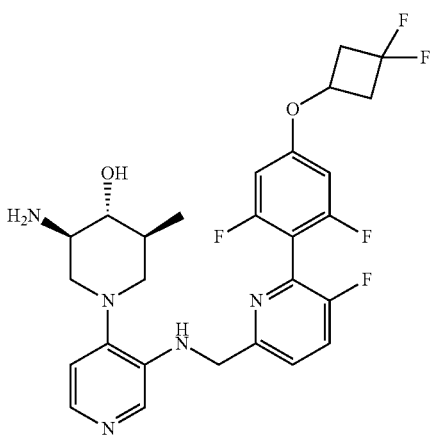 [SMILES: C[C@H]1CN(c2ccncc2NCc2ccc(F)c(-c3c(F)cc(OC4CC(F)(F)C4)cc3F)n2)C[C@@H](N)[C@@H]1O]

Step 1: 6-{4-[(3,3-Difluorocyclobutyl)oxy]-2,6-difluorophenyl}-5-fluoropyridine-2-carbaldehyde

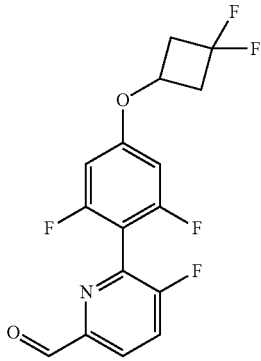 [SMILES: O=Cc1ccc(F)c(-c2c(F)cc(OC3CC(F)(F)C3)cc2F)n1]

This compound was prepared according to procedures analogous to those described for the synthesis of Example 73, Steps 1 to 5, using 3,3-difluorocyclobutanol (from Advanced Chemblocks) instead of (3S)-tetrahydrofuran-3-ol. LCMS calc. for $C_{16}H_{11}F_5NO_2$ (M+H)$^+$: 344.1; Found: 344.0.

Step 2. (3R,4R,5S)-3-Amino-1-(3-{[(6-{4-[(3,3-difluorocyclobutyl)oxy]-2,6-difluorophenyl}-5-fluoropyridin-2-yl)methyl]amino}pyridin-4-yl)-5-methylpiperidin-4-ol This compound was prepared as a TFA salt by using procedures analogous to those described for the synthesis of Example 73, Step 6 starting from tert-butyl [(3S,5R)-1-(3-aminopyridin-4-yl)-5-methylpiperidin-3-yl]carbamate (Prepared in Intermediate 2, Step 6) and 6-{4-[(3,3-difluorocyclobutyl)oxy]-2,6-difluorophenyl}-5-fluoropyridine-2-carbaldehyde. LCMS calc. for $C_{27}H_{29}F_5N_5O_2$ (M+H)$^+$: 550.2; Found: 550.2.

Example 81

4-[(3S,5R)-3-Amino-5-methylpiperidin-1-yl]-N-[(6-{4-[(3,3-difluorocyclobutyl)oxy]-2,6-difluorophenyl}-5-fluoropyridin-2-yl)methyl]pyridin-3-amine

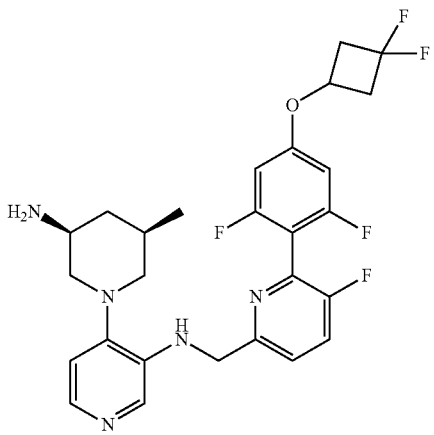 [SMILES: C[C@@H]1C[C@H](N)CN(c2ccncc2NCc2ccc(F)c(-c3c(F)cc(OC4CC(F)(F)C4)cc3F)n2)C1]

This compound was prepared as a TFA salt by using procedures analogous to those described for the synthesis of Example 73, Step 6 starting from tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11) and 6-{4-[(3,3-difluorocyclobutyl)oxy]-2,6-difluorophenyl}-5-fluoropyridine-2-carbaldehyde (Prepared in Example 80, Step 1). LCMS calc. for $C_{27}H_{29}F_5N_5O$ (M+H)$^+$: 534.2; Found: 534.2.

Example 82

(3R,4R,5S)-3-Amino-1-[3-({[6-(2,6-difluoro-4-methoxyphenyl)-5-fluoropyridin-2-yl]methyl}amino)pyridin-4-yl]-5-methylpiperidin-4-ol

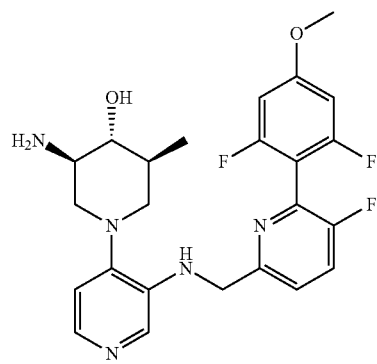 [SMILES: COc1cc(F)c(-c2nc(CNc3cnccc3N3C[C@@H](N)[C@H](O)[C@@H](C)C3)ccc2F)c(F)c1]

A mixture of (2,6-difluoro-4-methoxyphenyl)boronic acid (from Aldrich, 9.40 mg, 0.0500 mmol), tert-butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (Intermediate 1, 31.2 mg, 0.0500 mmol), dicyclohexyl(2',4',6'-triisopropylbiphenyl-2-yl)phosphine-(2'-aminobiphenyl-2-yl)(chloro)palladium (1:1) (3.93 mg, 0.00500 mmol) and cesium carbonate (32.6 mg, 0.100 mmol) was evacuated and recharged with nitrogen. Then 1,4-dioxane (0.25 mL) and water (0.15 mL) was added, and re-evacuated and recharged with N$_2$ three times. The reaction mixture was stirred at 70° C. for 1 h. After cooling, the mixture was diluted with EtOAc, washed with water and brine. The organic layer was dried over MgSO$_4$, filtered and concentrated under reduced pressure. The residue was treated with 4N HCl in dioxane (1.0 mL) and methanol (0.5 mL). The mixture was stirred at room temperature for 1 h. diluted with methanol, and purified by RP-HPLC (XBridge C18 column, gradient elution with acetonitrile/water containing 0.05% TFA, at flow rate of 60 mL/min) to afford the desired product as TFA salt. LCMS calc. for $C_{24}H_{27}F_3N_5O_2$ (M+H)$^+$: 474.2; Found: 474.2.

Example 83

4-[(3S,5R)-3-Amino-5-methylpiperidin-1-yl]-N-{[6-(2,6-difluoro-4-methoxyphenyl)-5-fluoropyridin-2-yl]methyl}pyridin-3-amine

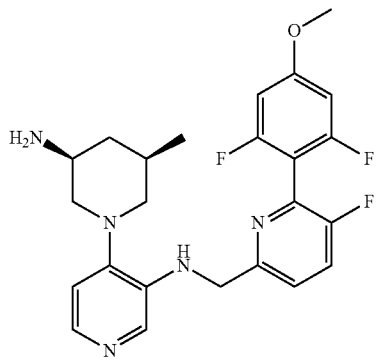 [SMILES: COc1cc(F)c(-c2nc(CNc3cnccc3N3C[C@H](C)C[C@H](N)C3)ccc2F)c(F)c1]

This compound was prepared as a TFA salt by using procedures analogous to those described for the synthesis of Example 82, Step 4 starting from tert-butyl [(3S,5R)-1-(3-{[(6-bromo-5-fluoropyridin-2-yl)methyl]amino}pyridin-4-yl)-5-methylpiperidin-3-yl]carbamate (Intermediate 2) and (2,6-difluoro-4-methoxyphenyl)boronic acid. LCMS calc. for $C_{24}H_{27}F_3N_5O$ (M+H)$^+$: 458.2; Found: 458.2.

Example 84

4-{6-[({4-[(3S,5R)-3-Amino-5-methylpiperidin-1-yl]pyridin-3-yl}amino)methyl]-3-fluoropyridin-2-yl}-3-fluorobenzonitrile

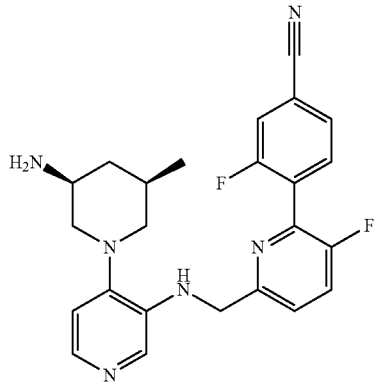 [SMILES: C[C@@H]1C[C@H](N)CN(c2ccncc2NCc2ccc(F)c(-c3ccc(C#N)cc3F)n2)C1]

This compound was prepared as a TFA salt by using procedures analogous to those described for the synthesis of Example 82, Step 4 starting from tert-butyl [(3S,5R)-1-(3-{[(6-bromo-5-fluoropyridin-2-yl)methyl]amino}pyridin-4-yl)-5-methylpiperidin-3-yl]carbamate (Intermediate 2) and (4-cyano-2-fluorophenyl)boronic acid (from Combi-Blocks). LCMS calc. for $C_{24}H_{25}F_2N_6$ (M+H)$^+$: 435.2; Found: 435.2.

Example 85

4-[(3S,5R)-3-Amino-5-methylpiperidin-1-yl]-N-{[6-(1-benzothien-5-yl)-5-fluoropyridin-2-yl]methyl}pyridin-3-amine

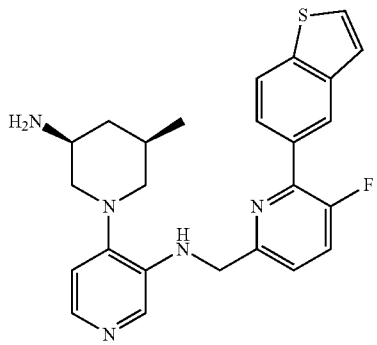 [SMILES: C[C@@H]1C[C@H](N)CN(c2ccncc2NCc2ccc(F)c(-c3ccc4sccc4c3)n2)C1]

This compound was prepared as a TFA salt by using procedures analogous to those described for the synthesis of Example 82, Step 4 starting from tert-butyl [(3S,5R)-1-(3-{[(6-bromo-5-fluoropyridin-2-yl)methyl]amino}pyridin-4-yl)-5-methylpiperidin-3-yl]carbamate (Intermediate 2) and 2-(1-benzothien-5-yl)-4,4,5,5-tetramethyl-1,3,2-dioxaborolane (from Maybridge). LCMS calc. for $C_{25}H_{27}FN_5S$ (M+H)$^+$: 448.2; Found: 448.2.

Example 86

6-{6-[({4-[(3S,5R)-3-Amino-5-methylpiperidin-1-yl]pyridin-3-yl}amino)methyl]-3-fluoropyridin-2-yl}-1,3-dihydro-2H-indol-2-one

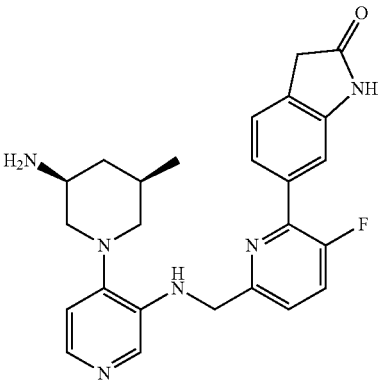 [SMILES: C[C@@H]1C[C@H](N)CN(c2ccncc2NCc2ccc(F)c(-c3ccc4c(c3)NC(=O)C4)n2)C1]

This compound was prepared as a TFA salt by using procedures analogous to those described for the synthesis of Example 82, Step 4 starting from tert-butyl [(3S,5R)-1-(3-{[(6-bromo-5-fluoropyridin-2-yl)methyl]amino}pyridin-4-yl)-5-methylpiperidin-3-yl]carbamate (Intermediate 2) and (2-oxo-2,3-dihydro-1H-indol-6-yl)boronic acid (from Combi-Blocks). LCMS calc. for $C_{25}H_{28}FN_6O$ (M+H)$^+$: 447.2; Found: 447.2.

Example 87

(7S)-4-[(3S,5R)-3-Amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol and (7R)-4-[(3S,5R)-3-Amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol

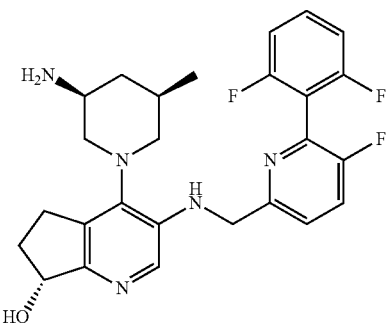 [SMILES: C[C@@H]1C[C@H](N)CN(c2c(NCc3ccc(F)c(-c4c(F)cccc4F)n3)cnc3c2CC[C@H]3O)C1]

Step 1: 6,7-Dihydro-5H-cyclopenta[b]pyridine 1-oxide

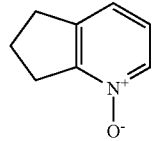

mCPBA (10.0 g, 44.6 mmol) was added slowly to a mixture of 6,7-dihydro-5H-cyclopenta[b]pyridine (from Aldrich, 5.0 g, 42 mmol) in DCM (50 mL). The reaction mixture was stirred at room temperature for 2 h. The solution was then washed with aqueous $Na_2S_2O_3$ (50 mL) and 1M NaOH (50 mL). The aqueous layer was extracted with DCM (5×70 mL). The combined organic layers were dried, filtered and concentrated under reduced pressure to give the sub-title compound (4.5 g, 79%). LCMS calc. for $C_8H_{10}NO$ (M+H)$^+$: m/z=136.1. Found: 136.2.

Step 2: 4-Chloro-6,7-dihydro-5H-cyclopenta[b]pyridine

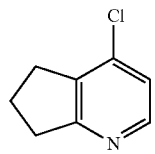

6,7-Dihydro-5H-cyclopenta[b]pyridine 1-oxide (2.5 g, 18 mmol) was mixed with $POCl_3$ (20 mL). The reaction mixture was stirred at 120° C. for 3 h. The excess $POCl_3$ was removed under reduced pressure. The residue was dissolved in EtOAc (80 mL) and neutralized with aq. $Na_2CO_3$. After filtration, the aqueous layer was extracted with EtOAc twice. The combined organic layers were dried, filtered and concentrated under reduced pressure to give the sub-title compound (2.6 g, 93%). LCMS calc. for $C_8H_9ClN$ (M+H)$^+$: m/z=154.0. Found: 154.3.

Step 3: 4-Methoxy-6,7-dihydro-5H-cyclopenta[b]pyridine

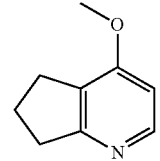

A mixture of 4-chloro-6,7-dihydro-5H-cyclopenta[b]pyridine (2.8 g, 18 mmol), MeOH (20 mL) and sodium methoxide (3.0 g, 56 mmol) was sealed in a pressurized flask and heated at 110° C. for 18 h. The mixture was diluted with EtOAc and neutralized with HCl to pH=1. The organic solvent was removed under reduced pressure. The resulting mixture was washed with ether twice, and then neutralized with $Na_2CO_3$ solution. The aqueous layer was extracted twice with EtOAc. The combined organic layers were dried, filtered and concentrated under reduced pressure to give the sub-title compound (1.20 g, 44%). LCMS calc. for $C_9H_{12}NO$ (M+H)$^+$: m/z=150.1. Found: 150.2.

Step 4: 4-Methoxy-3-nitro-6,7-dihydro-5H-cyclopenta[b]pyridine

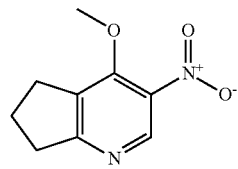

4-Methoxy-6,7-dihydro-5H-cyclopenta[b]pyridine (2.90 g, 19.4 mmol) was mixed with concentrated sulfuric acid (17.0 g, 173 mmol) at 0° C., then a mixture of potassium nitrate (5.3 g, 52 mmol) in another portion of concentrated sulfuric acid (26.5 g, 270 mmol) was added slowly. The reaction mixture was heated at 80° C. for 4 h. The crude mixture was slowly poured onto crushed ice (50 g), and neutralized carefully with 50% aqueous NaOH to pH 8-9. The resulting mixture was extracted with EtOAc five times. The combined organic extracts were dried and concentrated under reduced pressure to give the crude sub-title compound as brown gum (1.56 g, 41%), which was used without further purification. LCMS calc. for $C_9H_{11}N_2O_3$ (M+H)$^+$: m/z=195.1. Found: 195.2.

Step 5: 3-Nitro-6,7-dihydro-5H-cyclopenta[b]pyridin-4-ol

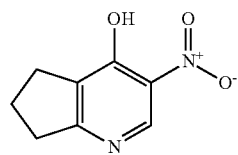

A mixture of 4-methoxy-3-nitro-6,7-dihydro-5H-cyclopenta[b]pyridine (1.535 g, 7.905 mmol) in acetic acid (2.6 mL) was treated 48% aqueous HBr (2.6 mL, 23 mmol). The flask containing the reaction mixture was sealed and heated at 130° C. for 40 min., then allowed to cool. The resulting reaction mixture was concentrated under reduced pressure, the residue was neutralized to pH=7-8 using 50% NaOH with cooling. After further concentrating, the residue was diluted with MeOH and THF, dried, filtered and concentrated to give the crude sub-title compound as light brown powder, which was used without further purification. LCMS calc. for $C_8H_9N_2O_3$ $(M+H)^+$: m/z=181.1. Found: 181.2.

Step 6: 4-Chloro-3-nitro-6,7-dihydro-5H-cyclopenta[b]pyridine

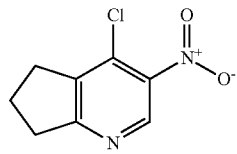 [SMILES: O=[N+]([O-])c1cnc2c(c1Cl)CCC2]

A solution of 3-nitro-6,7-dihydro-5H-cyclopenta[b]pyridin-4-ol (1.424 g, 7.904 mmol) in $POCl_3$ (11.0 mL) was heated at 110° C. in a sealed flask under $N_2$ for 2 h. The crude mixture was cooled to room temperature, and concentrated under reduced pressure. The residue was carefully quenched with ice, and neutralized with 50% NaOH to pH 7. The resulting mixture was extracted with EtOAc three times. The combined organic layers were dried, filtered and concentrated under reduced pressure to give the crude sub-title compound as a brown solid (0.82 g, 52%), which was used without further purification. LCMS calc. for $C_8H_8N_2O_2$ $(M+H)^+$: m/z=199.0. Found: 199.2.

Step 7: tert-Butyl [(3S,5R)-5-methyl-1-(3-nitro-6,7-dihydro-5H-cyclopenta[b]pyridin-4-yl)piperidin-3-yl]carbamate

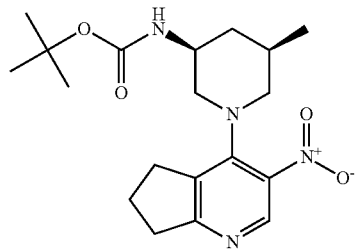 [SMILES: C[C@@H]1C[C@H](NC(=O)OC(C)(C)C)CN(c2c([N+](=O)[O-])cnc3c2CCC3)C1]

A mixture of 4-chloro-3-nitro-6,7-dihydro-5H-cyclopenta[b]pyridine (19.4 mg, 0.10 mmol), tert-butyl [(3S,5R)-5-methylpiperidin-3-yl]carbamate (Prepared in Intermediate 2, Step 4; 22.0 mg, 0.10 mmol) and triethylamine (40.9 µL, 0.29 mmol) in isopropyl alcohol (0.224 mL) was stirred at 100° C. for 40 min. The reaction mixture was concentrated under vacuum and the residue was purified by silica gel column chromatography using CombiFlash®(gradient elution with 0 to 50% EtOAc in hexanes) to give the sub-title compound as pale yellow powder (36.8 mg, 100%). LCMS calc. for $C_{19}H_{29}N_4O_4$ $(M+H)^+$: m/z=377.1. Found: 377.1.

Step 8. tert-Butyl [(3S,5R)-5-methyl-1-(3-nitro-1-oxido-6,7-dihydro-5H-cyclopenta[b]pyridin-4-yl)piperidin-3-yl]carbamate

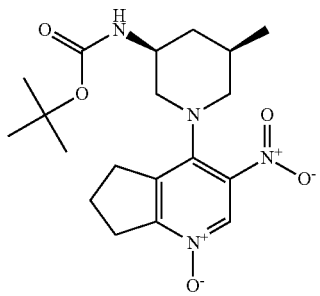 [SMILES: C[C@@H]1C[C@H](NC(=O)OC(C)(C)C)CN(c2c([N+](=O)[O-])c[n+]([O-])c3c2CCC3)C1]

To a solution of tert-butyl [(3S,5R)-5-methyl-1-(3-nitro-6,7-dihydro-5H-cyclopenta[b]pyridin-4-yl)piperidin-3-yl]carbamate (32.3 mg, 0.086 mmol) in DCM (0.50 mL) at 0° C. was added mCPBA (25.0 mg, 0.112 mmol). The reaction mixture was stirred at room temperature for 1 h. The mixture was treated with $Na_2S_2O_3$ solution, followed by the addition of 1N NaOH, and stirred for 30 min. at room temperature. The organic layer was separated, dried, filtered and concentrated under vacuum to give the crude N-oxide product. The crude product was purified by preparative LCMS (XBridge™ preparative C18 5 µm OBD™ column, 30×10 mm, 60 mL/min., gradient elution with MeCN and water with 0.1% $NH_4OH$) to afford the sub-title compound (20 mg, 40%). LCMS calc. for $C_{19}H_{29}N_4O_5$ $(M+H)^+$: m/z=393.2. Found: 393.1.

Step 9. 4-{(3S,5R)-3-[(tert-Butoxycarbonyl)amino]-5-methylpiperidin-1-yl}-3-nitro-6,7-dihydro-5H-cyclopenta[b]pyridin-7-yl acetate

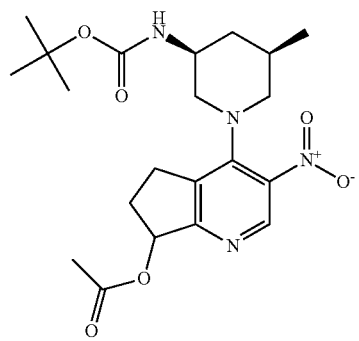 [SMILES: CC(=O)OC1CCc2c1ncc([N+](=O)[O-])c2N1C[C@H](C)C[C@H](NC(=O)OC(C)(C)C)C1]

Acetic anhydride (15.6 mg, 0.153 mmol) was added to the N-oxide tert-butyl [(3S,5R)-5-methyl-1-(3-nitro-1-oxido-6,7-dihydro-5H-cyclopenta[b]pyridin-4-yl)piperidin-3-yl]carbamate (10.0 mg, 0.026 mmol) in a sealed tube. The reaction mixture was heated at 90° C. for 30 min. and the solution was then concentrated under reduced pressure. The residue was then dissolved in DCM, then poured into ice cold $Na_2CO_3$ solution. The aqueous layer was extracted with DCM twice. The combined organic layers were dried, filtered and concentrated under reduced pressure to give the sub-title compound as off-white powder (11.2 mg, 95%). LCMS calc. for $C_{21}H_{31}N_4O_6$ $(M+H)^+$: m/z=435.2. Found: 435.1.

191

Step 10: 3-Amino-4-{(3S,5R)-3-[(tert-butoxycarbo-nyl)amino]-5-methylpiperidin-1-yl}-6,7-dihydro-5H-cyclopenta[b]pyridin-7-yl acetate

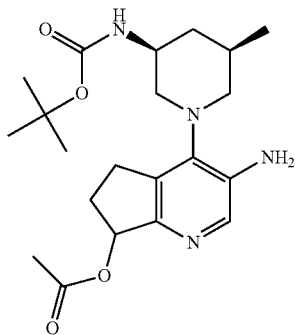 [SMILES: CC(=O)OC1CCc2c1ncc(N)c2N1C[C@H](C)C[C@H](NC(=O)OC(C)(C)C)C1]

A mixture of 4-{(3S,5R)-3-[(tert-butoxycarbonyl)amino]-5-methylpiperidin-1-yl}-3-nitro-6,7-dihydro-5H-cyclopenta[b]pyridin-7-yl acetate (11.2 mg, 0.026 mmol), acetic acid (73.3 µL) and iron powder (14.4 mg, 0.26 mmol) was stirred at room temperature for 3 h. The reaction mixture was diluted with EtOAc, filtered and washed with more EtOAc. The filtrate was concentrated under vacuum, and the residue was diluted with EtOAc and neutralized with $Na_2CO_3$ solution. The mixture was stirred at room temperature for 30 min. The organic layer was separated, dried over $Na_2SO_4$, filtered and concentrated under vacuum to give the sub-title compound as a yellow solid (10.0 mg, 96%). LCMS calc. for $C_{21}H_{33}N_4O_4$ $(M+H)^+$: m/z=405.2. Found: 405.1.

Step 11: 4-{(3S,5R)-3-[(tert-Butoxycarbonyl) amino]-5-methylpiperidin-1-yl}-3-({[6-(2,6-difluorophenyl)-5-fluoropyridin-2-yl]methyl}amino)-6,7-dihydro-5H-cyclopenta[b]pyridin-7-yl acetate

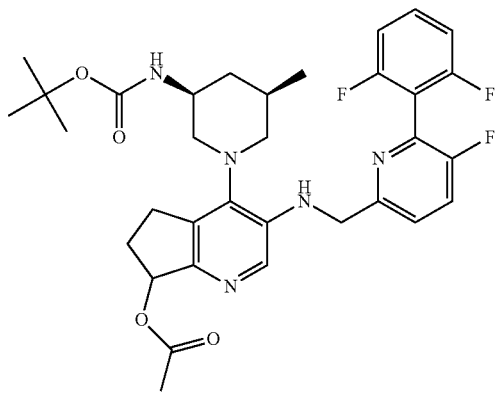 [SMILES: CC(=O)OC1CCc2c1ncc(NCc1ccc(F)c(-c3c(F)cccc3F)n1)c2N1C[C@H](C)C[C@H](NC(=O)OC(C)(C)C)C1]

3-Amino-4-{(3S,5R)-3-[(tert-butoxycarbonyl)amino]-5-methylpiperidin-1-yl}-6,7-dihydro-5H-cyclopenta[b]pyridin-7-yl acetate (18.8 mg, 0.046 mmol) and 6-(2,6-difluorophenyl)-5-fluoropyridine-2-carbaldehyde (Prepared in Example 66, Step 4; 10.0 mg, 0.042 mmol) were dissolved in toluene (0.9 mL) and AcOH (catalytic amount) was added. The reaction mixture was heated at 120 Celsius for 3 h. The solvent was evaporated under vacuum and methanol (0.94 mL) was added, followed by the addition of sodium tetrahydroborate (4.0 mg, 0.10 mmol). The reaction mixture

192 was stirred at room temperature for 30 min. The crude product was purified by prep LCMS (XBridge™ PrepC18 5 µm OBD™ column, 30×10 mm, 60 mL/min, gradient elution with MeCN and water with $NH_4OH$) to give the desired product (8.0 mg). LCMS calc. for $C_{33}H_{39}F_3N_5O_4$ $(M+H)^+$: m/z=626.3. Found: 626.3.

Step 12: (7S)-4-[(3S,5R)-3-Amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol and (7R)-4-[(3S,5R)-3-Amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol 4-{(3S,5R)-3-[(tert-Butoxycarbonyl)amino]-5-methylpiperidin-1-yl}-3-({[6-(2,6-difluorophenyl)-5-fluoropyridin-2-yl]methyl}amino)-6,7-dihydro-5H-cyclopenta[b]pyridin-7-yl acetate (8.0 mg, 0.013 mmol) was mixed with methanol (0.03 mL), tetrahydrofuran (0.2 mL) and 1.0M sodium hydroxide in water (0.064 mL, 0.064 mmol). The reaction mixture was stirred at room temperature for 20 min. The organic solvents and trace of water were removed under vacuum to give the crude intermediate, which was treated with 4.0M hydrogen chloride in dioxane (0.16 mL, 0.64 mmol). The mixture was stirred at room temperature for 10 min. After concentration, the residue was diluted with $NH_4OH$ and MeOH, filtered and purified by prep LCMS (XBridge™ PrepC18 5 µm OBD™ column, 30×10 mm, 60 mL/min, gradient elution with MeCN and water with $NH_4OH$) to give two diastereomers (Diastereoisomers 1 and 2) which were tentatively assigned as (7S)-4-[(3S,5R)-3-amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol and (7R)-4-[(3S,5R)-3-amino-5-methylpiperidin-1-yl]-3-({[6-(2,6-difluorophenyl)-5-fluoropyridin-2-yl]methyl}amino)-6,7-dihydro-5H-cyclopenta[b]pyridin-7-ol. Analytical data were obtained for the second diasteromer eluted (1.2 mg). LCMS calc. for $C_{26}H_{29}F_3N_5O$ $(M+H)^+$: m/z=484.2. Found: 484.2.

Example 88

(3R,4R,5S)-3-Amino-1-[5-({[6-(2,6-difluorophenyl)-5-fluoropyridin-2-yl]methyl}amino)-2,3-dihydrofuro[2,3-b]pyridin-4-yl]-5-methylpiperidin-4-ol

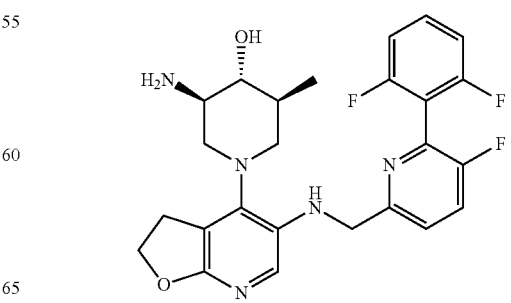

Step 1. 2-(2-Fluoro-4-iodopyridin-3-yl)ethanol

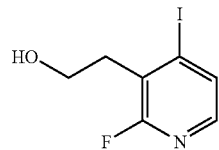 [SMILES: OCCc1c(I)ccnc1F]

A solution of 2.0M lithium diisopropylamide in heptane/THF/ethylbenzene (8.10 mL, 16.2 mmol) was added to a solution of 2-fluoro-4-iodopyridine (Ark Pharm, 2.989 g, 13.40 mmol) in THF (50 mL) at −78° C., then the mixture was stirred at −78° C. for 90 min. With the temperature maintained at −78° C., a solution of 1,3,2-dioxathiolane 2,2-dioxide (2.206 g, 17.77 mmol) in THF (30 mL) was added slowly over a period of 20 min., the solution was stirred at −78° C. for a further 20 min., then allowed to warm to room temperature and stirred for 2 h at that temperature. The mixture was then cooled to 0° C., and 12.0M aqueous HCl (5.0 mL, 60. mmol) was added. The reaction mixture was allowed to warm to room temperature and stirred at that temperature for 3 h. Saturated aqueous NaHCO$_3$ (250 mL) was added, then the reaction mixture was extracted with EtOAc (3×150 mL). The combined extracts were washed with brine (250 mL), dried over Na$_2$SO$_4$ and concentrated under reduced pressure. The residue was purified by chromatography on silica gel (gradient elution with 0-100% EtOAc in hexanes) to give the sub-title compound as a white solid (3.13 g, 87%). LCMS calc. for C$_7$H$_8$FINO (M+H)$^+$: m/z=268.0; found 268.0.

Step 2. 4-Iodo-2,3-dihydrofuro[2,3-b]pyridine

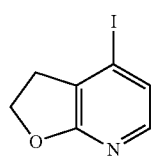

Potassium phosphate (10.0 g, 47.1 mmol) was added to a solution of 2-(2-fluoro-4-iodopyridin-3-yl)ethanol (3.13 g, 11.7 mmol) in 1,4-dioxane (100 mL). The mixture was heated under reflux for 36 h. The reaction mixture was filtered, and the filter cake was washed with EtOAc. The combined filtrates were concentrated under reduced pressure. The residue was dissolved in DCM (100 mL), washed with brine (2×100 mL), dried over Na$_2$SO$_4$ and concentrated under reduced pressure. The resulting residue (2.55 g) containing the sub-title compound was used in the next step directly without further purification. LCMS calc. for C$_7$H$_7$INO (M+H)$^+$: m/z=247.9; found 248.0.

Step 3. 4-Iodo-5-nitro-2,3-dihydrofuro[2,3-b]pyridine

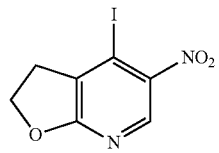 [SMILES: O=[N+]([O-])c1cnc2c(c1I)CCO2]

A solution of fuming nitric acid (15.0 mL, 358 mmol) in concentrated sulfuric acid (15.0 mL, 281 mmol) was added slowly over a period of 15 min. to a stirred solution of 4-iodo-2,3-dihydrofuro[2,3-b]pyridine (2.237 g, 9.055 mmol) in sulfuric acid (10.0 mL, 188 mmol) at −10° C. The reaction mixture was allowed to warm to room temperature, and stirred for a further 16 h. The reaction mixture was quenched by pouring onto crushed ice and was then extracted with EtOAc (6×100 mL). The organic extracts were combined and washed with saturated aqueous NaHCO$_3$ (2×300 mL) and brine (300 mL), then dried over Na$_2$SO$_4$, and concentrated under reduced pressure. The residue was purified by chromatography on silica gel (gradient elution with 0-100% EtOAc in hexanes) to give the sub-title compound as a pale yellow solid (2.43 g, 92%). LCMS calc. for C$_7$H$_6$IN$_2$O$_3$ (M+H)$^+$: m/z=292.9; found 293.0.

Step 4. tert-Butyl [(3R,4R,5S)-4-{[tert-butyl(dimethyl)silyl]oxy}-5-methyl-1-(5-nitro-2,3-dihydrofuro[2,3-b]pyridin-4-yl)piperidin-3-yl]carbamate

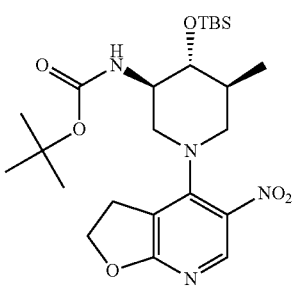 [SMILES: C[C@H]1CN(c2c([N+](=O)[O-])cnc3c2CCO3)C[C@@H](NC(=O)OC(C)(C)C)[C@@H]1O[Si](C)(C)C(C)(C)C]

To a mixture of 4-iodo-5-nitro-2,3-dihydrofuro[2,3-b]pyridine (110.4 mg, 0.3780 mmol) and tert-butyl ((3R,4R,5S)-4-{[tert-butyl(dimethyl)silyl]oxy}-5-methylpiperidin-3-yl)carbamate (Prepared in Intermediate 1, Step 9; 100.0 mg, 0.2902 mmol) was added EtOH (2.0 mL) followed by the addition of DIPEA (163.8 mg, 1.267 mmol). The reaction mixture was heated at 100° C. for 15 h, and then concentrated under reduced pressure. The residue was purified by chromatography on silica gel (gradient elution with 0-50% EtOAc in hexanes) to afford the sub-title compound as a yellow solid (118.2 mg, 80%). LCMS calc. for C$_{24}$H$_{41}$N$_4$O$_6$Si (M+H)$^+$: m/z=509.3; found 509.3.

Step 5. tert-Butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate

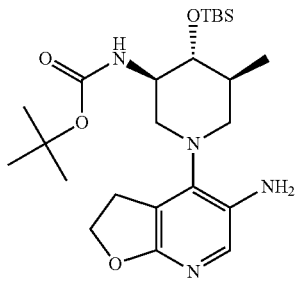 [SMILES: C[C@H]1CN(c2c(N)cnc3c2CCO3)C[C@@H](NC(=O)OC(C)(C)C)[C@@H]1O[Si](C)(C)C(C)(C)C]

To a mixture of tert-butyl [(3R,4R,5S)-4-{[tert-butyl(dimethyl)silyl]oxy}-5-methyl-1-(5-nitro-2,3-dihydrofuro[2,3-b]pyridin-4-yl)piperidin-3-yl]carbamate (73.4 mg, 0.144 mmol), iron powder (89.0 mg, 1.59 mmol), and ammonium chloride (151.4 mg, 2.830 mmol) was added EtOH (2.0 mL), followed by the addition of water (0.50 mL, 28 mmol). The reaction mixture was stirred at 80° C. for 1 h. The reaction mixture was filtered through a pad of diatomaceous earth. The diatomaceous earth pad was eluted with a 10% aqueous solution of $K_3PO_4$ (20 mL), and EtOAc (20 mL). The organic layers were washed with brine (20 mL), dried over $Na_2SO_4$, and concentrated to give the crude sub-title compound (67.8 mg). The crude product was used directly in the next step without further purification. LCMS calc. for $C_{24}H_{43}N_4O_4Si$ (M+H)$^+$: m/z=479.3; found 479.3.

Step 6: tert-Butyl {(3R,4R,5S)-4-{[tert-butyl(dimethyl)silyl]oxy}-1-[5-({[6-(2,6-difluorophenyl)-5-fluoropyridin-2-yl]methyl}amino)-2,3-dihydrofuro[2,3-b]pyridin-4-yl]-5-methylpiperidin-3-yl}carbamate

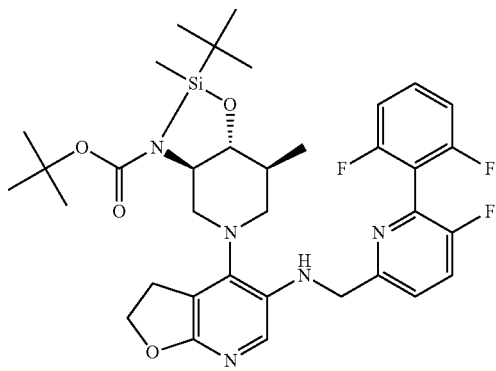

tert-Butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (31.1 mg, 0.065 mmol) and 6-(2,6-difluorophenyl)-5-fluoropyridine-2-carbaldehyde (Prepared in Example 66, Step 4; 14.0 mg, 0.06 mmol) were dissolved in toluene (0.60 mL) and AcOH (catalytic amount) was added. The reaction mixture was heated at 125° C. for 3 h. The solvent was evaporated under vacuum and methanol (0.60 mL) was added, followed by the addition of sodium tetrahydroborate (11 mg, 0.30 mmol) at 0° C. The reaction mixture was stirred at room temperature for 30 min. After formation of the desired product, as determined by LCMS, the reaction mixture was concentrated and the residue was used directly in the next step. LCMS calc. for $C_{36}H_{49}F_3N_5O_4Si$ (M+H)$^+$: m/z=700.3. Found: 700.3.

Step 7: (3R,4R,5S)-3-Amino-1-[5-({[6-(2,6-difluorophenyl)-5-fluoropyridin-2-yl]methyl}amino)-2,3-dihydrofuro[2,3-b]pyridin-4-yl]-5-methylpiperidin-4-ol tert-Butyl {(3R,4R,5S)-4-{[tert-butyl(dimethyl)silyl]oxy}-1-[5-({[6-(2,6-difluorophenyl)-5-fluoropyridin-2-yl]methyl}amino)-2,3-dihydrofuro[2,3-b]pyridin-4-yl]-5-methylpiperidin-3-yl}carbamate (9.8 mg, 0.014 mmol) was mixed with methanol (0.11 mL) and 4.0M hydrogen chloride in dioxane (0.17 mL, 0.70 mmol). The reaction mixture was stirred at room temperature for 20 min. After concentrated under reduced pressure, the residue was dissolved in NH$_4$OH and MeOH, filtered and purified by prep LCMS (XBridge™ PrepC18 5 μm OBD™ column, 30×10 mm, 60 mL/min, gradient elution with MeCN and water with NH$_4$OH) to give the desired product as white powders (4.5 mg, 66%). LCMS calc. for $C_{25}H_{27}F_3N_5O_2$ (M+H)$^+$: m/z=486.2. Found: 486.2.

Example 89

4-[(3S,5R)-3-Amino-5-methylpiperidin-1-yl]-N-{[6-(2,6-difluorophenyl)-5-fluoropyridin-2-yl]methyl}-6,7-dihydro-5H-cyclopenta[b]pyridin-3-amine

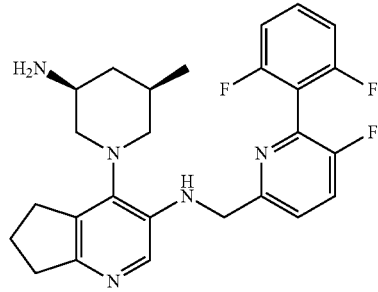 [SMILES: C[C@@H]1C[C@H](N)CN(c2c(NCc3ccc(F)c(-c4c(F)cccc4F)n3)cnc3c2CCC3)C1]

Step 1. tert-Butyl [(3S,5R)-1-(3-amino-6,7-dihydro-5H-cyclopenta[b]pyridin-4-yl)-5-methylpiperidin-3-yl]carbamate

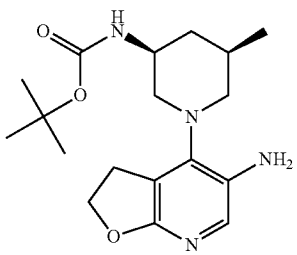 [SMILES: C[C@@H]1C[C@H](NC(=O)OC(C)(C)C)CN(c2c(N)cnc3c2CCO3)C1]

A mixture of tert-Butyl [(3S,5R)-5-methyl-1-(3-nitro-6,7-dihydro-5H-cyclopenta[b]pyridin-4-yl)piperidin-3-yl]carbamate (from Example 87 step 7, 0.435 g, 1.16 mmol), acetic acid (6.5 mL) and iron powder (1.32 g, 23.6 mmol) were stirred at rt for 3 h. The reaction mixture was diluted with EtOAc, filtered through a celite pad. The filtrate was concentrated under vacuum, diluted with dichloromethane and neutralized with NaOH (2N). The organic layer was separated, dried over $K_2CO_3$, filtered and concentrated under vacuum to give the desired product as light brown powders (365 mg, 91%). LCMS calcd for $C_{19}H_{31}N_4O_2$ (M+H)$^+$: m/z=347.2. Found: 347.1.

Step 2: tert-Butyl {(3S,5R)-1-[3-({[6-(2,6-difluorophenyl)-5-fluoropyridin-2-yl]methyl}amino)-6,7-dihydro-5H-cyclopenta[b]pyridin-4-yl]-5-methylpiperidin-3-yl}carbamate

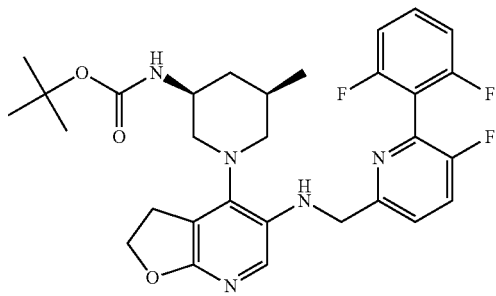 [SMILES: C[C@@H]1C[C@H](NC(=O)OC(C)(C)C)CN(c2c(NCc3ccc(F)c(-c4c(F)cccc4F)n3)cnc3c2CCO3)C1]

tert-Butyl [(3S,5R)-1-(3-amino-6,7-dihydro-5H-cyclopenta[b]pyridin-4-yl)-5-methylpiperidin-3-yl]carbamate (22.5 mg, 0.065 mmol) and 6-(2,6-difluorophenyl)-5-fluoropyridine-2-carbaldehyde (Prepared in Example 66, Step 4; 14.0 mg, 0.059 mmol) were dissolved in toluene (0.60 mL) and AcOH (catalytic amount) was added. The reaction mixture was heated at 125° C. for 3 h. The solvent was evaporated and methanol (0.6 mL) was added, followed by the addition of sodium tetrahydroborate (11 mg, 0.3 mmol) at 0° C. The reaction mixture was stirred at room temperature for 30 min and then concentrated under reduced pressure and directly used in the next step. LCMS calc. for $C_{31}H_{37}F_3N_5O_2$ (M+H)$^+$: m/z=568.3. Found: 568.3.

Step 3: 4-[(3S,5R)-3-Amino-5-methylpiperidin-1-yl]-N-{[6-(2,6-difluorophenyl)-5-fluoropyridin-2-yl]methyl}-6,7-dihydro-5H-cyclopenta[b]pyridin-3-amine tert-Butyl {(3S,5R)-1-[3-({[6-(2,6-difluorophenyl)-5-fluoropyridin-2-yl]methyl}amino)-6,7-dihydro-5H-cyclopenta[b]pyridin-4-yl]-5-methylpiperidin-3-yl}carbamate (11.0 mg, 0.019 mmol) was mixed with methanol (0.16 mL) and 4.0M hydrogen chloride in dioxane (0.24 mL, 0.97 mmol). The reaction mixture was stirred at room temperature for 20 min. After concentrated under reduced pressure, the residue was dissolved in $NH_4OH$ and MeOH, filtered and purified by prep LCMS (XBridge™ PrepC18 5 μm OBD™ column, 30×10 mm, 60 mL/min, gradient elution with MeCN and water with $NH_4OH$) to give the desired product as white powder (3.4 mg, 38%). LCMS calc. for $C_{26}H_{29}F_3N_5$ (M+H)$^+$: m/z=468.2. Found: 468.2.

Example 90

4-[(3R,4R)-3-Amino-4-fluoropiperidin-1-yl]-N-{[6-(2,6-difluorophenyl)-5-fluoropyridin-2-yl]methyl}pyridin-3-amine

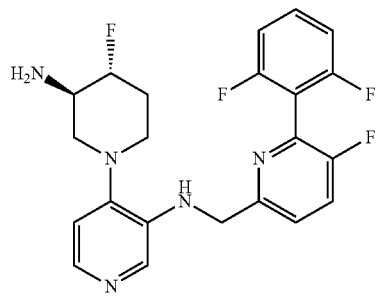 [SMILES: N[C@@H]1CN(c2ccncc2NCc2ccc(F)c(-c3c(F)cccc3F)n2)CC[C@H]1F]

Step 1: tert-Butyl [(3R,4R)-4-fluoro-1-(3-nitropyridin-4-yl)piperidin-3-yl]carbamate

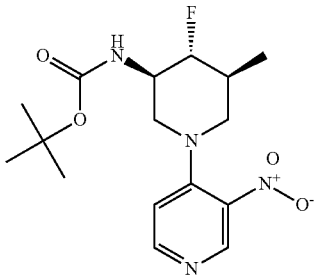

A mixture of 4-chloro-3-nitropyridine (191 mg, 1.20 mmol), tert-butyl [(3R,4R)-4-fluoropiperidin-3-yl]carbamate (from Synnovator, 250 mg, 1.15 mmol) and triethylamine (0.48 mL, 3.4 mmol) in isopropyl alcohol (1.23 mL) was stirred at 100° C. for 60 min. The reaction mixture was purified by Biotage column to give the pure product as pale yellow powder (452 mg, 100% yield). LCMS calc. for $C_{15}H_{22}FN_4O_4$ (M+H)$^+$: m/z=341.2. Found: 341.3.

Step 2: tert-Butyl [(3R,4R)-1-(3-aminopyridin-4-yl)-4-fluoropiperidin-3-yl]carbamate

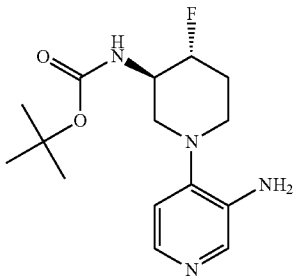 [SMILES: CC(C)(C)OC(=O)N[C@@H]1CN(c2ccncc2N)CC[C@H]1F]

tert-Butyl [(3R,4R)-4-fluoro-1-(3-nitropyridin-4-yl)piperidin-3-yl]carbamate (0.39 g, 1.14 mmol) was dissolved in methanol (8 mL). To the above solution was added palladium hydroxide (0.12 g) (20% palladium on carbon) under nitrogen. The system was de-gassed and recharged with hydrogen three times and then the reaction mixture was shaken under Parr-sharker at 45 psi of $H_2$ for 1 h. The mixture was filtered through a pad of diatomaceous earth and rinsed with MeOH. The filtrate was concentrated under reduced pressure to afford the desired product (356 mg, 100%) as light brown powder. LCMS calc. for $C_{15}H_{24}FN_4O_2$ (M+H)$^+$: m/z=311.2. Found: 311.2.

Step 3: tert-Butyl {(3R,4R)-1-[3-({[6-(2,6-difluorophenyl)-5-fluoropyridin-2-yl]methyl}amino)pyridin-4-yl]-4-fluoropiperidin-3-yl}carbamate

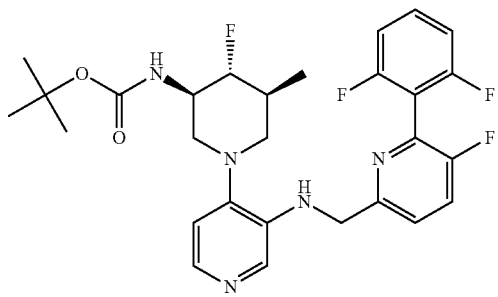 [SMILES: C[C@H]1CN(c2ccncc2NCc2ccc(F)c(-c3c(F)cccc3F)n2)C[C@@H](NC(=O)OC(C)(C)C)[C@@H]1F]

tert-Butyl [(3R,4R)-1-(3-aminopyridin-4-yl)-4-fluoropiperidin-3-yl]carbamate (20.2 mg, 0.065 mmol) and 6-(2,6-difluorophenyl)-5-fluoropyridine-2-carbaldehyde (Prepared in Example 66, Step 4; 14.0 mg, 0.059 mmol) were dissolved in toluene (0.65 mL) and AcOH (catalytic amount) was added. The reaction mixture was heated at 130° C. for 3 h. The solvent was evaporated under vacuum and methanol (0.6 mL) was added, followed by the addition of sodium tetrahydroborate (22.3 mg, 0.59 mmol) at 0° C. The reaction mixture was stirred at room temperature for 50 min and then concentrated under vacuum to give the desired crude product. LCMS calc. for $C_{27}H_{30}F_4N_5O_2$ (M+H)$^+$: m/z=532.2. Found: 532.2.

Step 4: 4-[(3R,4R)-3-Amino-4-fluoropiperidin-1-yl]-N-{[6-(2,6-difluorophenyl)-5-fluoropyridin-2-yl]methyl}pyridin-3-amine tert-Butyl {(3R,4R)-1-[3-({[6-(2,6-difluorophenyl)-5-fluoropyridin-2-yl]methyl}amino)pyridin-4-yl]-4-fluoropiperidin-3-yl}carbamate (31.0 mg, 0.058 mmol) was mixed with methanol (0.5 mL) and 4.0M hydrogen chloride in dioxane (0.73 mL, 2.9 mmol). The reaction mixture was stirred at room temperature for 30 min. After concentrated under reduced pressure, the residue was dissolved in NH$_4$OH and MeOH, filtered and purified by prep LCMS (XBridge™ PrepC18 5 μm OBD™ column, 30×10 mm, 60 mL/min, gradient elution with MeCN and water with NH$_4$OH) to give the desired product as a white powder (13.3 mg, 53%). LCMS calc. for $C_{22}H_{22}F_4N_5$ (M+H)$^+$: m/z=432.2. Found: 432.2.

Example 91

4-[(3S,5R)-3-Amino-5-methylpiperidin-1-yl]-N-{[7-(2,3-dihydro-1-benzofuran-6-yl)quinolin-2-yl]methyl}pyridin-3-amine

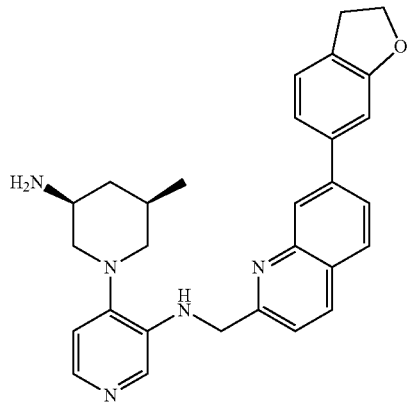

Step 1: (7-Bromoquinolin-2-yl)methanol

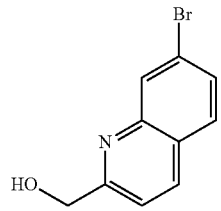 [SMILES: OCc1ccc2ccc(Br)cc2n1]

To a mixture of 7-bromoquinoline-2-carboxylic acid (from Aldrich, 0.80 g, 3.2 mmol) and triethylamine (0.49 mL, 3.5 mmol) in tetrahydrofuran (20 mL) was slowly added isobutyl chloroformate (0.45 mL, 3.8 mmol). The reaction mixture was stirred at room temperature for 1 h. The presipitate was removed by filtration. The filtrate was cooled in an ice bath and a solution of sodium borohydride (1.20 g, 4.0 mmol) in water (15.0 mL) was added dropwise. The mixture was stirred for 1 h, quenched with NaHCO$_3$ (aqueous) solution, extracted with EtOAc, washed with brine, dried over MgSO$_4$ and concentrated to give the desired product. LCMS calc. for $C_{10}H_9BrNO$ (M+H)$^+$: m/z=238.0. Found: 238.0.

Step 2: 7-Bromoquinoline-2-carbaldehyde

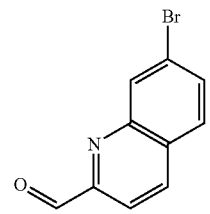 [SMILES: O=Cc1ccc2ccc(Br)cc2n1]

A solution of (7-bromoquinolin-2-yl)methanol (0.77 g, 3.2 mmol) in DCM (10 mL) at 0° C. was added Dess-Martin periodinane (2.0 g, 4.7 mmol). The reaction mixture was stirred at room temperature overnight and then concentrated under vacuum. The crude residue was purified by silica gel column chromatography (gradient elution with EtOAc in hexanes 0-50%) to give the desired product as a colorless solid. LCMS calc. for $C_{10}H_7BrNO$ $(M+H)^+$: m/z=236.0. Found: 235.9.

Step 3: tert-Butyl [(3S,5R)-1-(3-{[(7-bromoquinolin-2-yl)methyl]amino}pyridin-4-yl)-5-methylpiperidin-3-yl]carbamate

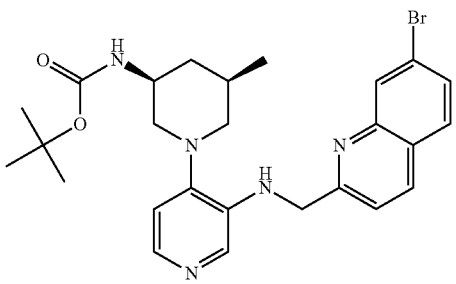 [SMILES: C[C@@H]1C[C@H](NC(=O)OC(C)(C)C)CN(c2ccncc2NCc2ccc3ccc(Br)cc3n2)C1]

tert-Butyl [(3S,5R)-1-(3-aminopyridin-4-yl)-5-methylpiperidin-3-yl]carbamate (Prepared in Intermediate 2, Step 6; 0.23 g, 0.75 mmol) and 7-bromoquinoline-2-carbaldehyde (0.16 g, 0.68 mmol) were dissolved in toluene (7.5 mL) and AcOH (catalytic amount) was added. The reaction mixture was heated at 130° C. for 3 h. The solvent was evaporated under vacuum and methanol (6.9 mL) was added, followed by the addition of sodium tetrahydroborate (0.26 g, 6.82 mmol) at 0° C. The reaction mixture was stirred at room temperature for 50 min, then concentrated under reduced pressure and purified by silica gel column chromatography (gradient elution with 0-100% EtOAc in hexanes) to give the desired product as a light yellow powder. LCMS calc. for $C_{26}H_{33}BrN_5O_2$ $(M+H)^+$: m/z=526.2. Found: 526.2.

Step 4: 4-[(3S,5R)-3-Amino-5-methylpiperidin-1-yl]-N-{[7-(2,3-dihydro-1-benzofuran-6-yl)quinolin-2-yl]methyl}pyridin-3-amine 6-(4,4,5,5-Tetramethyl-1,3,2-dioxaborolan-2-yl)-2,3-dihydro-1-benzofuran (from Ark Pharma, 0.018 g, 0.072 mmol), tert-butyl [(3S,5R)-1-(3-{[(7-bromoquinolin-2-yl)methyl]amino}pyridin-4-yl)-5-methylpiperidin-3-yl]carbamate (16.0 mg, 0.03 mmol), 1,4-dioxane (0.17 mL) and DIPEA (17.3 mg, 0.134 mmol) and water (0.017 mL) were mixed together. The mixture was flushed with nitrogen and then bis(tri-tert-butylphosphine)palladium (7.0 mg, 0.01 mmol) was added. The reaction mixture was sealed and heated at 120° C. for 2 h. The reaction mixture was cooled, filtered and concentrated under vacuum. The residue was dissolved in MeOH (1 mL), followed by the addition of 4N HCl in dioxane (2.0 mL) to the resultant solution. The reaction mixture was stirred at room temperature for 2 h, and the solvents were removed under vacuum. The residue was purified by prep LCMS (XBridge™ PrepC18 5 µm OBD™ column, 30×10 mm, 60 mL/min, gradient elution with MeCN and water with $NH_4OH$) to give the desired product as a white powder. LCMS calc. for $C_{29}H_{32}N_5O$ $(M+H)^+$: m/z=466.3. Found: 466.3.

Example 92

4-[(3S,5R)-3-Amino-5-methylpiperidin-1-yl]-N-[(7-imidazo[1,2-a]pyridin-7-ylquinolin-2-yl)methyl]pyridin-3-amine

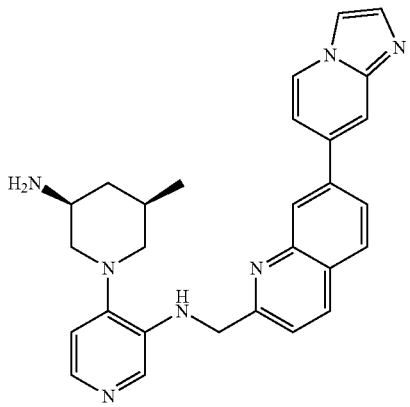 [SMILES: C[C@@H]1C[C@H](N)CN(c2ccncc2NCc2ccc3ccc(-c4ccn5ccnc5c4)cc3n2)C1]

7-(4,4,5,5-Tetramethyl-1,3,2-dioxaborolan-2-yl)imidazo[1,2-a]pyridine (from J&W Pharma, 10.0 mg, 0.041 mmol), tert-butyl [(3S,5R)-1-(3-{[(7-bromoquinolin-2-yl)methyl]amino}pyridin-4-yl)-5-methylpiperidin-3-yl]carbamate (Prepared in Example 91, Step 3; 16.0 mg, 0.03 mmol), 1,4-dioxane (0.17 mL) and N,N-diisopropylethylamine (17.3 mg, 0.134 mmol) and water (0.02 mL) were mixed together. The reaction mixture was flushed with nitrogen and then bis(tri-t-butylphosphine)palladium (7.0 mg, 0.01 mmol) was added. The reaction mixture was sealed and heated at 120° C. for 2 h. The reaction mixture was filtered and concentrated under vacuum. The residue was dissolved in MeOH (1.0 mL), followed by the addition of 4N HCl in dioxane (2.0 mL). The reaction mixture was stirred at room temperature for 1 h. The solvents were removed under vacuum. The residue was purified by prep LCMS (XBridge™ PrepC18 5 µm OBD™ column, 30×10 mm, 60 mL/min, gradient elution with MeCN and water with $NH_4OH$) to give the desired product as a white powder. LCMS calc. for $C_{28}H_{30}N_7$ $(M+H)^+$: m/z=464.3. Found: 464.3.

Example 93

(3R,4R,5S)-3-Amino-1-(3-{[(7-imidazo[1,2-a]pyridin-7-ylquinolin-2-yl)methyl]amino}pyridin-4-yl)-5-methylpiperidin-4-ol

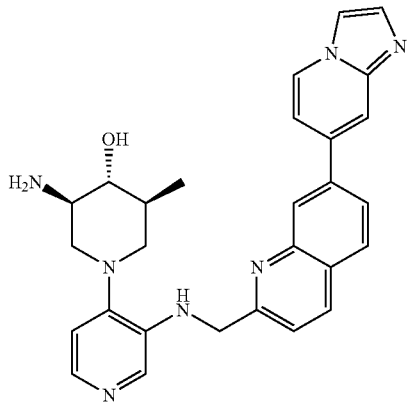 [SMILES: C[C@H]1CN(c2ccncc2NCc2ccc3ccc(-c4ccn5ccnc5c4)cc3n2)C[C@@H](N)[C@@H]1O]

Step 1: tert-Butyl ((3R,4R,5S)-1-(3-{[(7-bromoquinolin-2-yl)methyl]amino}pyridin-4-yl)-4-{[tert-butyl(dimethyl)silyl]oxy}-5-methylpiperidin-3-yl)carbamate

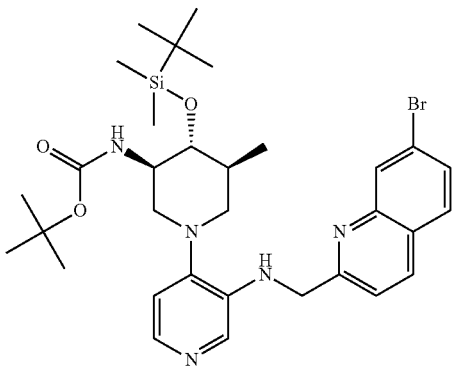 [SMILES: C[C@H]1CN(c2ccncc2NCc2ccc3ccc(Br)cc3n2)C[C@@H](NC(=O)OC(C)(C)C)[C@@H]1O[Si](C)(C)C(C)(C)C]

tert-Butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 0.30 g, 0.68 mmol) and 7-bromoquinoline-2-carbaldehyde (Prepared in Example 91, Step 2; 0.16 g, 0.68 mmol) were dissolved in toluene (7.5 mL) and acetic acid (catalytic amount) was added. The reaction mixture was heated at 130° C. for 3 h. The solvent was evaporated and methanol (6.9 mL) was added, followed by the addition of sodium tetrahydroborate (0.258 g, 6.8 mmol) at 0° C. The reaction mixture was stirred at room temperature for 50 min and concentrated under vacuum. The residue was diluted with EtOAc and NaHCO$_3$ aqueous solution. The aqueous layer was extracted with EtOAc twice. The organic layers were combined, filtered and concentrated. The crude product was purified by silica gel column chromatography (0-100% EtOAc in hexanes, then 0-30% MeOH in EtOAc) to give the desired product as a light yellow powder. LCMS calc. for C$_{32}$H$_{47}$BrN$_5$O$_3$Si (M+H)$^+$: m/z=656.3. Found: 656.2.

Step 2: (3R,4R,5S)-3-Amino-1-(3-{[(7-imidazo[1,2-a]pyridin-7-ylquinolin-2-yl)methyl]amino}pyridin-4-yl)-5-methylpiperidin-4-ol 7-(4,4,5,5-Tetramethyl-1,3,2-dioxaborolan-2-yl)imidazo[1,2-a]pyridine (10.0 mg, 0.041 mmol), tert-butyl ((3R,4R,5S)-1-(3-{[(7-bromoquinolin-2-yl)methyl]amino}pyridin-4-yl)-4-{[tert-butyl(dimethyl)silyl]oxy}-5-methylpiperidin-3-yl)carbamate (20.0 mg, 0.030 mmol), 1,4-dioxane (0.17 mL) and N,N-diisopropylethylamine (17.3 mg, 0.13 mmol) and water (0.017 mL) were mixed together. The reaction mixture was flushed with nitrogen and then bis(tri-tert-butylphosphine)palladium (7.0 mg, 0.01 mmol) was added. The reaction mixture was sealed and heated at 120° C. for 2 h. The reaction mixture was concentrated under vacuum. The residue was treated with 4N HCl in dioxane (2.0 mL) at room temperature for 2 h. The solvents were removed under vacuum. The residue was purified by prep LCMS (XBridge™ PrepC18 5 µm OBD™ column, 30×10 mm, 60 mL/min, gradient elution with MeCN and water with NH$_4$OH) to give the desired product as a white powder. LCMS calc. for C$_{28}$H$_{30}$N$_7$O (M+H)$^+$: m/z=480.2. Found: 480.3.

Example 94

(3R,4R,5S)-3-Amino-1-{3-[({6-[2,6-difluoro-4-(1-methyl-1H-pyrazol-4-yl)phenyl]-5-fluoropyridin-2-yl}methyl)amino]pyridin-4-yl}-5-methylpiperidin-4-ol

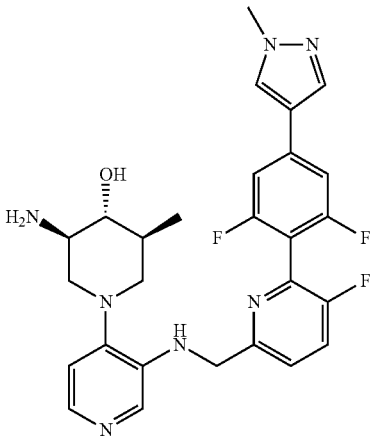 [SMILES: C[C@H]1CN(c2ccncc2NCc2ccc(F)c(-c3c(F)cc(-c4cnn(C)c4)cc3F)n2)C[C@@H](N)[C@@H]1O]

Step 1: 4-(3,5Difluorophenyl)-1-methyl-1H-pyrazole

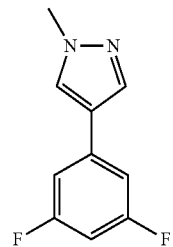

To a degassed mixture of 1-methyl-4-(4,4,5,5-tetramethyl-1,3,2-dioxaborolan-2-yl)-1H-pyrazole (from Aldrich, 0.30 g, 1.4 mmol), 1-bromo-3,5-difluorobenzene (from Aldrich, 0.28 g, 1.4 mmol), 1,4-dioxane (3.5 mL), N,N-diisopropylethylamine (0.35 g, 2.7 mmol) and water (0.35 mL) were added bis(tri-t-butylphosphine)palladium (0.10 g, 0.30 mmol). The reaction mixture was sealed in a microwave tube and heated at 120° C. for 1 h. The mixture was filtered. The filtrate was concentrated and purified by silica gel column chromatography (eluted with EtOAc in hexanes 0-50%) to give the desired product (0.23 g, 82%). LCMS calc. for $C_{10}H_9F_2N_2$ (M+H)$^+$: m/z=195.1. Found: 195.1.

Step 2: 4-[3,5-Difluoro-4-(4,4,5,5-tetramethyl-1,3,2-dioxaborolan-2-yl)phenyl]-1-methyl-1H-pyrazole

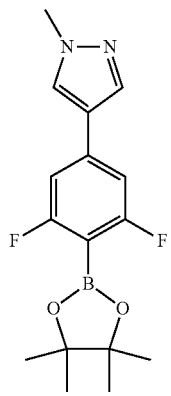

To a solution of 4-(3,5-difluorophenyl)-1-methyl-1H-pyrazole (0.23 g, 1.2 mmol) in tetrahydrofuran (4 mL) at −78° C. was added 2.5M n-butyllithium in hexane (1.4 mL, 3.6 mmol). The reaction mixture was stirred at −78° C. for 1 h, followed by the addition of 2-isopropoxy-4,4,5,5-tetramethyl-1,3,2-dioxaborolane (0.60 mL, 2.96 mmol). The mixture was allowed to warm up to rt and stirred for one hour. The mixture was diluted with EtOAc and NaHCO$_3$ (aq) was added. The organic layer was washed with brine, dried over Na$_2$SO$_4$, filtered and concentrated under vacuum. The residue was purified by silica gel column chromatography (eluted with EtOAc in hexanes 0-100%) to give the desired product (0.24 g, 63%) as brown oil. LCMS calc. for $C_{16}H_{20}BF_2N_2O_2$ (M+H)$^+$: m/z=321.2. Found: 321.2.

Step 3: (3R,4R,5S)-3-Amino-1-{3-[({6-[2,6-difluoro-4-(1-methyl-1H-pyrazol-4-yl)phenyl]-5-fluoropyridin-2-yl}methyl)amino]pyridin-4-yl}-5-methylpiperidin-4-ol 4-[3,5-Difluoro-4-(4,4,5,5-tetramethyl-1,3,2-dioxaborolan-2-yl)phenyl]-1-methyl-1H-pyrazole (15.0 mg, 0.046 mmol), tert-butyl ((3R,4R,5S)-1-(3-{[(6-bromo-5-fluoropyridin-2-yl)methyl]amino}pyridin-4-yl)-4-{[tert-butyl(dimethyl)silyl]oxy}-5-methylpiperidin-3-yl)carbamate (Intermediate 1, 12.0 mg, 0.02 mmol), 1,4-dioxane (0.11 mL), N,N-diisopropylethylamine (11.2 mg, 0.09 mmol) and water (0.011 mL) were mixed together. The reaction mixture was flushed with nitrogen and then bis(tri-tert-butylphosphine)palladium (4.0 mg, 0.009 mmol) was added. The mixture was sealed and heated at 120° C. for 2 h. The reaction mixture was filtered and concentrated under vacuum to give the crude intermediate, which was treated with 4N HCl in dioxane (2.0 mL). The reaction mixture was stirred at room temperature for 2 h, and the solvents were removed under vacuum. The residue was purified by prep LCMS (XBridge™ PrepC18 5 μm OBD™ column, 30×10 mm, 60 mL/min, gradient elution with MeCN and water with NH$_4$OH) to give the desired product as a white powder. LCMS calc. for $C_{27}H_{29}F_3N_7O$ (M+H)$^+$: m/z=524.2. Found: 524.3.

Example 95

(3R,4R,5S)-3-Amino-1-(3-{[(3-isopropylfuro[3,2-b]pyridin-5-yl)methyl]amino}pyridin-4-yl)-5-methylpiperidin-4-ol

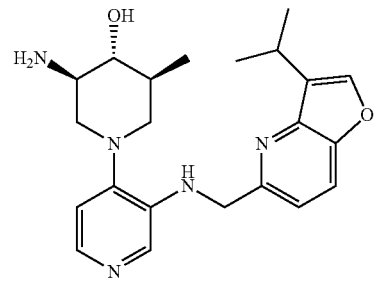 [SMILES: CC(C)c1coc2ccc(CNc3cnccc3N3C[C@@H](N)[C@H](O)[C@@H](C)C3)nc12]

Step 1. tert-Butyl [(3R,4R,5S)-4-{[tert-butyl(dimethyl)silyl]oxy}-1-(3-{[(3-isopropenylfuro[3,2-b]pyridin-5-yl)methyl]amino}pyridin-4-yl)-5-methylpiperidin-3-yl]carbamate

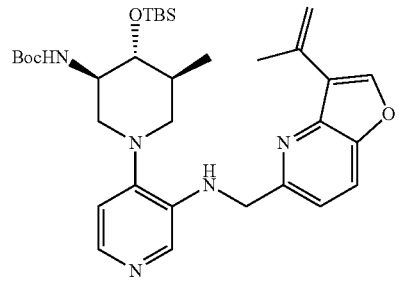 [SMILES: C=C(C)c1coc2ccc(CNc3cnccc3N3C[C@H](C)[C@@H](O[Si](C)(C)C(C)(C)C)[C@H](NC(=O)OC(C)(C)C)C3)nc12]

tert-Butyl ((3R,4R,5S)-1-(3-{[(3-bromofuro[3,2-b]pyridin-5-yl)methyl]amino}pyridin-4-yl)-4-{[tert-butyl(dimethyl)silyl]oxy}-5-methylpiperidin-3-yl)carbamate (Intermediate 4, 20.0 mg, 0.0309 mmol), chloro(2-dicyclohexylphosphino-2',4',6'-triisopropyl-1,1'-biphenyl)[2-(2'-amino-1,1'-biphenyl)]palladium(II) (Pd XPhos G2) (2.5 mg, 0.0032 mmol), potassium phosphate (20 mg, 0.096 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-isopropenyl-4,4,5,5-tetramethyl-1,3,2-dioxaborolane (from Aldrich, 8.3 mg, 0.049 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The crude product was purified by Biotage Isolera to give the desired compound (18 mg, 99%). LCMS calc. for $C_{33}H_{50}N_5O_4Si$ (M+H)$^+$ m/z=608.4; found: 608.4.

Step 2. tert-Butyl [(3R,4R,5S)-4-{[tert-butyl(dimethyl)silyl]oxy}-1-(3-{[(3-isopropylfuro[3,2-b]pyridin-5-yl)methyl]amino}pyridin-4-yl)-5-methylpiperidin-3-yl]carbamate

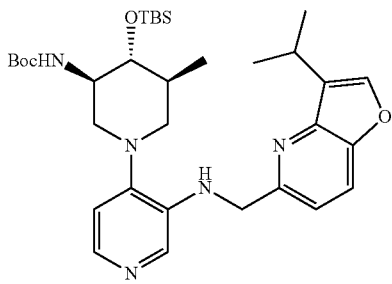 [SMILES: CC(C)c1coc2ccc(CNc3cnccc3N3C[C@H](C)[C@@H](O[Si](C)(C)C(C)(C)C)[C@H](NC(=O)OC(C)(C)C)C3)nc12]

To a stirred solution of tert-butyl [(3R,4R,5S)-4-{[tert-butyl(dimethyl)silyl]oxy}-1-(3-{[(3-isopropenylfuro[3,2-b]pyridin-5-yl)methyl]amino}pyridin-4-yl)-5-methylpiperidin-3-yl]carbamate (18 mg, 0.03 mmol) in methanol (10 mL) was added 5 w % of Pd on carbon (31 mg, 0.015 mmol). A vial was closed with septum and was connected to a balloon with hydrogen.

After stirring at room temperature for 3 h, the reaction mixture was filtered through a pad of diatomaceous earth and the solvent was evaporated under reduced pressure. The resulting crude product was used in the next step without further purification (18 mg, 99%). LCMS calc. for $C_{33}H_{52}N_5O_4Si$ (M+H)$^+$ m/z=610.4; found: 610.5.

Step 3. (3R,4R,5S)-3-Amino-1-(3-{[(3-isopropylfuro[3,2-b]pyridin-5-yl)methyl]amino}pyridin-4-yl)-5-methylpiperidin-4-ol tert-Butyl ((3R,4R,5S)-4-{[tert-butyl(dimethyl)silyl]oxy}-1-(3-{[(3-isopropylfuro[3,2-b]pyridin-5-yl)methyl]amino}pyridin-4-yl)-5-methylpiperidin-3-yl]carbamate (19 mg, 0.032 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 µm particle size, gradient elution with acetonitrile/water containing 0.1% NH$_4$OH, at flow rate of 60 mL/min). LCMS calc. for $C_{22}H_{30}N_5O_2$ (M+H)$^+$ m/z=396.2; found: 396.3.

Example 96

(3R,4R,5S)-3-amino-1-(3-(((3-(2,6-difluoro-4-(hydroxymethyl)phenyl)furo[3,2-b]pyridin-5-yl)methyl)amino)pyridin-4-yl)-5-methylpiperidin-4-ol

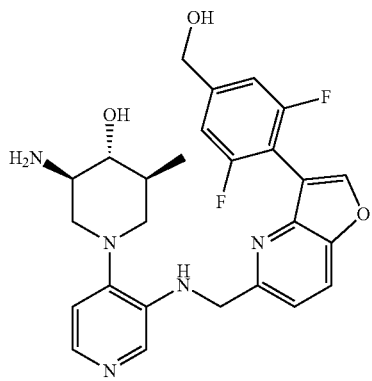 [SMILES: C[C@H]1CN(c2ccncc2NCc2ccc3occ(-c4c(F)cc(CO)cc4F)c3n2)C[C@@H](N)[C@@H]1O]

This compound was synthesized according to the procedures described in Example 95, using (3,5-difluoro-4-(4,4,5,5-tetramethyl-1,3,2-dioxaborolan-2-yl)phenyl)methanol (from Example 35 Step 1) to replace 2-isopropenyl-4,4,5,5-tetramethyl-1,3,2-dioxaborolane in Step 1. LCMS calc. for $C_{26}H_{28}F_2N_5O_3$ (M+H)$^+$ m/z=496.2; found: 496.2.

Example 97

(3R,4R,5S)-3-amino-1-(3-(((3-(2-fluoro-4-(hydroxymethyl)phenyl)furo[3,2-b]pyridin-5-yl)methyl)amino)pyridin-4-yl)-5-methylpiperidin-4-ol

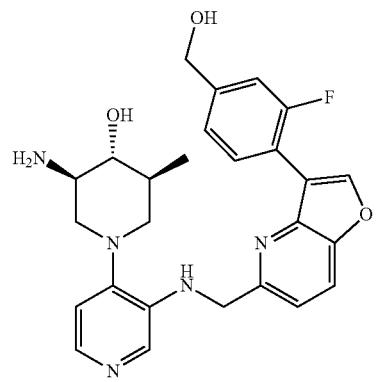 [SMILES: C[C@H]1CN(c2ccncc2NCc2ccc3occ(-c4ccc(CO)cc4F)c3n2)C[C@@H](N)[C@@H]1O]

This compound was synthesized according to the procedures described in Example 95, using 2-fluoro-4-(hydroxymethyl)phenylboronic acid (from Combi-Blocks) to replace 2-isopropenyl-4,4,5,5-tetramethyl-1,3,2-dioxaborolane in Step 1. LCMS calc. for $C_{26}H_{29}FN_5O_3$ (M+H)$^+$ m/z=478.2; found: 478.2.

Example 98

4-[(3S,5R)-3-Amino-5-methylpiperidin-1-yl]-N-[(3-isopropylfuro[3,2-b]pyridin-5-yl)methyl]pyridin-3-amine

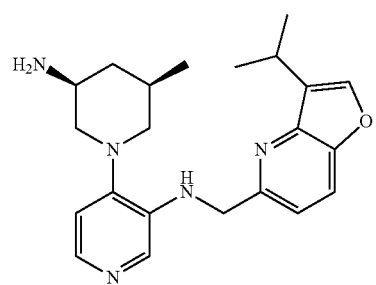 [SMILES: CC(C)c1coc2ccc(CNc3cnccc3N3C[C@H](C)C[C@H](N)C3)nc12]

Step 1. tert-Butyl [(3S,5R)-1-(3-{[(3-isopropenyl-furo[3,2-b]pyridin-5-yl)methyl]amino}pyridin-4-yl)-5-methylpiperidin-3-yl]carbamate

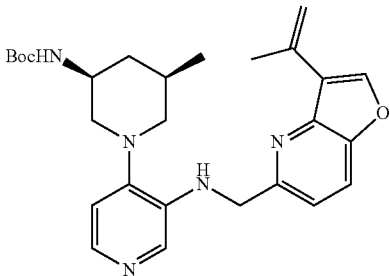 [SMILES: C=C(C)c1coc2ccc(CNc3cnccc3N3C[C@H](C)C[C@H](NC(=O)OC(C)(C)C)C3)nc12]

tert-Butyl [(3S,5R)-1-(3-{[(3-bromofuro[3,2-b]pyridin-5-yl)methyl]amino}pyridin-4-yl)-5-methylpiperidin-3-yl]carbamate (Intermediate 5, 20.0 mg, 0.0387 mmol), chloro(2-dicyclohexylphosphino-2',4',6'-triisopropyl-1,1'-biphenyl)[2-(2'-amino-1,1'-biphenyl)]palladium(II) (Pd XPhos G2) (23.0 mg, 0.0039 mmol), potassium phosphate (25 mg, 0.12 mmol) and magnet bar were placed in a vial with septum. The vial was then evacuated and backfilled with nitrogen three times. 1,4-Dioxane (2.5 mL) and degassed water (0.3 mL) were added to the reaction mixture. Finally 2-isopropenyl-4,4,5,5-tetramethyl-1,3,2-dioxaborolane (10. mg, 0.062 mmol) was added and the reaction mixture was stirred at 65° C. for 1 h. Then the reaction mixture was diluted with EtOAc. The resulting solution was washed with brine, dried over Na$_2$SO$_4$ and solvent evaporated. The crude product was purified by Biotage Isolera to give the desired compound (19 mg, 99%). LCMS calc. for C$_{27}$H$_{36}$N$_5$O$_3$ (M+H)$^+$ m/z=478.3; found: 478.3.

Step 2. tert-Butyl [(3S,5R)-1-(3-{[(3-isopropylfuro[3,2-b]pyridin-5-yl)methyl]amino}pyridin-4-yl)-5-methylpiperidin-3-yl]carbamate

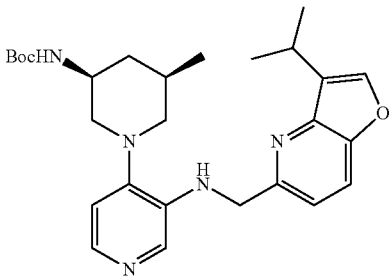 [SMILES: CC(C)c1coc2ccc(CNc3cnccc3N3C[C@H](C)C[C@H](NC(=O)OC(C)(C)C)C3)nc12]

To a stirred solution of tert-butyl [(3S,5R)-1-(3-{[(3-isopropenylfuro[3,2-b]pyridin-5-yl)methyl]amino}pyridin-4-yl)-5-methylpiperidin-3-yl]carbamate (19 mg, 0.040 mmol) in methanol (10 mL) was added 5 w % of Pd on carbon (31 mg, 0.015 mmol). A vial was closed with septum and was connected to a balloon with hydrogen. After stirring at room temperature for 3 h, the reaction was filtered through a pad of diatomaceous earth and the solvent was evaporated under reduced pressure. The resulting crude product was used in the next step without further purification (18 mg, 99%). LCMS calc. for C$_{27}$H$_{38}$N$_5$O$_3$ (M+H)$^+$ m/z=480.3; found: 480.3.

Step 3. 4-[(3S,5R)-3-Amino-5-methylpiperidin-1-yl]-N-[(3-isopropylfuro[3,2-b]pyridin-5-yl)methyl]pyridin-3-amine tert-Butyl [(3S,5R)-1-(3-{[(3-isopropylfuro[3,2-b]pyridin-5-yl)methyl]amino}pyridin-4-yl)-5-methylpiperidin-3-yl]carbamate (18 mg, 0.038 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 µm particle size, gradient elution with acetonitrile/water containing 0.1% NH$_4$OH, at flow rate of 60 mL/min). LCMS calc. for C$_{22}$H$_{30}$N$_5$O (M+H)$^+$ m/z=380.2; found: 380.2. $^1$H NMR (400 MHz, DMSO-d6) δ 8.06 (d, J=0.9 Hz, 1H), 7.96 (d, J=8.5 Hz, 1H), 7.86 (s, 1H), 7.83 (d, J=5.0 Hz, 1H), 7.36 (d, J=8.5 Hz, 1H), 6.86 (d, J=5.1 Hz, 1H), 5.76 (t, J=5.5 Hz, 1H), 4.65-4.51 (m, 2H), 3.26-3.24 (m, 2H), 3.22-3.15 (m, 2H), 3.07-2.94 (m, 1H), 2.16 (t, J=10.6 Hz, 1H), 2.08 (t, J=11.0 Hz, 1H), 2.02-1.89 (m, 2H), 1.39 (d, J=6.9 Hz, 6H), 0.90 (d, J=6.3 Hz, 3H), 0.87-0.76 (m, 1H) ppm.

Example 99

(4-(5-((4-((3S,5R)-3-amino-5-methylpiperidin-1-yl)pyridin-3-ylamino)methyl)furo[3,2-b]pyridin-3-yl)-3,5-difluorophenyl)methanol

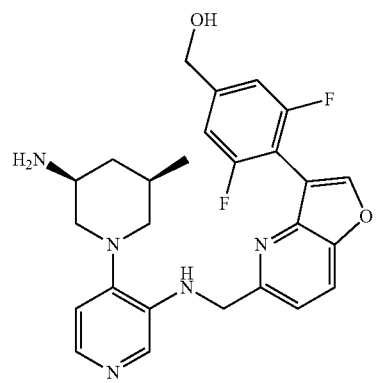 [SMILES: C[C@@H]1C[C@H](N)CN(c2ccncc2NCc2ccc3occ(-c4c(F)cc(CO)cc4F)c3n2)C1]

This compound was synthesized using similar procedures as described in Example 98, using (3,5-difluoro-4-(4,4,5,5-tetramethyl-1,3,2-dioxaborolan-2-yl)phenyl)methanol to replace 2-isopropenyl-4,4,5,5-tetramethyl-1,3,2-dioxaborolane in Step 1. LCMS calc. for C$_{26}$H$_{28}$F$_2$N$_5$O$_2$ (M+H)$^+$ m/z=480.2; found: 480.2. $^1$H NMR (400 MHz, DMSO-d6) δ 8.58 (s, 1H), 8.18 (d, J=8.6 Hz, 1H), 7.86 (s, 1H), 7.83 (d, J=5.0 Hz, 1H), 7.48 (d, J=8.6 Hz, 1H), 7.23 (d, J=8.2 Hz, 2H), 6.79 (d, J=5.1 Hz, 1H), 5.84-5.77 (m, 1H), 4.65 (s, 2H), 4.64-4.42 (m, 2H), 3.52 (s, 1H), 3.14-3.03 (m, 2H), 2.48-2.41 (m, 1H), 2.17 (t, J=10.5 Hz, 2H), 1.81 (t, J=11.2 Hz, 2H), 1.67 (d, J=12.2 Hz, 1H), 1.41 (s, 1H), 0.71 (d, J=6.6 Hz, 3H), 0.68-0.60 (m, 1H) ppm.

Example 100

(4-(5-((4-((3S,5R)-3-amino-5-methylpiperidin-1-yl)pyridin-3-ylamino)methyl)furo[3,2-b]pyridin-3-yl)-3-fluorophenyl)methanol

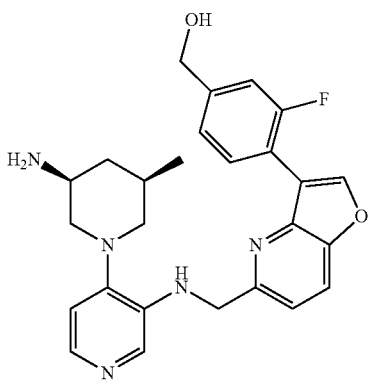 [SMILES: C[C@@H]1C[C@H](N)CN(c2ccncc2NCc2ccc3occ(-c4ccc(CO)cc4F)c3n2)C1]

This compound was synthesized according to the procedures described in Example 98, using (2-fluoro-4-(hydroxymethyl)phenylboronic acid to replace 2-isopropenyl-4,4,5,5-tetramethyl-1,3,2-dioxaborolane in Step 1. LCMS calc. for $C_{26}H_{29}FN_5O_2$ (M+H)+ m/z=462.2; found: 462.2. 1H NMR (400 MHz, DMSO-d6) δ 8.64 (d, J=2.5 Hz, 1H), 8.45 (t, J=7.9 Hz, 1H), 8.14 (d, J=8.6 Hz, 1H), 7.85 (s, 1H), 7.81 (d, J=5.0 Hz, 1H), 7.48 (d, J=8.6 Hz, 1H), 7.34-7.21 (m, 2H), 6.83 (d, J=5.1 Hz, 1H), 5.68 (t, J=5.5 Hz, 1H), 4.70-4.54 (m, 4H), 3.23 (d, J=7.0 Hz, 2H), 3.13 (d, J=9.2 Hz, 2H), 2.89-2.74 (m, 1H), 2.13 (t, J=10.6 Hz, 1H), 1.99 (t, J=11.1 Hz, 1H), 1.84-1.66 (m, 2H), 0.79 (d, J=6.5 Hz, 3H), 0.72 (q, J=11.8 Hz, 1H) ppm.

Example 101

(3R,4R,5S)-3-Amino-1-(3-{[(3-cyclopropylfuro[3,2-b]pyridin-5-yl)methyl]amino}pyridin-4-yl)-5-methylpiperidin-4-ol

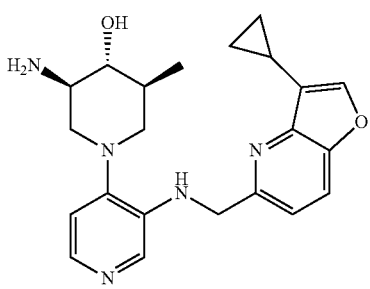 [SMILES: C[C@H]1CN(c2ccncc2NCc2ccc3occ(C4CC4)c3n2)C[C@@H](N)[C@@H]1O]

Step 1. tert-Butyl [(3R,4R,5S)-4-{[tert-butyl(dimethyl)silyl]oxy}-1-(3-{[(3-cyclopropylfuro[3,2-b]pyridin-5-yl)methyl]amino}pyridin-4-yl)-5-methylpiperidin-3-yl]carbamate

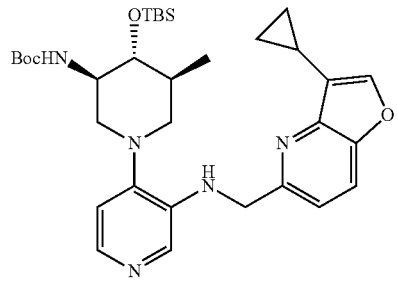 [SMILES: C[C@H]1CN(c2ccncc2NCc2ccc3occ(C4CC4)c3n2)C[C@@H](NC(=O)OC(C)(C)C)[C@@H]1O[Si](C)(C)C(C)(C)C]

tert-Butyl ((3R,4R,5S)-1-(3-{[(3-bromofuro[3,2-b]pyridin-5-yl)methyl]amino}pyridin-4-yl)-4-{[tert-butyl(dimethyl)silyl]oxy}-5-methylpiperidin-3-yl)carbamate (Intermediate 4, 20.0 mg, 0.0309 mmol), potassium cyclopropyltrifluoroborate (from Aldrich, 9.2 mg, 0.062 mmol), cesium carbonate (30.2 mg, 0.0928 mmol), palladium acetate (1.0 mg, 0.0046 mmol) and di-1-adamantyl(butyl)phosphine (3.3 mg, 0.0093 mmol) were placed in a vial. The vial was sealed and evacuated and filled with nitrogen three times. Toluene (1.0 mL) and water (100 μL) were added and the reaction mixture was stirred at 100° C. overnight. Then the reaction mixture was diluted with EtOAc. Obtained solution was washed with brine, dried over $Na_2SO_4$ and solvent was evaporated under reduced pressure. The resulting crude product was used in the next step without further purification. LCMS calc. for $C_{33}H_{50}N_5O_4Si$ (M+H)+ m/z=608.4; found: 608.4.

Step 2. (3R,4R,5S)-3-Amino-1-(3-{[(3-cyclopropylfuro[3,2-b]pyridin-5-yl)methyl]amino}pyridin-4-yl)-5-methylpiperidin-4-ol tert-Butyl [(3R,4R,5S)-4-{[tert-butyl(dimethyl)silyl]oxy}-1-(3-{[(3-cyclopropylfuro[3,2-b]pyridin-5-yl)methyl]amino}pyridin-4-yl)-5-methylpiperidin-3-yl]carbamate (18 mg, 0.03 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{22}H_{28}N_5O_2$ (M+H)+ m/z=394.2; found: 394.2.

Example 102

4-[(3S,5R)-3-Amino-5-methylpiperidin-1-yl]-N-[(3-cyclopropylfuro[3,2-b]pyridin-5-yl)methyl]pyridin-3-amine

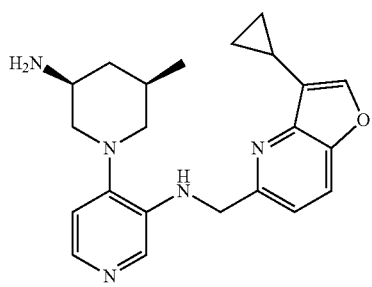 [SMILES: C[C@@H]1C[C@H](N)CN(c2ccncc2NCc2ccc3occ(C4CC4)c3n2)C1]

Step 1. tert-Butyl [(3S,5R)-1-(3-{[(3-cyclopropylfuro[3,2-b]pyridin-5-yl)methyl]amino}pyridin-4-yl)-5-methylpiperidin-3-yl]carbamate

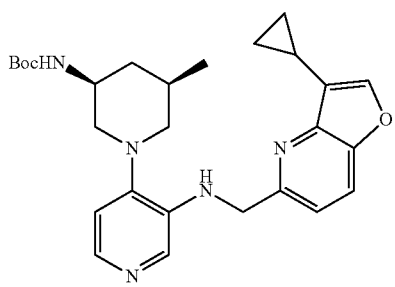 [SMILES: C[C@@H]1C[C@H](NC(=O)OC(C)(C)C)CN(c2ccncc2NCc2ccc3occ(C4CC4)c3n2)C1]

tert-Butyl [(3S,5R)-1-(3-{[(3-bromofuro[3,2-b]pyridin-5-yl)methyl]amino}pyridin-4-yl)-5-methylpiperidin-3-yl]carbamate (Intermediate 5, 16.0 mg, 0.0309 mmol), potassium cyclopropyltrifluoroborate (9.2 mg, 0.062 mmol), cesium carbonate (30.2 mg, 0.0928 mmol), palladium acetate (1.0 mg, 0.0046 mmol) and di-1-adamantyl(butyl)phosphine (3.3 mg, 0.0093 mmol) were placed in a vial. The vial was sealed and evacuated and filled with nitrogen three times. Toluene (1.0 mL) and water (100 μL) were added and the reaction mixture was stirred at 100° C. overnight. Then the reaction mixture was diluted with EtOAc. Obtained solution was washed with brine, dried over $Na_2SO_4$ and solvent was evaporated under reduced pressure. The resulting crude product was used in the next step without further purification. LCMS calc. for $C_{27}H_{36}N_5O_3$ $(M+H)^+$ m/z=478.3; found: 478.3.

Step 2. 4-[(3S,5R)-3-Amino-5-methylpiperidin-1-yl]-N-[(3-cyclopropylfuro[3,2-b]pyridin-5-yl)methyl]pyridin-3-amine tert-Butyl [(3S,5R)-1-(3-{[(3-cyclopropylfuro[3,2-b]pyridin-5-yl)methyl]amino}pyridin-4-yl)-5-methylpiperidin-3-yl]carbamate (14 mg, 0.03 mmol) was dissolved in methanol (2 mL). Then 4.0M solution of HCl in dioxane (1 mL, 4 mmol) was added to the reaction mixture. The reaction mixture was stirred at room temperature overnight. Then the reaction mixture was neutralized by addition of the ammonia solution and purified by RP-HPLC (water XBridge C18 column, 30 mm×100 mm, 5 μm particle size, gradient elution with acetonitrile/water containing 0.1% $NH_4OH$, at flow rate of 60 mL/min). LCMS calc. for $C_{22}H_{28}N_5O$ $(M+H)^+$ m/z=378.2; found: 378.2. $^1$H NMR (400 MHz, DMSO-d6) δ 8.05 (s, 1H), 7.94 (d, J=8.5 Hz, 1H), 7.85-7.79 (m, 2H), 7.34 (d, J=8.5 Hz, 1H), 6.85 (d, J=5.1 Hz, 1H), 5.72 (t, J=5.4 Hz, 1H), 4.59-4.53 (m, 2H), 3.27 (d, J=8.4 Hz, 1H), 3.20-3.16 (m, 1H), 3.06-2.92 (m, 1H), 2.21-1.85 (m, 6H), 1.01-0.91 (m, 4H), 0.89 (d, J=6.3 Hz, 3H), 0.85-0.72 (m, 1H) ppm.

Example 103

1-(4-{6-[({4-[(3S,5R)-3-Amino-5-methylpiperidin-1-yl]pyridin-3-yl}amino)methyl]-3-fluoropyridin-2-yl}-3,5-difluorophenoxy)-2-methylpropan-2-ol

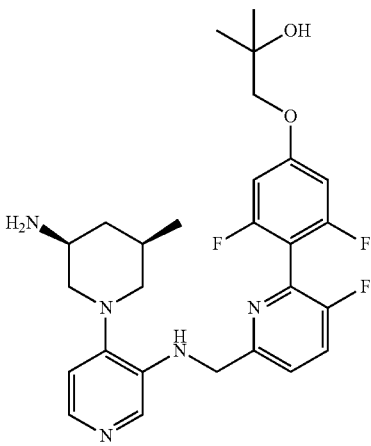 [SMILES: C[C@@H]1C[C@H](N)CN(c2ccncc2NCc2ccc(F)c(-c3c(F)cc(OCC(C)(C)O)cc3F)n2)C1]

Step 1. 1-(3,5-Difluorophenoxy)-2-methylpropan-2-ol

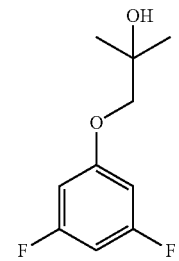

A mixture of 3,5-difluorophenol (from Aldrich, 1.0 g, 7.7 mmol), 2,2-dimethyloxirane (from Aldrich, 1.9 mL, 23 mmol) and potassium carbonate (2.1 g, 15 mmol) in N,N-dimethylformamide (8 mL) was microwaved at 150° C. for 30 min. The reaction mixture was diluted with water, extracted with EtOAc, concentrated and purified on silica gel column (gradient elution with 0-50% EtOAc/hexanes) to give the desired product (1.6 g, 100%). LCMS calc. for $C_{10}H_{13}F_2O_2$ $(M+H)^+$ m/z=203.1; found: 203.1.

Step 2. 1-[3,5-Difluoro-4-(4,4,5,5-tetramethyl-1,3,2-dioxaborolan-2-yl)phenoxy]-2-methylpropan-2-ol

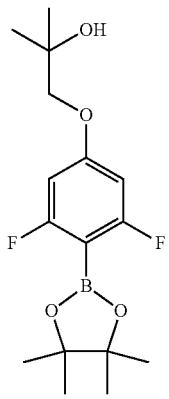

To a mixture of 1-(3,5-difluorophenoxy)-2-methylpropan-2-ol (1.6 g, 7.9 mmol) in tetrahydrofuran (31 mL) cooled at −78° C. was slowly added 2.5M n-butyllithium in hexanes (7.9 mL, 20 mmol). When addition completed the mixture was stirred at −78° C. for 1 h. 2-Isopropoxy-4,4,5,5-tetramethyl-1,3,2-dioxaborolane (4.84 mL, 23.7 mmol) was then added to the reaction mixture in one portion. The reaction mixture was allowed to warm to room temperature and stirred at that temperature for 1 h. The reaction mixture was poured into a mixture of EtOAc and saturated aqueous NaHCO$_3$ solution. The organic layer was washed with brine, dried over MgSO$_4$ and concentrated to give the product (2.6 g, 100%), which was used in the next step directly. LCMS calc. for C$_{16}$H$_{24}$BF$_2$O$_4$ (M+H)$^+$ m/z=329.2; found: 329.2.

Step 3. Methyl 6-[2,6-difluoro-4-(2-hydroxy-2-methylpropoxy)phenyl]-5-fluoropyridine-2-carboxylate

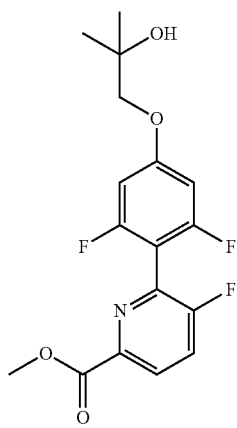 [SMILES: COC(=O)c1ccc(F)c(-c2c(F)cc(OCC(C)(C)O)cc2F)n1]

A mixture of methyl 6-bromo-5-fluoropyridine-2-carboxylate (1.8 g, 7.5 mmol), dicyclohexyl(2',4',6'-triisopropylbiphenyl-2-yl)phosphine-(2'-aminobiphenyl-2-yl)(chloro)palladium (1:1) (0.62 g, 0.79 mmol) and cesium carbonate (5.2 g, 16 mmol) was evacuated and backfilled with nitrogen three times. A solution of 1-[3,5-difluoro-4-(4,4,5,5-tetramethyl-1,3,2-dioxaborolan-2-yl)phenoxy]-2-methylpropan-2-ol (2.6 g, 7.9 mmol) in 1,4-dioxane (19.74 mL) was added, followed by the addition of degassed water (9.87 mL). The reaction mixture was stirred at 55° C. overnight. The reaction mixture was filtered, concentrated, diluted with EtOAc, washed with water, concentrated and purified on silica gel column (gradient elution with 0-100% EtOAC/hexanes) to give the desired product (1.0 g, 37%). LCMS calc. for C$_{17}$H$_{17}$F$_3$NO$_4$ (M+H)$^+$ m/z=356.1; found: 356.1.

Step 4. 6-[2,6-Difluoro-4-(2-hydroxy-2-methylpropoxy)phenyl]-5-fluoropyridine-2-carboxylic acid

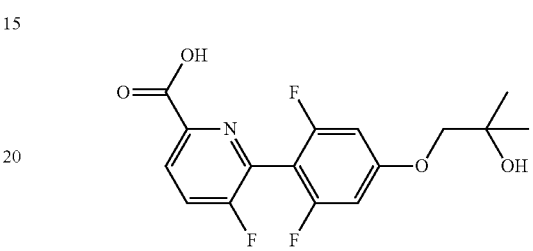

A mixture of methyl 6-[2,6-difluoro-4-(2-hydroxy-2-methylpropoxy)phenyl]-5-fluoropyridine-2-carboxylate (1.0 g, 2.8 mmol) and 1.0M sodium hydroxide in water (11 mL, 11 mmol) in tetrahydrofuran (20 mL)/methanol (20 mL) was stirred at room temperature for 1 h. The mixture was concentrated, and the residue was acidified by addition of aqueous 4N HCl solution. The mixture was extracted with EtOAc. The combined organic layers were dried over MgSO$_4$ and concentrated to give the crude product (0.8 g, 80%). LCMS calc. for C$_{16}$H$_{15}$F$_3$NO$_4$ (M+H)$^+$ m/z=342.1; found: 342.0.

Step 5. 1-{3,5-Difluoro-4-[3-fluoro-6-(hydroxymethyl)pyridin-2-yl]phenoxy}-2-methylpropan-2-ol

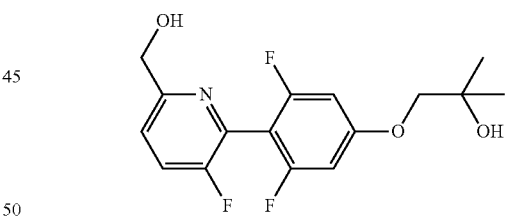

To a mixture of 6-[2,6-difluoro-4-(2-hydroxy-2-methylpropoxy)phenyl]-5-fluoropyridine-2-carboxylic acid (0.80 g, 2.3 mmol) and triethylamine (0.343 mL, 2.46 mmol) in tetrahydrofuran (10 mL) was added tert-butyl chloridocarbonate (0.322 mL, 2.46 mmol) dropwise. The reaction mixture was stirred for 1 h. The precipitate was collected by filtration. The filtrate was cooled in an ice bath and a solution of sodium tetrahydroborate (0.18 g, 4.7 mmol) in water (0.8 mL) was added dropwise. The reaction mixture was stirred for 30 min, then quenched with aqueous saturated NaHCO$_3$ solution, extracted with EtOAc. The organic layers were combined, concentrated and purified on silica gel column (gradient elution with 0-100% EtOAc/hexanes) to give the desired product (0.47 g, 61%). LCMS calc. for C$_{16}$H$_{17}$F$_3$NO$_3$ (M+H)$^+$ m/z=328.1; found: 328.2.

Step 6. 6-(2,6-difluoro-4-(2-hydroxy-2-methylpropoxy)phenyl)-5-fluoropicolinaldehyde

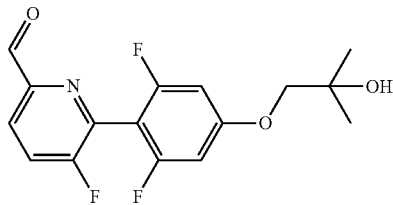 [SMILES: CC(C)(O)COc1cc(F)c(-c2nc(C=O)ccc2F)c(F)c1]

To a mixture of 1-{3,5-difluoro-4-[3-fluoro-6-(hydroxymethyl)pyridin-2-yl]phenoxy}-2-methylpropan-2-ol (470 mg, 1.4 mmol) and pyridine (0.14 mL, 1.7 mmol) in DCM (9 mL) was added Dess-Martin periodinane (0.67 g, 1.6 mmol) at 0° C. The reaction mixture was stirred at room temperature for 2 h. The reaction mixture was quenched with aqueous saturated NaHCO$_3$ solution and aqueous saturated Na$_2$S$_2$O$_3$ solution (1:1), extracted with DCM. The combined organic layers were concentrated and purified on silica gel (gradient elution with 0-100% EtOAc/hexanes) to give the desired product (0.44 g, 94%). LCMS calc. for C$_{16}$H$_{15}$F$_3$NO$_3$ (M+H)$^+$ m/z=326.1; found: 326.1.

Step 7. tert-Butyl ((3S,5R)-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-3-yl)carbamate

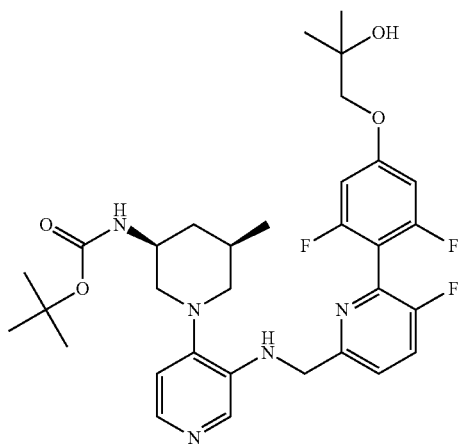 [SMILES: C[C@@H]1C[C@H](NC(=O)OC(C)(C)C)CN(c2ccncc2NCc2ccc(F)c(-c3c(F)cc(OCC(C)(C)O)cc3F)n2)C1]

A mixture of tert-butyl [(3S,5R)-1-(3-aminopyridin-4-yl)-5-methylpiperidin-3-yl]carbamate (Prepared in Intermediate 2, Step 6; 47 mg, 0.15 mmol), 6-(2,6-difluoro-4-(2-hydroxy-2-methylpropoxy)phenyl)-5-fluoropicolinaldehyde (51 mg, 0.16 mmol) and acetic acid (7.2 µL, 0.13 mmol) in toluene (5.6 mL) was heated at 100° C. for 2 h. Then solvent was evaporated and methanol (5.6 mL) was added. After addition of sodium tetrahydroborate (12 mg, 0.32 mmol) at 0° C., the resulting reaction mixture was stirred for 10 min. The solvent was removed, and the residue was diluted with water and extracted with EtOAc. The combined organic layers were dried over MgSO$_4$ and concentrated to give the crude product (32 mg, 33%). LCMS calc. for C$_{32}$H$_{41}$F$_3$N$_5$O$_4$ (M+H)$^+$ m/z=616.1; found: 616.3.

Step 8. 1-(4-{6-[({4-[(3S,5R)-3-Amino-5-methylpiperidin-1-yl]pyridin-3-yl}amino)methyl]-3-fluoropyridin-2-yl}-3,5-difluorophenoxy)-2-methylpropan-2-ol tert-Butyl ((3S,5R)-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-3-yl)carbamate (0.032 g, 0.052 mmol) was treated with 4.0M hydrogen chloride in dioxane (0.065 mL, 0.26 mmol) in DCM (1 mL) at room temperature for 1 h. The reaction mixture was concentrated to dryness and the resultant residue was purified on prep-LCMS (Waters Sunfire C18, 5 um particle size, 30×100 mm; mobile phases: water (0.1% TFA)/acetonitrile at a flow rate of 60 ml/min; Gradient: 8.5-28.5% acetonitrile in 5 min) to give the desired product (5 mg, 19%). LCMS calc. for C$_{27}$H$_{33}$F$_3$N$_5$O$_2$ (M+H)$^+$ m/z=516.3; found: 516.3.

Example 104

(3R,4R,5S)-3-Amino-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-4-ol

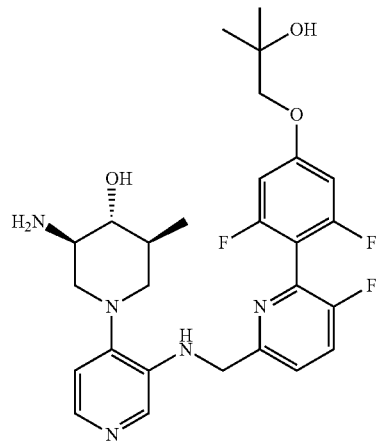

Step 1. tert-Butyl ((3R,4R,5S)-4-{[tert-butyl(dimethyl)silyl]oxy}-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-3-yl)carbamate

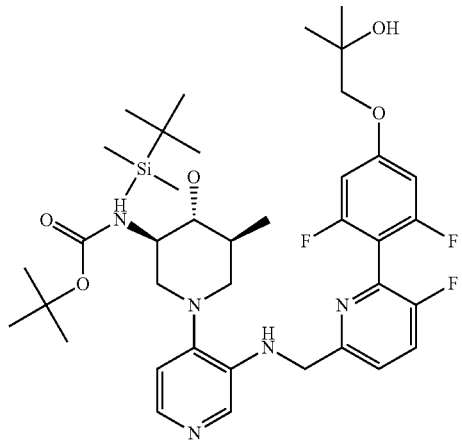

A mixture of tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 67 mg, 0.15 mmol), 6-(2,6-difluoro-4-(2-hydroxy-2-methylpropoxy)phenyl)-5-fluoropicolinaldehyde (Prepared in Example 103, Step 6; 51 mg, 0.16 mmol) and acetic acid (7.2 µL, 0.13 mmol) in toluene (5.6 mL) was heated at 100° C. for 2 h. Then solvent was evaporated and methanol (5.6 mL) was added. After addition of sodium tetrahydroborate (12 mg, 0.32 mmol) at 0° C., the resulting reaction mixture was stirred for 10 min. The solvent was removed, the residue was diluted with water, extracted with EtOAc. The combined organic layers were dried over MgSO$_4$ and concentrated under reduced pressure to give the crude product (38 mg, 33%). LCMS calc. for $C_{38}H_{55}F_3N_5O_5Si$ (M+H)$^+$ m/z=746.4; found: 746.3.

Step 2. (3R,4R,5S)-3-Amino-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(2-hydroxy-2-methylpropoxy)phenyl]-5-fluoropyridin-2-yl}methyl)amino]pyridin-4-yl}-5-methylpiperidin-3-yl)carbamate (0.038 g, 0.052 mmol) was treated with 4.0M hydrogen chloride in dioxane (0.065 mL, 0.26 mmol) in DCM (1 mL) at room temperature for 1 h. The mixture was concentrated to dryness and the residue was purified on prep-LCMS (Waters Sunfire C18, 5 um particle size, 30×100 mm; mobile phases: water (0.1% TFA)/acetonitrile at a flow rate of 60 ml/min; Gradient: 8.5-28.5% acetonitrile in 5 min) to give the desired product (5 mg, 18%). LCMS calc. for $C_{27}H_{33}F_3N_5O_3$ (M+H)$^+$ m/z=532.3; found: 532.2.

Example 105

2-(4-{6-[({4-[(3S,5R)-3-Amino-5-methylpiperidin-1-yl]pyridin-3-yl}amino)methyl]-3-fluoropyridin-2-yl}-3,5-difluorophenyl)propan-2-ol

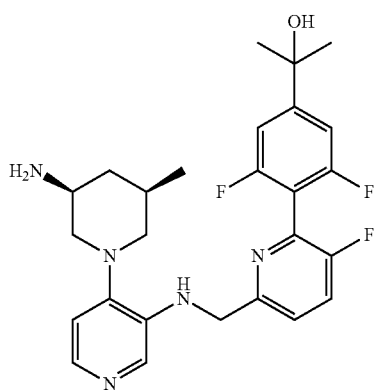 [SMILES: C[C@@H]1C[C@H](N)CN(c2ccncc2NCc2ccc(F)c(-c3c(F)cc(C(C)(C)O)cc3F)n2)C1]

Step 1. 2-(3,5-Difluorophenyl)propan-2-ol

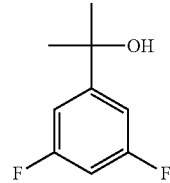

To a solution of acetone (0.20 mL, 2.7 mmol) in tetrahydrofuran (4.1 mL) cooled at 0° C. was added 0.5M bromo(2,6-difluorophenyl)magnesium in THF (from Aldrich, 6.0 mL, 3.0 mmol) slowly. The reaction was stirred overnight, then quenched with aq. NH$_4$Cl solution, extracted with EtOAc. The combined organic extracts were washed with brine, dried over MgSO$_4$ and concentrated to give the crude product (0.34 g, 72%), which was used in the next step without further purification.

Step 2. 2-[3,5-Difluoro-4-(4,4,5,5-tetramethyl-1,3,2-dioxaborolan-2-yl)phenyl]propan-2-ol

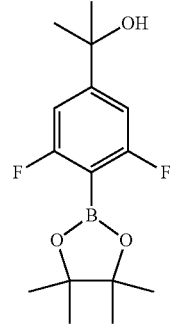 [SMILES: CC(C)(O)c1cc(F)c(B2OC(C)(C)C(C)(C)O2)c(F)c1]

To a mixture of 2-(3,5-difluorophenyl)propan-2-ol (340 mg, 2.0 mmol) in tetrahydrofuran (7.8 mL) cooled at −78° C. was slowly added 2.5M n-butyllithium in hexanes (2.0 mL, 4.9 mmol). The mixture was stirred at −78° C. for 1 h. 2-isopropoxy-4,4,5,5-tetramethyl-1,3,2-dioxaborolane (from Aldrich, 1.21 mL, 5.92 mmol) was then added in one portion. The mixture was allowed to warm up to rt and stirred at rt for 1 h, then worked up in EtOAc and NaHCO$_3$ solution. The organic layer was washed with brine, dried over MgSO$_4$ and concentrated to give the crude product (0.5 g, 90%), which was used in the next step without purification.

Step 3. Methyl 6-[2,6-difluoro-4-(1-hydroxy-1-methylethyl)phenyl]-5-fluoropyridine-2-carboxylate

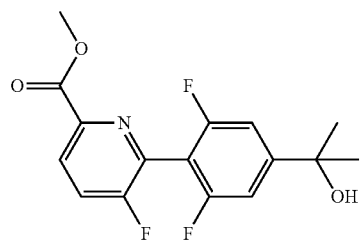 [SMILES: COC(=O)c1ccc(F)c(-c2c(F)cc(C(C)(C)O)cc2F)n1]

A mixture of methyl 6-bromo-5-fluoropyridine-2-carboxylate (230 mg, 0.97 mmol), dicyclohexyl(2',4',6'-triisopropylbiphenyl-2-yl)phosphine-(2'-aminobiphenyl-2-yl) (chloro)palladium (1:1) (76 mg, 0.097 mmol) and cesium carbonate (0.63 g, 1.9 mmol) was evacuated and backfilled with nitrogen three times. A solution of 2-[3,5-difluoro-4-(4,4,5,5-tetramethyl-1,3,2-dioxaborolan-2-yl)phenyl]propan-2-ol (290 mg, 0.97 mmol) in 1,4-dioxane (2.424 mL) was added, followed by the addition of degassed water (1.21 mL). The reaction mixture was stirred at 55° C. for 1 h. The reaction mixture was purified on silica gel (gradient elution with 0-100% EtOAC/hexanes) to give the desired product (100 mg, 32%). LCMS calc. for $C_{16}H_{15}F_3NO_3$ $(M+H)^+$ m/z=326.1; found: 326.1.

Step 4. 6-[2,6-Difluoro-4-(1-hydroxy-1-methylethyl) phenyl]-5-fluoropyridine-2-carboxylic acid

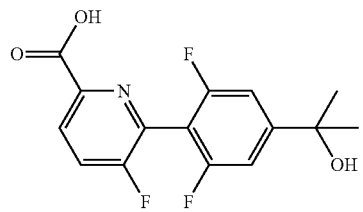 [SMILES: CC(C)(O)c1cc(F)c(-c2nc(C(=O)O)ccc2F)c(F)c1]

A mixture of methyl 6-[2,6-difluoro-4-(1-hydroxy-1-methylethyl)phenyl]-5-fluoropyridine-2-carboxylate (99 mg, 0.30 mmol) and 1.0M sodium hydroxide in water (2 mL, 2 mmol) in tetrahydrofuran (2 mL)/methanol (2 mL) was stirred at room temperature for 1 h. The reaction mixture was concentrated, and the residue was acidified by addition of aqueous 4N HCl solution. The mixture was extracted with EtOAc. The combined extracted were dried over MgSO₄ and concentrated to give the crude product (90 mg, 100%). LCMS calc. for $C_{15}H_{13}F_3NO_3$ $(M+H)^+$ m/z=312.1; found: 312.0.

Step 5. 2-{3,5-Difluoro-4-[3-fluoro-6-(hydroxymethyl)pyridin-2-yl]phenyl}propan-2-ol

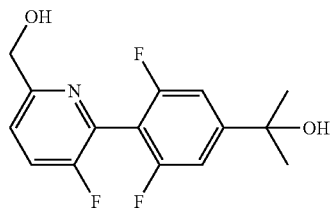 [SMILES: CC(C)(O)c1cc(F)c(-c2nc(CO)ccc2F)c(F)c1]

To a mixture of 6-[2,6-difluoro-4-(1-hydroxy-1-methylethyl)phenyl]-5-fluoropyridine-2-carboxylic acid (0.17 g, 0.55 mmol) and triethylamine (0.0799 mL, 0.573 mmol) in tetrahydrofuran (3 mL) was added tert-butyl chloridocarbonate (0.075 mL, 0.573 mmol) dropwise. The reaction mixture was stirred for 1 h. The precipitate was removed by filtration. The filtrate was cooled in an ice bath and a solution of sodium tetrahydroborate (0.041 g, 1.1 mmol) in water (0.2 mL) was added dropwise. The reaction mixture was stirred for 1 h, and then quenched with saturated aq. NaHCO₃, extracted with EtOAc. The combined organic layers were concentrated under reduced pressure and the resultant residue was purified on silica gel (gradient elution with 0-100% EtOAc/hexanes) to give the desired product (70 mg, 40%). LCMS calc. for $C_{15}H_{15}F_3NO_2$ $(M+H)^+$ m/z=298.1; found: 298.1.

Step 6. 6-[2,6-Difluoro-4-(1-hydroxy-1-methylethyl) phenyl]-5-fluoropyridine-2-carbaldehyde

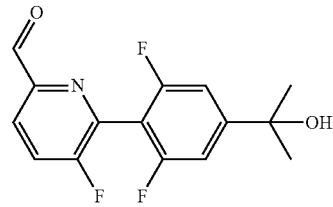 [SMILES: CC(C)(O)c1cc(F)c(-c2nc(C=O)ccc2F)c(F)c1]

To a mixture of 2-{3,5-difluoro-4-[3-fluoro-6-(hydroxymethyl)pyridin-2-yl]phenyl}propan-2-ol (0.070 g, 0.24 mmol) and pyridine (0.023 mL, 0.28 mmol) in DCM (2 mL) was added Dess-Martin periodinane (0.11 g, 0.26 mmol) at 0° C. The reaction mixture was stirred for 2 h. The reaction mixture was quenched with a mixture of aqueous saturated NaHCO₃ solution and aqueous saturated Na₂S₂O₃ solution (1:1), extracted with DCM. The combined organic layers were concentrated under reduced pressure and purified on silica gel (gradient elution with 0-100% EtOAc/hexanes) to give the desired product (70 mg, 100%). LCMS calc. for $C_{15}H_{13}F_3NO_2$ $(M+H)^+$ m/z=296.1; found: 296.1.

Step 7. tert-Butyl ((3S,5R)-1-{3-[({6-[2,6-difluoro-4-(1-hydroxy-1-methylethyl)phenyl]-5-fluoropyridin-2-yl}methyl)amino]pyridin-4-yl}-5-methylpiperidin-3-yl)carbamate

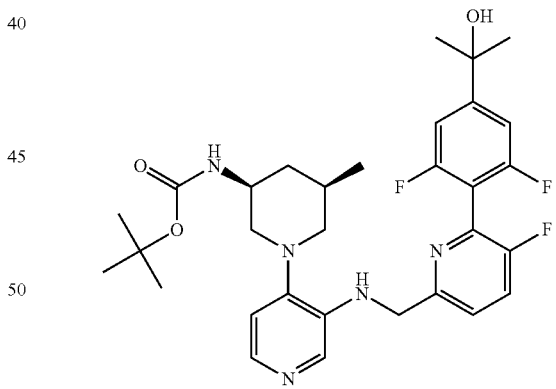

A mixture of tert-butyl [(3S,5R)-1-(3-aminopyridin-4-yl)-5-methylpiperidin-3-yl]carbamate (Prepared in Intermediate 2, Step 6; 0.035 g, 0.12 mmol), 6-[2,6-difluoro-4-(1-hydroxy-1-methylethyl)phenyl]-5-fluoropyridine-2-carbaldehyde (35 mg, 0.12 mmol) and acetic acid (5.5 µL, 0.096 mmol) in toluene (4.2 mL) was heated at 100° C. for 2 h. Then solvent was evaporated and methanol (4.2 mL) was added. After addition of sodium tetrahydroborate (9.1 mg, 0.24 mmol) at 0° C., the reaction mixture was stirred for 10 min. The solvent was removed, and the resultant residue was diluted with water, extracted with EtOAc. The organic layers were combined, dried over MgSO₄ and concentrated to give the crude product (30 mg, 48%). LCMS calc. for C$_{31}$H$_{39}$F$_3$N$_5$O$_3$ (M+H)$^+$ m/z=586.3; found: 586.2.

Step 8. 2-(4-{6-[({4-[(3S,5R)-3-Amino-5-methylpiperidin-1-yl]pyridin-3-yl}amino)methyl]-3-fluoropyridin-2-yl}-3,5-difluorophenyl)propan-2-ol tert-Butyl ((3S,5R)-1-{3-[({6-[2,6-difluoro-4-(1-hydroxy-1-methylethyl)phenyl]-5-fluoropyridin-2-yl}methyl)amino]pyridin-4-yl}-5-methylpiperidin-3-yl)carbamate (0.030 g, 0.052 mmol) was treated with 4.0M hydrogen chloride in dioxane (0.065 mL, 0.26 mmol) in DCM (1 mL) at room temperature for 1 h. The reaction mixture was concentrated to dryness and the residue was purified on prep-LCMS (Waters Sunfire C18, 5 um particle size, 30×100 mm; mobile phases: water (0.1% TFA)/acetonitrile at a flow rate of 60 ml/min; Gradient: 8.5-28.5% acetonitrile in 5 min) to give the desired product (5 mg, 20%). LCMS calc. for C$_{26}$H$_{31}$F$_3$N$_5$O (M+H)$^+$ m/z=486.2; found: 486.2.

Example 106

(3R,4R,5S)-3-Amino-1-{3-[({6-[2,6-difluoro-4-(1-hydroxy-1-methylethyl)phenyl]-5-fluoropyridin-2-yl}methyl)amino]pyridin-4-yl}-5-methylpiperidin-4-ol

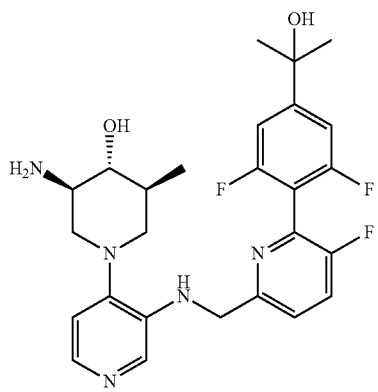

Step 1. tert-Butyl ((3R,4R,5S)-4-{[tert-butyl(dimethyl)silyl]oxy}-1-{3-[({6-[2,6-difluoro-4-(1-hydroxy-1-methylethyl)phenyl]-5-fluoropyridin-2-yl}methyl)amino]pyridin-4-yl}-5-methylpiperidin-3-yl)carbamate

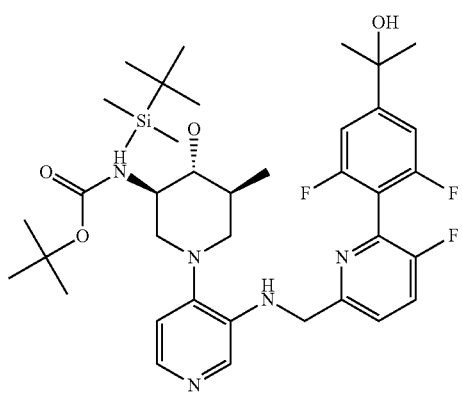

A mixture of tert-butyl ((3R,4R,5S)-1-(3-aminopyridin-4-yl)-4-{[tert-butyl(dimethyl)silyl]oxy}-5-methylpiperidin-3-yl)carbamate (Prepared in Intermediate 1, Step 11; 0.050 g, 0.12 mmol), 6-[2,6-difluoro-4-(1-hydroxy-1-methylethyl)phenyl]-5-fluoropyridine-2-carbaldehyde (Prepared in Example 105, Step 4; 35 mg, 0.12 mmol) and acetic acid (5.5 μL, 0.096 mmol) in toluene (4.2 mL) was heated at 100° C. for 2 h. Then solvent was evaporated and methanol (4.2 mL) was added. After addition of sodium tetrahydroborate (9.1 mg, 0.24 mmol) at 0° C., the reaction mixture was stirred for 10 min. The solvent was removed, diluted with water, extracted with EtOAc. The organic extracts were combined, dried over MgSO$_4$ and concentrated to give the crude product (37 mg, 46%). LCMS calc. for C$_{37}$H$_{53}$F$_3$N$_5$O$_4$Si (M+H)$^+$ m/z=716.4; found: 716.3.

Step 2. (3R,4R,5S)-3-Amino-1-{3-[({6-[2,6-difluoro-4-(1-hydroxy-1-methylethyl)phenyl]-5-fluoropyridin-2-yl}methyl)amino]pyridin-4-yl}-5-methylpiperidin-4-ol tert-Butyl ((3R,4R,5S)-4-{[tert-butyl(dimethyl)silyl]oxy}-1-{3-[({6-[2,6-difluoro-4-(1-hydroxy-1-methylethyl)phenyl]-5-fluoropyridin-2-yl}methyl)amino]pyridin-4-yl}-5-methylpiperidin-3-yl)carbamate (0.037 g, 0.052 mmol) was treated with 4.0M hydrogen chloride in dioxane (0.065 mL, 0.26 mmol) in DCM (1 mL) at room temperature for 1 h. The mixture was concentrated to dryness under reduced pressure and the residue was purified on prep-LCMS (Waters Sunfire C18, 5 um particle size, 30×100 mm; mobile phases: water (0.1% TFA)/acetonitrile at a flow rate of 60 ml/min; Gradient: 8.5-28.5% acetonitrile in 5 min) to give the desired product (5 mg, 19%). LCMS calc. for C$_{26}$H$_{31}$F$_3$N$_5$O$_2$ (M+H)$^+$ m/z=502.2; found: 502.2.

Example 107

4-{2-[({4-[(3R,4R,5S)-3-Amino-4-hydroxy-5-methylpiperidin-1-yl]pyridin-3-yl}amino)methyl]quinolin-7-yl}-3-fluoro-1-methylpyridin-2(1H)-one

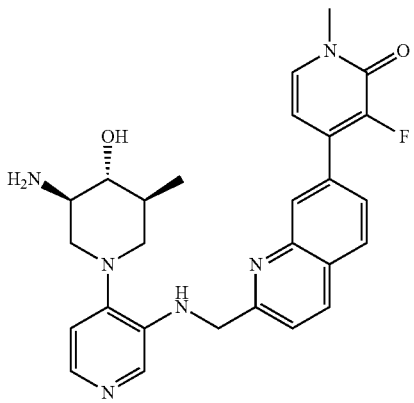 [SMILES: C[C@H]1CN(c2ccncc2NCc2ccc3ccc(-c4ccn(C)c(=O)c4F)cc3n2)C[C@@H](N)[C@@H]1O]

Step 1. tert-Butyl ((3R,4R,5S)-1-(3-{[(7-bromoquinolin-2-yl)methyl]amino}pyridin-4-yl)-4-{[tert-butyl(dimethyl)silyl]oxy}-5-methylpiperidin-3-yl)carbamate

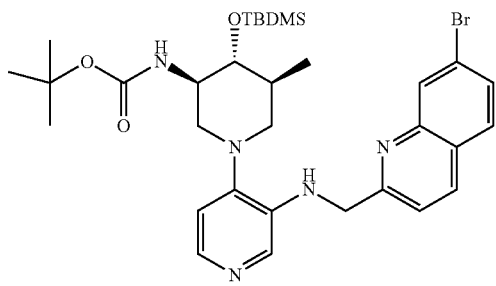 [SMILES: C[C@H]1CN(c2ccncc2NCc2ccc3ccc(Br)cc3n2)C[C@@H](NC(=O)OC(C)(C)C)[C@@H]1O[Si](C)(C)C(C)(C)C]

A mixture tert-butyl ((3R,4R,5 S)-1-(3-aminopyridin-4-yl)-4-{[tert-butyl(dimethyl)silyl]oxy}-5-methylpiperidin-3-yl)carbamate (Prepared in Intermediate 1, Step 11; 300 mg, 0.68 mmol), 7-bromoquinoline-2-carbaldehyde (Prepared in Example 91, Step 2; 200 mg, 0.846 mmol) and acetic acid (39 µL, 0.68 mmol) in Toluene (30 mL) was heated at 100° C. for 2 h. Then solvent was evaporated and methanol (30 mL) was added. After addition of sodium tetrahydroborate (65 mg, 1.7 mmol) at 0° C., the reaction mixture was stirred for 1 h. The solvent was removed. The residue was diluted with water, then extracted with EtOAc. The combined organic layers were dried over MgSO₄, concentrated and purified by Combi-flash Chromatography with 20-100% EtOAc/hexane as eluents to give the product (0.40 g, 89%). LCMS calc. for $C_{32}H_{47}BrN_5O_3Si$ (M+H)⁺ m/z: 656.3; found: 656.1.

Step 2. tert-Butyl {(3R,4R,5S)-4-{[tert-butyl(dimethyl)silyl]oxy}-5-methyl-1-[3-({[7-(4,4,5,5-tetramethyl-1,3,2-dioxaborolan-2-yl)quinolin-2-yl]methyl}amino)pyridin-4-yl]piperidin-3-yl}carbamate

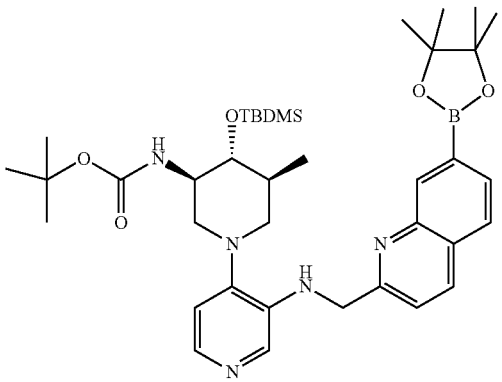 [SMILES: C[C@H]1CN(c2ccncc2NCc2ccc3ccc(B4OC(C)(C)C(C)(C)O4)cc3n2)C[C@@H](NC(=O)OC(C)(C)C)[C@@H]1O[Si](C)(C)C(C)(C)C]

A mixture of tert-butyl ((3R,4R,5 S)-1-(3-{[(7-bromoquinolin-2-yl)methyl]amino}pyridin-4-yl)-4-{[tert-butyl(dimethyl)silyl]oxy}-5-methylpiperidin-3-yl)carbamate (0.098 g, 0.15 mmol), 4,4,5,5,4',4',5',5'-octamethyl-[2,2']bi[[1,3,2]dioxaborolanyl](0.0454 g, 0.179 mmol), potassium acetate (0.029 g, 0.30 mmol) and [1,1'-bis(diphenylphosphino)ferrocene]dichloropalladium (II) (0.011 g, 0.015 mmol) in 1,4-dioxane (0.5 mL) was vacuumed and refilled with N₂ for 3 times, then sealed and heated at 95° C. for 2 h. The reaction mixture was cooled to r.t and used directly in the next step without further purification. LCMS calc. for $C_{38}H_{59}BN_5O_5Si$ (M+H)⁺ m/z: 704.4; found: 704.4.

Step 3. 3-Fluoro-4-iodopyridin-2(1H)-one

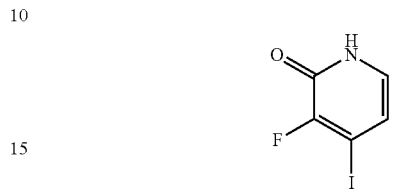

A mixture of 2,3-difluoro-4-iodopyridine (from Ark Pharm, 3.0 g, 12 mmol) in acetic acid (30 mL) and water (15 mL) was heated to reflux overnight. Most of the solvent was removed by vacuum and the remaining was neutralized with aq. NaHCO₃ and extracted by EtOAc. The organic layers were combined, dried and concentrated. The white solid crude product obtained (2.5 g, 84%) was used directly in the next step without further purifications. LCMS calc. for $C_5H_4FINO$ (M+H)⁺ m/z=239.9; found, 240.0.

Step 4. 3-Fluoro-4-iodo-1-methylpyridin-2(1H)-one

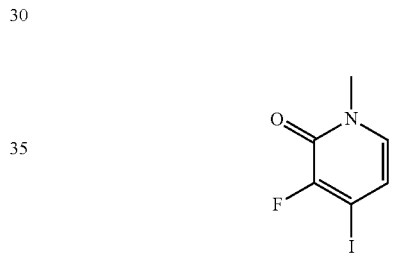

To a mixture of 3-fluoro-4-iodopyridin-2(1H)-one (2.5 g, 10 mmol) and potassium carbonate (3.5 g, 25 mmol) in N,N-dimethylformamide (10 mL) was added iodomethane (3.9 g, 25 mmol). The reaction mixture was stirred at rt overnight, then worked up with aq NaHCO₃ and EtOAc. The organic layer was separated, dried over Na₂SO₄ and concentrated by vacuum. The resulting residue was purified with Combi-flash chromatography (eluting with 0-100% EtOAc in hexanes) to give 2.0 g (77%) of the desired product. LCMS calc. for $C_6H_6FINO$ (M+H)⁺ m/z=253.9; found: 254.1.

Step 5. 4-{2-[({4-[(3R,4R,5S)-3-Amino-4-hydroxy-5-methylpiperidin-1-yl]pyridin-3-yl}amino)methyl]quinolin-7-yl}-3-fluoro-1-methylpyridin-2(1H)-one In a sealed tube a mixture of tert-butyl {(3R,4R,5S)-4-{[tert-butyl(dimethyl)silyl]oxy}-5-methyl-1-[3-({[7-(4,4,5,5-tetramethyl-1,3,2-dioxaborolan-2-yl)quinolin-2-yl]methyl}amino)pyridin-4-yl]piperidin-3-yl}carbamate (100 mg, 0.1 mmol), 3-fluoro-4-iodo-1-methylpyridin-2(1H)-one (48 mg, 0.19 mmol), and N,N-diisopropylethylamine (0.076 mL, 0.44 mmol) in 1,4-dioxane (4.0 mL) and water (0.40 mL) was stirred together and flushed with N₂ bubble for 5 min before bis(tri-t-butylphosphine)palladium (20 mg, 0.04 mmol) was added to the reaction mixture. The reaction mixture was then heated at 110° C. for 1 h. The crude was purified by silica gel column chromatography (40 g column, gradient elution with 0-100% EtOAc in hexanes, 5% MeOH)) to give the desired Suzuki product.

Above product was dissolved in small amount of MeOH and 4N HCl was added and the resultant reaction mixture was stirred for 1 h at room temperature Most of solvent was removed under reduced pressure and the resulting residue was purified with prep-HPLC (Waters Sunfire C18, 5 um particle size, 30×100 mm; mobile phases: water (0.15% ammonium hydroxide)/acetonitrile at a flow rate of 60 ml/min) to give the desired product (10.0 mg, 15%). LCMS calc. for $C_{27}H_{28}FN_6O_3$ (M+H)$^+$ m/z: 503.2; found: 503.1.

Example 108

2-[({4-[(3S,5R)-3-Amino-5-methylpiperidin-1-yl]pyridin-3-yl}amino)methyl]-6-(2,6-difluorophenyl)-5-fluoropyridin-3-amine

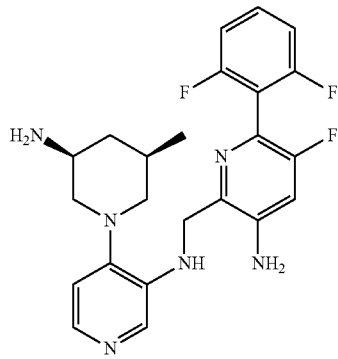 [SMILES: C[C@@H]1C[C@H](N)CN(c2ccncc2NCc2nc(-c3c(F)cccc3F)c(F)cc2N)C1]

Step 1. tert-Butyl [6-(2,6-difluorophenyl)-5-fluoro-2-(hydroxymethyl)pyridin-3-yl]carbamate

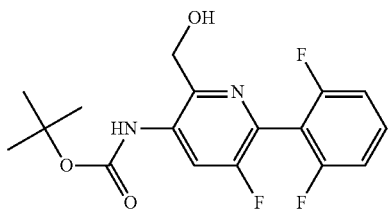 [SMILES: CC(C)(C)OC(=O)Nc1cc(F)c(-c2c(F)cccc2F)nc1CO]

To a mixture of 3-[(tert-butoxycarbonyl)amino]-6-(2,6-difluorophenyl)-5-fluoropyridine-2-carboxylic acid (from Infinity, 700 mg, 2 mmol) and triethylamine (278 μL, 2.00 mmol) in tetrahydrofuran (14 mL) was added isobutyl chloroformate (0.259 mL, 2.00 mmol) at 0° C. The reaction mixture was stirred at 0° C. for 30 min. The resulting precipitate was removed by filtration. To the filtrate was added sodium tetrehydroborate (140 mg, 3.8 mmol) in water (0.9 mL). The reaction mixture was stirred at r.t for 1 h, then quenched with water, extracted with EtOAc. The combined organic layers were washed with brine, dried and solvent evaporated. The residue was purified with combi-flash using 0-50% hexanes/EtOAc to give the desired product (230 mg, 30%). LCMS calc. for $C_{17}H_{18}F_3N_2O_3$ (M+H)$^+$ m/z: 355.1; found: 355.1.

Step 2. tert-Butyl [6-(2,6-difluorophenyl)-5-fluoro-2-formylpyridin-3-yl]carbamate

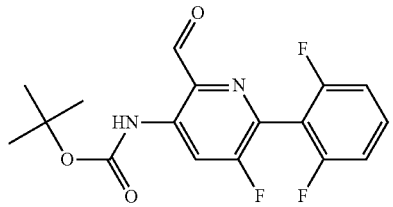 [SMILES: CC(C)(C)OC(=O)Nc1cc(F)c(-c2c(F)cccc2F)nc1C=O]

To a stirred solution of tert-butyl [6-(2,6-difluorophenyl)-5-fluoro-2-(hydroxymethyl)pyridin-3-yl]carbamate (200 mg, 0.58 mmol) in DCM (4 mL, 60 mmol) at 0° C. was added pyridine (56 μL, 0.69 mmol) and Dess-Martin periodinane (257 mg, 0.605 mmol). The reaction mixture was stirred overnight at room temperature Solution of NaHCO$_3$ and Na$_2$S$_2$O$_3$ was added and the resulting reaction mixture was stirred for 30 min, and then extracted with DCM. The combined organic layers were dried, concentrated under reduced pressure. The residue was purified by Combi-flash chromatography using 10-50% EtOAc in hexanes as eluents to give the desired product (180 mg, 90%). LCMS calc. for $C_{17}H_{16}F_3N_2O_3$ (M+H)$^+$ m/z: 353.1; found: 353.1.

Step 3. 2-[({4-[(3S,5R)-3-Amino-5-methylpiperidin-1-yl]pyridin-3-yl}amino)methyl]-6-(2,6-difluorophenyl)-5-fluoropyridin-3-amine tert-Butyl [(3 S,5R)-1-(3-aminopyridin-4-yl)-5-methylpiperidin-3-yl]carbamate (Prepared in Intermediate 2, Step 6; 14 mg, 0.046 mmol) and tert-butyl [6-(2,6-difluorophenyl)-5-fluoro-2-formylpyridin-3-yl]carbamate (18 mg, 0.050 mmol) were dissolved in toluene (2.0 mL) and catalitic amount of acetic acid was added. The reaction mixture was heated at 100° C. for 2 h. Then solvent was evaporated and methanol (2.0 mL) was added. After addition of sodium tetrahydroborate (4.3 mg, 0.11 mmol), the reaction was stirred for 30 min, and then concentrated under reduced pressure. The residue was dissolved in methanol (0.5 mL) and 4.0M hydrogen chloride in dioxane (2 mL, 8 mmol) was added. The reaction mixture was stirred for 30 min. Solvent was removed and the resulting residue was purified with prep-HPLC (Waters Sunfire C18, 5 um particle size, 30×100 mm; mobile phases: water (0.1% TFA)/acetonitrile at a flow rate of 60 ml/min) to give the desired product (5 mg, 30%). LCMS calc. for $C_{23}H_{27}F_2N_6$ (M+H)$^+$ m/z: 425.2; found: 425.1. $^1$H NMR (DMSO-d$_6$, 300 MHz): δ 8.05 (s, 1H); 7.85 (d, 1H); 7.60 (m, 1H); 7.20 (t. 2H); 7.00 (d, 1H); 6.80 (d, 1H); 6.05 (s, 2H); 5.90 (m, 1H); 4.25 (d, 1H); 4.15 (d, 1H); 3.10 (d, 2H); 2.65 (m, 1H); 2.15 (t, 1H); 1.85 (t, 1H); 1.55 (m, 4H); 0.65 (m, 4H) ppm.

Example 109

2-[({4-[(3S,5R)-3-Amino-5-(trifluoromethyl)piperidin-1-yl]pyridin-3-yl}amino)methyl]-6-(2,6-difluorophenyl)-5-fluoropyridin-3-amine

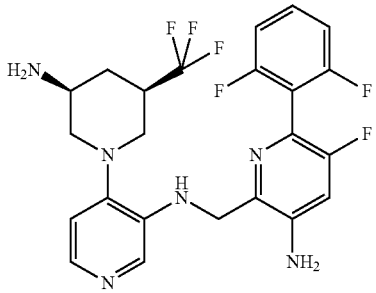 [SMILES: Nc1cc(F)c(-c2c(F)cccc2F)nc1CNc1cnccc1N1C[C@@H](N)C[C@@H](C(F)(F)F)C1]

tert-Butyl [(3 S,5R)-1-(3-aminopyridin-4-yl)-5-(trifluoromethyl)piperidin-3-yl]carbamate (Prepared in Intermediate 3, Step 4; 16 mg, 0.050 mmol) and tert-butyl [6-(2,6-difluorophenyl)-5-fluoro-2-formylpyridin-3-yl]carbamate (Prepared in Example 108, Step 2; 18 mg, 0.050 mmol) were dissolved in toluene (2.0 mL) and catalitic amount of acetic acid was added. The reaction mixture was heated at 100° C. for 2 h. Then solvent was evaporated and methanol (2.0 mL) was added. After addition of sodium tetrahydroborate (4.3 mg, 0.11 mmol), the reaction mixture was stirred for 30 min, then concentrated under reduced pressure.

The residue was dissolved in methanol (0.5 mL) and 4.0M hydrogen chloride in dioxane (2 mL) was added, the mixture was stirred for 30 min. Solvent was removed and the residue was purified with prep-HPLC (Waters Sunfire C18, 5 um particle size, 30×100 mm; mobile phases: water (0.1% TFA)/acetonitrile at a flow rate of 60 ml/min) to give the desired product (11.5 mg, 70%). LCMS calc. for $C_{23}H_{24}F_5N_6$ (M+H)$^+$ m/z: 479.2; found: 497.1. $^1$H NMR (DMSO-d$_6$, 300 MHz): δ 8.05 (s, 1H); 7.85 (d, 1H); 7.65 (m, 1H); 7.20 (m. 2H); 7.00 (d, 1H); 6.90 (d, 1H); 6.05 (s, 2H); 5.90 (m, 1H); 4.30 (d, 1H); 4.15 (d, 1H); 3.10 (d, 1H); 2.65 (m, 1H); 2.30 (m, 4H); 1.85 (d, 1H); 1.10 (m, 1H) ppm.

Example 110

4-[(3S,5R)-3-Amino-5-methylpiperidin-1-yl]-N-{[6-(2,6-difluorophenyl)-5-fluoropyridin-2-yl]methyl}-2-fluoropyridin-3-amine

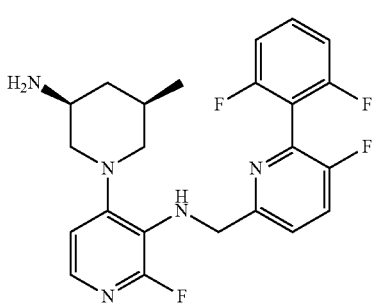 [SMILES: C[C@@H]1C[C@H](N)CN(c2ccnc(F)c2NCc2ccc(F)c(-c3c(F)cccc3F)n2)C1]

Step 1. tert-Butyl [(3S,5R)-1-(2-fluoro-3-nitropyridin-4-yl)-5-methylpiperidin-3-yl]carbamate

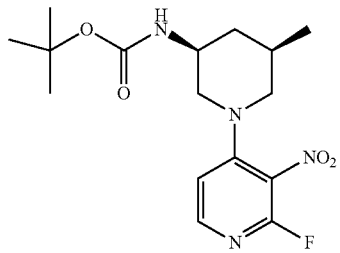 [SMILES: C[C@@H]1C[C@H](NC(=O)OC(C)(C)C)CN(c2ccnc(F)c2[N+](=O)[O-])C1]

A mixture of 2,4-difluoro-3-nitropyridine (from Combi-Blocks, 0.20 g, 1.2 mmol), tert-butyl [(3 S,5R)-5-methylpiperidin-3-yl]carbamate (Prepared in Intermediate 2, Step 4; 0.31 g, 1.4 mmol) and triethylamine (0.06 mL, 0.4 mmol) in isopropyl alcohol (0.29 mL) was stirred at r.t for 1 h. The solvent was removed by rotavap and the residue was purified with combi-flash with EtOAc/hexanes (10-60%) to give the desired product (0.40 g, 90%). LCMS calc. for $C_{16}H_{24}FN_4O_4$ (M+H)$^+$ m/z: 355.2; found: 355.2.

Step 2. tert-Butyl [(3S,5R)-1-(3-amino-2-fluoropyridin-4-yl)-5-methylpiperidin-3-yl]carbamate

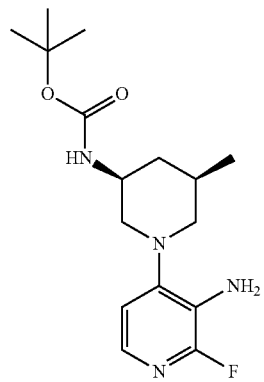 [SMILES: C[C@@H]1C[C@H](NC(=O)OC(C)(C)C)CN(c2ccnc(F)c2N)C1]

A mixture of tert-butyl [(3 S,5R)-1-(2-fluoro-3-nitropyridin-4-yl)-5-methylpiperidin-3-yl]carbamate (0.40 g, 1.2 mmol), methanol (20 mL) and 10% palladium on carbon (0.49 g) was hydrogenated under positive pressure of H$_2$ at room temperature for 2 h. The reaction mixture was filtered and concentrated under reduced pressure to give the desired product (0.35 g, 90%). LCMS calc. for $C_{15}H_{24}FN_4O_2$ (M+H)$^+$ m/z: 311.2; found: 311.2.

Step 3. tert-Butyl [(3S,5R)-1-(3-{[(6-bromo-5-fluoropyridin-2-yl)methyl]amino}-2-fluoropyridin-4-yl)-5-methylpiperidin-3-yl]carbamate

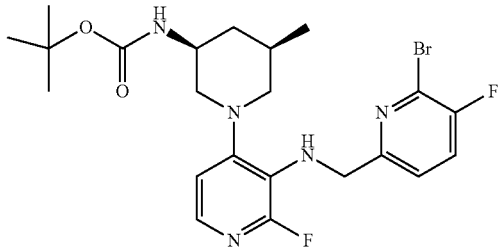 [SMILES: C[C@@H]1C[C@H](NC(=O)OC(C)(C)C)CN(c2ccnc(F)c2NCc2ccc(F)c(Br)n2)C1]

tert-Butyl [(3 S,5R)-1-(3-amino-2-fluoropyridin-4-yl)-5-methylpiperidin-3-yl]carbamate (290 mg, 0.89 mmol) and 6-bromo-5-fluoropyridine-2-carbaldehyde (Prepared in Intermediate 1, Step 2; 200 mg, 0.980 mmol) were dissolved in toluene (39 mL) and catalitic amount of acetic acid was added. The reaction mixture was heated at 110° C. for 2 h. Then solvent was evaporated and methanol (39 mL) was added. After addition of sodium tetrahydroborate (84 mg, 2.2 mmol), the reaction mixture was stirred for 30 min. Solvent was removed and the resulting residue was purified with Combi-flash chromatography with 20-100% EtOAc/hexane as eluents to give the desired product as yellow solid (0.40 g, 85%). LCMS calc. for $C_{22}H_{29}BrF_2N_5O_2$ $(M+H)^+$ m/z: 512.2; found: 512.1.

Step 4. 4-[(3S,5R)-3-Amino-5-methylpiperidin-1-yl]-N-{[6-(2,6-difluorophenyl)-5-fluoropyridin-2-yl]methyl}-2-fluoropyridin-3-amine In a microwave tube, a mixture tert-butyl [(3S,5R)-1-(3-{[(6-bromo-5-fluoropyridin-2-yl)methyl]amino}-2-fluoropyridin-4-yl)-5-methylpiperidin-3-yl]carbamate (50 mg, 0.1 mmol), (2,6-difluorophenyl)boronic acid (from Aldrich, 20 mg, 0.13 mmol), and N,N-diisopropylethylamine (0.051 mL, 0.29 mmol) in 1,4-dioxane (2.7 mL) and water (0.26 mL) was stirred together and purged with $N_2$ for 5 min before bis(tri-t-butylphosphine)palladium (10 mg, 0.03 mmol) was added. The reaction mixture was then heated at 110° C. for 1 h. The reaction mixture was worked up with $NaHCO_3$ solution and EtOAc. Layers were separated and the organic layer was dried and concentrated. The resultant residue was dissolved in small amount of MeOH and 4N HCl was added. The reaction mixture was stirred for 1 h at room temperature Solvent was removed under reduced pressure and the residue was purified with prep-HPLC (Waters Sunfire C18, 5 um particle size, 30×100 mm; mobile phases: water (0.15% ammonium hydroxide)/acetonitrile at a flow rate of 60 ml/min) to give the desired product (8.0 mg, 20%). LCMS calc. for $C_{23}H_{24}F_4N_5$ $(M+H)^+$ m/z: 446.2; found: 446.1.

Example 111

4-[(3S,5R)-3-Amino-5-methylpiperidin-1-yl]-N-{1-[6-(2,6-difluorophenyl)-5-fluoropyridin-2-yl]ethyl}pyridin-3-amine

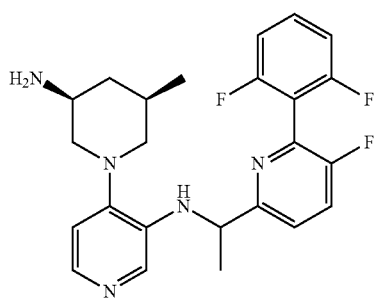 [SMILES: CC(Nc1cnccc1N1C[C@H](C)C[C@H](N)C1)c1ccc(F)c(-c2c(F)cccc2F)n1]

Step 1. 6-(2,6-Difluorophenyl)-5-fluoro-N-methoxy-N-methylpyridine-2-carboxamide

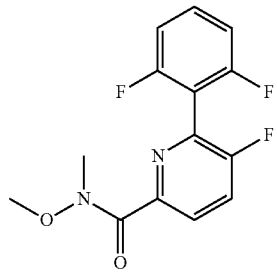 [SMILES: CON(C)C(=O)c1ccc(F)c(-c2c(F)cccc2F)n1]

To a solution of 6-(2,6-difluorophenyl)-5-fluoropyridine-2-carboxylic acid (0.97 g, 3.8 mmol) and N,O-dimethylhydroxylamine hydrochloride (0.357 g, 3.66 mmol) in DMF (10 mL) was added N,N,N',N'-tetramethyl-O-(7-azabenzotriazol-1-yl)uronium hexafluorophosphate (1.70 g, 4.47 mmol) and N,N-diisopropylethylamine (2.0 mL, 12 mmol). The reaction mixture was stirred at room temperature overnight. The reaction mixture was diluted with water, extracted with DCM. The combined organic layers were dried over $Na_2SO_4$, filtered and concentrated. The residue was purified with flash chromatography (eluting with 0-30% EtOAc in hexanes) to give the desired product (1.06 g, 98%). LCMS calc. for $C_{14}H_{12}F_3N_2O_2$ $(M+H)^+$ m/z: 297.1; found: 297.1.

Step 2. 1-[6-(2,6-Difluorophenyl)-5-fluoropyridin-2-yl]ethanone

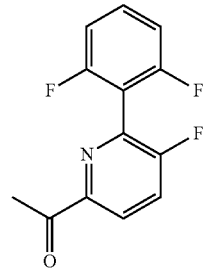 [SMILES: CC(=O)c1ccc(F)c(-c2c(F)cccc2F)n1]

To a mixture of 6-(2,6-difluorophenyl)-5-fluoro-N-methoxy-N-methylpyridine-2-carboxamide (1.06 g, 3.58 mmol) in tetrahydrofuran (20 mL) at 0° C. was added 3.0M methylmagnesium bromide in ether (1.25 mL, 3.76 mmol) slowly. Ther reaction mixture was stirred at 0° C. until complete conversion was detected by LCMS, then the reaction was quenched with $NH_4Cl$ solution, and then the reaction mixture was extracted with EtOAc. The combined organic layers were washed with brine, dried and solvent evaporated. The residue was purified with flash chromatography (0-20% EtOAc in hexanes) to give the desired product as colorless solid.

Step 3. 4-[(3S,5R)-3-Amino-5-methylpiperidin-1-yl]-N-{1-[6-(2,6-difluorophenyl)-5-fluoropyridin-2-yl]ethyl}pyridin-3-amine To a mixture of sodium triacetoxyborohydride (147 mg, 0.694 mmol) in DCM (2.0 mL) was added trifluoroacetic acid (178 μL, 2.31 mmol). After stirring for 5 min, tert-butyl

[(3S,5R)-1-(3-aminopyridin-4-yl)-5-methylpiperidin-3-yl] carbamate (Prepared in Intermediate 2, Step 6; 51.0 mg, 0.166 mmol) was added followed by the addition of a solution of 1-[6-(2,6-difluorophenyl)-5-fluoropyridin-2-yl] ethanone (50 mg, 0.20 mmol) in DCM (1 mL) dropwise. The reaction mixture was stirred for 3 h, then quenched with DCM and water. The organic layer was concentrated under reduced pressure and purified with flash chromatography (0-15% methanol in DCM) to give the reductive amination product. The intermediate was treated with 1:1 DCM/TFA (2 mL) and stirred for 1 h. The solvent was removed and the residue was dissolved in methanol and purified with prep-LCMS (Waters Sunfire C18, 5 um particle size, 30×100 mm; mobile phases: water (0.15% ammonium hydroxide)/acetonitrile at a flow rate of 60 ml/min) to give the desired product as white solid. LCMS calc. for $C_{24}H_{27}F_3N_5$ $(M+H)^+$ m/z: 442.2; found: 442.2.

Example A. Pim Enzyme Assays

Pim-1 and Pim-3 kinase assays-20 µL reactions were run in white 384 well polystyrene plates dotted with 0.8 µL compound/DMSO in the assay buffer (50 mM Tris, pH 7.5, 0.01% Tween-20, 5 mM mgCl$_2$, 0.01% BSA, 5 mM DTT), containing 0.05M Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 µL STOP Buffer (150 mM Tris, pH=7.5, 150 mM NaCl, 75 mM EDTA, 0.01% Tween-20, 0.3% BSA,) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 µg/mL each. Supplementation of the STOP buffer with beads and stopping the reactions were done under reduced light. Prior to the stopping reactions STOP buffer with beads was preincubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay—20 µL reactions were run in white 384 well polystyrene plates dotted with 0.8 µL compound/DMSO in the assay buffer (50 mM Tris, pH 7.5, 0.01% Tween-20, 5 mM mgCl$_2$, 0.01% BSA, 5 mM DTT), containing 0.05M Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 µL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an IC$_{50}$ of 2M or less when tested for PIM kinase activity under the assay conditions disclosed above are considered active.

Although the above in vitro assays are conducted at 1 mM ATP compounds can also be evaluated for potency and in vitro activity against PIM targets utilizing K$_m$ conditions, where the concentration of ATP is set to the K$_m$ value and the assay is more sensitive to PIM inhibition activity.

Example B. Pim Cellular Assays

One or more compounds of the invention were tested for inhibitory activity of PIM according to at least one of the following cellular assays. Compounds of the invention having an IC$_{50}$ of 10 µM or less when tested for PIM kinase activity under the cellular assay conditions disclosed below would be and were considered active.

Pim Cell Proliferation Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the anti-proliferation activity of test compounds, both cell lines are plated with the culture medium ($2×10^3$ cells/well/in 200 µL) into 96-well polystyrene ultralow binding (Costar,) in the presence or absence of a concentration range of test compounds. After 4 days, [$^3$H]-thymidine, 1 µCi/10 µL/well (PerkinElmer, Boston, Mass.) in culture medium is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim Cell Proliferation Assay

MOLM-16 cells are purchased from DSMZ (Germany) and maintained in the culture medium recommended, RPMI, 20% FBS. To measure the anti-proliferation activity of test compounds, the cells are plated with the RPMI, 10% FBS ($1×10^4$ cells/well/in 200 µL) into 96-well polystyrene ultralow binding plates (Costar) in the presence or absence of a concentration range of test compounds. After 4 days, [$^3$H]-thymidine, 1 µCi/10 µL/well (PerkinElmer, Boston, Mass.) in RPMI, 10% FBS is then added to the cell culture for an additional 16 h before the incorporated radioactivity is separated by filtration with a Packard Micro plate Harvester with water through a 0.3% PEI pre wetted GF/B filter plates (Packard Bioscience/PerkinElmer, Boston, Mass.). The plate is measured by liquid scintillation counting with a TopCount (PerkinElmer). IC$_{50}$ determination is performed by fitting the curve of percent inhibition versus the log of the inhibitor concentration using the GraphPad Prism 5.0 software.

Pim pBAD Signaling Assay

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium ($1×10^6$/well/100 µL for KG1A and $4×10^5$ cells/well/in 100 µL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS. 12.BM cells and 4 h for KG1-A cells. Plates are centrifuged at 2000 RPM for 10 min. and supernatants aspirated. 100 µL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80° C. To measure the pBAD activity, a Cell Signaling ELISA kit (Cell Signaling Path Scan phosphor pBAD ELISA) is utilized. 50 µL of the lysate is tested per the ELISA protocol and the data analysis is performed by software on a SpectrMax5 plate reader (Molecular Devices, Sunnyvale, Calif.). $IC_{50}$ determination is performed by fitting the curve of percent inhibition versus the log of the inhibitor concentration using the GraphPad Prism 5.0 software.

Data obtained for the Example compounds, obtained using the methods described in Example A, are provided in Table 1.

TABLE 1

Pim Enzyme Assay Data

| Example No. | Pim1 $IC_{50}$ (nM)[a] | Pim2 $IC_{50}$ (nM)[b] | Pim3 $IC_{50}$ (nM)[a] |
|---|---|---|---|
| 1 | * | + | * |
| 2 | + | + | * |
| 3 | * | + | * |
| 4 | * | + | * |
| 5 | * | + | * |
| 6 | * | + | * |
| 7 | * | + | * |
| 8 | * | ++ | * |
| 9 | * | ++ | * |
| 10 | * | + | * |
| 11 | * | ++ | * |
| 12 | * | + | * |
| 13 | * | + | * |
| 14 | * | + | * |
| 15 | * | ++ | * |
| 16 | * | ++ | * |
| 17 | * | ++ | * |
| 18 | * | ++ | * |
| 19 | * | + | * |
| 20 | * | +++ | ** |
| 21 | * | ++ | * |
| 22 | * | ++ | * |
| 23 | * | ++ | * |
| 24 | * | + | * |
| 24A | * | + | * |
| 24B | * | ++ | * |
| 25 | * | ++ | * |
| 26 | * | ++ | * |
| 27 | * | ++ | * |
| 28 | * | ++ | * |
| 29 | * | ++ | * |
| 30 | ** | +++ | ** |
| 31 | * | +++ | ** |
| 32 | * | + | * |
| 33 | * | + | * |
| 34 | * | + | * |
| 35 | * | + | * |
| 36 | * | + | * |
| 37 | * | ++ | * |
| 38 | * | ++ | * |
| 39 | * | + | * |
| 40 | * | ++ | * |
| 41 | * | ++ | * |
| 42 | * | + | * |
| 43 | * | + | * |
| 44 | * | + | * |
| 45 | * | + | * |
| 46 | * | + | * |
| 47 | * | + | * |
| 48 | * | + | * |
| 49 | * | ++ | * |
| 50 | * | ++ | * |
| 51 | * | + | * |
| 52 | * | + | * |
| 53 | * | + | * |
| 54 | * | + | * |
| 55 | * | + | * |
| 56 | * | + | * |
| 57 | * | ++ | * |
| 58 | * | ++ | ** |
| 59 | * | ++ | * |
| 60 | * | ++ | * |
| 61 | * | + | * |
| 62 | * | + | * |
| 63 | * | + | * |

TABLE 1-continued

Pim Enzyme Assay Data

| Example No. | Pim1 $IC_{50}$ (nM)[a] | Pim2 $IC_{50}$ (nM)[b] | Pim3 $IC_{50}$ (nM)[a] |
|---|---|---|---|
| 64 | * | + | * |
| 65 | * | + | * |
| 66 | * | ++ | * |
| 67 | * | ++ | * |
| 68 | * | ++ | * |
| 69 | * | +++ | * |
| 70 | * | ++ | * |
| 71 | * | + | * |
| 72 | * | + | * |
| 73 | * | + | * |
| 74 | * | + | * |
| 75 | * | + | * |
| 76 | * | + | * |
| 77 | * | + | * |
| 78 | * | + | * |
| 79 | n/a | n/a | n/a |
| 80 | n/a | n/a | n/a |
| 81 | n/a | n/a | n/a |
| 82 | * | + | * |
| 83 | * | + | * |
| 84 | * | ++ | * |
| 85 | * | ++ | * |
| 86 | * | ++ | * |
| 87 (Diastereoisomer 1) | * | +++ | ** |
| 87 (Diastereoisomer 2) | * | ++ | ** |
| 88 | * | +++ | * |
| 89 | * | ++ | * |
| 90 | * | +++ | * |
| 91 | * | ++ | * |
| 92 | * | ++ | * |
| 93 | * | ++ | * |
| 94 | n/a | n/a | n/a |
| 95 | n/a | n/a | n/a |
| 96 | * | ++ | * |
| 97 | ** | ++ | * |
| 98 | * | ++ | * |
| 99 | * | + | * |
| 100 | * | + | * |
| 101 | n/a | n/a | n/a |
| 102 | * | ++ | * |
| 103 | * | + | * |
| 104 | * | ++ | * |
| 105 | * | + | * |
| 106 | * | + | * |
| 107 | * | + | * |
| 108 | * | + | * |
| 109 | * | + | * |
| 110 | * | + | * |
| 111 | * | + | * |

[a] $IC_{50}$ ≤10 nM: *; 10 nM < $IC_{50}$ ≤ 50 nM: ; 50 nM < $IC_{50}$ ≤ 500 nM: *; 500 nM < $IC_{50}$ ≤ 2000 nM: ****. Assays performed at 1 mM ATP.
[b] $IC_{50}$ ≤100 nM: +; 100 nM < $IC_{50}$ ≤ 1000 nM: ++; 1000 nM < $IC_{50}$ ≤ 10000 nM: +++. Assays performed at 1 mM ATP.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound which is 4-[(3S,5R)-3-amino-5-methylpiperidin-1-yl]-N-{[6-(2,6-difluorophenyl)-5-fluoropyridin-2-yl]methyl}-6,7-dihydro-5H-cyclopenta[b]pyridin-3-amine, or a pharmaceutically acceptable salt thereof.

2. A composition comprising the compound of claim 1, or a pharmaceutically acceptable salt thereof, and at least one pharmaceutically acceptable carrier.

3. A method of inhibiting Pim1, Pim2, or Pim3 enzyme comprising contacting the enzyme with the compound of claim 1, or a pharmaceutically acceptable salt thereof.

4. A method of inhibiting Pim1 enzyme comprising contacting the enzyme with the compound of claim 1, or a pharmaceutically acceptable salt thereof.

5. A method of inhibiting Pim2 enzyme comprising contacting the enzyme with the compound of claim 1, or a pharmaceutically acceptable salt thereof.

6. A method of inhibiting Pim3 enzyme comprising contacting the enzyme with the compound of claim 1, or a pharmaceutically acceptable salt thereof.

7. A method of treating cancer comprising administering to a patient in need of such treatment a therapeutically effective amount of the compound of claim 1, or a pharmaceutically acceptable salt thereof.

8. The method of claim 7, wherein the cancer is a cancer wherein the expression or activity of at least one of Pim1, Pim2, and Pim3 is upregulated.

9. The method of claim 7, wherein the cancer is a cancer wherein an oncogene is activated.

10. The method of claim 7, wherein the cancer is a cancer wherein Myc or Bcl2 is activated.

11. The method of claim 7, wherein the cancer is a solid tumor or a hematological cancer.

12. The method of claim 7, wherein the cancer is prostate cancer, colon cancer, esophageal cancer, endometrial cancer, ovarian cancer, uterine cancer, renal cancer, hepatic cancer, pancreatic cancer, gastric cancer, breast cancer, lung cancer, cancer of the head or neck, thyroid cancer, glioblastoma, sarcoma, bladder cancer, lymphoma, leukemia, acute lymphoblastic leukemia, acute myelogenous leukemia, chronic lymphocytic leukemia, chronic myelogenous leukemia, diffuse large-B cell lymphoma, mantle cell lymphoma, non-Hodgkin lymphoma, Hodgkin lymphoma or multiple myeloma.

13. A method of treating myeloproliferative disorder, comprising administering to a patient in need of such treatment a therapeutically effective amount of the compound of claim 1, or a pharmaceutically acceptable salt thereof, wherein the myeloproliferative disorder is polycythemia vera, essential thrombocythemia, chronic myelogenous leukemia, myelofibrosis, primary myelofibrosis, post polycythemia vera/essential thrombocythemia myelofibrosis, post-essential thrombocythemia myelofibrosis or post polycythemia vera myelofibrosis.

14. A method of treating an immune disorder comprising administering to a patient in need of such treatment a therapeutically effective amount of compound of claim 1, or a pharmaceutically acceptable salt thereof, wherein the immune disorder is multiple sclerosis, rheumatoid arthritis, allergy, food allergy, asthma, lupus, inflammatory bowel disease or ulcerative colitis, Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft vs host disease, Sjogren's syndrome, glomerulonephritis or type I diabetes mellitus.

15. A method of treating atherosclerosis comprising administering to a patient in need of such treatment a therapeutically effective amount of the compound of claim 1, or a pharmaceutically acceptable salt thereof.

16. A method of reducing angiogenesis or tumor metastasis, comprising administering to a patient in need of such treatment a therapeutically effective amount of the compound of claim 1, or a pharmaceutically acceptable salt thereof.

* * * * *